(12) United States Patent
Sadar et al.

(10) Patent No.: US 9,388,112 B2
(45) Date of Patent: *Jul. 12, 2016

(54) BISPHENOL DERIVATIVES AND THEIR USE AS ANDROGEN RECEPTOR ACTIVITY MODULATORS

(75) Inventors: Marianne D. Sadar, West Vancouver (CA); Nasrin R. Mawji, Burnaby (CA); Carmen Adriana Banuelos, Vancouver (CA); Raymond J. Andersen, Vancouver (CA); Javier Garcia Fernandez, Gijon (ES)

(73) Assignees: The University of British Columbia, Vancouver, BC (CA); Brittish Columbia Cancer Agency Branch, Vancouver, BC (CA)

( * ) Notice: Subject to any disclaimer, the term of this patent is extended or adjusted under 35 U.S.C. 154(b) by 506 days.

This patent is subject to a terminal disclaimer.

(21) Appl. No.: 13/520,729

(22) PCT Filed: Jan. 6, 2011

(86) PCT No.: PCT/CA2011/000019
§ 371 (c)(1),
(2), (4) Date: Jan. 9, 2013

(87) PCT Pub. No.: WO2011/082487
PCT Pub. Date: Jul. 14, 2011

(65) Prior Publication Data
US 2013/0131167 A1     May 23, 2013

Related U.S. Application Data

(60) Provisional application No. 61/282,238, filed on Jan. 6, 2010.

(51) Int. Cl.
| | |
|---|---|
| C07C 43/23 | (2006.01) |
| C07D 401/06 | (2006.01) |
| C07C 15/16 | (2006.01) |
| C07C 57/38 | (2006.01) |
| A61K 31/09 | (2006.01) |
| A61K 31/22 | (2006.01) |
| C07C 69/63 | (2006.01) |
| C07C 43/225 | (2006.01) |

(52) U.S. Cl.
CPC ............... *C07C 57/38* (2013.01); *A61K 31/09* (2013.01); *A61K 31/22* (2013.01); *C07C 15/16* (2013.01); *C07C 43/225* (2013.01); *C07C 43/23* (2013.01); *C07C 69/63* (2013.01); *C07D 401/06* (2013.01)

(58) Field of Classification Search
CPC ....... C07C 15/16; C07C 43/23; C07D 401/06
See application file for complete search history.

(56) References Cited

U.S. PATENT DOCUMENTS

| | | |
|---|---|---|
| 2,571,217 A | 10/1951 | Davis et al. |
| 2,890,189 A | 6/1959 | Greenlee |
| 4,284,574 A | 8/1981 | Bagga |
| 4,369,298 A | 1/1983 | Kida et al. |
| 4,855,184 A | 8/1989 | Klun et al. |
| 4,904,760 A | 2/1990 | Gaku et al. |
| 5,043,375 A | 8/1991 | Henning et al. |
| 5,155,196 A | 10/1992 | Kolb et al. |
| 5,362,615 A | 11/1994 | Hagemann et al. |
| 5,403,697 A | 4/1995 | Doessel et al. |
| 5,753,730 A | 5/1998 | Nagata et al. |
| 5,998,674 A | 12/1999 | Taketani et al. |
| 6,218,430 B1 | 4/2001 | Allegretto et al. |
| 6,245,117 B1 | 6/2001 | Nishikawa et al. |
| 7,183,323 B2 | 2/2007 | Chinn et al. |
| 7,674,795 B2 | 3/2010 | Mailliet et al. |
| 8,686,050 B2 | 4/2014 | Sadar et al. |
| 2003/0092724 A1* | 5/2003 | Kao .............. A61K 9/208 514/282 |
| 2003/0105268 A1 | 6/2003 | Boriack et al. |
| 2004/0049004 A1 | 3/2004 | Boriak et al. |
| 2004/0243316 A1 | 12/2004 | Weinmann et al. |
| 2008/0153837 A1 | 6/2008 | Mailliet et al. |
| 2008/0193380 A1 | 8/2008 | Dalton et al. |
| 2008/0255395 A1 | 10/2008 | Dai et al. |
| 2009/0105349 A1 | 4/2009 | Barvian et al. |
| 2011/0230556 A1 | 9/2011 | Sadar et al. |
| 2013/0045204 A1 | 2/2013 | Andersen et al. |
| 2013/0109758 A1 | 5/2013 | Sadar et al. |
| 2013/0245129 A1 | 9/2013 | Sadar et al. |
| 2013/0336962 A1 | 12/2013 | Andersen et al. |
| 2014/0248263 A1 | 9/2014 | Andersen et al. |
| 2014/0335080 A1 | 11/2014 | Andersen et al. |

(Continued)

FOREIGN PATENT DOCUMENTS

| | | |
|---|---|---|
| CA | 2 339 775 A1 | 3/2000 |
| CA | 2 606 262 A1 | 11/2006 |

(Continued)

OTHER PUBLICATIONS

Poouthree et al. Electrophoresis, 2007, vol. 28, pp. 3705-3711.*
Petersen et al. Eur. Food Res. Technol., 2003, vol. 216, pp. 355-364.*
Andersen et al., "Aziridine Bisphenol Ethers and Related Compounds and Methods for Their Use," U.S. Appl. No. 13/863,849, filed Apr. 16, 2013, 120 pages.
Andersen et al., "Bisphenol Compounds and Methods for Their Use," U.S. Appl. No. 14/110,615, filed Oct. 8, 2013, 157 pages.
Bao et al., "Androgen signaling is required for the vitamin D-mediated growth inhibition in human prostate cancer cells," *Nature Publishing Group* 23:3350-3360, 2004.

(Continued)

*Primary Examiner* — Samira Jean-Louis
(74) *Attorney, Agent, or Firm* — Cooley LLP

(57) ABSTRACT

This invention provides bisphenol derivatives having a structure of formula 1. Said compounds are modulators of the androgen receptor activity and are useful in the treatment of various diseases, including prostate cancer, breast cancer, ovarian cancer, endometrial cancer, acne, ovarian cysts, polycystic ovarian disease, age-related macular degeneration, precocious puberty, hirsutism and hair loss.

34 Claims, 7 Drawing Sheets

(56) References Cited

U.S. PATENT DOCUMENTS

| | | | |
|---|---|---|---|
| 2015/0010469 | A1 | 1/2015 | Andersen et al. |
| 2015/0125389 | A1 | 5/2015 | Andersen et al. |

FOREIGN PATENT DOCUMENTS

| | | |
|---|---|---|
| EP | 0056175 A1 | 7/1982 |
| EP | 0 293 768 A1 | 12/1988 |
| EP | 0515128 A1 | 11/1992 |
| FR | 1389005 | 2/1965 |
| JP | B-S45-008432 | 3/1970 |
| JP | 63-196675 | 8/1988 |
| JP | H01-503541 | 11/1989 |
| JP | H02-4815 | 1/1990 |
| JP | 6-049473 A2 | 4/1994 |
| JP | 9-176240 A | 7/1997 |
| JP | A-H10-316803 | 12/1998 |
| JP | 11-166087 A2 | 6/1999 |
| JP | 2000-072705 A2 | 3/2000 |
| JP | 2005-325301 A | 11/2005 |
| JP | 2006-208607 A | 8/2006 |
| JP | 2006-265351 A2 | 10/2006 |
| JP | 2007-290980 | 11/2007 |
| PL | 135932 | 9/1984 |
| WO | WO 88/09782 | 12/1988 |
| WO | WO 98/34930 A1 | 8/1998 |
| WO | 00/01813 A2 | 1/2000 |
| WO | 00/10958 A1 | 3/2000 |
| WO | 01/88013 A2 | 11/2001 |
| WO | WO 02/05813 | 1/2002 |
| WO | 03/004481 A1 | 1/2003 |
| WO | WO 2005/042464 A1 | 5/2005 |
| WO | 2005/077967 A1 | 8/2005 |
| WO | WO 2008/101806 A2 | 8/2008 |
| WO | 2010/000066 A1 | 1/2010 |
| WO | 2011/082487 A1 | 7/2011 |
| WO | 2011/082488 A1 | 7/2011 |
| WO | 2012/139039 A2 | 10/2012 |
| WO | 2012/145328 A1 | 10/2012 |
| WO | 2012/145330 A1 | 10/2012 |
| WO | 2013/028791 A1 | 2/2013 |
| WO | WO 2013/028572 A1 | 2/2013 |
| WO | WO 2014/179867 A1 | 11/2014 |

OTHER PUBLICATIONS

Biles et al., "Determination of the Diglycidyl Ether of Bisphenol A and Its Derivatives in Canned Foods," *Journal. Agric. Food Chem.* 47:1965-1969, 1999.
Bisson et al., "Discovery of antiandrogen activity of nonsteroidal scaffolds of marketed drugs," *PNAS* 104(29):11927-11932, Jul. 17, 2007.
Blaszczyk et al., "Osteoblast-Derived Factors Induce Androgen-Independent Proliferation and Expression of Prostate-Specific Antigen in Human Prostate Cancer Cells," *Clinical Cancer Research* 10:1860-1869, Mar. 1, 2004.
Chang et al., "Development of Peptide Antagonists for the Androgen Receptor Using Combinatorial Peptide Phage Display," *Molecular Endocrinology* 19(10):2478-2490, 2005.
Dehm et al., "Ligand-independent Androgen Receptor Activity Is Activation Function-2-independent and Resistant to Antiandrogens in Androgen Refractory Prostate Cancer Cells," *The Journal of Biological Chemistry* 281(38):27882-27893, Sep. 22, 2006.
Dehm et al., "Splicing of a Novel *Androgen Receptor* Exon Generates a Constitutively Active Androgen Receptor that Mediates Prostate Cancer Therapy Resistance," *Cancer Res* 68(13):5469-5477, Jul. 1, 2008.
Estébanez-Perpiñá et al., "A surface on the androgen receptor that allosterically regulates coactivator binding," *PNAS* 104:15224-15229, Sep. 19, 2007.
Estébanez-Perpiñá et al., "The Molecular Mechanisms of Coactivator Utilization in Ligand-dependent Transactivation by the Androgen Receptor," *The Journal of Biological Chemistry* 280(9):8060-8068, 2005.

Fehlberg et al., "Bisphenol A diglycidyl ether induces apoptosis in tumor cells independently of peroxisome proliferator-activated receptor-$\gamma$, in caspase-dependent and—independent manners," *Biochem. J.* 362:573-578, 2002.
Gregory et al., "Epidermal Growth Factor Increases Coactivation of the Androgen Receptor in Recurrent Prostate Cancer," *The Journal of Biological Chemistry* 279(8):7119-7130, 2004.
Guo et al., "A Novel Androgen Receptor Splice Variant Is Up-regulated during Prostate Cancer Progression and Promotes Androgen Depletion-Resistant Growth," *Cancer Res* 69(6):2305-2313, Mar. 15, 2009.
He et al., "Structural Basis for Androgen Receptor Interdomain and Coactivator Interactions Suggests a Transition in Nuclear Receptor Activation Function Dominance," *Molecular Cell* 16: 425-438, Nov. 5, 2004.
Hur et al., "Recognition and Accommodation at the Androgen Receptor Coactivator Binding Interface," *PLOS Biology* 2(9):1303-1312, Sep. 2004.
Kolbel et al., "Design of Liquid Crystalline Block Molecules with Nonconventional Mesophase Morphologies: Calamitic Bolaamphiphiles with Lateral Alkyl Chains," *J. Am. Chem. Soc.* 123:6809-6818, 2001.
Kumar et al., "Synthesis of new crown analogs derived from bisphenol," *Indian Journal Chemistry* 36B:656-661, Aug. 1997.
Loren et al., "Synthesis of achiral and racemic catenanes based on terpyridine and a directionalized terpyridine mimic, pyridyl-phenanthroline," *Org. Biomol. Chem.* 3(17):3105-3116, 2005.
20 Martin et al., "A new precursor for the radiosynthesis of [$^{18}$F]FLT," *Nuclear Medicine and Biology* 29:263-273, 2002.
Paris et al., "Phenylphenols, biphenols, bisphenol-A and 4-*tert*-octylphenol exhibit $\alpha$ and $\beta$ estrogen activities and antiandrogen activity in reporter cell lines," *Molecular and Cellular Endocrinology* 193:43-49, 2002.
Quayle et al., "Androgen receptor decoy molecules block the growth of prostate cancer," *PNAS* 104(4):1331-1336, Jan. 23, 2007.
Reid et al., "Conformational Analysis of the Androgen Receptor Amino-terminal Domain Involved in Transactivation," *The Journal of Biological Chemistry* 277(22):20079-20086, 2002.
Sadar et al., "Prostate cancer: molecular biology of early progression to androgen independence," *Endocrine-Related Cancer* 6:487-502, 1999.
Sadar, "Androgen-independent Induction of Prostate-specific Antigen Gene Expression via Cross-talk between the Androgen Receptor and Protein Kinase A Signal Transduction Pathways," *The Journal of Biological Chemistry* 274(12):7777-7783, 1999.
Satoh et al., "Study on anti-androgenic effects of bisphenol a diglycidyl ether (BADGE), bisphenol F diglycidyl ether (BFDGE) and their derivatives using cells stably transfected with human androgen receptor, AR-EcoScreen," *Food and Chemical Toxicology* 42(6):983-993, Jun. 2004.
Schafer et al., "Migration from can coatings: Part 3. Synthesis, identification and quantification of migrating epoxy-based substances below 1000 Da," *Food Additives Contaminants* 21(4):390-405, Apr. 2004.
Taplin et al., "Selection for Androgen Receptor Mutations in Prostate Cancers Treated with Androgen Antagonist[1]," *Cancer Research* 59:2511-2515, Jun. 1, 1999.
Ueda et al., "Activation of the Androgen Receptor N-terminal Domain by Interleukin-6 via MAPK and STAT3 Signal Transduction Pathways," *The Journal of Biological Chemistry* 277(9):7076-7085, 2002.
Ueda et al., "Ligand-independent Activation of the Androgen Receptor by Interleukin-6 and the Role of Steroid Receptor Coactivator-1 in Prostate Cancer Cells," *The Journal of Biological Chemistry* 277(41):38087-38094, Oct. 11, 2002.
Uematsu et al., "Chlorohydrins of bisphenol A diglycidyl ether (BADGE) and of bisphenol F diglycidyl ether (BFDGE) in canned foods and ready-to-drink coffees from the Japanese market," *Food Additives and Contaminants* 18(2):177-185, 2001.
van Scherpenzeel et al., "Nanomolar affinity, iminosugar-based chemical probes for specific labeling of lysosomal glucocerebrosidase," *Bioorg. Med. Chem.* 18(1):267-273, 2010.

(56) References Cited

OTHER PUBLICATIONS

Anderson, R. et al., "Regression of Castrate-Recurrent Prostate Cancer by a Small-Molecule Inhibitor of the Amino-Terminus Domain of the Androgen Receptor", *Cancer Cell*, 17:535-546 (2010).
Brzozowski, Z. et al., "Precursors for bisphenolic resins", CAPLUS Database Accession No. 1990:36690, Document No. 112:33690, (1987), 1 page (Abstract).
Choi, K. M. et al., "New Families of Photocurable Oligomeric Fluoromonomers for Use in Dental Composites", *Chemistry of Materials*, 8(12):2704-2707 (1996).
Crivello, J. V. et al., "Synthesis and photopolymerization of multifunctional propenyl ether monomers," Database CAPLUS [online], Chemical Abstracts Service, Columbus, Ohio, US, XP002729292, retrieved from STN CA Caesar Accession No. 1994-606067 (1994), 3 pages.
Crivello, J. V. et al., "Synthesis and photopolymerization of multifunctional propenyl ether monomers", *Journal of Macromolecular Science, Pure and Applied Chemistry*, A31(9):1105-1119 (1994).
Cook, W. D., "Fracture and Structure of Highly Crosslinked Polymer Composites", *Journal of Applied Polymer Science*, 42:1259-1269 (1991).
Danquah, M. et al., "Micellar Delivery of Bicalutamide and Embelin for Treating Prostate Cancer", *Pharmaceutical Research*, 26:2081-2092 (2009).
Gallart-Ayala, H. et al., "The analysis of bisphenol A-diglycidyl ether (BADGE), bisphenol F-diglycidyl ether (BFDGE) and their derivatives in canned food and beverages by LC-MS/MS", *Thermo Fisher Scientific Inc.*, 4 pages (2011).
Garuti, L., et al., "Irreversible Protein Kinase Inhibitors", *Current Medicinal Chemistry*, 18:2981-2994 (2011).
Hu, R. et al., "Ligand-Independent Androgen Receptor Variants Derived from Splicing of Cryptic Exons Signify Hormone-Refractory Prostate Cancer", *Cancer Research*, 69:16-22 (2009).
L'Heureux, A. et al., "Aminodifluorosulfinium Salts: Selective Fluorination Reagents with Enhanced Thermal Stability and Ease of Handling", *J. Org. Chem*, 75:3401-3411 (2010).
Myung, J-K et al., "An androgen receptor N-terminal domain antagonist for treating prostate cancer", *The Journal of Clinical Investigation*, 123(7):2948-2960 (2013).
Nedolya, N. A. et al., Zhurnal Organicheskoi Khimii, 30(8):1163-1166 (1994).
Penczek, P. et al., "Synthesis and cyclotrimerization of dipropargyl derivatives of diepoxides," Database CAPLUS [Online] Chemical Abstracts Service, Columbus, Ohio, retrieved from STN CA Caesar Accession No. 1995:741510 (1995), 2 pages.
Penczek, P. et al., "Synthesis and cyclotrimerization of dipropargyl derivatives of diepoxides," Polimery, (Warsaw), 40(5):274-2777 (1995).
Reader, C. E. L., "Epoxy Resin Derivatives for Stoving Systems", *Surface Coatings Australia*, 25(10):6-9 (1988).
Rusu, E. et al.: "Photosensitive compounds with chloromethyl groups", *Revue Roumaine de Chimie*, 45(5):451-456 (2000).
Silverman, R. B., The Organic Chemistry of Drug Design and Drug Action, Academic Press, Inc., Harcourt Brace Jovanovich, pp. 15-20, 9 pages (1992).
Sun, S. et al., "Castration resistance in human prostate cancer is conferred by a frequently occurring androgen receptor splice variant", *The Journal of Clinical Investigation*, 120(8):2715-30 (2010).
Taskeen, A. et al., "Analysis of bisphenol A in canned food: A mini review", *Asian Journal of Chemistry*, 22(5):4133-4135 (2010).
Zuhayra, M. et al., "New approach for the synthesis of [$^{18}$F]fluoroethyltyrosine for cancer imaging: Simple, fast, and high yielding automated synthesis", *Bioorganic & Medicinal Chemistry*, 17:7441-7448 (2009).
Supplementary European Search Report in EP Application No. 09771876.1 dated Jun. 20, 2011, 5 pages.
Supplementary European Search Report in EP Application No. 11731645.5 dated mailed Jun. 2, 2013, 11 pages.
Decision of Refusal for Japanese Application No. 2011-515039, mailed Dec. 2, 2014, 18 pages (English translation).
International Preliminary Report on Patentability for PCT/CA2009/000902 issued Jan. 5, 2011, 7 pages.
International Search Report for PCT/CA2009/000902 mailed Sep. 1, 2009, 4 pages.
Written Opinion for PCT/CA2009/000902 mailed Sep. 1, 2009, 6 pages.
International Preliminary Report on Patentability for PCT/US2012/032584 issued Oct. 8, 2013, 6 pages.
International Search Report for PCT/US2012/032584 mailed Jul. 31, 2012, 3 pages.
Written Opinion for PCT/US2012/032584 mailed Jul. 31, 2012, 5 pages.
International Preliminary Report on Patentability for PCT/US2012/033959 dated Oct. 22, 2013, 8 pages.
International Search Report for PCT/US2012/033959 mailed Jul. 18, 2012, 3 pages.
Written Opinion for PCT/US2012/033959 mailed Jul. 18, 2012, 7 pages.
International Preliminary Report on Patentability for PCT/US2012/033957 dated Oct. 22, 2013, 6 pages.
International Search Report for PCT/US2012/033957 mailed Jul. 18, 2012, 3 pages.
Written Opinion for PCT/US2012/033957 mailed Jul. 18, 2012, 5 pages.
International Preliminary Report on Patentability for PCT/CA2011/000019 dated Jul. 10, 2012, 8 pages.
International Search Report for PCT/CA2011/000019 mailed Mar. 21, 2011, 7 pages.
Written Opinion for PCT/CA2011/000019 mailed Mar. 21, 2011, 7 pages.
International Preliminary Report on Patentability for PCT/CA2011/000021 dated Jul. 10, 2012, 8 pages.
International Search Report for PCT/CA2011/000021 mailed Apr. 11, 2011, 8 pages.
Written Opinion for PCT/CA2011/000021 mailed Apr. 11, 2011, 7 pages.
International Preliminary Report on Patentability for PCT/US2012/051481 dated Feb. 25, 2014, 8 pages.
International Search Report for PCT/US2012/051481 mailed Nov. 26, 2012, 4 pages.
Written Opinion for PCT/US2012/051481 mailed Nov. 26, 2012, 7 pages.
International Preliminary Report on Patentability for PCT/US2012/051923 dated Feb. 25, 2014, 9 pages.
International Search Report for PCT/US2012/051923 mailed Jan. 28, 2013, 4 pages.
Written Opinion for PCT/US2012/051923 mailed Jan. 28, 2013, 8 pages.
Extended European Search Report in Application No. EP 12768410.8 dated Sep. 22, 2014, 10 pages.
International Search Report and Written Opinion for PCT/CA2014/000414 mailed Dec. 4, 2014, 6 pages.
International Search Report and Written Opinion for PCT/CA2014/000685 mailed Dec. 4, 2014, 13 pages.
Anton, R. et al., Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A diglycidyl ether, BADGE), REF. No. 13510 and 39700 (EFSA-Q-2003-178), *The EFSA Journal*, 86:1-40 (2004).
Auzou et al., *European Journal of Medicinal Chemistry*, 9(5):548-554 (1974) (with English Abstract).
Balbay, M.D. et al., "Highly Metastatic Human Prostate Cancer Growing within the Prostate of Athymic Mice Overexpresses Vascular Endothelial Growth Factor", *Clinical Cancer Research*, 5:783-789 (1999).
Berge, S.M. et al., "Pharmaceutical Salts", *Pharmaceutical Sciences*, 66(1):1-19 (1977).

(56) References Cited

OTHER PUBLICATIONS

Berger, U. et al., "Identification of Derivatives of Bisphenol A Diglycidyl Ether and Novolac Glycidyl Ether in Can Coatings by Liquid Chromatography/Ion Trap Mass Spectrometry," Journal of AOAC International, *Food Chemical Contaminants*, 83(6):1367-1376 (2000).
Bohler, Paul et al., "Identification of Migrants from Coatings of Food Cans and Tubes: Reaction Products of Bisphenol-A-Diglycidyl Ether (BADGE) with Phenols and Solvents", *Mitt. Gebiete Lebensm. Hyg.*, 89:529-547 (1998).
Bruckheimer, E.M. et al., "Apoptosis in prostate carcinogenesis A growth regulator and a therapeutic target", *Cell Tissue Res*, 301:153-162 (2000).
Clinton, G.M. et al., "Estrogen action in human ovarian cancer", *Critical Reviews in Oncology/Hematology*, 25:1-9 (1997).
Culig, Zoran et al., "Androgen Receptor Activation in Prostatic Tumor Cell Lines by Insulin-like Growth Factor-I, Keratinocyte Growth Factor", and Epidermal Growth Factor, *Cancer Research*, 54:5474-5478 (1994).
Das, Debasish et al., "Sulfonic acid functionalized mesoporous MCM-41 silica as a convenient catalyst for Bisphenol-A synthesis", *Chemical Communications*, pp. 2178-2179 (2001).
Edmondson, J.M. et al., "The human ovarian surface epithelium is an androgen responsive tissue", *British Journal of Cancer*, 86:879-885 (2002).
Cleave, Martin et al., "Acceleration of Human Prostate Cancer Growth in Vivo by Factors Produced by Prostate and Bone Fibroblasts", *Cancer Research*, 51:3753-3761 (1991).
Guinan, P.D. et al., "Impotence Therapy and Cancer of the Prostate", *The American Journal of Surgery*, 131:599-600 (1976).
Haggstrom, Stina et al., "Testosterone Induces Vascular Endothelial Growth Factor Synthesis in the Ventral Prostate in Castrated Rats", *The Journal of Urology*, 161:1620-1625 (1999).
Harper et al., "Expression of Androgen Receptor and Growth Factors in Premalignant Lesions of the Prostate", *Journal of Pathology*, 186:169-177 (1998).
He, B. et al., "Activation Function 2 in the Human Androgen Receptor Ligand Binding Domain Mediates Interdomain Communication with the $NH_2$-terminal Domain", *The Journal of Biological Chemistry*, 274(52):37219-37225 (1999).
Heinlein, Cynthia A., et al., "Androgen Receptor in Prostate Cancer", *Endocrine Reviews*, 25(2):276-308 (2004).
Helzlsouer, Kathy J., et al., "Serum Gonadotropins and Steroid Hormones and the Development of Ovarian Cancer", *JAMA*, 274(24):1926-1930 (1995).
Horoszewicz, J.S. et al., "LNCaP Model of Human Prostatic Carcinoma", *Cancer Research*, 43:1809-1818 (1983).
Huber, P.R. et al., "Prostate Specific Antigen. Experimental and Clinical Observations", *Scand. J. Urol Nephrol.*, 104:33-39 (1987).
Isaacs, J.T., et al., "New Biochemical Methods to Determine Androgen Sensitivity of Prostatic Cancer: The Relative Enzymatic Index (REI)", *Prostate Cancer and Hormone Receptors*, pp. 133-144 (1979).
Isaacs, J.T., "Antagonistic Effect of Androgen on Prostatic Cell Death", *The Prostate*, 5:545-557 (1984).
Jackson, J.A. et al., "Prostatic Complications of Testosterone Replacement Therapy", *Arch Intern Med.*, 149:2365-2366 (1989).
Jenster, G. et al., "Domains of the Human Androgen Receptor Involved in Steroid Binding, Transcriptional Activation, and Subcellular Localization", *Molecular Endocrinology*, 5:1396-1404 (1991).
Jia, L. et al., "Androgen Receptor Signaling: Mechanism of Interleukin-6 Inhibition", *Cancer Research*, 64:2619-2626 (2004).
Jia, L. et al., "Androgen Receptor-Dependent PSA Expression in Androgen-Independent Prostate Cancer Cells Does Not Involve Androgen Receptor Occupancy of the PSA Locus", *Cancer Research*, 65:8003-8008 (2005).
Kaighn, M.E. et al., "Prostate Carcinoma: Tissue Culture Cell Lines", *National Cancer Institute Monograph* No. 49, pp. 17-21 (1978).
Kemppainen, J.A. et al., "Distinguishing ANDROGEN Receptor Agonists and Antagonists: Distinct Mechanisms of Activation by Medroxyprogesterone Acetate and Dihydrotestosterone", *Mol. Endocrinol.*, 13:440-454 (1999).
Kim, D. et al., "Androgen Receptor Expression and Cellular Proliferation During Transition from Androgen-Dependent to Recurrent Growth after Castration in the CWR22 Prostate Cancer Xenograft", *American Journal of Pathology*, 160(1):219-226 (2002).
Langley, E. et al., "Evidence for an Anti-parallel Orientation of the Ligand-activated Human Androgen Receptor Dimer", *The Journal of Biological Chemistry*, 270(50):29983-29990 (1995).
Lannoye, G.S. et al., "N-Fluoroalkylated and N-alkylated analogs of the dopaminergic D-2 receptor antagonist raclopride", *J. Med. Chem.*, 33(9):2430-2437 (1990).
Louie, M.C. et al., "Androgen-induced recruitment of RNA polymerase II to a nuclear receptor—p160 coactivator complex", *PNAS*, 100(5)2226-2230 (2003).
Masiello, D. et al., "Bicalutamide Functions as an Androgen Receptor Antagonist by Assembly of a Transcriptionally Inactive Receptor", *The Journal of Biological Chemistry*, 277(29):26321-26326 (2002).
Melnyk, O. et al., "Neutralizing Ant-Vascular Endothelial Growth Factor Antibody Inhibits Further Growth of Established Prostate Cancer and Metastases in a Pre-Clinical Model", *The Journal of Urology*, 161:960-963 (1999).
Miller, J.I. et al., "The Clinical Usefulness of Serum Prostate Specific Antigen After Hormonal Therapy of Metastatic Prostate Cancer", *The Journal of Urology*, 147:956-961 (1992).
Mitsiades, C.S. et al., "Molecular biology and cellular physiology of refractoriness to androgen ablation therapy in advanced prostate cancer", *Expert Opin. Investig. Drugs*,10(6):1099-1115 (2001).
Nakazawa, H. et al., "In vitro assay of hydrolysis and chlorohydroxy derivatives of bisphenol A diglycidyl ether for estrogenic activity", *Food and Chemical Toxicology*, 40:1827-1832 (2002).
Nazareth, L.V. et al, "Activation of the Human Androgen Receptor through a Protein Kinase A Signaling Pathway", *The Journal of Biological Chemistry*, 271(33):19900-19907 (1996).
Noble, R.L., "The development of prostatic adenocarcinoma in Nb Rats following prolonged sex hormone administration", *Cancer Research*, 37:1929-1933 (1977).
Noble, R.L., "Sex steroids as a cause of adenocarcinoma of the dorsal prostate in Nb Rats, and their influence on the growth of transplants", *Oncology*, 34:138-141 (1977).
Ogawa, Y. et al., "Estrogenic activities of chemicals related to food contact plastics and rubbers tested by the yeast two-hybrid assay," *Food Additives and Contaminants*, 23:4, 422-430 (2006).
Poustka, J. et al., "Determination and occurrence of bisphenol A, bisphenol A diglycidyl ether, and bisphenol F diglycidyl ether, including their derivatives, in canned foodstuffs' from the Czech retail market," *Czech J. Food Sci.*, 25(4):221-229 (2006).
Rao, B.R. et al., "Endocrine Factors in Common Epithelial Ovarian Cancer", *Endocrine Reviews*, 12(1):14-26 (1991).
Risch, H.A., "Hormonal Etiology of Epithelial Ovarian Cancer, With a Hypothesis Concerning the Role of Androgens and Progesterone", *Journal of the National Cancer Institute*, 90(23):1774-1786 (1998).
Roberts, J.T. et al., "Adenocarcinoma of Prostate in 40-Year-Old Body-Builder", *Lancet*, 2:742 (1986).
Rokicki, G. et al., "Reactions of 4-chloromethyl-1,3-dioxolan-2-one with phenols as a new route to polyols and cyclic carbonates", *Journal f. prakt. Chemie.*, 327:718-722 (1985).
Ross, R.K. et al., "Androgen Metabolism and Prostate Cancer: Establishing a Model of Genetic Susceptibility", *European Urology*, 35:355-361 (1999).
Sadar, M.D. et al., "Characterization of a New in Vivo Hollow Fiber Model for the Study of Progression of Prostate Cancer to Androgen Independence", *Molecular Cancer Therapeutics*, 1:629-637 (2002).
Sato, N. et al., "Intermittent Androgen Suppression Delays Progression to Androgen-independent Regulation of Prostate-specific Antigen Gene in the LNCaP Prostate Tumour Model", *J. Steroid Biochem. Mol. Biol.*, 58:139-146 (1996).
Sato, N. et al., "A Metastatic and Androgen-sensitive Human Prostate Cancer Model Using Intraprostatic Inoculation of LNCaP Cells in SCID Mice", *Cancer Research*, 57:1584-1589 (1997).

(56) References Cited

OTHER PUBLICATIONS

Snoek, R. et al., "Induction of Cell-free, In Vitro Transcription by Recombinant Androgen Receptor Peptides", *J. Steroid Biochem. Mol. Biol.*, 59:243-250 (1996).

Still, W. C. et al., "Rapid Chromatographic Technique for Preparative Separations with Moderate Resolution", *J. Org. Chem.*, 43(14):2923-2925 (1978).

Tanji, N. et al., "Growth Factors: Rules in Andrology", *Archives of Andrology*, 47:1-7 (2001).

Thomson, A.A., "Role of androgens and fibroblast growth factors in prostatic development", *Reproduction*, 121:187-195 (2001).

Van Der Kwast, T.H. et al., "Androgen Receptors in Endocrine-Therapy-Resistant Human Prostate Cancer", *Inter. J. Cancer*, 48:189-193 (1991).

Wang, G. et al., "Identification of genes targeted by the androgen and PKA signaling pathways in prostate cancer cells", *Oncogene*, 25:7311-7323 (2006).

Wang, Q. et al., "Spatial and Temporal Recruitment of Androgen Receptor and Its Coactivators Involves Chromosomal Looping and Polymerase Tracking", *Molecular Cell*, 19:631-642 (2005).

Wetherill, Y. B. et al., "In vitro molecular mechanisms of bisphenol A action," *Reproductive Toxicology*, 24:178-198 (2007).

Wilding, G., "The Importance of Steroid Hormones in Prostate Cancer", *Cancer Surveys*, 14:113-130 (1992).

Wilson, J.D. et al., "Long-Term Consequences of Castration in Men: Lessons from the Skoptzy and the Eunuchs of the Chinese and Ottoman Courts", *The Journal of Clinical Endocrinology & Metabolism*, 84:4324-4331 (1999).

Wong, C. et al., "Steroid Requirement for Androgen Receptor Dimerization and DNA Binding", *J. Biol. Chem.*, 268(25):19004-19012 (1993).

Xu, X. et al, "Synthesis and Stability Study of Dental Monomers Containing Methacrylamidoethyl Phosphonic Acids", *Journal of Polymer Science: Part A Polymer Chemistry*, 45:99-110 (2007).

Ye, Deyong, "An Introduction to Computer-Aided Drug Design", 3 pages, Jan. 31, 2004.

Patani and LaVoie, "Bioisosterism: A Rational Approach in Drug Design", Chem. Rev., 96: 3147-3176 (1996).

Strub and McKim, "Dimethyl Sulfoxide USP, PhEur in Approved Pharmaceutical Products and Medical Devices", PharmaTech.com, 6 pages (2008). http://www.pharmtech.com/print/224268?page=full&rel=canonical.

Alvarez, C. et al., "Confirmational and Experimental Studies on the Dipole Moments of Models of Comblike Polymers", Macromolecules, 30(20): 6369-6375 (1997).

Henke, H., "Selektive präparative gelchromatographische Trennung niedermolekularer Verbindungen an Sephadex LH-20", Journal of Chromatography, 254: 296-308 (1983).

Riu, A. et al., "Characterization of Novel Ligands of ERα, ERβ, and PPARγ: The Case of Halogenated Bisphenol A and Their Conjugated Metabolites", Toxicology Sciences, 122(2): 372-382 (2011).

Wilcox and Cowart, "New Approaches to Synthetic Receptors. Synthesis and Host Properties of a Water Soluble Macrocyclic Analog of Troger's Base", Tetrahedron Letters, 27(46): 5563-5566 (1986).

International Preliminary Report on Patentability for PCT/CA2014/000414 mailed Nov. 10, 2015, 7 pages.

\* cited by examiner

BISPHENOL DERIVATIVES AND THEIR USE AS ANDROGEN RECEPTOR ACTIVITY MODULATORS

CROSS REFERENCE TO RELATED APPLICATIONS

This application is a National Stage Filing of International PCT Patent Application No. PCT/CA2011/000019, filed 6 Jan. 2011 which claims the benefit of U.S. Provisional Patent Application Ser. No. 61/282,238 entitled "ACHIRAL GROUP CONTAINING BISPHENOL DERIVATIVE THERAPEUTICS AND METHODS FOR THEIR USE" filed on 6 Jan. 2010, which application is incorporated herein by reference in its entirety.

TECHNICAL FIELD

This invention relates to therapeutics, their uses and methods for the treatment of various indications, including various cancers. In particular the invention relates to therapies and methods of treatment for cancers such as prostate cancer, including all stages and androgen dependent, androgen-sensitive and androgen-independent (also referred to as hormone refractory, castration resistant, androgen deprivation resistant, androgen ablation resistant, androgen depletion-independent, castration-recurrent, anti-androgen-recurrent).

BACKGROUND

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Urol* 35, 355-361 (1999); A. A. Thomson, *Reproduction* 121, 187-195 (2001); N. Tanji, K. Aoki & M. Yokoyama, *Arch Androl* 47, 1-7 (2001)). Several lines of evidence show that androgens are associated with the development of prostate carcinogenesis. Firstly, androgens induce prostatic carcinogenesis in rodent models (R. L. Noble, *Cancer Res* 37, 1929-1933 (1977); R. L. Noble, *Oncology* 34, 138-141 (1977)) and men receiving androgens in the form of anabolic steroids have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 2365-2366 (1989); P. D. Guinan, W. Sadoughi, H. Alsheik, R. J. Ablin, D. Alrenga & I. M. Bush, *Am J Surg* 131, 599-600 (1976)). Secondly, prostate cancer does not develop if humans or dogs are castrated before puberty (J. D. Wilson & C. Roehrborn, *J Clin Endocrinol Metab* 84, 4324-4331 (1999); G. Wilding, *Cancer Surv* 14, 113-130 (1992)). Castration of adult males causes involution of the prostate and apoptosis of prostatic epithelium while eliciting no effect on other male external genitalia (E. M. Bruckheimer & N. Kyprianou, *Cell Tissue Res* 301, 153-162 (2000); J. T. Isaacs, *Prostate* 5, 545-557 (1984)). This dependency on androgens provides the underlying rationale for treating prostate cancer with chemical or surgical castration (androgen ablation).

Androgens also play a role in female cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, *JAMA* 274, 1926-1930 (1995); R. J. Edmondson, J. M. Monaghan & B. R. Davies, *Br J Cancer* 86, 879-885 (2002)). The AR has been detected in a majority of ovarian cancers (H. A. Risch, *J Natl Cancer Inst* 90, 1774-1786 (1998); B. R. Rao & B. J. Slotman, *Endocr Rev* 12, 14-26 (1991); G. M. Clinton & W. Hua, *Crit Rev Oncol Hematol* 25, 1-9 (1997)), whereas estrogen receptor-alpha (ERa) and the progesterone receptor are detected in less than 50% of ovarian tumors.

The only effective treatment available for advanced prostate cancer is the withdrawal of androgens which are essential for the survival of prostate epithelial cells. Androgen ablation therapy causes a temporary reduction in tumor burden concomitant with a decrease in serum prostate-specific antigen (PSA). Unfortunately prostate cancer can eventually grow again in the absence of androgens (androgen-independent disease) (Huber et al 1987 *Scand J. Urol Nephrol.* 104, 33-39). Androgen-independent disease is biochemically characterized before the onset of symptoms by a rising titre of serum PSA (Miller et al 1992 *J. Urol.* 147, 956-961). Once the disease becomes androgen-independent most patients succumb to their disease within two years.

The AR has distinct functional domains that include the carboxy-terminal ligand-binding domain (LBD), a DNA-binding domain (DBD) comprising two zinc finger motifs, and an N-terminus domain (NTD) that contains one or more transcriptional activation domains. Binding of androgen (ligand) to the LBD of the AR results in its activation such that the receptor can effectively bind to its specific DNA consensus site, termed the androgen response element (ARE), on the promoter and enhancer regions of "normally" androgen regulated genes, such as PSA, to initiate transcription. The AR can be activated in the absence of androgen by stimulation of the cAMP-dependent protein kinase (PKA) pathway, with interleukin-6 (IL-6) and by various growth factors (Culig et al 1994 *Cancer Res.* 54, 5474-5478; Nazareth et al 1996 *J. Biol. Chem.* 271, 19900-19907; Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The mechanism of ligand-independent transformation of the AR has been shown to involve: 1) increased nuclear AR protein suggesting nuclear translocation; 2) increased AR/ARE complex formation; and 3) the AR-NTD (Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The AR may be activated in the absence of testicular androgens by alternative signal transduction pathways in androgen-independent disease, which is consistent with the finding that nuclear AR protein is present in secondary prostate cancer tumors (Kim et al 2002 *Am. J. Pathol.* 160, 219-226; and van der Kwast et al 1991 *Inter. J. Cancer* 48, 189-193).

Available inhibitors of the AR include nonsteroidal antiandrogens such as bicalutamide (Casodex™), nilutamide, and flutamide and the steroidal antiandrogen, cyproterone acetate. These antiandrogens target the LBD of the AR and predominantly fail presumably due to poor affinity and mutations that lead to activation of the AR by these same antiandrogens (Taplin, M. E., Bubley, G. J., Kom Y. J., Small E. J., Uptonm M., Rajeshkumarm B., Balkm S. P., *Cancer Res.*, 59, 2511-2515 (1999)). These antiandrogens would also have no effect on the recently discovered AR splice variants that lack the ligand-binding domain (LBD) to result in a constitutively active receptor which promotes progression of androgen-independent prostate cancer (Dehm S M, Schmidt L J, Heemers H V, Vessella R L, Tindall D J., *Cancer Res* 68, 5469-77, 2008; Guo Z, Yang X, Sun F, Jiang R, Linn D E, Chen H, Chen H, Kong X, Melamed J, Tepper C G, Kung H J, Brodie A M, Edwards J, Qiu Y., *Cancer Res.* 69, 2305-13, 2009).

Conventional therapy has concentrated on androgen-dependent activation of the AR through its C-terminal domain. Recent studies developing antagonists to the AR have concentrated on the C-terminus and specifically: 1) the allosteric pocket and AF-2 activity (Estébanez-Perpiñà et al 2007, *PNAS* 104, 16074-16079); 2) in silico "drug repurposing" procedure for identification of nonsteroidal antagonists (Bisson et al 2007, *PNAS* 104, 11927-11932); and coactivator or corepressor interactions (Chang et al 2005, *Mol Endocrinology* 19, 2478-2490; Hur et al 2004, *PLoS Biol* 2, E274; Estébanez-Perpiñà et al 2005, *JBC* 280, 8060-8068; He et al 2004, *Mol Cell* 16, 425-438).

The AR-NTD is also a target for drug development (e.g. WO 2000/001813), since the NTD plays a role in activation of the AR in the absence of androgens (Sadar, M. D. 1999 *J. Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 1860-9; Dehm et al 2006 *J Biol Chem.* 28, 27882-93; Gregory et al 2004 *J Biol Chem.* 279, 7119-30). The AR-NTD is important in hormonal progression of prostate cancer as shown by application of decoy molecules (Quayle et al 2007, *Proc Natl Acad Sci USA.* 104, 1331-1336).

While the crystal structure has been resolved for the AR C-terminus LBD, this has not been the case for the NTD due to its high flexibility and intrinisic disorder in solution (Reid et al 2002 *J. Biol. Chem.* 277, 20079-20086) thereby hampering virtual docking drug discovery approaches.

SUMMARY

This invention is based in part on the fortuitous discovery that compounds described herein modulate androgen receptor (AR) activity. Specifically, compounds identified herein, show inhibition of AR activity, which may be useful for blocking in vivo tumor growth in the presence and absence of androgens. The discovery was particularly fortuitous because the initial screen of marine invertebrate extracts was testing for inhibition of AR activity and some of the compounds identified in that initial screen were determined to have a structural resemblance to BADGE (Bisphenol A Diglycidic Ether). The resemblance to BADGE suggests that these compounds are most likely of industrial origin and were bioaccumulated by the sponge from the contaminated seawater. Accordingly, due to the known activities for Badge compounds, the present BADGE derivatives are very unlikely to have been screened in the assay under any other circumstances.

The compounds described herein may be used for in vivo or in vitro research uses (i.e. non-clinical) to investigate the mechanisms of orphan and nuclear receptors (including steroid receptors such as the androgen receptor). Furthermore, these compounds may be used individually or as part of a kit for in vivo or in vitro research to investigate signal transduction pathways and/or the activation of orphan and nuclear receptors using recombinant proteins, cells maintained in culture, and/or animal models.

This invention is also based in part on the surprising discovery that the compounds described herein, may also be used to modulate the androgen receptor activity either in vivo or in vitro for both research and therapeutic uses. The compounds may be used in an effective amount so that androgen receptor activity may be modulated. The androgen receptor may be mammalian. Alternatively, the androgen receptor may be human. In particular, the compounds may be used to inhibit the AR. The compounds modulatory activity may be used in either an in vivo or an in vitro model for the study of at least one of the following indications: prostate cancer, breast cancer, ovarian cancer, endometrial cancer, hair loss, acne, hirsutism, ovarian cysts, polycystic ovary disease, precocious puberty, and age-related macular degeneration. Furthermore, the compounds modulatory activity may be used for the treatment of at least one of the following indications: prostate cancer, breast cancer, ovarian cancer, endometrial cancer, hair loss, acne, hirsutism, ovarian cysts, polycystic ovary disease, precocious puberty (testoxicosis) and age-related macular degeneration. The indication for treatment may be prostate cancer. The prostate cancer may be androgen-independent prostate cancer. The prostate cancer may be androgen-dependent prostate cancer.

In accordance with one embodiment, there is provided a use of a compound having a structure of Formula I

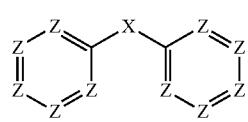

I or a pharmaceutically acceptable salt thereof,
wherein: X may be $CH_2$, $CHR^1$, or $CR^1R^2$; each of $R^1$ and $R^2$ may independently be linear or branched, substituted or unsubstituted, saturated or unsaturated $C_1$-$C_{10}$ alkyl, or $R^1$ and $R^2$ together may form a substituted or unsubstituted, saturated or unsaturated cyclic $C_3$-$C_{10}$ alkyl, wherein the optional substituent may be selected from the group consisting of oxo, $OJ'''$, COOH, $R^3$, OH, $OR^3$, F, Cl, Br, I, $NH_2$, $NHR^3$, $NR^3_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3_2$, $NHR^6$, $OPO_3H_3$, $CONR^3R^6$, $NR^3R^6$, and $NO_2$, wherein each $R^3$ may independently be unsubstituted $C_1$-$C_{10}$ alkyl and each $R^6$ may independently be $C_1$-$C_{10}$ acyl; at least one Z of one aromatic ring may independently be C-Q, at least one Z of the other aromatic ring may independently be C-T, CF, CCl, CBr, CI, COH, $CG^1$, $COG^1$, $CNH_2$, $CNHG^1$, $CNG^1_2$, $COSO_3H$, $COPO_3H_2$, $CSG^1$, $CSOG^1$, or $CSO_2G^1$, and each remaining Z may independently be C-T, N, CH, CF, CCl, CBr, CI, COH, $CG^1$, $COG^1$, $CNH_2$, $CNHG^1$, $CNG^1_2$, $COSO_3H$, $COPO_3H_2$, $CSG^1$, $CSOG^1$, or $CSO_2G^1$; Q may be

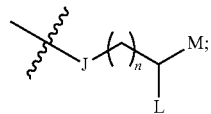

J may be $G^1$, O, $CH_2$, $CHG^1$, $CG^1_2$, S, NH, $NG^1$, SO, $SO_2$, or NR; M may be H, Cl, Br, $CH_2Cl$, $CHCl_2$, $CCl_3$, $CH_2Br$, $CHBr_2$, $CBr_3$, or C≡CH; L may be H or A-D; A may be O, S, NH, $NG^1$, $N^+H_2$, or $N^+HG^1$; D may be H, $G^1$, R,

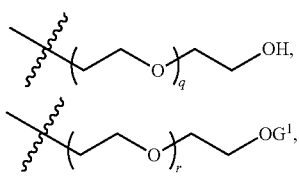

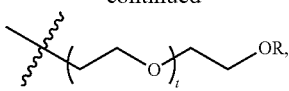

or a moiety selected from TABLE 1; each of q, r and t may independently be 0, 1, 2, 3, 4, 5, 6 or 7; n may be 0, 1, 2, 3, 4, 5, 6, 7 or 8; T may be

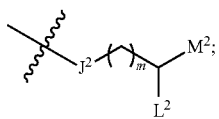

$J^2$ may be $G^1$, O, $CH_2$, $CHG^1$, $CG^1{}_2$, S, NH, $NG^1$, SO, $SO_2$, or NR; $M^2$ may be H, $CH_3$, Cl, Br, $CH_2Cl$, $CHCl_2$, $CCl_3$, $CH_2Br$, $CHBr_2$, $CBr_3$, $CH_2OH$, $CH_2OJ'''$, $G^1$, $CH_2OG^1$, $CH_2OR$, $CH_2OG^{1''}OG^{1''}$, $G^1OG^{1''}$, $G^1OG^{1''}OG^{1'''}$, $CH_2SG^1$, $CH_2NH_2$, $CH_2NHG^1$, $CH_2NG^1{}_2$, or C≡CH; $L^2$ may be H or $A^2$-$D^2$; $A^2$ may be O, S, SO, $SO_2$, NH, $NG^1$, $N^+H_2$, or $N^+HG^1$; $D^2$ may be H, $G^1$, R,

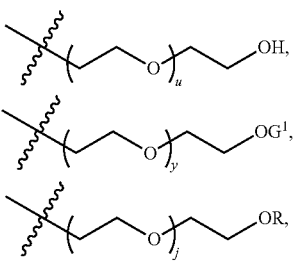

or a moiety selected from TABLE 1; each of u, y and j may independently be 0, 1, 2, 3, 4, 5, 6 or 7; m may be 0, 1, 2, 3, 4, 5, 6, 7 or 8; each of J'' and 0.1° may independently be a moiety selected from TABLE 1; each $G^1$ $G^{1''}$ and $G^{1'''}$ may independently be linear or branched, or aromatic cyclic or non-aromatic cyclic, substituted or unsubstituted, saturated or unsaturated $C_1$-$C_{10}$ alkyl, wherein the optional substituent may be selected from the group consisting of oxo, OJ''', COOH, $R^4$, OH, $OR^4$, F, Cl, Br, I, $NH_2$, $NHR^4$, $NR^4{}_2$, CN, SH, $SR^4$, $SO_3H$, $SO_3R^4$, $SO_2R^4$, $OSO_3R^4$, $OR^5$, $CO_2R^4$, $CONH_2$, $CONHR^4$, $CONHR^5$, $CONR^4{}_2$, $NHR^5$, $OPO_3H_3$, $CONR^4R^5$, $NR^4R^5$, and $NO_2$, wherein each $R^4$ may independently be unsubstituted $C_1$-$C_{10}$ alkyl and each $R^5$ may independently be $C_1$-$C_{10}$ acyl; and R may be $C_1$-$C_{10}$ acyl, for modulating androgen receptor (AR) activity.

In accordance with another embodiment, there is provided a use of a compound having a structure of Formula I

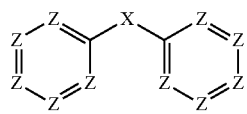      I or a pharmaceutically acceptable salt thereof,
wherein: X may be $CH_2$, $CHR^1$, or $CR^1R^2$; each of $R^1$ and $R^2$ may independently be linear or branched, substituted or unsubstituted, saturated or unsaturated $C_1$-$C_{10}$ alkyl, or $R^1$ and $R^2$ together may form a substituted or unsubstituted, saturated or unsaturated cyclic $C_3$-$C_{10}$ alkyl, wherein the optional substituent may be selected from the group consisting of oxo, OJ''', COOH, $R^3$, OH, $OR^3$, F, Cl, Br, I, $NH_2$, $NHR^3$, $NR^3{}_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3{}_2$, $NHR^6$, $OPO_3H_3$, $CONR^3R^6$, $NR^3R^6$, and $NO_2$, wherein each $R^3$ may independently be unsubstituted $C_1$-$C_{10}$ alkyl and each $R^6$ may independently be $C_1$-$C_{10}$ acyl; at least one Z of one aromatic ring may independently be C-Q, at least one Z of the other aromatic ring may independently be C-T, CF, CCl, CBr, CI, COH, $CG^1$, $COG^1$, $CNH_2$, $CNHG^1$, $CNG^1{}_2$, $COSO_3H$, $COPO_3H_2$, $CSG^1$, $CSOG^1$, or $CSO_2G^1$, and each remaining Z may independently be C-T, N, CH, CF, CCl, CBr, CI, COH, $CG^1$, $COG^1$, $CNH_2$, $CNHG^1$, $CNG^1{}_2$, $COSO_3H$, $COPO_3H_2$, $CSG^1$, $CSOG^1$, or $CSO_2G^1$; Q may be

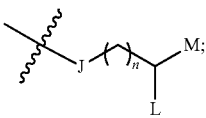

J may be $G^1$, O, $CH_2$, $CHG^1$, $CG^1{}_2$, S, NH, $NG^1$, SO, $SO_2$, or NR; M may be H, Cl, Br, $CH_2Cl$, $CHCl_2$, $CCl_3$, $CH_2Br$, $CHBr_2$, $CBr_3$, or C≡CH; L may be H or A-D; A may be O, S, NH, $NG^1$, $N^+H_2$, or $N^+HG^1$; D may be H, $G^1$, R,

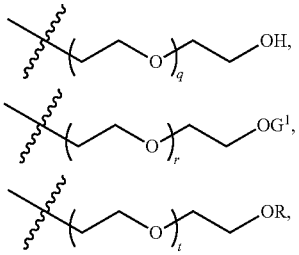

or a moiety selected from TABLE 1; each of q, r and t may independently be 0, 1, 2, 3, 4, 5, 6 or 7; n may be 0, 1, 2, 3, 4, 5, 6, 7 or 8; T may be

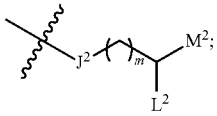

$J^2$ may be $G^1$, O, $CH_2$, $CHG^1$, $CG^1{}_2$, S, NH, $NG^1$, SO, $SO_2$, or NR; $M^2$ may be H, $CH_3$, Cl, Br, $CH_2Cl$, $CHCl_2$, $CCl_3$, $CH_2Br$, $CHBr_2$, $CBr_3$, $CH_2OH$, $CH_2OJ'''$, $G^1$, $CH_2OG^1$, $CH_2OR$, $CH_2OG^{1''}OG^{1''}$, $G^1OG^{1''}$, $G^1OG^{1''}OG^{1'''}$, $CH_2SG^1$, $CH_2NH_2$, $CH_2NHG^1$, $CH_2NG^1{}_2$, or C≡CH; $L^2$ may be H or $A^2$-$D^2$; $A^2$ may be O, S, SO, $SO_2$, NH, $NG^1$, $N^+H_2$, or $N^+HG^1$; $D^2$ may be H, $G^1$, R,

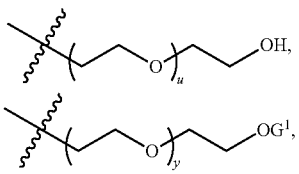

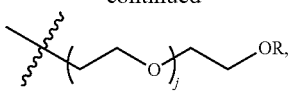

or a moiety selected from TABLE 1; each of u, y and j may independently be 0, 1, 2, 3, 4, 5, 6 or 7; m may be 0, 1, 2, 3, 4, 5, 6, 7 or 8; each of J'' and J''' may independently be a moiety selected from TABLE 1; each $G^1$ $G^{1'}$ and $G^{1'''}$ may independently be linear or branched, or aromatic cyclic or non-aromatic cyclic, substituted or unsubstituted, saturated or unsaturated $C_1$-$C_{10}$ alkyl, wherein the optional substituent may be selected from the group consisting of oxo, OJ''', COOH, $R^4$, OH, $OR^4$, F, Cl, Br, I, $NH_2$, $NHR^4$, $NR^4{}_2$, CN, SH, $SR^4$, $SO_3H$, $SO_3R^4$, $SO_2R^4$, $OSO_3R^4$, $OR^5$, $CO_2R^4$, $CONH_2$, $CONHR^4$, $CONHR^5$, $CONR^4{}_2$, $NHR^5$, $OPO_3H_3$, $CONR^4R^5$, $NR^4R^5$, and $NO_2$, wherein each $R^4$ may independently be unsubstituted $C_1$-$C_{10}$ alkyl and each $R^5$ may independently be $C_1$-$C_{10}$ acyl; and R may be $C_1$-$C_{10}$ acyl, for modulating androgen receptor (AR) activity, provided that:

i) when one Z at the para position to X on the aromatic ring is C-Q; n is 1; J is $G^1$, O, $CH_2$, $CHG^1$, $CG^1{}_2$, S, NH, or $NG^1$; L is A-D; A is O, S, NH, $NG^1$, $N^+H_2$, or $N^+HG^1$; and D is H or a moiety selected from TABLE 1, then the Z at the para position to X on the other aromatic ring is N, CH, CF, CCl, CBr, CI, COH, $CNH_2$, $COSO_3H$, $COPO_3H_2$, C-T wherein when m is 1 and $J^2$ is $G^1$, O, $CH_2$, $CHG^1$, $CG^1{}_2$, S, NH, or $NG^1$, then $L^2$ is H or $A^2$-$D^2$ wherein $A^2$ is O, S, NH, $NG^1$, $N^+H_2$, or $N^+HG^1$, and $D^2$ is $G^1$, R,

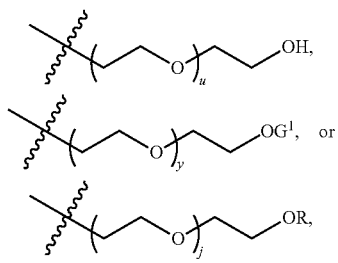

or C-Q wherein when n is 1 and J is $G^1$, O, $CH_2$, $CHG^1$, $CG^1{}_2$, S, NH, or $NG^1$, then L is H or A-D wherein A is O, S, NH, $NG^1$, $N^+H_2$, or $N^+HG^1$, and D is $G^1$, R,

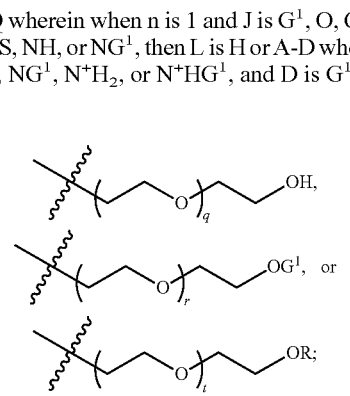

ii) when one Z at the para position to X on the aromatic ring is $CG^1$, $COG^1$, $CNHG^1$, $CNG^1{}_2$, $CSG^1$, $CSOG^1$, or $CSO_2G^1$, then the Z at the para position to X on the other aromatic ring is N, CH, CF, CCl, CBr, CI, COH, $CNH_2$, $COSO_3H$, $COPO_3H_2$, C-T wherein when m is 1 and $J^2$ is $G^1$, O, $CH_2$, $CHG^1$, $CG^1{}_2$, S, NH, or $NG^1$, then $L^2$ is H or $A^2$-$D^2$ wherein $A^2$ is O, S, NH, $NG^1$, $N^+H_2$, or $N^+HG^1$; and $D^2$ is $G^1$, R, or C-Q wherein when n is 1 and J is $G^1$, O, $CH_2$, $CHG^1$, $CG^1{}_2$, S, NH, or $NG^1$, then L is H or A-D wherein A is O, S, NH, $NG^1$, $N^+H_2$, or $N^+HG^1$, and D is $G^1$, R, and iii) when one Z at the para position to X on the aromatic ring is C-T; m is 1; $J^2$ is $G^1$, O, $CH_2$, $CHG^1$, $CG^1{}_2$, S, NH, or $NG^1$; $L^2$ is $A^2$-$D^2$; $A^2$ is O, S, NH, $NG^1$, $N^+H_2$, or $N^+HG^1$; and $D^2$ is H or a moiety selected from TABLE 1, then the Z at the para position to X on the other aromatic ring is N, CH, CF, CCl, CBr, CI, COH, $CNH_2$, $COSO_3H$, $COPO_3H_2$, C-Q wherein when n is 1 and J is $G^1$, O, $CH_2$, $CHG^1$, $CG^1{}_2$, S, NH, or $NG^1$, then L is H or A-D wherein A is O, S, NH, $NG^1$, $N^+H_2$, or $N^+HG^1$; and D is $G^1$, R, or C-T wherein when m is 1 and $J^2$ is $G^1$, O, $CH_2$, $CHG^1$, $CG^1{}_2$, S, NH, or $NG^1$, then $L^2$ is H or $A^2$-$D^2$ wherein $A^2$ is O, S, NH, $NG^1$, $N^+H_2$, or $N^+HG^1$, and $D^2$ is $G^1$, R,

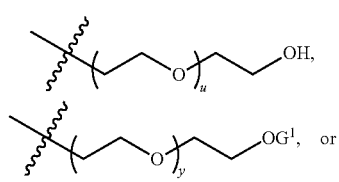

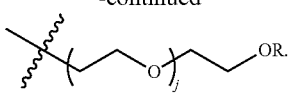

In accordance with another embodiment, there is provided a use of a compound having a structure of Formula II

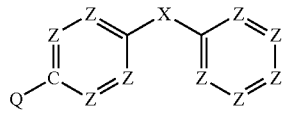

II or a pharmaceutically acceptable salt thereof, wherein each X, Z, and Q may independently be defined as anywhere herein. In accordance with another embodiment, there is provided a use of a compound having a structure of Formula III

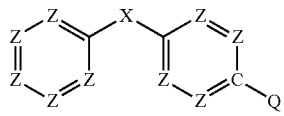

III or a pharmaceutically acceptable salt thereof, wherein each X, Z, and Q may independently be defined as anywhere herein. In accordance with another embodiment, there is provided a use of a compound having a structure of Formula IV

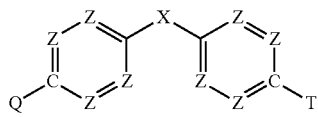

IV or a pharmaceutically acceptable salt thereof, wherein each X, Z, Q, and T may independently be defined as anywhere herein. In accordance with another embodiment, there is provided a use of a compound having a structure of Formula V

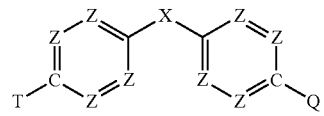

V or a pharmaceutically acceptable salt thereof, wherein each X, Z, Q, and T may independently be defined as anywhere herein. In accordance with another embodiment, there is provided a use of a compound having a structure of Formula VI

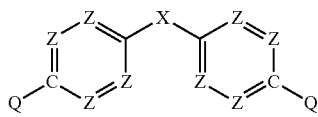

VI or a pharmaceutically acceptable salt thereof, wherein each X, Z, and Q may independently be defined as anywhere herein. In accordance with another embodiment, there is provided a use of a compound having a structure of Formula VII

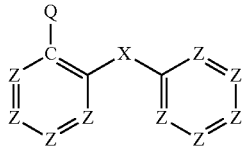

VII or a pharmaceutically acceptable salt thereof, wherein each X, Z, and Q may independently be defined as anywhere herein. In accordance with another embodiment, there is provided a use of a compound having a structure of Formula VIII

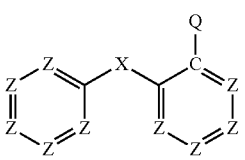

VIII or a pharmaceutically acceptable salt thereof, wherein each X, Z, and Q may independently be defined as anywhere herein. In accordance with another embodiment, there is provided a use of a compound having a structure of Formula IX

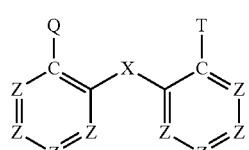

IX or a pharmaceutically acceptable salt thereof, wherein each X, Z, Q, and T may independently be defined as anywhere herein. In accordance with another embodiment, there is provided a use of a compound having a structure of Formula X

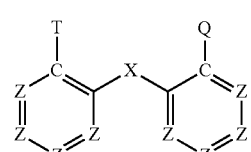

X or a pharmaceutically acceptable salt thereof, wherein each X, Z, Q, and T may independently be defined as anywhere herein. In accordance with another embodiment, there is provided a use of a compound having a structure of Formula XI

XI or a pharmaceutically acceptable salt thereof, wherein each X, Z, and Q may independently be defined as anywhere herein. In accordance with another embodiment, there is provided a use of a compound having a structure of Formula XII

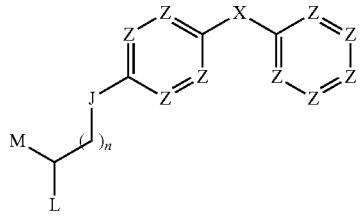

XII or a pharmaceutically acceptable salt thereof, wherein each X, Z, J, M, L, and n may independently be defined as anywhere herein. In accordance with another embodiment, there is provided a use of a compound having a structure of Formula XIII

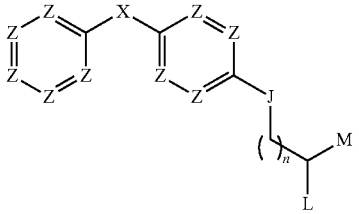

XIII or a pharmaceutically acceptable salt thereof, wherein each X, Z, J, M, L, and n may independently be defined as anywhere herein. In accordance with another embodiment, there is provided a use of a compound having a structure of Formula XIV

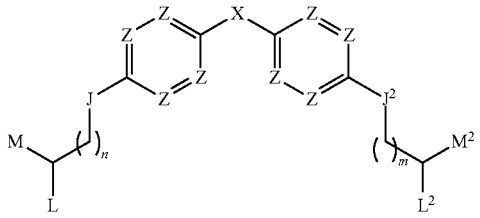

XIV or a pharmaceutically acceptable salt thereof, wherein each X, Z, J, J$^2$, M, M$^2$, L, L$^2$, n, and m may independently be defined as anywhere herein. In accordance with another embodiment, there is provided a use of a compound having a structure of Formula XV

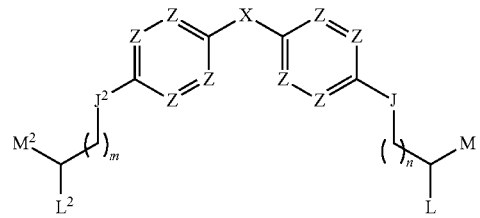

XV or a pharmaceutically acceptable salt thereof, wherein each X, Z, J, J$^2$, M, M$^2$, L, L$^2$, n, and m may independently be defined as anywhere herein. In accordance with another embodiment, there is provided a use of a compound having a structure of Formula XVI

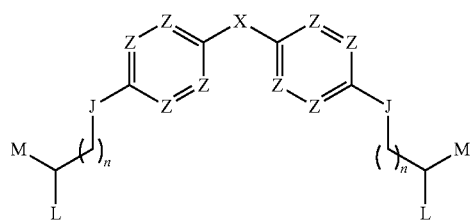

XVI or a pharmaceutically acceptable salt thereof, wherein each X, Z, J, M, L, and n may independently be defined as anywhere herein. In accordance with another embodiment, there is provided a use of a compound having a structure of Formula XVII

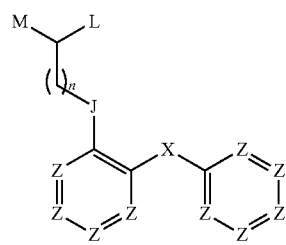

XVII or a pharmaceutically acceptable salt thereof, wherein each X, Z, J, M, L, and n may independently be defined as anywhere herein. In accordance with another embodiment, there is provided a use of a compound having a structure of Formula XVIII

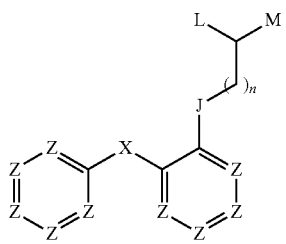

XVIII or a pharmaceutically acceptable salt thereof, wherein each X, Z, J, M, L, and n may independently be defined as anywhere herein. In accordance with another embodiment, there is provided a use of a compound having a structure of Formula XIX

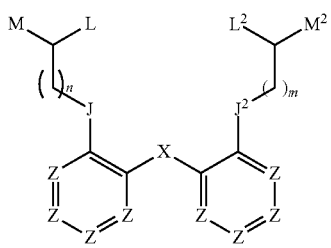

XIX or a pharmaceutically acceptable salt thereof, wherein each X, Z, J, J², M, M², L, L², n, and m may independently be defined as anywhere herein. In accordance with another embodiment, there is provided a use of a compound having a structure of Formula XX

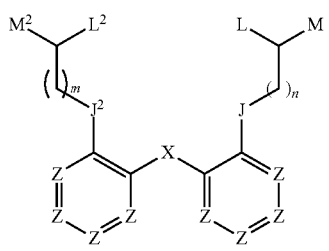

XX or a pharmaceutically acceptable salt thereof, wherein each X, Z, J, J², M, M², L, L², n, and m may independently be defined as anywhere herein. In accordance with another embodiment, there is provided a use of a compound having a structure of Formula XXI

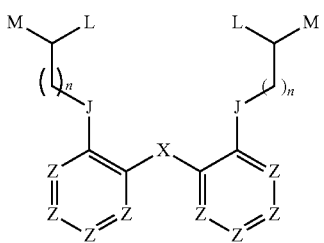

XXI or a pharmaceutically acceptable salt thereof, wherein each X, Z, J, M, L, and n may independently be defined as anywhere herein.

Each J may independently be $G^1$, O, $CH_2$, $CHG^1$, $CG^1_2$, S, NH, $NG^1$, SO, $SO_2$, or NR. Each J may independently be $G^1$, O, $CH_2$, $CHG^1$, $CG^1_2$, S, NH, or $NG^1$. Each J may independently be O, S, NH, $NG^1$, SO, $SO_2$, or NR. Each J may independently be O, S, SO, or $SO_2$. Each J may independently be O, NH, $NG^1$, or NR. Each J may independently be S, NH, $NG^1$, SO, $SO_2$, or NR. Each J may independently be S, SO, or $SO_2$. Each J may independently be NH, $NG^1$, or NR. Each J may independently be $G^1$, $CH_2$, $CHG^1$, or $CG^1_2$. Each J may independently be O, $CH_2$, S, or NH. Each J may independently be O, $CH_2$, or NH. Each J may independently be O, or $CH_2$. Each J may independently be $G^1$, O, $CHG^1$, or NH. Each J may independently be $G^1$, O, or $CHG^1$. Each J may independently be $G^1$, or O. Each J may independently be O, or S. Each J may independently be $G^1$. Each J may independently be $CH_2$. Each J may be $CHG^1$. Each J may be $CG^1_2$. Each J may be NR. Each J may be $SO_2$. Each J may be SO. Each J may be $NG^1$. Each J may be NH. Each J may be S. Each J may be O.

Each M may independently be H, Cl, Br, $CH_2Cl$, $CHCl_2$, $CCl_3$, $CH_2Br$, $CHBr_2$, $CBr_3$, or C≡CH. Each M may independently be Cl, Br, $CH_2Cl$, $CHCl_2$, $CCl_3$, $CH_2Br$, $CHBr_2$, or $CBr_3$. Each M may independently be Cl, $CH_2Cl$, $CHCl_2$, or $CCl_3$. Each M may independently be Br, $CH_2Br$, $CHBr_2$, or $CBr_3$. Each M may independently be Cl, or Br. Each M may independently be $CH_2Cl$, or $CH_2Br$. Each M may independently be $CHCl_2$, or $CHBr_2$. Each M may independently be $CCl_3$, or $CBr_3$. Each M may independently be $CH_2Cl$, $CHCl_2$, or $CCl_3$. Each M may independently be $CH_2Br$, $CHBr_2$, or $CBr_3$. Each M may independently be Cl, $CH_2Cl$, or $CHCl_2$. Each M may independently be Br, $CH_2Br$, or $CHBr_2$. Each M may independently be $CH_2Cl$, or $CHCl_2$. Each M may independently be $CH_2Br$, or $CHBr_2$. Each M may independently be Cl, or $CCl_3$. Each M may independently be Br, or $CBr_3$. Each M may be H. Each M may be Cl. Each M may be Br. Each M may be $CHCl_2$. Each M may be $CCl_3$. Each M may be $CH_2Br$. Each M may be $CHBr_2$. Each M may be $CBr_3$. Each M may be C≡CH. Each M may be $CH_2Cl$.

Each L may independently be H or A-D. Each L may be H. Each L may be A-D.

Each A may independently be O, S, NH, $NG^1$, $N^+H_2$, or $N^+HG^1$. Each A may independently be O, NH, or $N^+H_2$. Each A may independently be O, S, NH, or $N^+H_2$. Each A may independently be O, S, or NH. Each A may independently be O, or NH. Each A may independently be O, or S. Each A may be S. Each A may be NH. Each A may be $NG^1$. Each A may be $N^+H_2$. Each A may be $N^+HG^1$. Each A may be O.

Each D may independently be H, $G^1$, R,

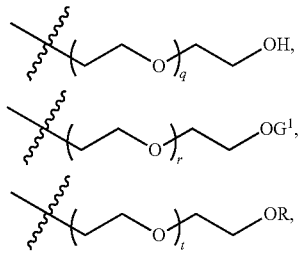

or a moiety selected from TABLE 1. Each D may independently be H, $G^1$, or R. Each D may independently be H, or R. Each D may independently be $G^1$, or R. Each D may independently be H, or $G^1$. Each D may independently be

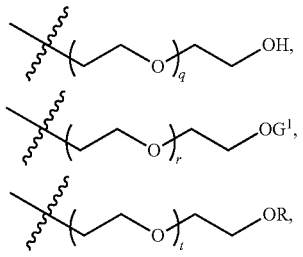

or a moiety selected from TABLE 1. Each D may independently be

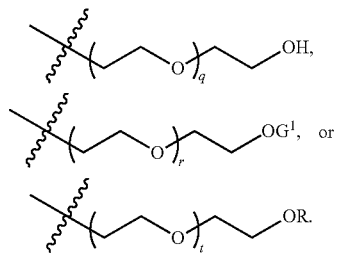

Each D may independently be

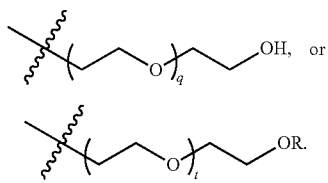

Each D may independently be

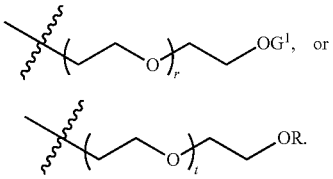

Each D may independently be

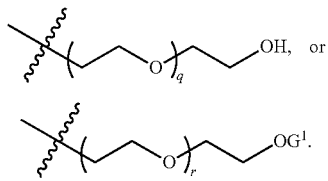

Each D may independently be

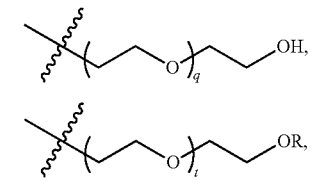

or a moiety selected from TABLE 1. Each D may independently be

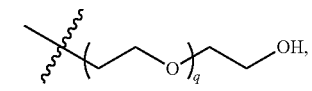

or a moiety selected from TABLE 1. Each D may be H. Each D may be $G^1$. Each D may be R. Each D may be

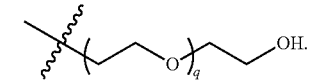

Each D may be

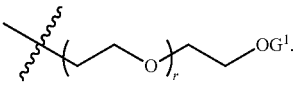

Each D may be

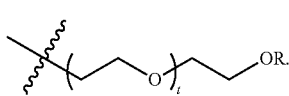

Each D may be a moiety selected from TABLE 1.

Each $J^2$ may independently be $G^1$, O, $CH_2$, $CHG^1$, $CG^1_2$, S, NH, $NG^1$, SO, $SO_2$, or NR. Each $J^2$ may independently be $G^1$, O, $CH_2$, $CHG^1$, $CG^1_2$, S, NH, or $NG^1$. Each $J^2$ may independently be O, S, NH, $NG^1$, SO, $SO_2$, or NR. Each $J^2$ may independently be O, S, SO, or $SO_2$. Each $J^2$ may independently be O, NH, $NG^1$, or NR. Each $J^2$ may independently be S, NH, $NG^1$, SO, $SO_2$, or NR. Each $J^2$ may independently be S, SO, or $SO_2$. Each $J^2$ may independently be NH, $NG^1$, or NR. Each $J^2$ may independently be $G^1$, $CH_2$, $CHG^1$, or $CG^1_2$. Each $J^2$ may independently be O, $CH_2$, S, or NH. Each $J^2$ may independently be O, $CH_2$, or NH. Each $J^2$ may independently be O, or $CH_2$. Each $J^2$ may independently be $G^1$, O, $CHG^1$, or NH. Each $J^2$ may independently be $G^1$, O, or $CHG^1$. Each $J^2$ may independently be $G^1$, or O. Each $J^2$ may independently be O, or S. Each $J^2$ may independently be $G^1$. Each $J^2$ may independently be $CH_2$. Each $J^2$ may be $CHG^1$. Each $J^2$ may be $CG^1_2$. Each $J^2$ may be NR. Each $J^2$ may be $SO_2$. Each $J^2$ may be SO. Each $J^2$ may be $NG^1$. Each $J^2$ may be NH. Each $J^2$ may be S. Each $J^2$ may be O.

Each $M^2$ may independently be H, $CH_3$, Cl, Br, $CH_2Cl$, $CHCl_2$, $CCl_3$, $CH_2Br$, $CHBr_2$, $CBr_3$, $CH_2OH$, $CH_2OJ''$, $G^1$, $CH_2OG^1$, $CH_2OR$, $CH_2OG^1OG^{1\prime}$, $G^1OG^{1\prime}$, $G^1OG^{1\prime}OG^{1\prime\prime}$, $CH_2SG^1$, $CH_2NH_2$, $CH_2NHG^1$, $CH_2NG^1_2$, or C≡CH. Each $M^2$ may independently be H, $CH_3$, $CH_2Cl$, $CH_2Br$, $CH_2OJ'''$, $CH_2OG$, $CH_2OGOG'$, $GOG'$, $GOG'OG''$, $CH_2SG$, $CH_2NH_2$, $CH_2NHG$, or $CH_2NG_2$. Each $M^2$ may independently be H, $CH_3$, $CH_2Cl$, $CH_2Br$, $CH_2OJ'''$, $CH_2OG$, or $CH_2OGOG'$. Each $M^2$ may independently be $CH_2Cl$, $CH_2Br$, $CH_2OH$, $CH_2OCH_3$, $CH_2O(isopropyl)$, or $CH_2OC_2H_4OC_4H_9$. Each $M^2$ may independently be H, $CH_3$, $CH_3OCH_3$, $CH_3OCH_2CH_3$, $CH_2Cl$, or $CH_2Br$. Each $M^2$ may independently be $CH_3$, $CH_3OCH_2CH_3$, $CH_2Cl$, $CH_2Br$, $CH_2OH$, $CH_2OCH_3$, or $CH_2O(isopropyl)$. Each $M^2$ may independently be $CH_3$, $CH_2Cl$, $CH_2Br$, $CH_2OH$, $CH_3OCH_2CH_3$, or $CH_2OCH_3$. Each $M^2$ may independently be $CH_3$, $CH_2Cl$, $CH_2Br$, $CH_2OH$, or $CH_2OCH_3$. Each $M^2$ may independently be $CH_3$, $CH_2OH$, $CH_2OCH_3$, or $CH_2OCH_2CH_3$. Each $M^2$ may independently be $CH_2Cl$, or $CH_2Br$. Each $M^2$ may independently be H, Cl, Br, $CH_2Cl$, $CHCl_2$, $CCl_3$, $CH_2Br$, $CHBr_2$, $CBr_3$, or CH—CH. Each $M^2$ may independently be Cl, Br, $CH_2Cl$, $CHCl_2$, $CCl_3$, $CH_2Br$, $CHBr_2$, or $CBr_3$. Each $M^2$ may independently be Cl, $CH_2Cl$, $CHCl_2$, or $CCl_3$. Each $M^2$ may independently be Br, $CH_2Br$, $CHBr_2$, or $CBr_3$. Each $M^2$ may independently be Cl, or Br. Each $M^2$ may independently be $CH_2Cl$, or $CH_2Br$. Each $M^2$ may independently be $CHCl_2$, or $CHBr_2$. Each $M^2$ may independently be $CCl_3$, or $CBr_3$. Each $M^2$ may independently be $CH_2Cl$, $CHCl_2$, or $CCl_3$. Each $M^2$ may independently be $CH_2Br$, $CHBr_2$, or $CBr_3$. Each $M^2$ may independently be Cl, $CH_2Cl$, or $CHCl_2$. Each $M^2$ may independently be Br, $CH_2Br$, or $CHBr_2$. Each $M^2$ may independently be CH$_2$Cl, or CHCl$_2$. Each M$^2$ may independently be CH$_2$Br, or CHBr$_2$. Each M$^2$ may independently be Cl, or CCl$_3$. Each M$^2$ may independently be Br, or CBr$_3$. Each M$^2$ may be H. Each M$^2$ may be CH$_3$. Each M$^2$ may be Cl. Each M$^2$ may be Br. Each M$^2$ may be CH$_2$Cl. Each M$^2$ may be CHCl$_2$. Each M$^2$ may be CCl$_3$. Each M$^2$ may be CH$_2$Br. Each M$^2$ may be CHBr$_2$. Each M$^2$ may be CBr$_3$. Each M$^2$ may be CH$_2$OH. Each M$^2$ may be CH$_2$OJ''. Each M$^2$ may be G$^1$. Each M$^2$ may be CH$_2$OG$^1$. Each M$^2$ may be CH$_2$OR. Each M$^2$ may be CH$_2$OG$^1$OG$^{1\prime}$. Each M$^2$ may be G$^1$OG$^{1\prime}$. Each M$^2$ may be G$^1$OG$^{1\prime}$OG$^{1\prime\prime}$. Each M$^2$ may be CH$_2$SG$^1$. Each M$^2$ may be CH$_2$NH$_2$. Each M$^2$ may be CH$_2$NHG$^1$. Each M$^2$ may be CH$_2$NG$^1{}_2$. Each M$^2$ may be C≡CH.

Each L$^2$ may independently be H or A$^2$-D$^2$. Each L$^2$ may be H. Each L$^2$ may be A$^2$-D$^2$.

Each A$^2$ may independently be O, S, SO, SO$_2$, NH, NG$^1$, N$^+$H$_2$, or N$^+$HG$^1$. Each A$^2$ may independently be O, S, SO, or SO$_2$. Each A$^2$ may independently be O, NH, NG$^1$, N$^+$H$_2$, or N$^+$HG$^1$. Each A$^2$ may independently be S, SO, SO$_2$, NH, NG$^1$, N$^+$H$_2$, or N$^+$HG$^1$. Each A$^2$ may independently be O, S, SO, SO$_2$, NH, or N$^+$H$_2$. Each A$^2$ may independently be S, SO, or SO$_2$. Each A$^2$ may independently be NH, NG$^1$, N$^+$H$_2$, or N$^+$HG$^1$. Each A$^2$ may independently be NH, or N$^+$H$_2$. Each A$^2$ may independently be O, S, NH, NG$^1$, N$^+$H$_2$, or N$^+$HG$^1$. Each A$^2$ may independently be O, NH, or N$^+$H$_2$. Each A$^2$ may independently be O, S, NH, or N$^+$H$_2$. Each A$^2$ may independently be O, S, or NH. Each A$^2$ may independently be O, or NH. Each A$^2$ may independently be O, or S. Each A$^2$ may be S. Each A$^2$ may be SO. Each A$^2$ may be SO$_2$. Each A$^2$ may be NH. Each A$^2$ may be NG$^1$. Each A$^2$ may be N$^+$H$_2$. Each A$^2$ may be N$^+$HG$^1$. Each A$^2$ may be O.

Each D$^2$ may independently be H, G$^1$, R,

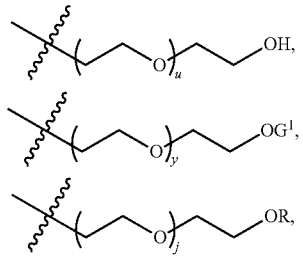

or a moiety selected from TABLE 1. Each D$^2$ may independently be H, G$^1$, or R. Each D$^2$ may independently be H, or R. Each D$^2$ may independently be G$^1$, or R. Each D$^2$ may independently be H, or G$^1$. Each D$^2$ may independently be

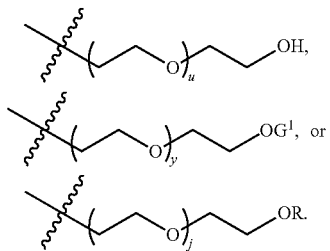

or a moiety selected from TABLE 1. Each D$^2$ may independently be


Each D$^2$ may independently be

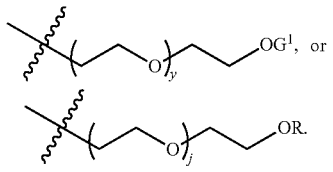

Each D$^2$ may independently be

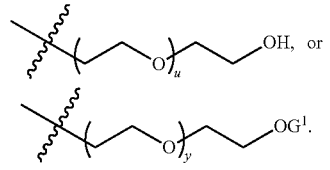

Each D$^2$ may independently be

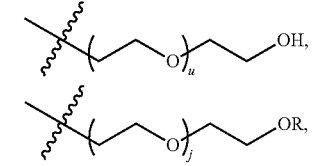

or a moiety selected from TABLE 1. Each D$^2$ may independently be

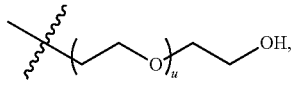

or a moiety selected from TABLE 1. Each D² may be H. Each D² may be G¹. Each D² may be R. Each D² may be
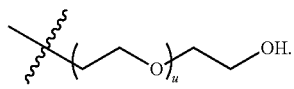
Each D² may be
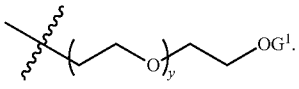
Each D² may be
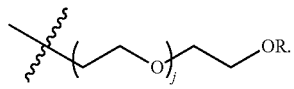
Each D² may be a moiety selected from TABLE 1.
Each Q may independently be
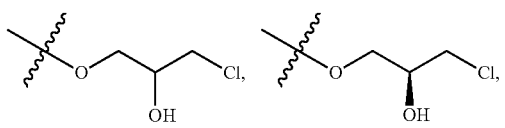
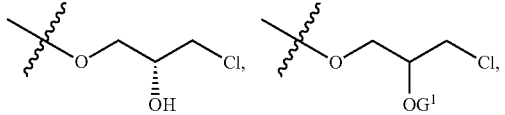
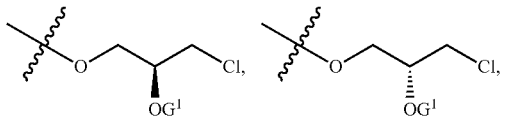
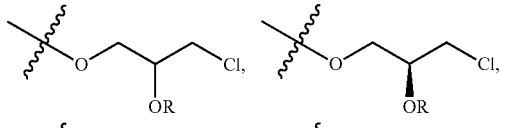
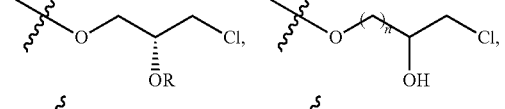
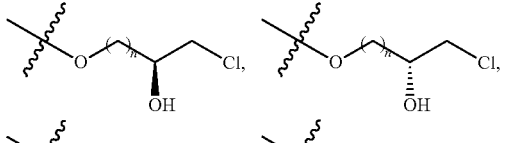

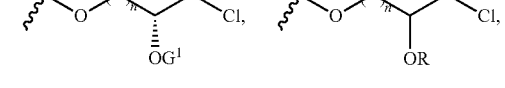
-continued
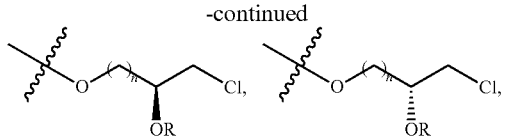
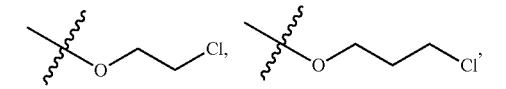
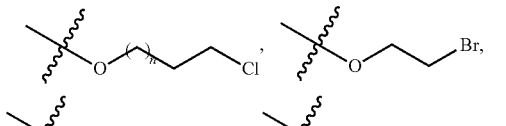
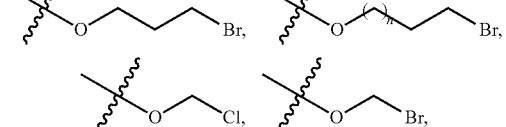
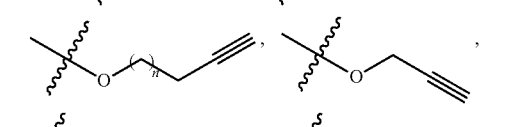
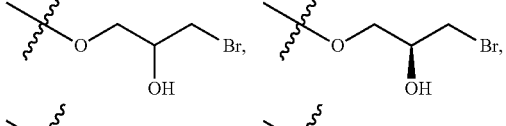
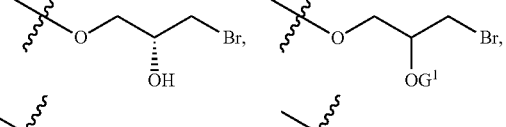
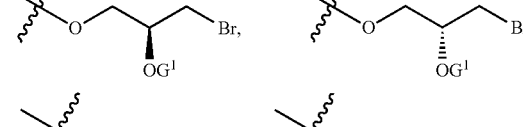
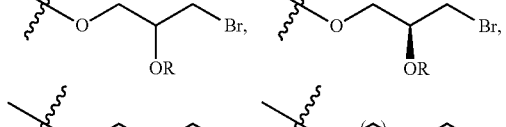
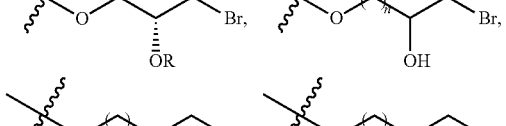
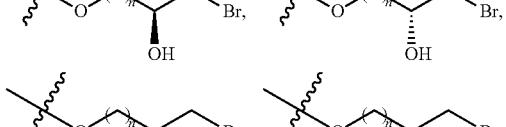
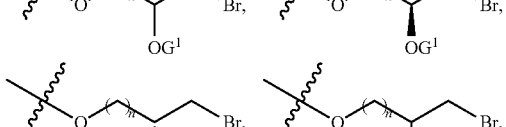
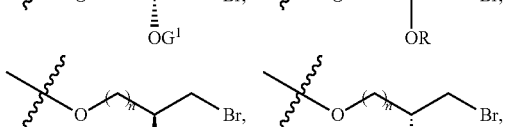
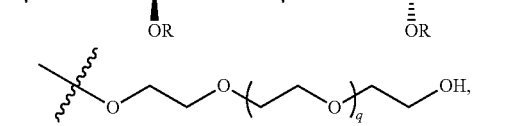

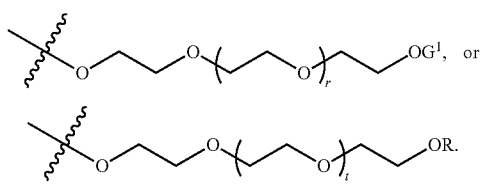
Each Q may independently be
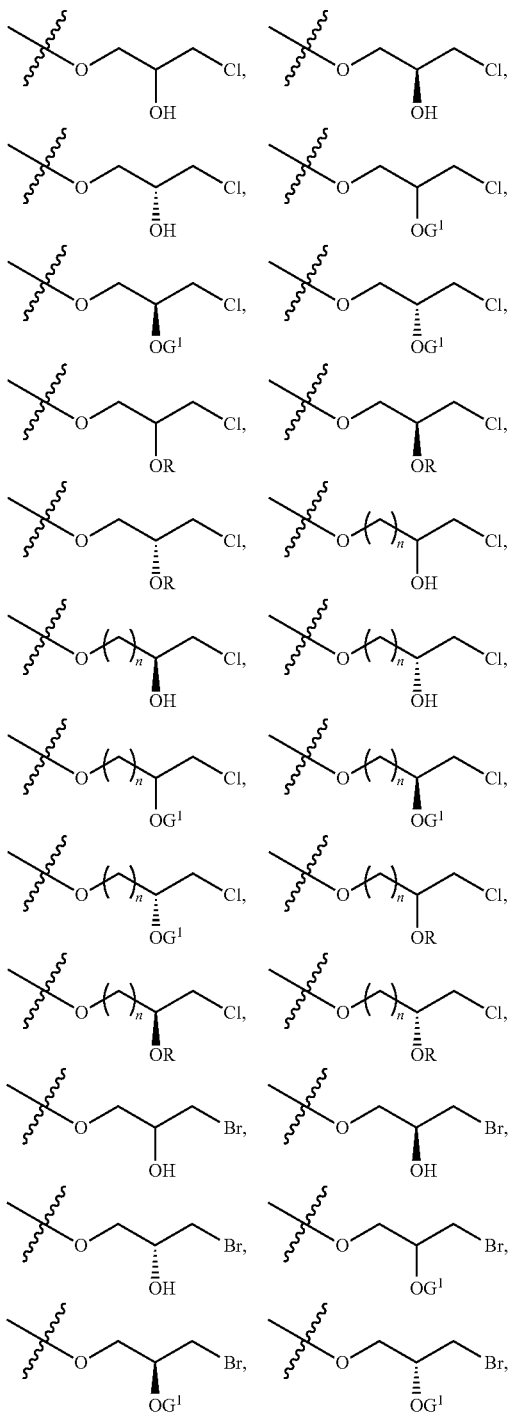
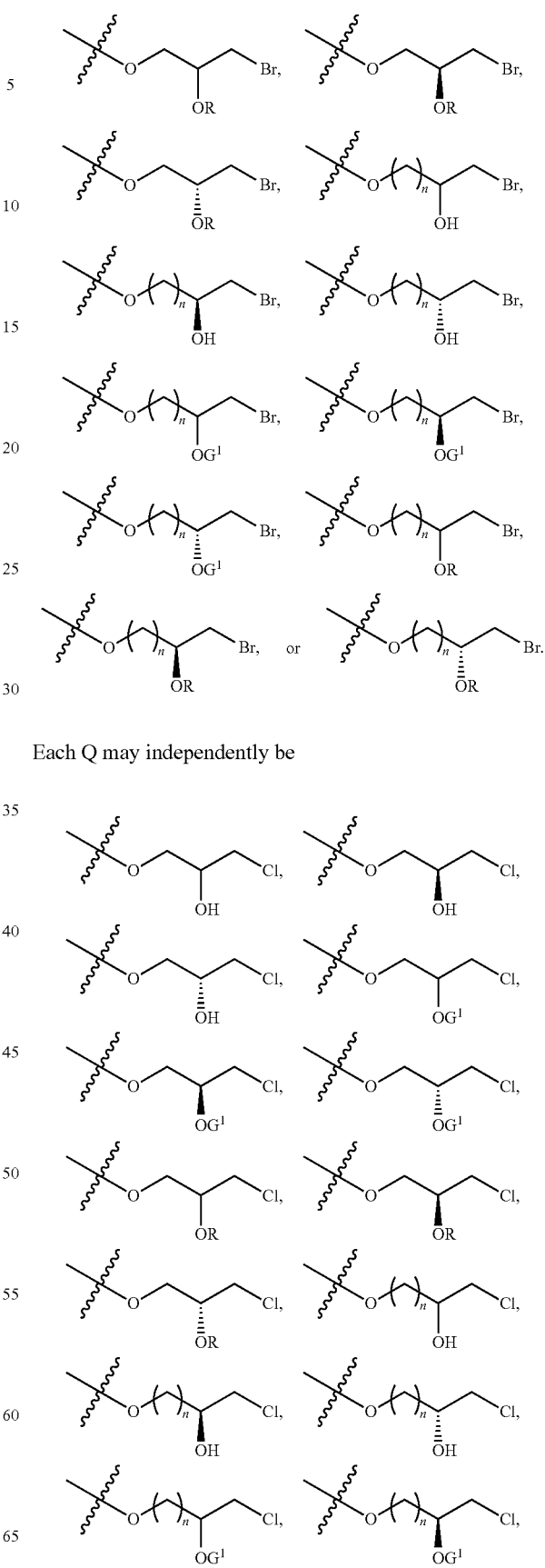
Each Q may independently be -continued
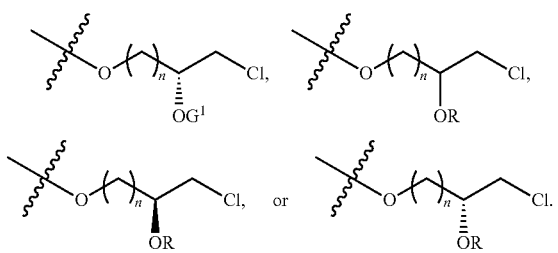
Each Q may independently be
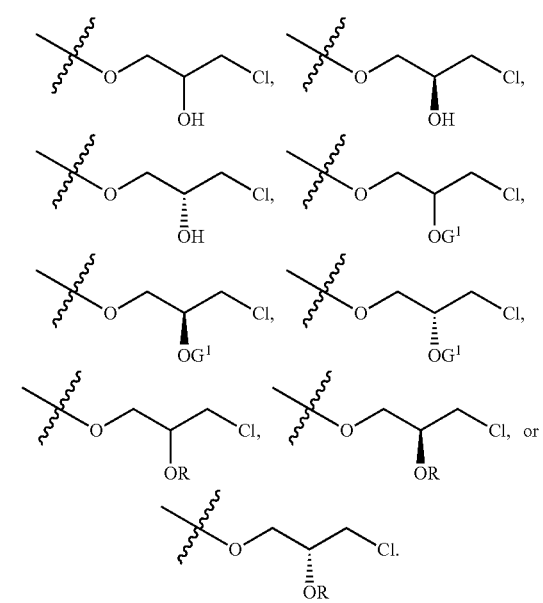
Each Q may independently be
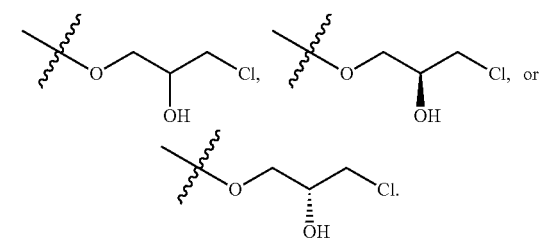
Each Q may independently be
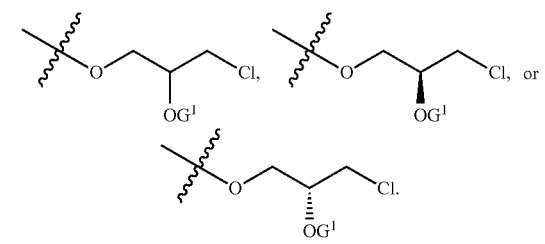
Each Q may independently be
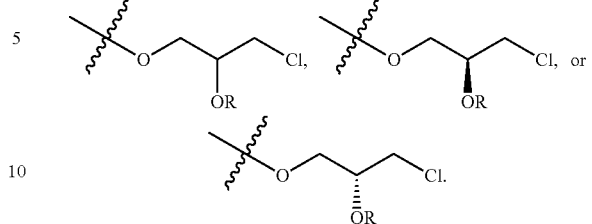
Each Q may independently be
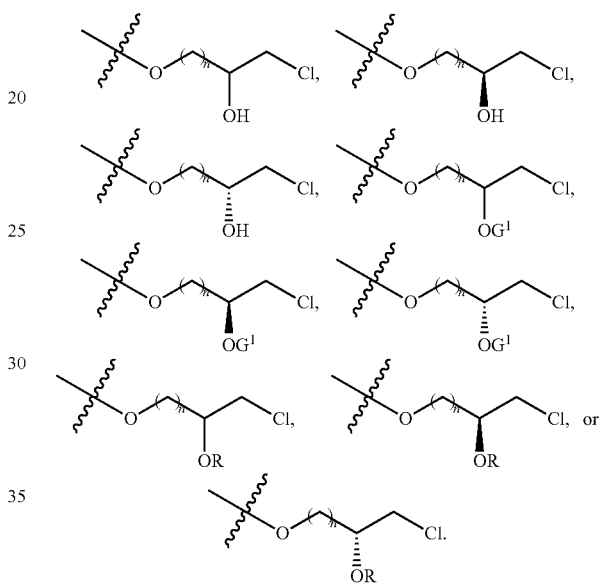
Each Q may independently be

Each Q may independently be

Each Q may independently be
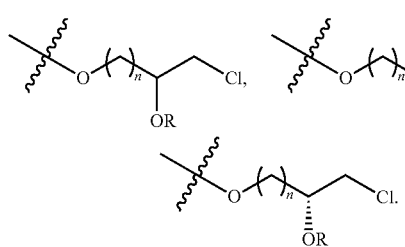
Each Q may independently be
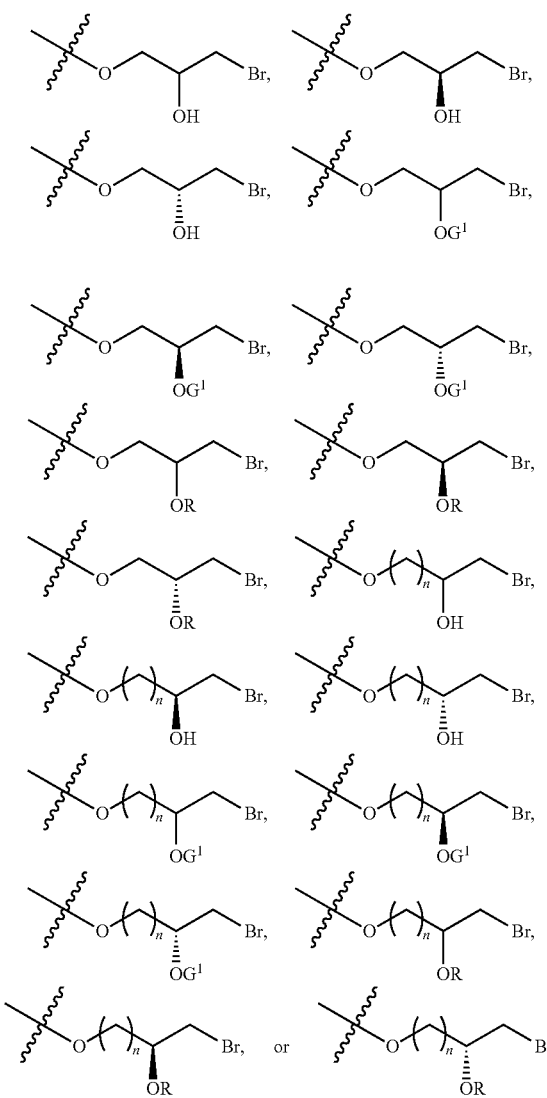
Each Q may independently be
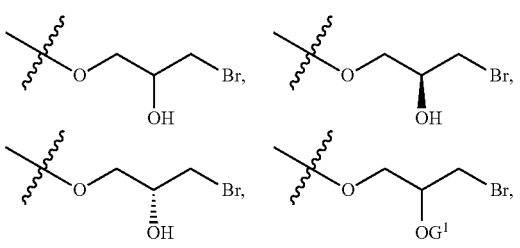
-continued
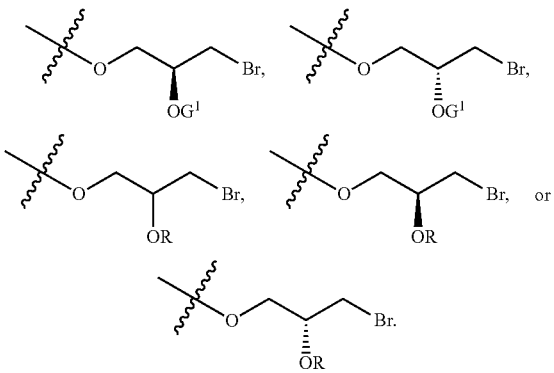
Each Q may independently be
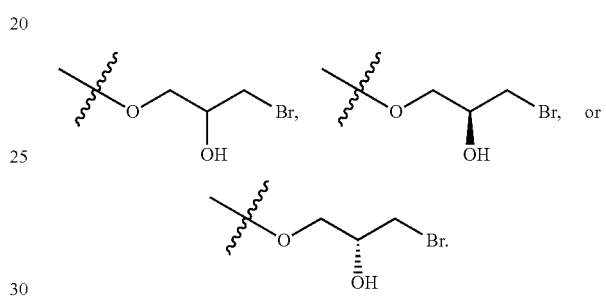
Each Q may independently be
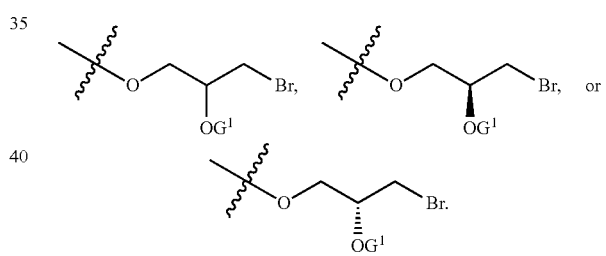
Each Q may independently be
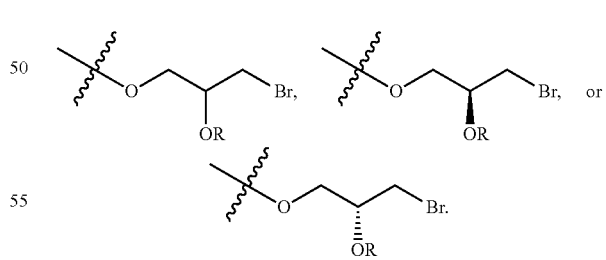
Each Q may independently be
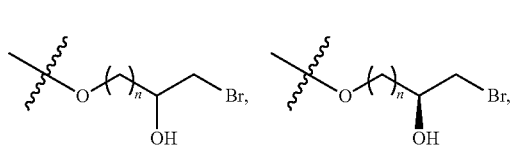

-continued
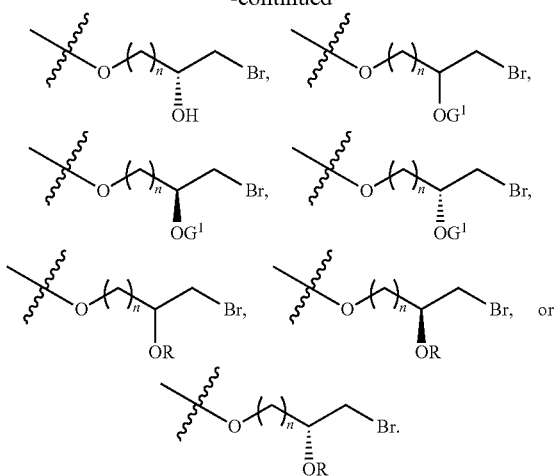
Each Q may independently be
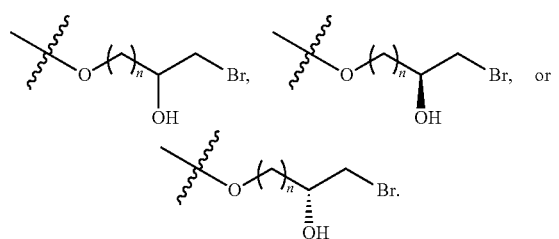
Each Q may independently be
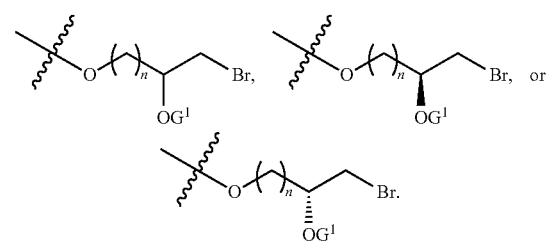
Each Q may independently be
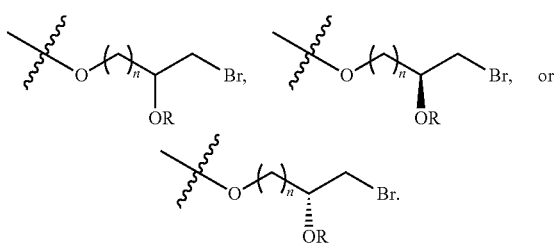
Each Q may independently be
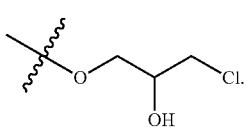 [SMILES: *OCC(O)CCl]
Each Q may independently be
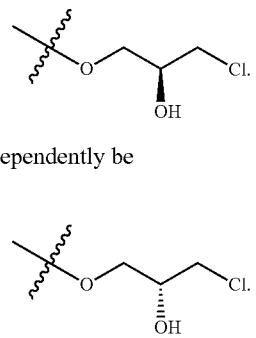
Each Q may independently be
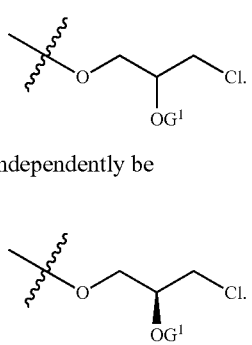
Each Q may independently be
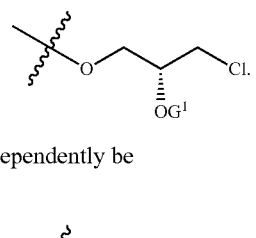
Each Q may independently be
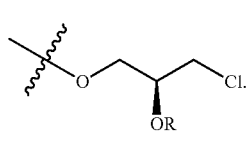
Each Q may independently be
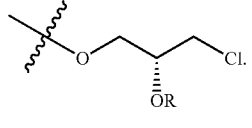

Each Q may independently be

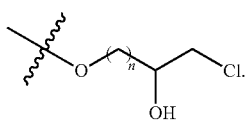

Each Q may independently be

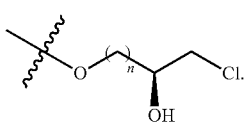

Each Q may independently be

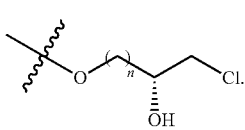

Each Q may independently be

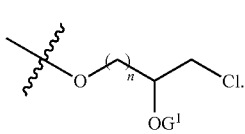

Each Q may independently be

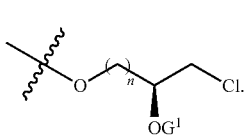

Each Q may independently be

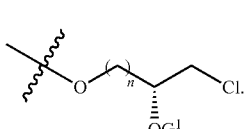

Each Q may independently be

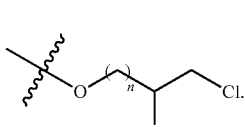

Each Q may independently be

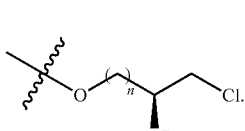

Each Q may independently be

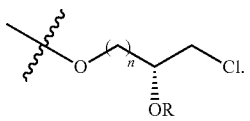

Each Q may independently be

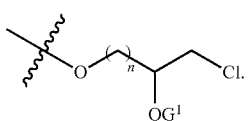

Each Q may independently be

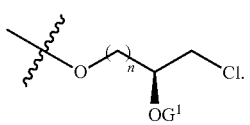

Each Q may independently be

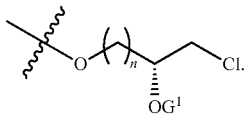

Each Q may independently be

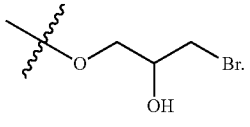 [SMILES: *OCC(O)CBr]

Each Q may independently be

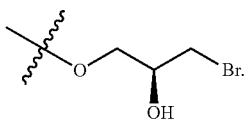 [SMILES: *OC[C@H](O)CBr]

Each Q may independently be

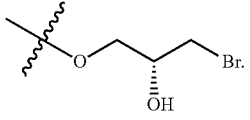

Each Q may independently be

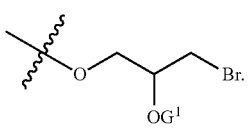

Each Q may independently be

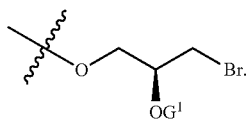

Each Q may independently be

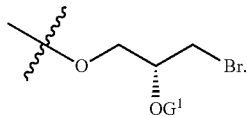

Each Q may independently be

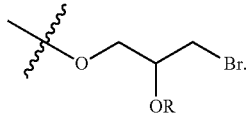

Each Q may independently be

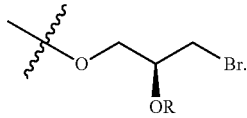

Each Q may independently be

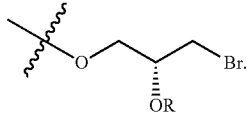

Each Q may independently be

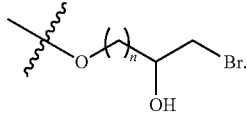

Each Q may independently be

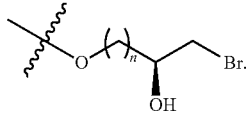

Each Q may independently be

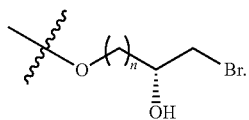

Each Q may independently be

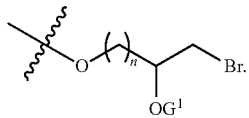

Each Q may independently be

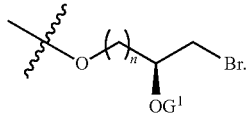

Each Q may independently be

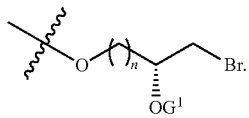

Each Q may independently be

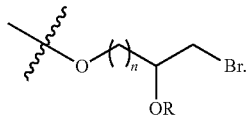

Each Q may independently be

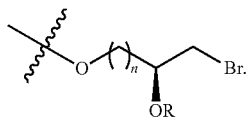

Each Q may

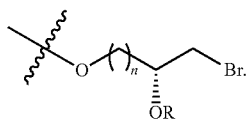

independently be
Each Q may independently be
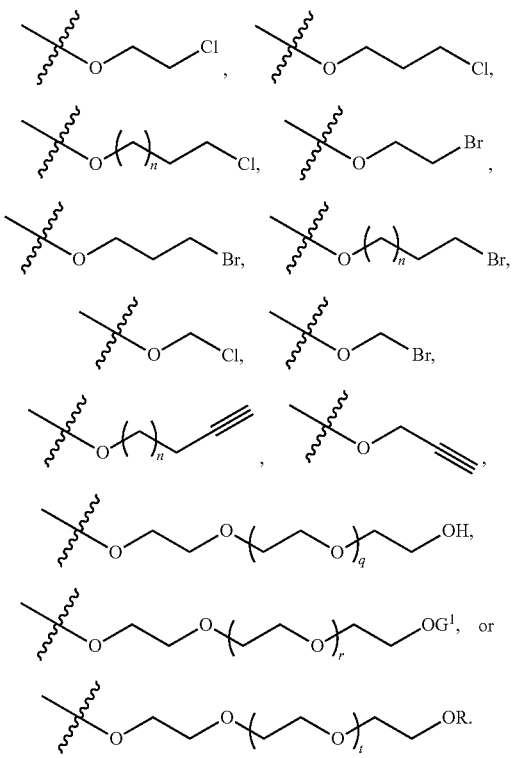
Each Q may independently be
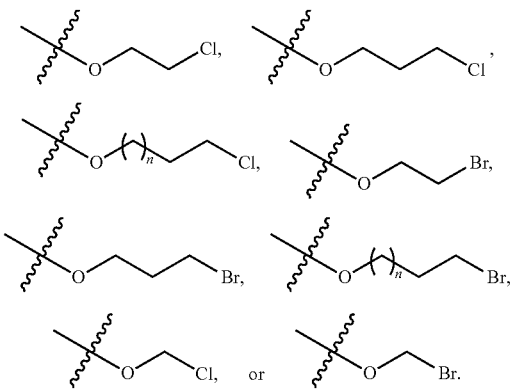
Each Q may independently be
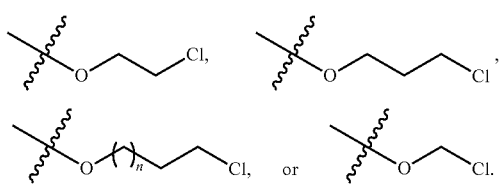
Each Q may independently be
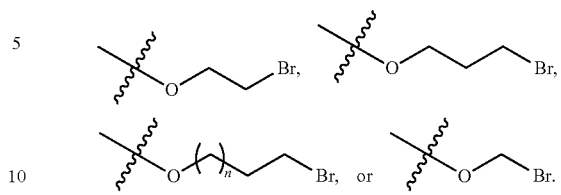
Each Q may independently be
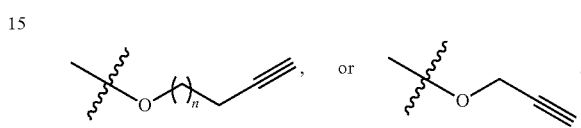
Each Q may independently be
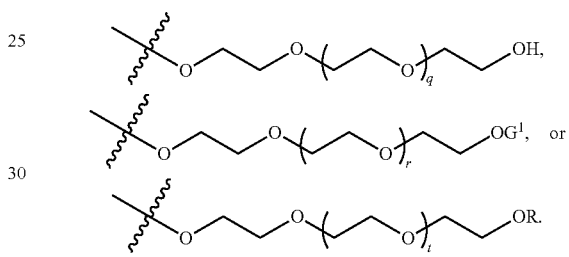
Each Q may be
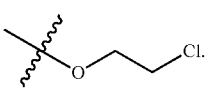 [SMILES: *OCCCl]
Each Q may be
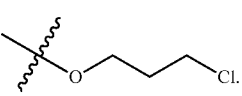
Each Q may independently be
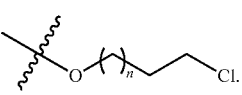
Each Q may be
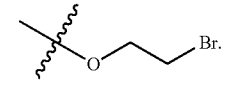 [SMILES: *OCCBr]

Each Q may be
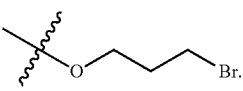
Each Q may independently be
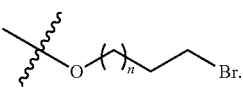
Each Q may be
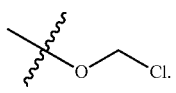 [SMILES: *OCCl]
Each Q may be
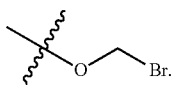 [SMILES: *OCBr]
Each Q may independently be
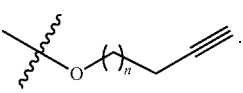
Each Q may be
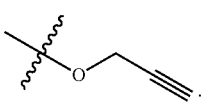 [SMILES: *OCC#C]
Each Q may independently be
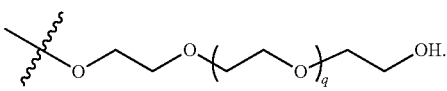
Each Q may independently be
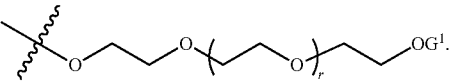
Each Q may independently be
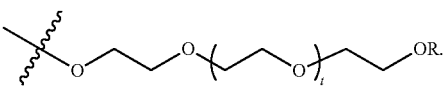
Each T may independently be
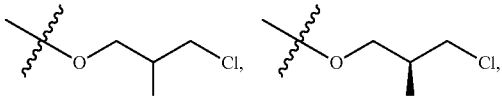
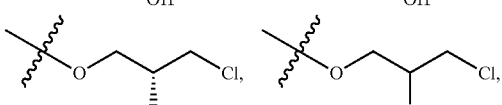
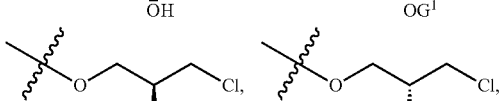
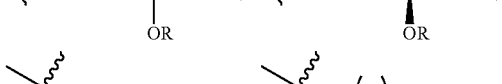
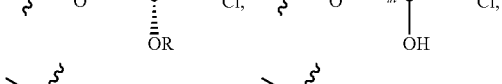
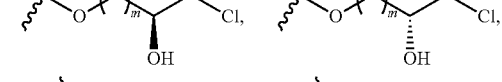
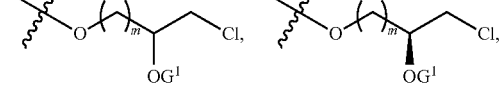
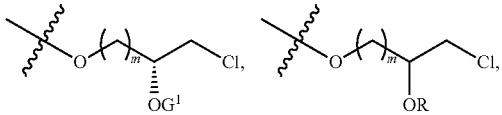
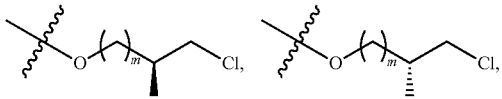
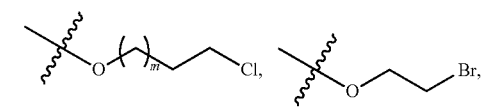
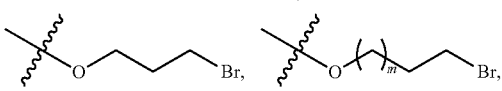
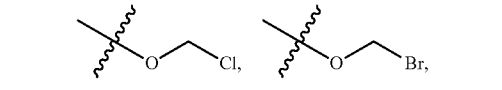

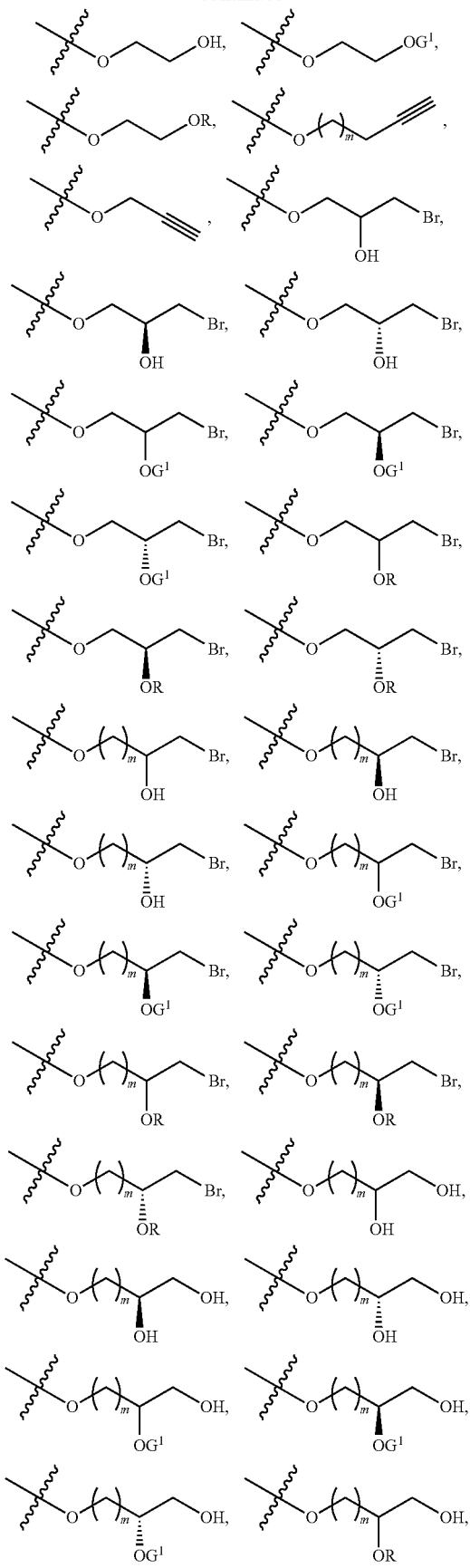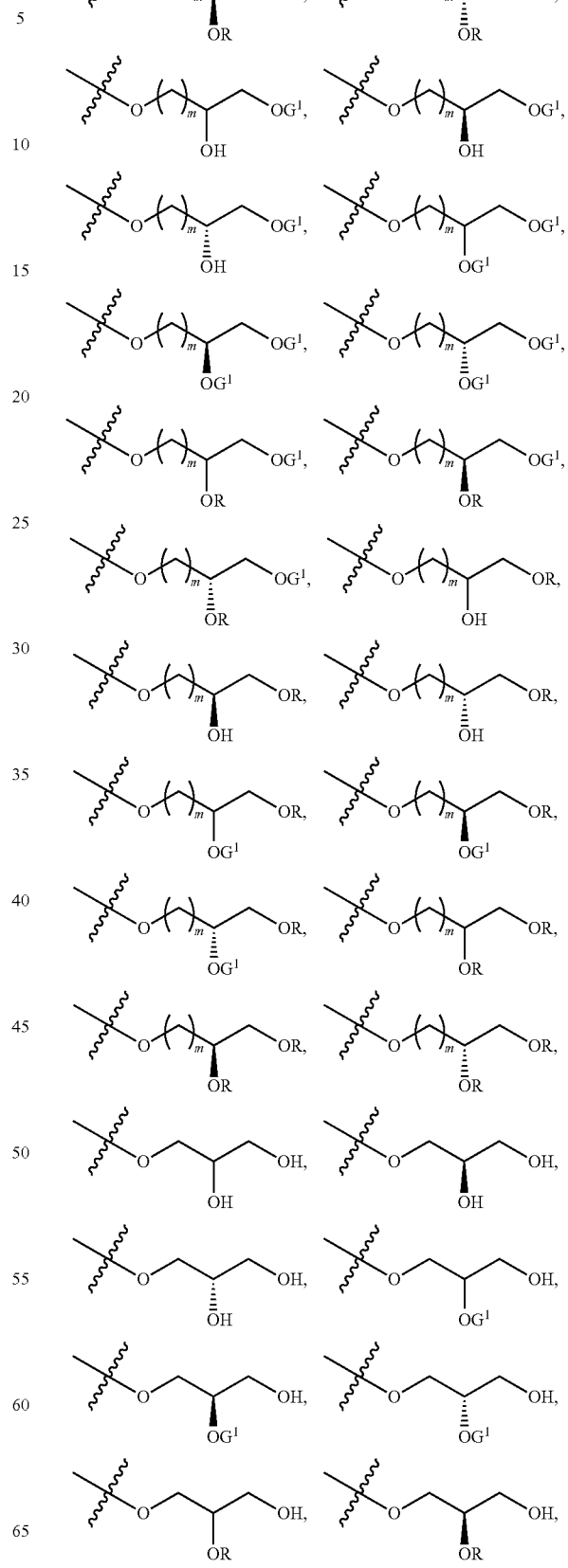

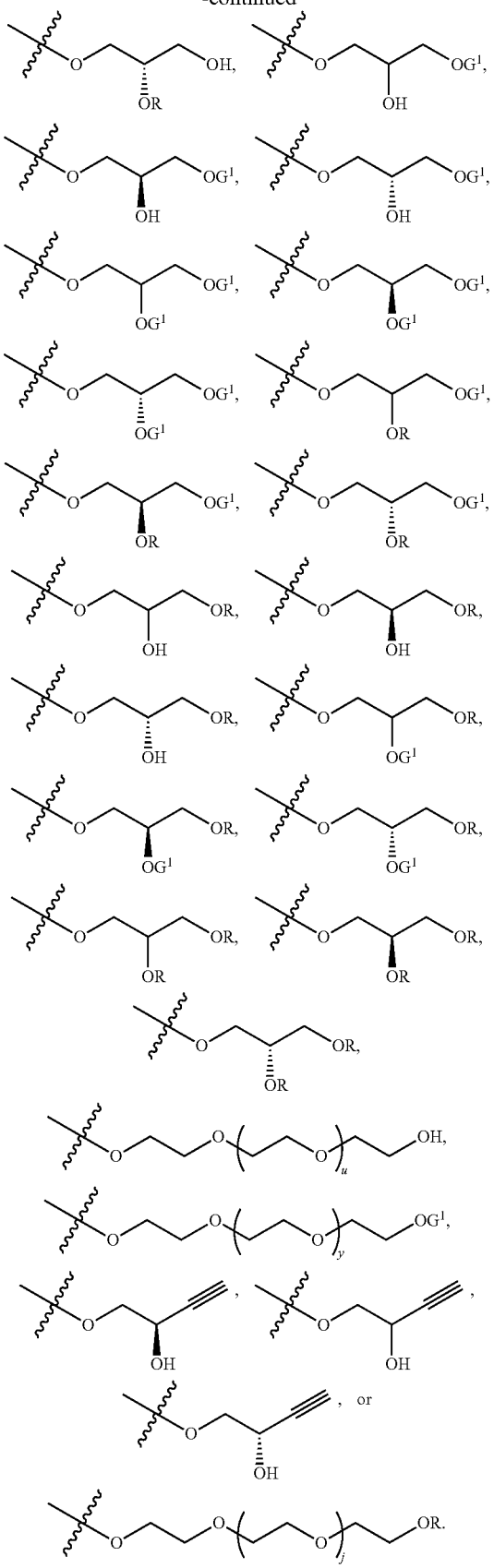
Each T may independently be
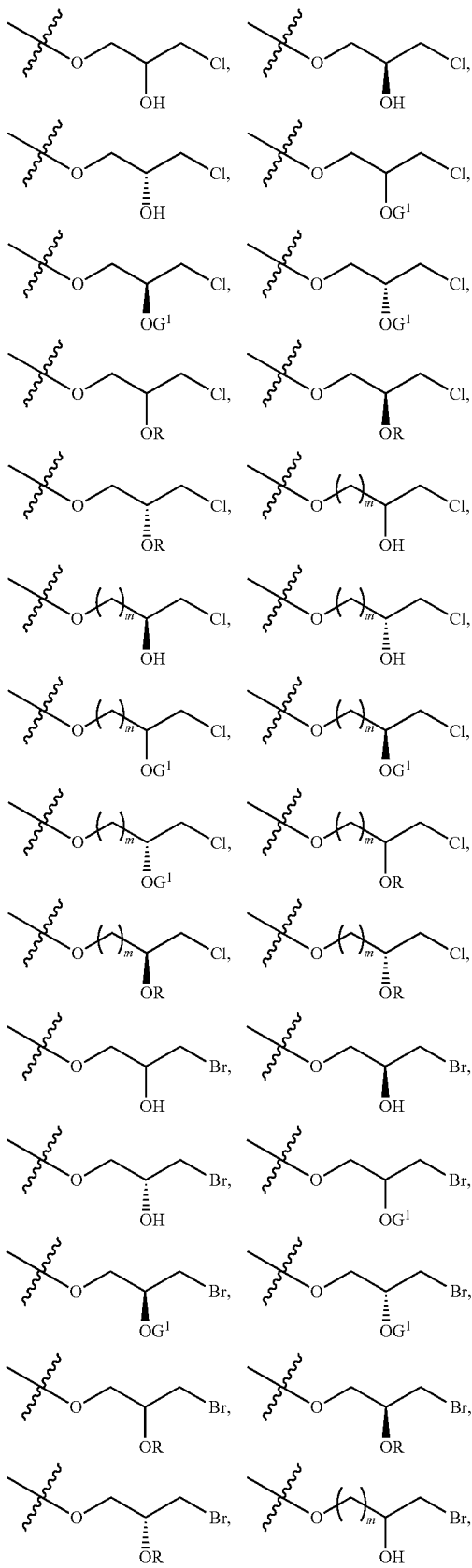

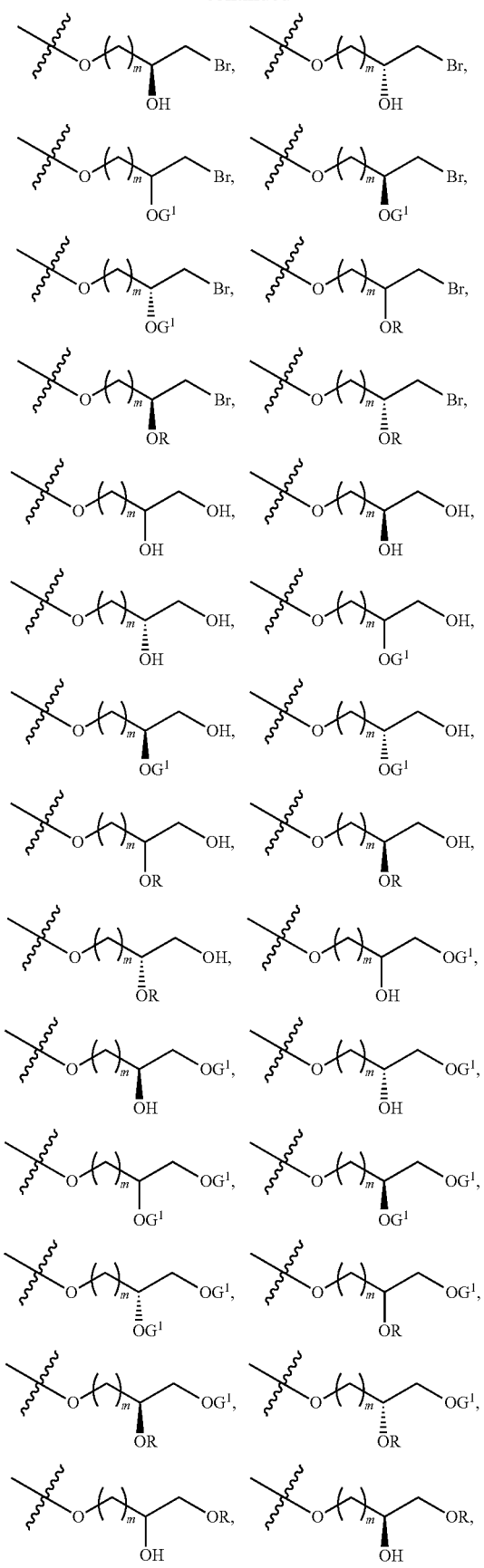
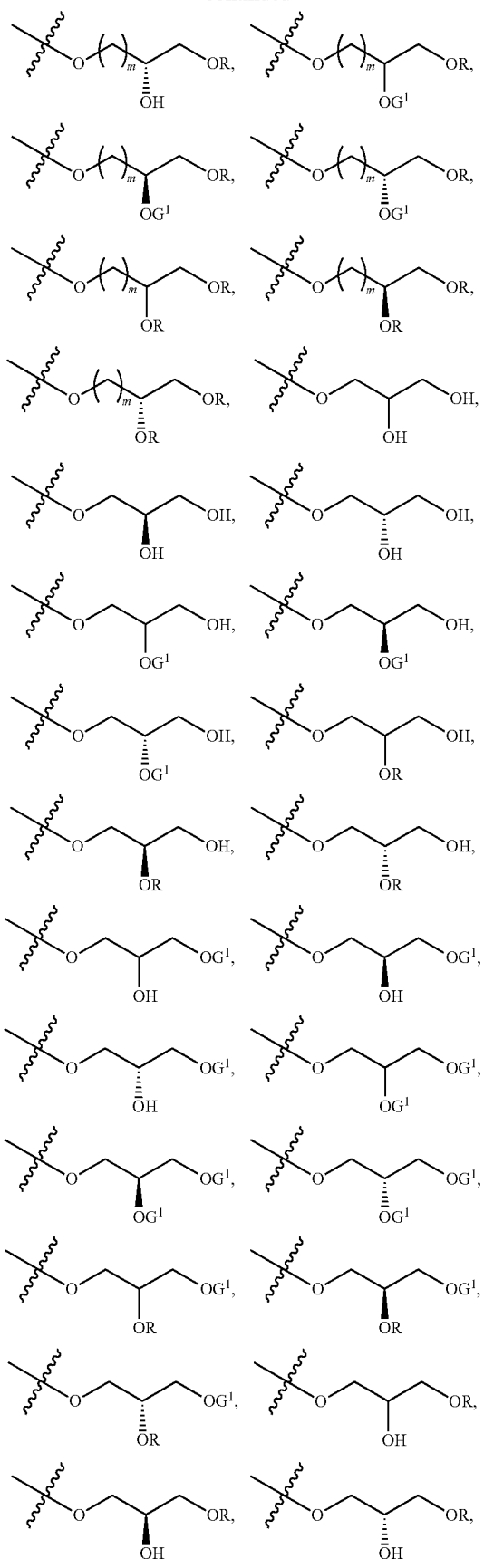

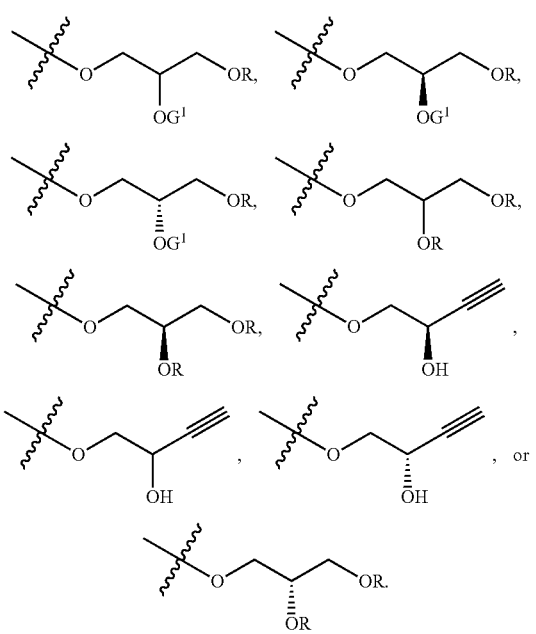
Each T may independently be
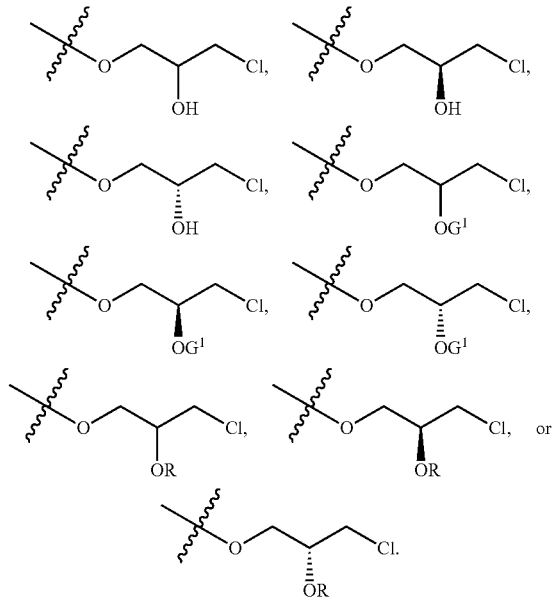
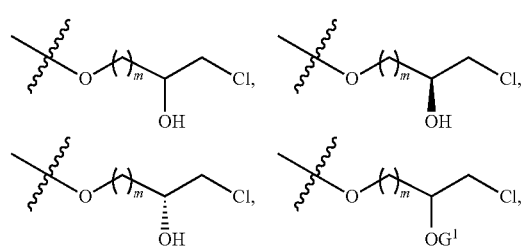
Each T may independently be
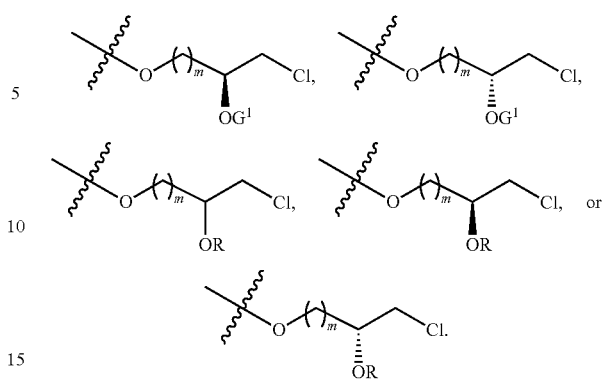
Each T may independently be
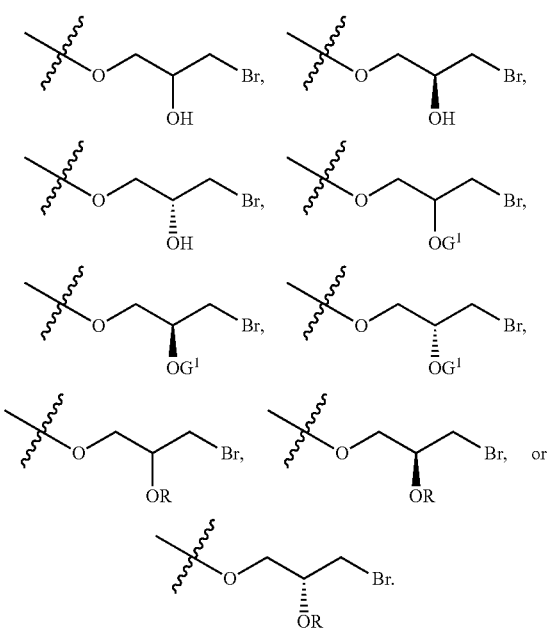
Each T may independently be
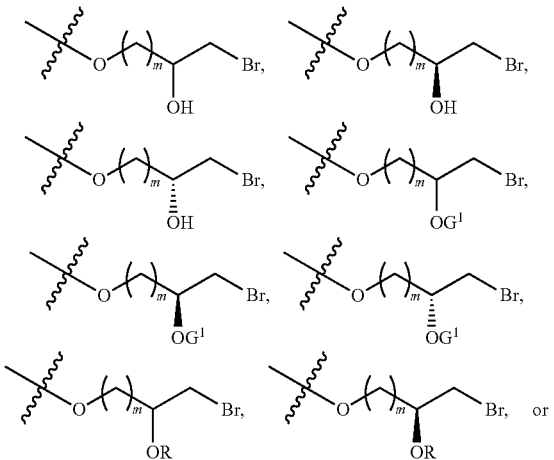

-continued
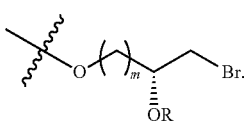
Each T may independently be
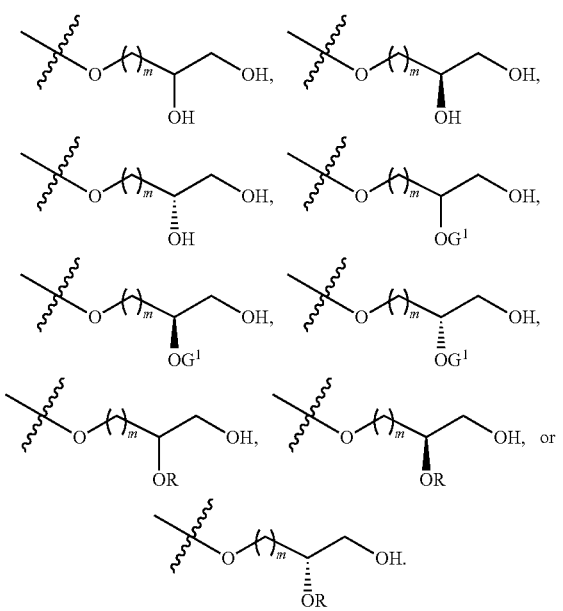
Each T may independently be
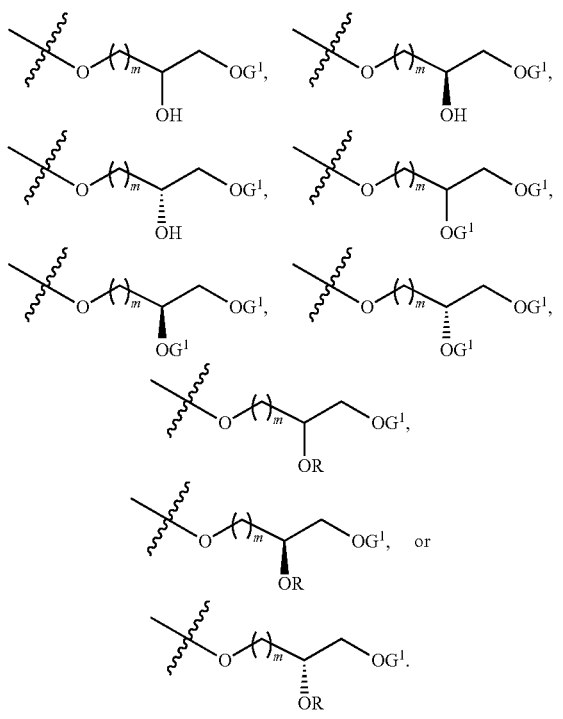
Each T may independently be
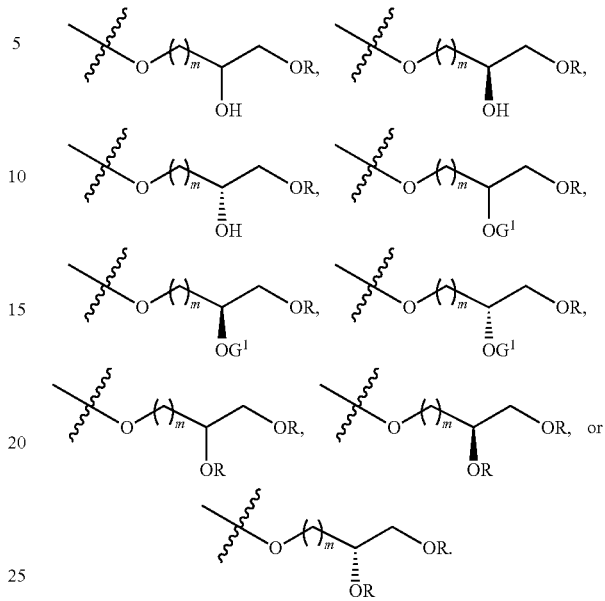
Each T may independently be
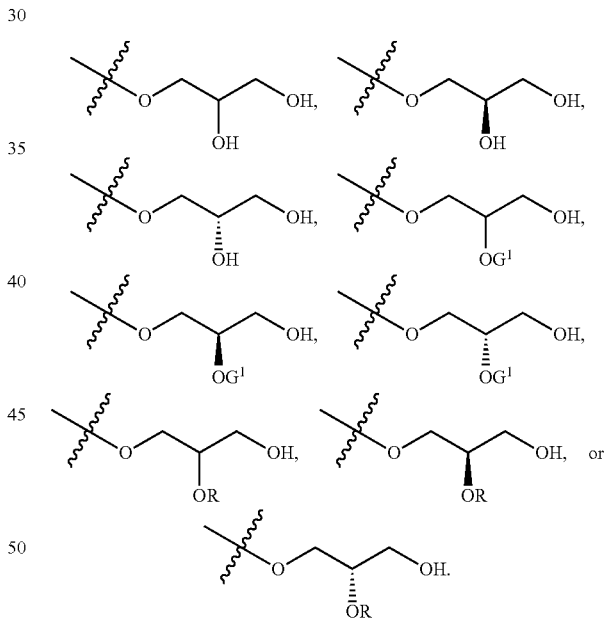
Each T may independently be
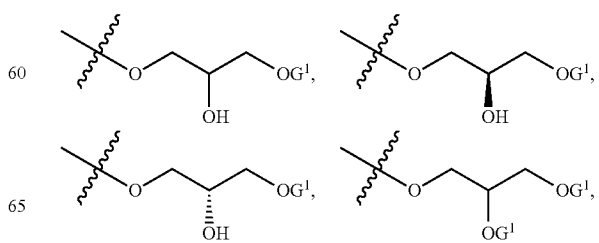

-continued
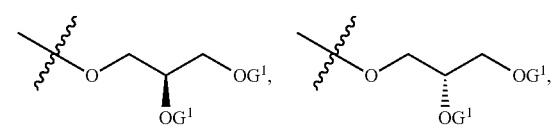
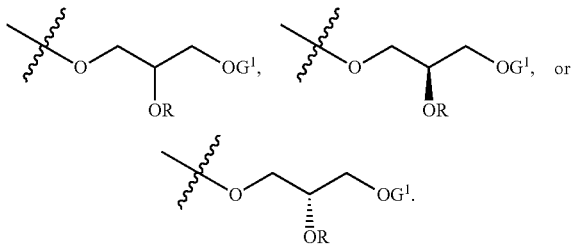
Each T may independently be
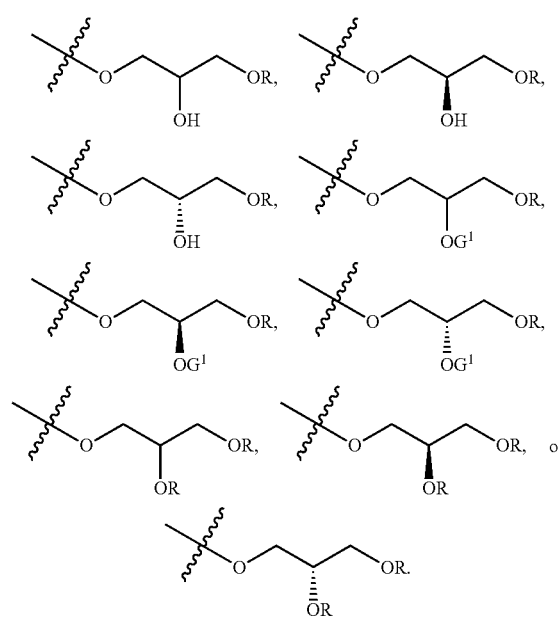
Each T may independently be
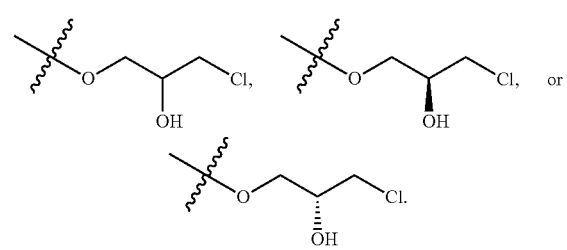
Each T may independently be
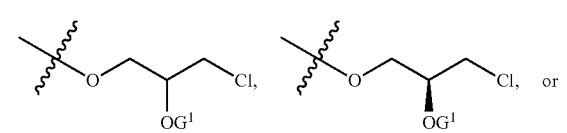
-continued
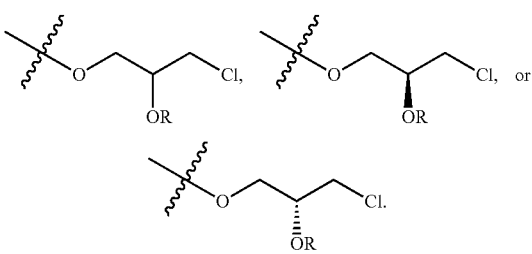
Each T may independently be
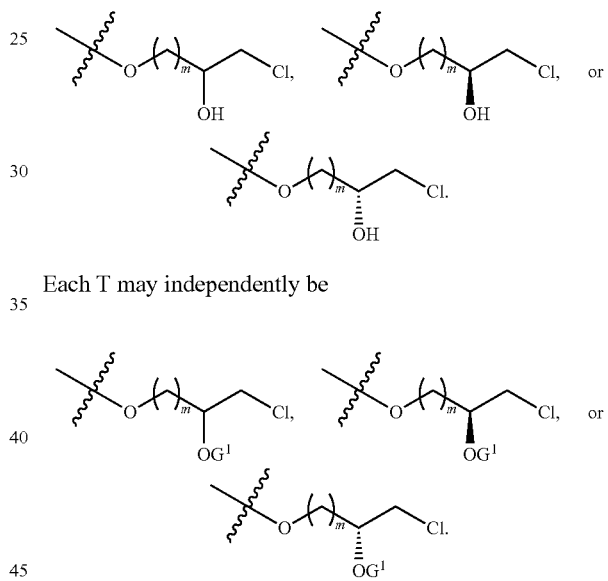
Each T may independently be
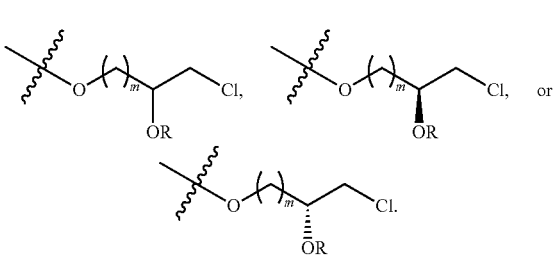
Each T may independently be
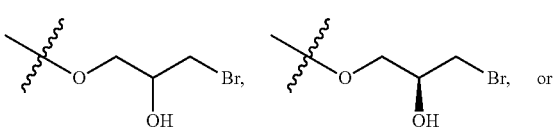

-continued
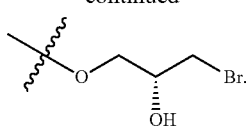
Each T may independently be
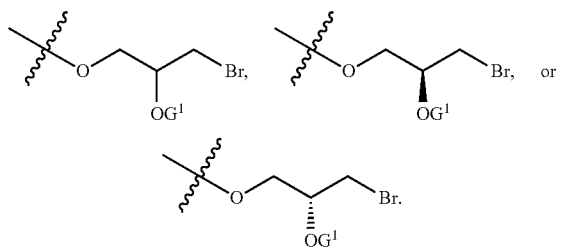
Each T may independently be
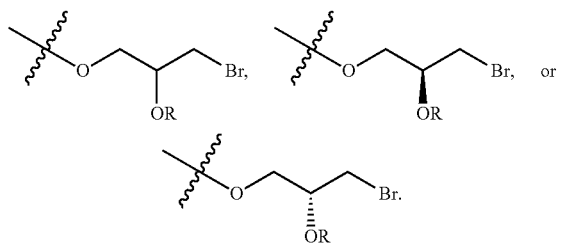
Each T may independently be
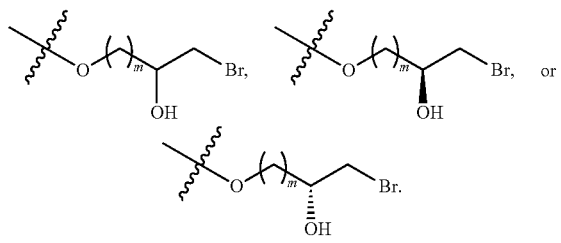
Each T may independently be
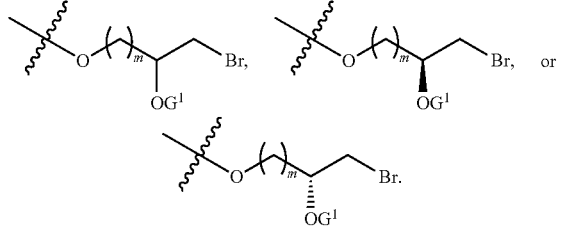
Each T may independently be
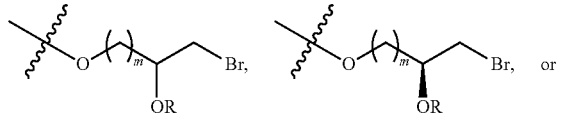
-continued
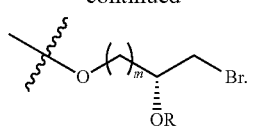
Each T may independently be
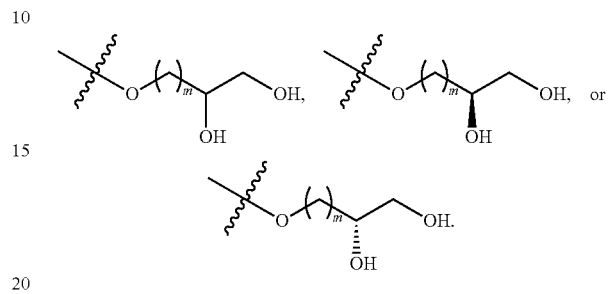
Each T may independently be
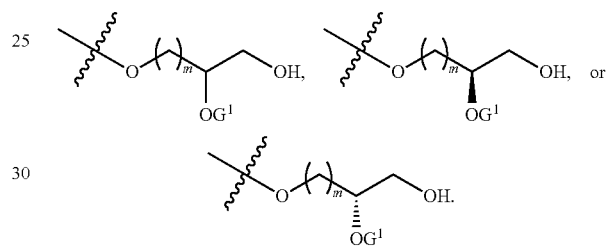
Each T may independently be
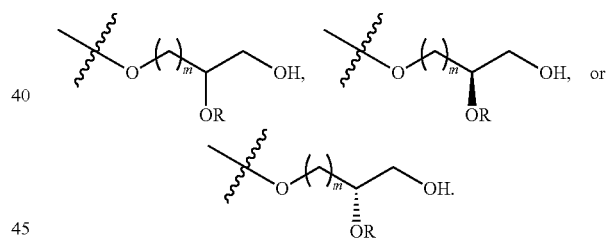
Each T may independently be
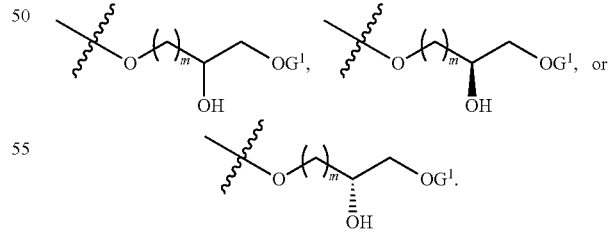
Each T may independently be
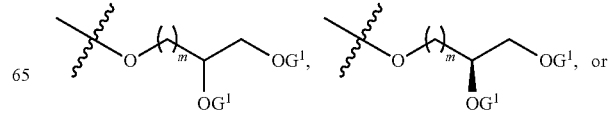

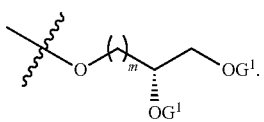
Each T may independently be
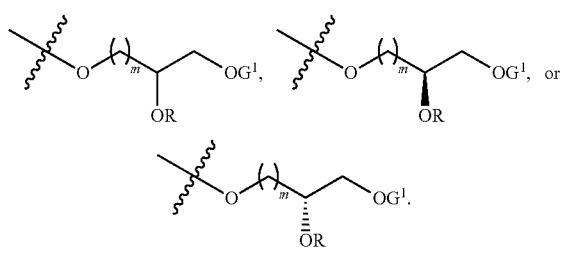
Each T may independently be
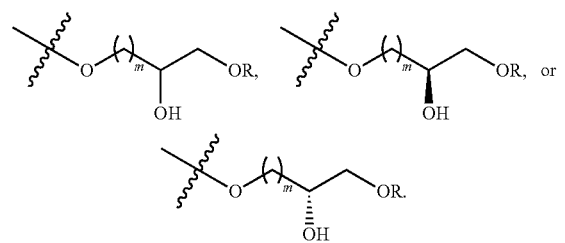
Each T may independently be
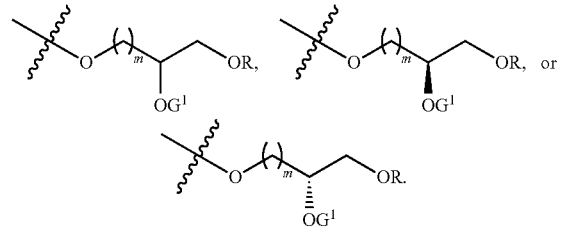
Each T may independently be
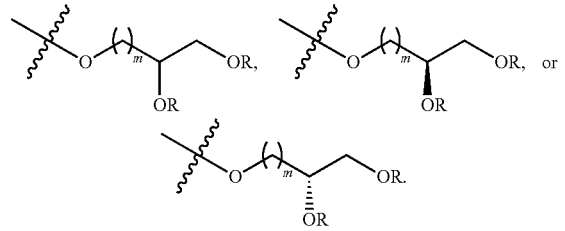
Each T may independently be
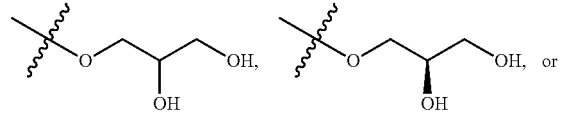
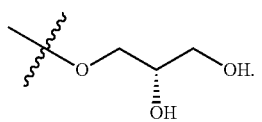
Each T may independently be
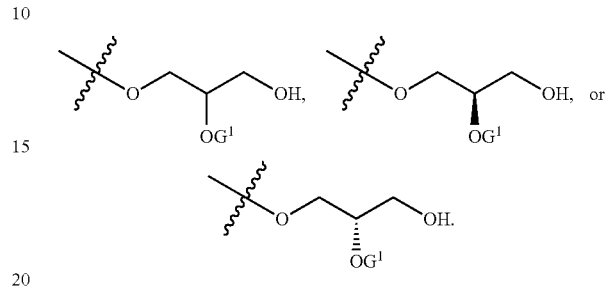
Each T may independently be
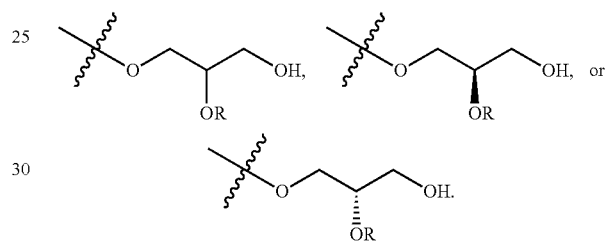
Each T may independently be
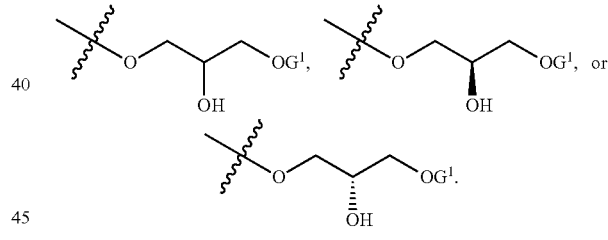
Each T may independently be
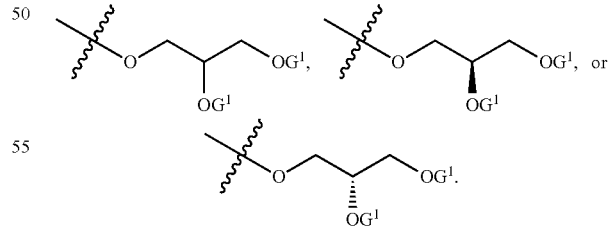
Each T may independently be
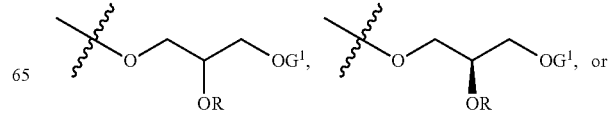

-continued

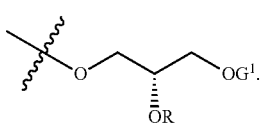

Each T may independently be

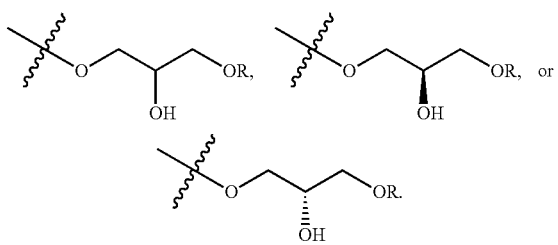

Each T may independently be

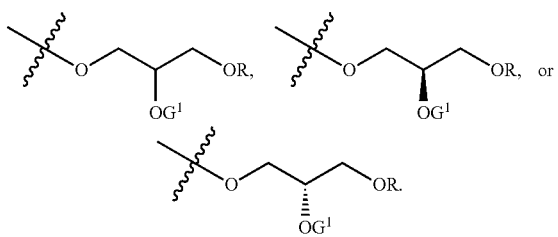

Each T may independently be

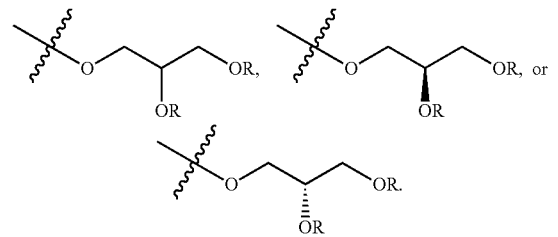

Each T may independently be

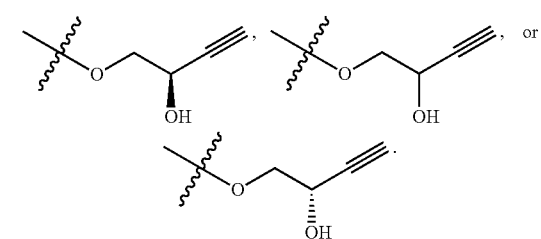

Each T may independently be

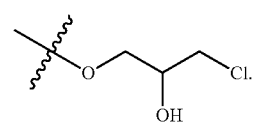 [SMILES: *OCC(O)CCl]

Each T may independently be

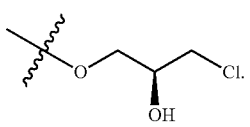

Each T may independently be

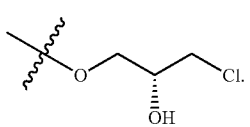

Each T may independently be

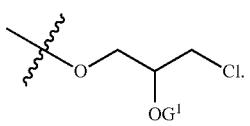

Each T may independently be

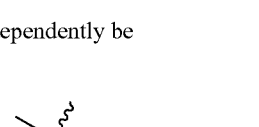

Each T may independently be

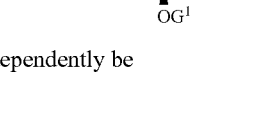

Each T may independently be

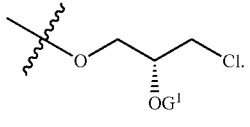

Each T may independently be

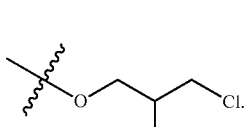

Each T may independently be

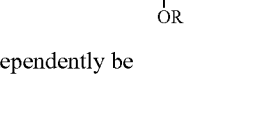

Each T may independently be

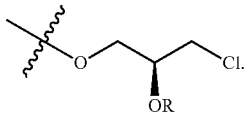

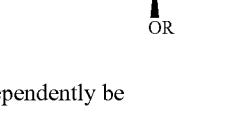

Each T may independently be

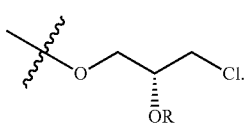

Each T may independently be

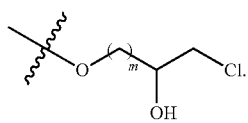

Each T may independently be

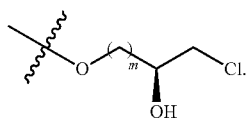

Each T may independently be

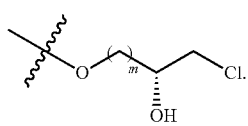

Each T may independently be

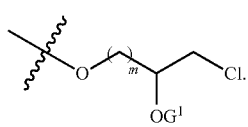

Each T may independently be

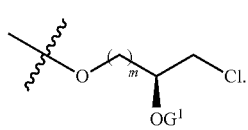

Each T may independently be

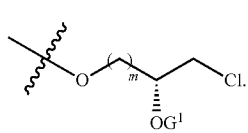

Each T may independently be

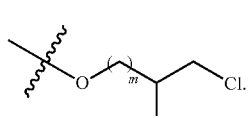

Each T may independently be

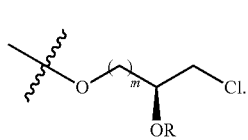

Each T may independently be

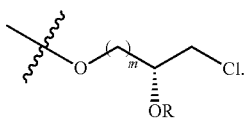

Each T may independently be

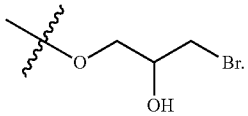

Each T may independently be

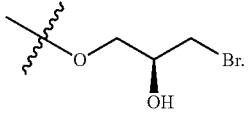

Each T may independently be

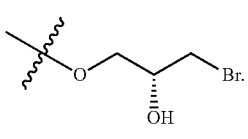 [SMILES: *OC[C@@H](O)CBr]

Each T may independently be

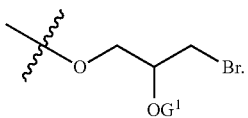

Each T may independently be

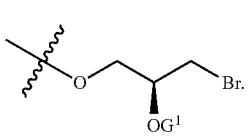

Each T may independently be

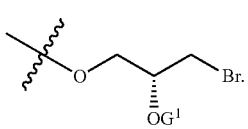

Each T may independently be

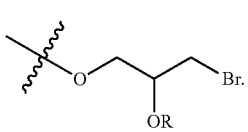

Each T may independently be

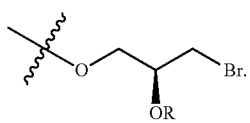

Each T may independently be

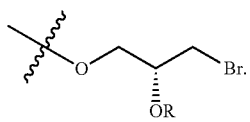

Each T may independently be

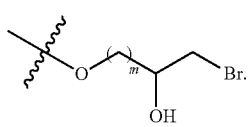

Each T may independently be

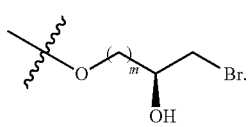

Each T may independently be

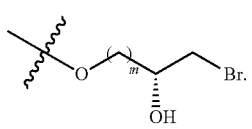

Each T may independently be

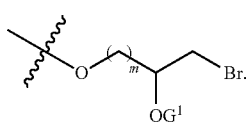

Each T may independently be

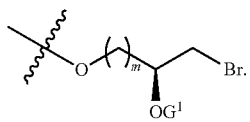

Each T may independently be

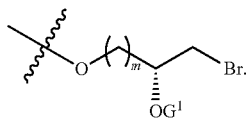

Each T may independently be

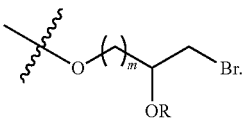

Each T may independently be

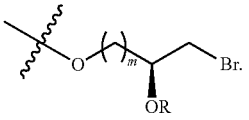

Each T may independently be

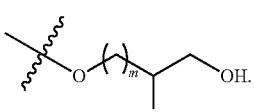

Each T may independently be

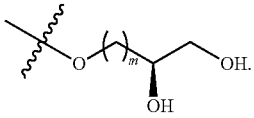

Each T may independently be

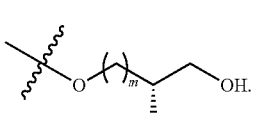

Each T may independently be

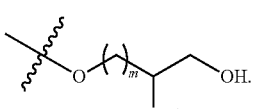

Each T may independently be

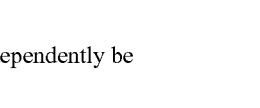

Each T may independently be

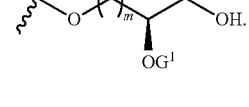

Each T may independently be

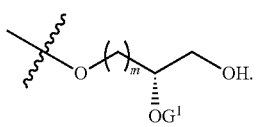

Each T may independently be

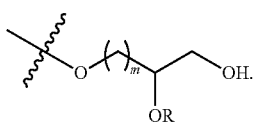

Each T may independently be

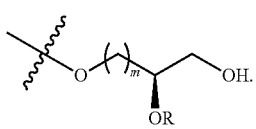

Each T may independently be

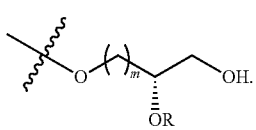

Each T may independently be

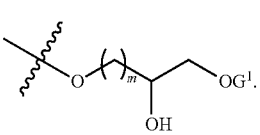

Each T may independently be

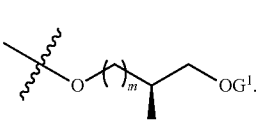

Each T may independently be

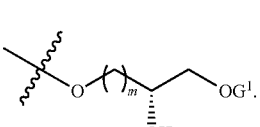

Each T may independently be

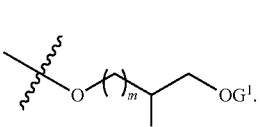

Each T may independently be

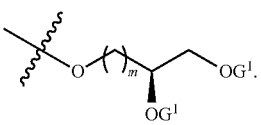

Each T may independently be

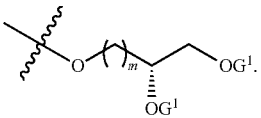

Each T may independently be

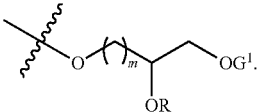

Each T may independently be

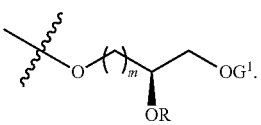

Each T may independently be

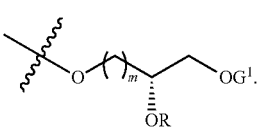

Each T may independently be

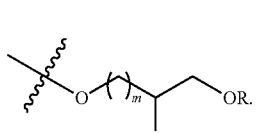

Each T may independently be

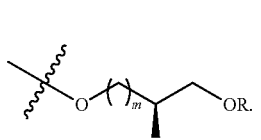

Each T may independently be

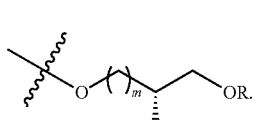

Each T may independently be

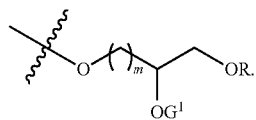

Each T may independently be

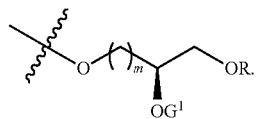

Each T may independently be

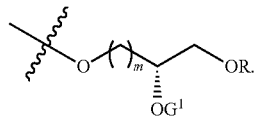

Each T may independently be

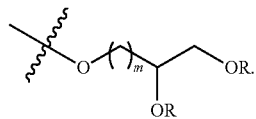

Each T may independently be

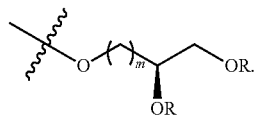

Each T may independently be

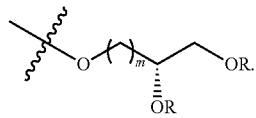

Each T may independently be

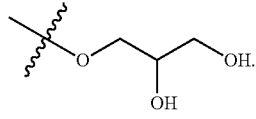 [SMILES: *OCC(O)CO]

Each T may independently be

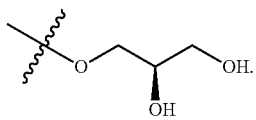 [SMILES: *OC[C@H](O)CO]

Each T may independently be

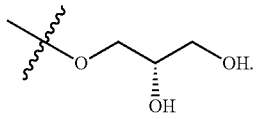

Each T may independently be

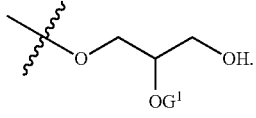

Each T may independently be

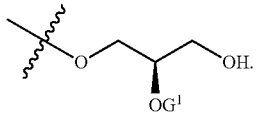

Each T may independently be

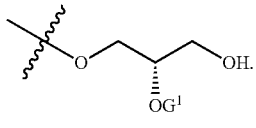

Each T may independently be

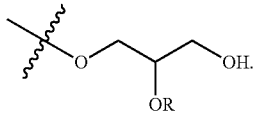

Each T may independently be

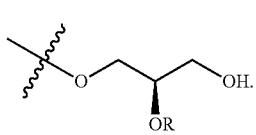

Each T may independently be
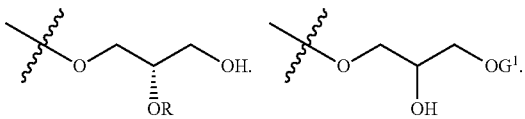
Each T may independently be
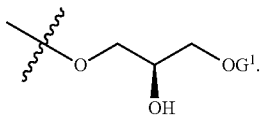
Each T may independently be
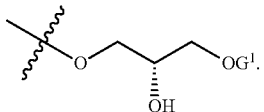
Each T may independently be
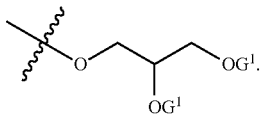
Each T may independently be
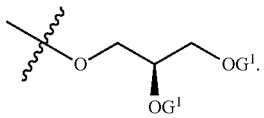
Each T may independently be
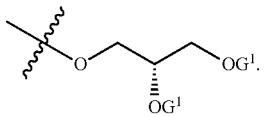
Each T may independently be
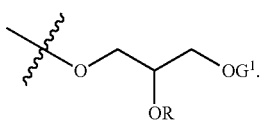
Each T may independently be
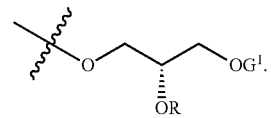
Each T may independently be
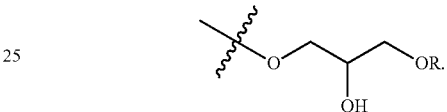
Each T may independently be
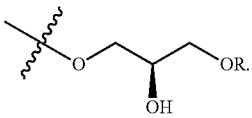
Each T may independently be
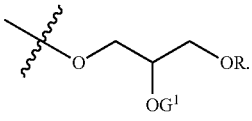
Each T may independently be
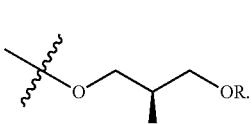
Each T may independently be
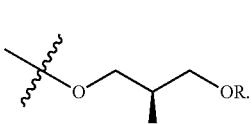

Each T may independently be

[structure: wavy-O-CH2-CH(OG¹)-CH2-OR]

Each T may independently be

[structure: wavy-O-CH2-CH(OR)-CH2-OR]

Each T may independently be

[structure: wavy-O-CH2-C(OR)(H)-CH2-OR, (S)]

Each T may independently be

[structure: wavy-O-CH2-C(OR)(H)-CH2-OR, (R)]

Each T may independently be

[structure: wavy-O-CH2-CH(OH)-C≡CH, (S)]

Each T may independently be

[structure: wavy-O-CH2-CH(OH)-C≡CH]

Each T may independently be

[structure: wavy-O-CH2-CH(OH)-C≡CH, (R)]

Each T may independently be

[structure: wavy-O-CH2CH2-Cl], [wavy-O-CH2CH2CH2-Cl],

[wavy-O-(CH2)m-CH2CH2-Cl], [wavy-O-CH2CH2-Br],

[wavy-O-CH2CH2CH2-Br], [wavy-O-(CH2)m-CH2CH2-Br],

[wavy-O-CH2-Cl], [wavy-O-CH2-Br],

[wavy-O-CH2CH2-OH], [wavy-O-CH2CH2-OG¹],

[wavy-O-CH2CH2-OR], [wavy-O-(CH2)m-C≡CH],

[wavy-O-CH2-C≡CH],

[wavy-O-CH2CH2-O-(CH2CH2O)u-CH2CH2-OH],

[wavy-O-CH2CH2-O-(CH2CH2O)y-CH2CH2-OG¹], or

[wavy-O-CH2CH2-O-(CH2CH2O)j-CH2CH2-OR].

Each T may independently be

[wavy-O-CH2CH2-Cl], [wavy-O-CH2CH2CH2-Cl],

[wavy-O-(CH2)m-CH2CH2-Cl], or [wavy-O-CH2-Cl].

Each T may independently be

[wavy-O-CH2CH2-Br], [wavy-O-CH2CH2CH2-Br],

[wavy-O-(CH2)m-CH2CH2-Br], or [wavy-O-CH2-Br].

Each T may independently be

[wavy-O-CH2CH2-OH], [wavy-O-CH2CH2-OG¹], or

[wavy-O-CH2CH2-OR].

Each T may independently be

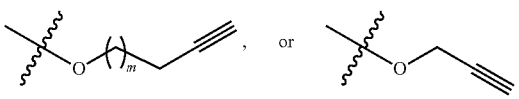, or 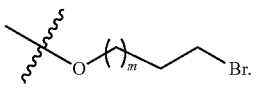.

Each T may independently be

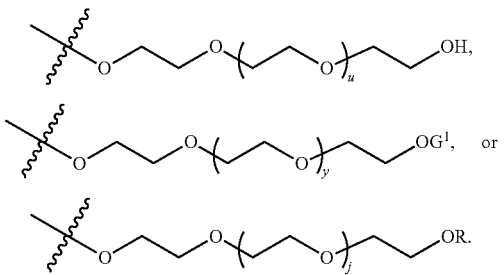

Each T may independently be

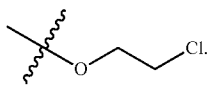

Each T may independently be

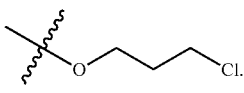 [SMILES: *OCCCCl]

Each T may independently be

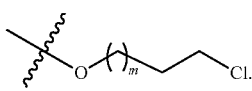

Each T may independently be

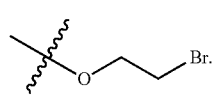 [SMILES: *OCCBr]

Each T may independently be

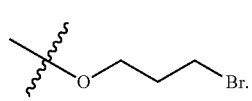 [SMILES: *OCCCBr]

Each T may independently be

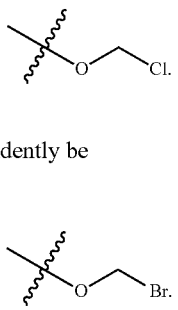

Each T may independently be

Each T may independently be

Each T may independently be

Each T may independently be

Each T may independently be

Each T may independently be

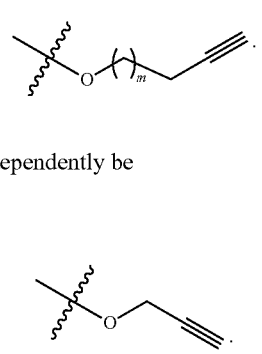

Each T may independently be

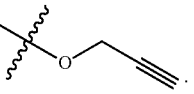.

Each T may independently be

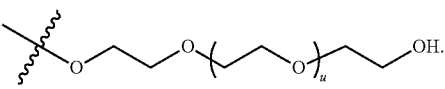

Each T may independently be

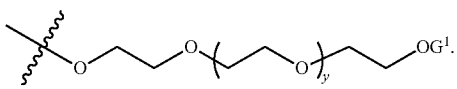

Each T may independently be

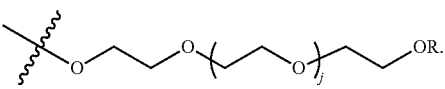

Each q may independently be 0, 1, 2, 3, 4, 5, 6 or 7. Each q may independently be 0 to 1, 0 to 2, 0 to 3, 0 to 4, 0 to 5, 0 to 6, or 0 to 7. Each q may independently be 1 to 2, 1 to 3, 1 to 4, 1 to 5, 1 to 6, or 1 to 7. Each q may independently be 2 to 3, 2 to 4, 2 to 5, 2 to 6, or 2 to 7. Each q may independently be 3 to 4, 3 to 5, 3 to 6, or 3 to 7. Each q may be 0. Each q may be 1. Each q may be 2. Each q may be 3. Each q may be 4. Each q may be 5. Each q may be 6. Each q may be 7.

Each r may independently be 0, 1, 2, 3, 4, 5, 6 or 7. Each r may independently be 0 to 1, 0 to 2, 0 to 3, 0 to 4, 0 to 5, 0 to 6, 0 to 7. Each r may independently be 1 to 2, 1 to 3, 1 to 4, 1 to 5, 1 to 6, or 1 to 7. Each r may independently be 2 to 3, 2 to 4, 2 to 5, 2 to 6, or 2 to 7. Each r may independently be 3 to 4, 3 to 5, 3 to 6, or 3 to 7. Each r may be 0. Each r may be 1. Each r may be 2. Each r may be 3. Each r may be 4. Each r may be 5. Each r may be 6. Each r may be 7.

Each t may independently be 0, 1, 2, 3, 4, 5, 6 or 7. Each t may independently be 0 to 1, 0 to 2, 0 to 3, 0 to 4, 0 to 5, 0 to 6, or 0 to 7. Each t may independently be 1 to 2, 1 to 3, 1 to 4, 1 to 5, 1 to 6, or 1 to 7. Each t may independently be 2 to 3, 2 to 4, 2 to 5, 2 to 6, or 2 to 7. Each t may independently be 3 to 4, 3 to 5, 3 to 6, or 3 to 7. Each t may be 0. Each t may be 1. Each t may be 2. Each t may be 3. Each t may be 4. Each t may be 5. Each t may be 6. Each t may be 7.

Each n may independently be 0, 1, 2, 3, 4, 5, 6, 7 or 8. Each n may independently be 0 to 1, 0 to 2, 0 to 3, 0 to 4, 0 to 5, 0 to 6, 0 to 7, or 0 to 8. Each n may independently be 1 to 2, 1 to 3, 1 to 4, 1 to 5, 1 to 6, 1 to 7, or 1 to 8. Each n may independently be 2 to 3, 2 to 4, 2 to 5, 2 to 6, 2 to 7, or 2 to 8. Each n may independently be 3 to 4, 3 to 5, 3 to 6, 3 to 7, or 3 to 8. Each n may be 0. Each n may be 1. Each n may be 2. Each n may be 3. Each n may be 4. Each n may be 5. Each n may be 6. Each n may be 7. Each n may be 8.

Each u may independently be 0, 1, 2, 3, 4, 5, 6 or 7. Each u may independently be 0 to 1, 0 to 2, 0 to 3, 0 to 4, 0 to 5, 0 to 6, 0 to 7. Each u may independently be 1 to 2, 1 to 3, 1 to 4, 1 to 5, 1 to 6, or 1 to 7. Each u may independently be 2 to 3, 2 to 4, 2 to 5, 2 to 6, or 2 to 7. Each u may independently be 3 to 4, 3 to 5, 3 to 6, or 3 to 7. Each u may be 0. Each u may be 1. Each u may be 2. Each u may be 3. Each u may be 4. Each u may be 5. Each u may be 6. Each u may be 7.

Each y may independently be 0, 1, 2, 3, 4, 5, 6 or 7. Each y may independently be 0 to 1, 0 to 2, 0 to 3, 0 to 4, 0 to 5, 0 to 6, or 0 to 7. Each y may independently be 1 to 2, 1 to 3, 1 to 4, 1 to 5, 1 to 6, or 1 to 7. Each y may independently be 2 to 3, 2 to 4, 2 to 5, 2 to 6, or 2 to 7. Each y may independently be 3 to 4, 3 to 5, 3 to 6, or 3 to 7. Each y may be 0. Each y may be 1. Each y may be 2. Each y may be 3. Each y may be 4. Each y may be 5. Each y may be 6. Each y may be 7.

Each j may independently be 0, 1, 2, 3, 4, 5, 6 or 7. Each j may independently be 0 to 1, 0 to 2, 0 to 3, 0 to 4, 0 to 5, 0 to 6, or 0 to 7. Each j may independently be 1 to 2, 1 to 3, 1 to 4, 1 to 5, 1 to 6, or 1 to 7. Each j may independently be 2 to 3, 2 to 4, 2 to 5, 2 to 6, or 2 to 7. Each j may independently be 3 to 4, 3 to 5, 3 to 6, or 3 to 7. Each j may be 0. Each j may be 1. Each j may be 2. Each j may be 3. Each j may be 4. Each j may be 5. Each j may be 6. Each j may be 7.

Each m may independently be 0, 1, 2, 3, 4, 5, 6, 7 or 8. Each m may independently be 0 to 1, 0 to 2, 0 to 3, 0 to 4, 0 to 5, 0 to 6, 0 to 7, or 0 to 8. Each m may independently be 1 to 2, 1 to 3, 1 to 4, 1 to 5, 1 to 6, 1 to 7, or 1 to 8. Each m may independently be 2 to 3, 2 to 4, 2 to 5, 2 to 6, 2 to 7, or 2 to 8. Each m may independently be 3 to 4, 3 to 5, 3 to 6, 3 to 7, or 3 to 8. Each m may be 0. Each m may be 1. Each m may be 2. Each m may be 3. Each m may be 4. Each m may be 5. Each m may be 6. Each m may be 7. Each m may be 8.

At least one Z of one aromatic ring may independently be C-Q, at least one Z of the other aromatic ring may independently be C-T, CF, CCl, CBr, CI, COH, $CG^1$, $COG^1$, $CNH_2$, $CNHG^1$, $CNG^1_2$, $COSO_3H$, $COPO_3H_2$, $CSG^1$, $CSOG^1$, or $CSO_2G^1$, and each remaining Z may independently be C-T, N, CH, CF, CCl, CBr, CI, COH, $CG^1$, $COG^1$, $CNH_2$, $CNHG^1$, $CNG^1_2$, $COSO_3H$, $COPO_3H_2$, $CSG^1$, $CSOG^1$, or $CSO_2G^1$. At least one Z of one aromatic ring may independently be C-Q, at least one Z of the other aromatic ring may independently be C-T, and each remaining Z may independently be N, CH, CF, CCl, CBr, CI, $CG^1$, or COH. At least one Z of one aromatic ring may independently be C-Q, at least one Z of the other aromatic ring may independently be COH, and each remaining Z may independently be N, CH, CF, CCl, CBr, CI, $CG^1$, or COH. At least one Z of one aromatic ring may independently be C-Q, at least one Z of the other aromatic ring may independently be C-T, and each remaining Z may independently be N, CH, CF, CCl, CBr, CI, or COH. At least one Z of one aromatic ring may independently be C-Q, at least one Z of the other aromatic ring may independently be COH, and each remaining Z may independently be N, CH, CF, CCl, CBr, CI, or COH. At least one Z of one aromatic ring may independently be C-Q, at least one Z of the other aromatic ring may independently be C-T, and each remaining Z may independently be CH. At least one Z of one aromatic ring may independently be C-Q, at least one Z of the other aromatic ring may independently be COH, and each remaining Z may independently be CH. Each remaining Z may independently be N, CH, CF, CCl, CBr, CI, COH, $CCH_3$, $CNH_2$, $COSO_3H$, or $COPO_3H_2$. Each remaining Z may independently be N, CH, CF, CCl, CBr, CI, COH, $CNH_2$, $COSO_3H$, or $COPO_3H_2$. Each remaining Z may independently be N, CH, CF, CCl, CBr, CI, or COH. Each remaining Z may independently be CH, CF, CCl, CBr, or CI. Each remaining Z may independently be CH, CCl, or CBr. Each remaining Z may be CH.

Each of J" and J'" may independently be a moiety selected from TABLE 1. Each of J", and J'" may independently be an amino acid based moiety or a polyethylene glycol based moiety selected from TABLE 1. Alternatively, each of J", and J'" may independently an amino acid based moiety selected from TABLE 1. Each J", and J'" may be Each G¹, G¹', and G¹'' may independently be linear or branched, or aromatic cyclic or non-aromatic cyclic, substituted or unsubstituted, saturated or unsaturated $C_1$-$C_{10}$ alkyl. Each G¹, G¹' and G¹'' may independently be a branched, linear, or non-aromatic cyclic, substituted or unsubstituted, saturated or unsaturated $C_1$-$C_{10}$ alkyl. Each G¹, G¹' and G¹'' may independently be a branched, linear, or non-aromatic cyclic, substituted or saturated or unsaturated $C_1$-$C_{10}$ alkyl. Each G¹, G¹' and G¹'' may independently be a branched, unbranched, or aromatic cyclic or non-aromatic cyclic, substituted or unsubstituted, saturated or unsaturated $C_1$-$C_9$ alkyl. Each G¹, G¹' and G¹'' may independently be a branched, unbranched, or aromatic cyclic or non-aromatic cyclic, substituted or unsubstituted, saturated or unsaturated $C_1$-$C_8$ alkyl. Each G¹, G¹', and G¹'' may independently be a branched, unbranched, or aromatic cyclic or non-aromatic cyclic, substituted or unsubstituted, saturated or unsaturated $C_1$-$C_7$ alkyl. Each G¹, G¹' and G¹'' may independently be a branched, unbranched, or aromatic cyclic or non-aromatic cyclic, substituted or unsubstituted, saturated or unsaturated $C_1$-$C_6$ alkyl. Each G¹, G¹, and G¹ may independently be a branched, unbranched, or aromatic cyclic or non-aromatic cyclic, substituted or unsubstituted, saturated or unsaturated $C_1$-$C_5$ alkyl. Each G¹, G¹' and G¹'' may independently be a branched, unbranched, or non-aromatic cyclic, substituted or unsubstituted, saturated or unsaturated $C_1$-$C_4$ alkyl. Each G¹, G¹' and G¹'' may independently be a branched, unbranched, or non-aromatic cyclic, substituted or unsubstituted, saturated or unsaturated $C_1$-$C_3$ alkyl. Each G¹, G¹' and G¹'' may independently be a branched, unbranched, or non-aromatic cyclic, substituted or unsubstituted, saturated or unsaturated $C_1$-$C_2$ alkyl.

An optional substituent may be selected from the group consisting of oxo, OJ''', COOH, $R^4$, OH, $OR^4$, F, Cl, Br, I, $NH_2$, $NHR^4$, $NR^4_2$, CN, SH, $SR^4$, $SO_3H$, $SO_3R^4$, $SO_2R^4$, $OSO_3R^4$, $OR^5$, $CO_2R^4$, $CONH_2$, $CONHR^4$, $CONHR^5$, $CONR^4_2$, $NHR^5$, $OPO_3H_3$, $CONR^4R^5$, $NR^4R^5$, and $NO_2$. An optional substituent may be selected from the group consisting of: oxo (i.e. =O), OJ''', COOH, $R^4$, OH, $OR^4$, F, Cl, Br, I, $NH_2$, $NHR^4$, $NR^4_2$, CN, SH, $SR^4$, $SO_3H$, $SO_3R^4$, $SO_2R^4$, $OSO_3R^4$, and $NO_2$. An optional substituent may be selected from the group consisting of: oxo (i.e. =O), OJ''', COOH, $R^4$, OH, $OR^4$, F, Cl, Br, I, $NH_2$, $NHR^4$, $NR^4_2$, $SO_3H$, $SO_3R^4$, $SO_2R^4$, and $NO_2$. An optional substituent may be selected from the group consisting of: oxo (i.e. =O), OJ''', COOH, $R^4$, OH, $OR^4$, F, Cl, Br, I, $NH_2$, and $NO_2$. An optional substituent may be selected from the group consisting of: oxo (i.e. =O), OJ''', COOH, $R^4$, OH, $OR^4$, F, Cl, Br, and I. An optional substituent may be selected from the group consisting of: oxo (i.e. =O), OJ''', COOH, OH, F, Cl, Br, and I. An optional substituent may be selected from the group consisting of: oxo (i.e. =O), OJ''', COOH, OH, F, and Cl. Each linear or branched, or aromatic cyclic or non-aromatic cyclic, saturated or unsaturated $C_1$-$C_{10}$ alkyl may be substituted with, for example, 1, 2, 3, 4, 5, or 6 substituents.

Each $R^4$ may independently be unsubstituted $C_1$-$C_{10}$ alkyl. Each $R^4$ may independently be unsubstituted $C_1$-$C_9$ alkyl. Each $R^4$ may independently be unsubstituted $C_1$-$C_8$ alkyl. Each $R^4$ may independently be unsubstituted $C_1$-$C_7$ alkyl. Each $R^4$ may independently be unsubstituted $C_1$-$C_6$ alkyl. Each $R^4$ may independently be unsubstituted $C_1$-$C_5$ alkyl. Each $R^4$ may independently be unsubstituted $C_1$-$C_4$ alkyl. Each $R^4$ may independently be unsubstituted $C_1$-$C_3$ alkyl. Each $R^4$ may independently be unsubstituted $C_1$-$C_2$ alkyl. Each $R^4$ may independently be unsubstituted $C_1$ alkyl. Each $R^4$ may independently be unsubstituted $C_2$ alkyl. Each $R^4$ may independently be unsubstituted $C_3$ alkyl. Each $R^4$ may independently be unsubstituted $C_4$ alkyl. Each $R^4$ may independently be unsubstituted $C_5$ alkyl. Each $R^4$ may independently be unsubstituted $C_6$ alkyl. Each $R^4$ may independently be unsubstituted $C_7$ alkyl. Each $R^4$ may independently be unsubstituted $C_8$ alkyl. Each $R^4$ may independently be unsubstituted $C_9$ alkyl. Each $R^4$ may independently be unsubstituted $C_{10}$ alkyl.

Each $R^5$ may independently be $C_1$-$C_{10}$ acyl. Each $R^5$ may independently be $C_1$-$C_9$ acyl. Each $R^5$ may independently be $C_1$-$C_8$ acyl. Each $R^5$ may independently be $C_1$-$C_7$ acyl. Each $R^5$ may independently be $C_1$-$C_6$ acyl. Each $R^5$ may independently be $C_1$-$C_5$ acyl. Each $R^5$ may independently be $C_1$-$C_4$ acyl. Each $R^5$ may independently be $C_1$-$C_3$ acyl. Each $R^5$ may independently be $C_1$-$C_2$ acyl. Each $R^5$ may independently be $C_1$ acyl. Each $R^5$ may independently be $C_2$ acyl. Each $R^5$ may independently be $C_3$ acyl. Each $R^5$ may independently be $C_4$ acyl. Each $R^5$ may independently be $C_5$ acyl. Each $R^5$ may independently be $C_6$ acyl. Each $R^5$ may independently be $C_7$ acyl. Each $R^5$ may independently be $C_8$ acyl. Each $R^5$ may independently be $C_9$ acyl. Each $R^5$ may independently be $C_{10}$ acyl.

Each R may independently be $C_1$-$C_{10}$ acyl. Each R may independently be $C_1$-$C_9$ acyl. Each R may independently be $C_1$-$C_8$ acyl. Each R may independently be $C_1$-$C_7$ acyl. Each R may independently be $C_1$-$C_6$ acyl. Each R may independently be $C_1$-$C_5$ acyl. Each R may independently be $C_1$-$C_4$ acyl. Each R may independently be $C_1$-$C_3$ acyl. Each R may independently be $C_1$-$C_2$ acyl. Each R may independently be $C_1$ acyl. Each R may independently be $C_2$ acyl. Each R may independently be $C_3$ acyl. Each R may independently be $C_4$ acyl. Each R may independently be $C_5$ acyl. Each R may independently be $C_6$ acyl. Each R may independently be $C_7$ acyl. Each R may independently be $C_8$ acyl. Each R may independently be $C_9$ acyl. Each R may independently be $C_{10}$ acyl.

X may be $CH_2$, $CHR^1$, or $CR^1R^2$. X may be $CH_2$. X may be $CHR^1$. X may be $CR^1R^2$.

Each of $R^1$ and $R^2$ may independently be linear or branched, substituted or unsubstituted, saturated or unsaturated $C_1$-$C_{10}$ alkyl, or $R^1$ and $R^2$ together may form a substituted or unsubstituted, saturated or unsaturated cyclic $C_3$-$C_{10}$ alkyl. Each of $R^1$ and $R^2$ may independently be branched or unbranched, substituted or unsubstituted, saturated or unsaturated $C_1$-$C_{10}$ alkyl. Each of $R^1$ and $R^2$ may independently be branched or unbranched, substituted or unsubstituted, saturated or unsaturated $C_1$-$C_9$ alkyl. Each of $R^1$ and $R^2$ may independently be branched or unbranched, substituted or unsubstituted, saturated or unsaturated $C_1$-$C_8$ alkyl. Each of $R^1$ and $R^2$ may independently be branched or unbranched, substituted or unsubstituted, saturated or unsaturated $C_1$-$C_7$ alkyl. Each of $R^1$ and $R^2$ may independently be branched or unbranched, substituted or unsubstituted, saturated or unsaturated $C_1$-$C_6$ alkyl. Each of $R^1$ and $R^2$ may independently be branched or unbranched, substituted or unsubstituted, saturated or unsaturated $C_1$-$C_5$ alkyl. Each of $R^1$ and $R^2$ may independently be branched or unbranched, substituted or unsubstituted, saturated or unsaturated $C_1$-$C_4$ alkyl. Each of $R^1$ and $R^2$ may independently be branched or unbranched, substituted or unsubstituted, saturated or unsaturated $C_1$-$C_3$ alkyl. Each of $R^1$ and $R^2$ may independently be branched or unbranched, substituted or unsubstituted, saturated or unsaturated $C_1$-$C_2$ alkyl. Each of $R^1$ and $R^2$ may be $CH_3$. $R^1$ and $R^2$ together may form a substituted or unsubstituted, saturated or unsaturated cyclic $C_3$-$C_{10}$ alkyl. $R^1$ and $R^2$ together may form an unsubstituted, saturated cyclic $C_6$ alkyl.

An optional substituent may be selected from the group consisting of oxo, OJ''', COOH, $R^3$, OH, $OR^3$, F, Cl, Br, I, $NH_2$, $NHR^3$, $NR^3_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3_2$, $NHR^6$, $OPO_3H_3$, $CONR^3R^6$, $NR^3R^6$, and $NO_2$. An optional substituent may be selected from the group consisting of: oxo (i.e. =O), OJ''', COOH, $R^3$, OH, $OR^3$, F, Cl, Br, I, $NH_2$, $NHR^3$, $NR^3_2$, CN, SH, $SR^3$, $SOR^3$, $SO_3H$, $SO_3R^3$, $SO_2R^3$, $OSO_3R^3$, and $NO_2$. An optional substituent may be selected from the group consisting of: oxo (i.e. =O), OJ''', COOH, $R^3$, OH, $OR^3$, F, Cl, Br, I, $NH_2$, $NHR^3$, $NR^3_2$, $SO_3H$, $SO_3R^3$, $SO_2R^3$, and $NO_2$. An optional substituent may be selected from the group consisting of: oxo (i.e. =O), COOH, $R^3$, OH, $OR^3$, F, Cl, Br, I, $NH_2$, and $NO_2$. An optional substituent may be selected from the group consisting of: oxo (i.e. =O), OJ''', COOH, $R^3$, OH, $OR^3$, F, Cl, Br, and I. An optional substituent may be selected from the group consisting of: oxo (i.e. =O), OJ''', COOH, OH, F, Cl, Br, and I. An optional substituent may be selected from the group consisting of: oxo (i.e. =O), OJ''', COOH, OH, F, and Cl. Each linear or branched, saturated or unsaturated $C_1$-$C_{10}$ alkyl, or saturated or unsaturated cyclic $C_3$-$C_{10}$ alkyl may be substituted with, for example, 1, 2, 3, 4, 5, or 6 substituents.

Each $R^3$ may independently be unsubstituted $C_1$-$C_{10}$ alkyl. Each $R^3$ may independently be unsubstituted $C_1$-$C_9$ alkyl. Each $R^3$ may independently be unsubstituted $C_1$-$C_8$ alkyl. Each $R^3$ may independently be unsubstituted $C_1$-$C_7$ alkyl. Each $R^3$ may independently be unsubstituted $C_1$-$C_6$ alkyl. Each $R^3$ may independently be unsubstituted $C_1$-$C_5$ alkyl. Each $R^3$ may independently be unsubstituted $C_1$-$C_4$ alkyl. Each $R^3$ may independently be unsubstituted $C_1$-$C_3$ alkyl. Each $R^3$ may independently be unsubstituted $C_1$-$C_2$ alkyl. Each $R^3$ may independently be unsubstituted $C_1$ alkyl. Each $R^3$ may independently be unsubstituted $C_2$ alkyl. Each $R^3$ may independently be unsubstituted $C_3$ alkyl. Each $R^3$ may independently be unsubstituted $C_4$ alkyl. Each $R^3$ may independently be unsubstituted $C_5$ alkyl. Each $R^3$ may independently be unsubstituted $C_6$ alkyl. Each $R^3$ may independently be unsubstituted $C_7$ alkyl. Each $R^3$ may independently be unsubstituted $C_8$ alkyl. Each $R^3$ may independently be unsubstituted $C_9$ alkyl. Each $R^3$ may independently be unsubstituted $C_{10}$ alkyl.

Each $R^6$ may independently be $C_1$-$C_{10}$ acyl. Each $R^6$ may independently be $C_1$-$C_9$ acyl. Each $R^6$ may independently be $C_1$-$C_8$ acyl. Each $R^6$ may independently be $C_1$-$C_7$ acyl. Each $R^6$ may independently be $C_1$-$C_6$ acyl. Each $R^6$ may independently be $C_1$-$C_5$ acyl. Each $R^6$ may independently be $C_1$-$C_4$ acyl. Each $R^6$ may independently be $C_1$-$C_3$ acyl. Each $R^6$ may independently be $C_1$-$C_2$ acyl. Each $R^6$ may independently be $C_1$ acyl. Each $R^6$ may independently be $C_2$ acyl. Each $R^6$ may independently be $C_3$ acyl. Each $R^6$ may independently be $C_4$ acyl. Each $R^6$ may independently be $C_5$ acyl. Each $R^6$ may independently be $C_6$ acyl. Each $R^6$ may independently be $C_7$ acyl. Each $R^6$ may independently be $C_8$ acyl. Each $R^6$ may independently be $C_9$ acyl. Each $R^6$ may independently be $C_{10}$ acyl.

Each remaining Z may be independently CH, CF, CCl, CBr, or Cl. Each remaining Z may be CH. X may be $CH^2$. X may be $CHR^1$. X may be $CR^1R^2$. $R^2$ may be linear or branched, substituted or unsubstituted, saturated or unsaturated $C_1$-$C_{10}$ alkyl. $R^2$ may be $CH_3$. $R^1$ may be linear or branched, substituted or unsubstituted, saturated or unsaturated $C_1$-$C_{10}$ alkyl. $R^1$ may be $CH_3$. J may be O. $J^2$ may be O. J may be O; n may be 0, 1, 2, 3, 4, 5, 6, 7, or 8; M may be $CH_2Cl$; and L may be H. $J^2$ may be 0; m may be 0, 1, 2, 3, 4, 5, 6, 7, or 8; $M^2$ may be $CH_2Cl$; and $L^2$ may be H. J may be 0; n may be 1; M may be $CH_2Cl$; and L may be H. $J^2$ may be 0; m may be 1; $M^2$ may be $CH_2Cl$; and $L^2$ may be H. J may be O; n may be 0, 1, 2, 3, 4, 5, 6, 7, or 8; M may be H; L may be A-D; A may be O; and D may be H. $J^2$ may be O; m may be 0, 1, 2, 3, 4, 5, 6, 7, or 8; $M^2$ may be H; $L^2$ may be $A^2$-$D^2$; $A^2$ may be O; and $D^2$ may be H. J may be O; n may be 1; M may be H; L may be A-D; A may be O; and D may be H. $J^2$ may be O; m may be 1; $M^2$ may be H; $L^2$ may be $A^2$-$D^2$; $A^2$ may be O; and $D^2$ may be H. J may be O; n may be 0, 1, 2, 3, 4, 5, 6, 7, or 8; M may be H; L may be A-D; A may be O; and D may be

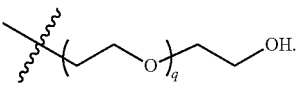

J may be O; n may be 0, 1, 2, 3, 4, 5, 6, 7, or 8; M may be H; L may be A-D; A may be O; and D may be

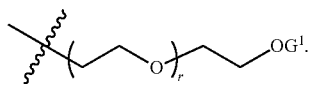

J may be O; n may be 0, 1, 2, 3, 4, 5, 6, 7, or 8; M may be H; L may be A-D; A may be O; and D may be

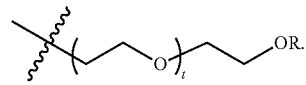

$J^2$ may be O; m may be 0, 1, 2, 3, 4, 5, 6, 7, or 8; $M^2$ may be H; $L^2$ may be $A^2$-$D^2$; $A^2$ may be O; and $D^2$ may be

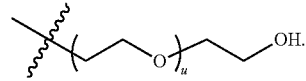

$J^2$ may be O; m may be 0, 1, 2, 3, 4, 5, 6, 7, or 8; $M^2$ may be H; $L^2$ may be $A^2$-$D^2$; $A^2$ may be O; and $D^2$ may be

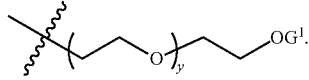

$J^2$ may be O; m may be 0, 1, 2, 3, 4, 5, 6, 7, or 8; $M^2$ may be H; $L^2$ may be $A^2$-$D^2$; $A^2$ may be O; and $D^2$ may be

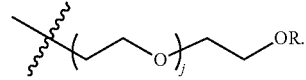

J may be O; n may be 1; M may be H; L may be A-D; A may be O; and D may be

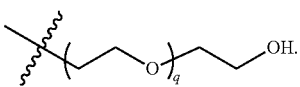

J may be O; n may be 1; M may be H; L may be A-D; A may be O; and D may be

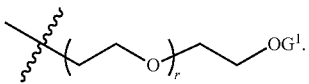

J may be O; n may be 1; M may be H; L may be A-D; A may be O; and D may be

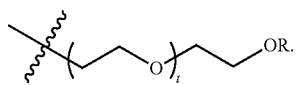

$J^2$ may be O; m may be 1; $M^2$ may be H; $L^2$ may be $A^2$-$D^2$; $A^2$ may be O; and $D^2$ may be

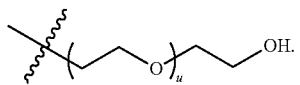

$J^2$ may be O; m may be 1; $M^2$ may be H; $L^2$ may be $A^2$-$D^2$; $A^2$ may be O; and $D^2$ may be

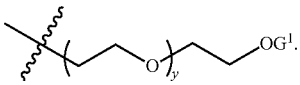

$J^2$ may be O; m may be 1; $M^2$ may be H; $L^2$ may be $A^2$-$D^2$; $A^2$ may be O; and $D^2$ may be

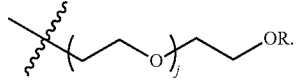

J may be O; n may be O; M may be C≡CH; and L may be H. $J^2$ may be O; m may be O; $M^2$ may be C≡CH; and $L^2$ may be H. J may be O; n may be 1; M may be C≡CH; L may be A-D; A may be O; and D may be H. $J^2$ may be O; m may be 1; $M^2$ may be C≡CH; $L^2$ may be $A^2$-$D^2$; $A^2$ may be O; and $D^2$ may be H.

In accordance with another embodiment, there is provided a use of a compound having a structure of Formula III

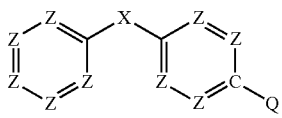

III wherein: X may be $CH_2$, $CHR^1$, or $CR^1R^2$; each of $R^1$ and $R^2$ may independently be linear or branched, substituted or unsubstituted, saturated or unsaturated $C_1$-$C_{10}$ alkyl, or $R^1$ and $R^2$ may together form a substituted or unsubstituted, saturated or unsaturated cyclic $C_3$-$C_{10}$ alkyl, wherein the optional substituent may be selected from the group consisting of oxo, OJ''', COOH, $R^3$, OH, $OR^3$, F, Cl, Br, I, $NH_2$, $NHR^3$, $NR^3_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3_2$, $NHR^6$, $OPO_3H_3$, $CONR^3R^6$, $NR^3R^6$, and $NO_2$; each $R^3$ may independently be unsubstituted $C_1$-$C_{10}$ alkyl; each $R^6$ may independently be $C_1$-$C_{10}$ acyl; at least one Z of the other aromatic ring may independently be C-T, and each remaining Z may independently be C-T, N, CH, CF, CCl, CBr, CI, COH, $CG^1$, $COG^1$, $CNH_2$, $CNHG^1$, $CNG^1_2$, $COSO_3H$, $COPO_3H_2$, $CSG^1$, $CSOG^1$, or $CSO_2G^1$; Q may be

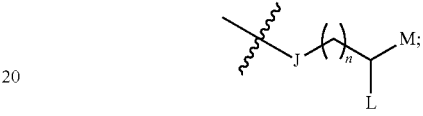

J may be $G^1$, O, $CH_2$, $CHG^1$, $CG^1_2$, S, NH, $NG^1$, SO, $SO_2$, or NR; M may be H, Cl, Br, $CH_2Cl$, $CHCl_2$, $CCl_3$, $CH_2Br$, $CHBr_2$, $CBr_3$, or C≡CH; L may be H or A-D; A may be O, S, NH, $NG^1$, $N^+H_2$, or $N^+HG^1$; D may be H, $G^1$, R,

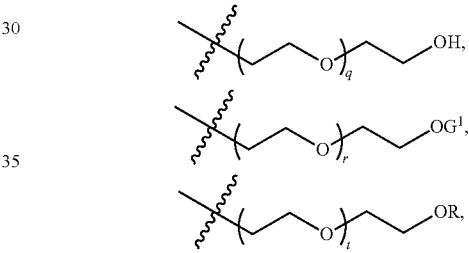

or a moiety selected from TABLE 1; each of q, r and t may independently be 0, 1, 2, 3, 4, 5, 6 or 7; n may be 0, 1, 2, 3, 4, 5, 6, 7 or 8; T may be

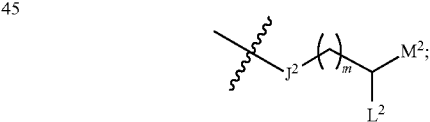

$J^2$ may be $G^1$, O, $CH_2$, $CHG^1$, $CG^1_2$, S, NH, $NG^1$, SO, $SO_2$, or NR; $M^2$ may be H, $CH_3$, Cl, Br, $CH_2Cl$, $CHCl_2$, $CCl_3$, $CH_2Br$, $CHBr_2$, $CBr_3$, $CH_2OH$, $CH_2OJ'''$, $G^1$, $CH_2OG^1$, $CH_2OR$, $CH_2OG^1OG^{1''}$, $G^1OG^{1''}$, $G^1OG^1OG^{1'''}$, $CH_2SG^1$, $CH_2NH_2$, $CH_2NHG^1$, $CH_2NG^1_2$, or C≡CH; $L^2$ may be H or $A^2$-$D^2$; $A^2$ may be O, S, SO, $SO_2$, NH, $NG^1$, $N^+H_2$, or $N^+HG^1$; $D^2$ may be H, $G^1$, R,

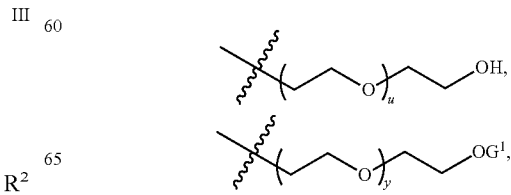

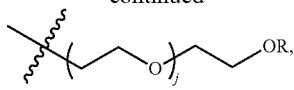

or a moiety selected from TABLE 1; each of u, y and j may independently be 0, 1, 2, 3, 4, 5, 6 or 7; m may be 0, 1, 2, 3, 4, 5, 6, 7 or 8; each of J" and J'" may independently be moiety selected from TABLE 1; each $G^1$ $G^{1'}$ and $G^{1'''}$ may independently be linear or branched, or aromatic cyclic or non-aromatic cyclic, substituted or unsubstituted, saturated or unsaturated $C_1$-$C_{10}$ alkyl, wherein the optional substituent may be selected from the group consisting of oxo, OJ'", COOH, $R^4$, OH, $OR^4$, F, Cl, Br, I, $NH_2$, $NHR^4$, $NR^4_2$, CN, SH, $SR^4$, $SO_3H$, $SO_3R^4$, $SO_2R^4$, $OSO_3R^4$, $OR^5$, $CO_2R^4$, $CONH_2$, $CONHR^4$, $CONHR^5$, $CONR^4_2$, $NHR^5$, $OPO_3H_3$, $CONR^4R^5$, $NR^4R^5$, and $NO_2$; each $R^4$ may independently be unsubstituted $C_1$-$C_{10}$ alkyl; each $R^5$ may independently be $C_1$-$C_{10}$ acyl; R may be $C_1$-$C_{10}$ acyl; and wherein one or more of the OH groups may be optionally substituted to replace the H with a moiety selected from TABLE 1. In accordance with another embodiment, there is provided a use of a compound having a structure of Formula IV

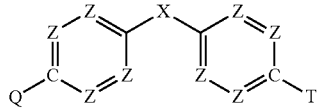

IV wherein: X may be $CH_2$, $CHR^1$, or $CR^1R^2$; each of $R^1$ and $R^2$ may independently be linear or branched, substituted or unsubstituted, saturated or unsaturated $C_1$-$C_{10}$ alkyl, or $R^1$ and $R^2$ may together form a substituted or unsubstituted, saturated or unsaturated cyclic $C_3$-$C_{10}$ alkyl, wherein the optional substituent may be selected from the group consisting of oxo, OJ'", COOH, $R^3$, OH, $OR^3$, F, Cl, Br, I, $NH_2$, $NHR^3$, $NR^3_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3_2$, $NHR^6$, $OPO_3H_3$, $CONR^3R^6$, $NR^3R^6$, and $NO_2$; each $R^3$ may independently be unsubstituted $C_1$-$C_{10}$ alkyl; each $R^6$ may independently be $C_1$-$C_{10}$ acyl; each remaining Z may independently be C-T, N, CH, CF, CCl, CBr, CI, COH, $CG^1$, $COG^1$, $CNH_2$, $CNHG^1$, $CNG^1_2$, $COSO_3H$, $COPO_3H_2$, $CSG^1$, $CSOG^1$, or $CSO_2G^1$; Q may be

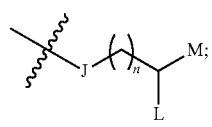

J may be $G^1$, O, $CH_2$, $CHG^1$, $CG^1_2$, S, NH, $NG^1$, SO, $SO_2$, or NR; M may be H, Cl, Br, $CH_2Cl$, $CHCl_2$, $CCl_3$, $CH_2Br$, $CHBr_2$, $CBr_3$, or C≡CH; L may be H or A-D; A may be O, S, NH, $NG^1$, $N^+H_2$, or $N^+HG^1$; D may be H, $G^1$, R,

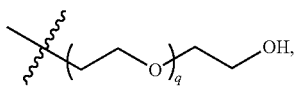

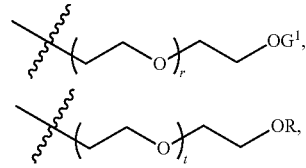

or a moiety selected from TABLE 1; each of q, r and t may independently be 0, 1, 2, 3, 4, 5, 6 or 7; n may be 0, 1, 2, 3, 4, 5, 6, 7 or 8; T may be

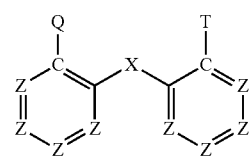

$J^2$ may be $G^1$, O, $CH_2$, $CHG^1$, $CG^1_2$, S, NH, $NG^1$, SO, $SO_2$, or NR; $M^2$ may be H, $CH_3$, Cl, Br, $CH_2Cl$, $CHCl_2$, $CCl_3$, $CH_2Br$, $CHBr_2$, $CBr_3$, $CH_2OH$, $CH_2OJ''$, $G^1$, $CH_2OG^1$, $CH_2OR$, $CH_2OG^1OG^{1'}$, $G^1OG^{1'}$, $G^1OG^{1'}OG^{1'''}$, $CH_2SG^1$, $CH_2NH_2$, $CH_2NHG^1$, $CH_2NG^1_2$, or C≡CH; $L^2$ may be H or $A^2$-$D^2$; $A^2$ may be O, S, SO, $SO_2$, NH, $NG^1$, $N^+H_2$, or $N^+HG^1$, $D^2$ may be H, $G^1$, R,

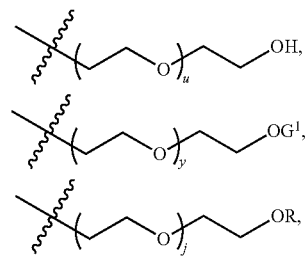

or a moiety selected from TABLE 1; each of u, y and j may independently be 0, 1, 2, 3, 4, 5, 6 or 7; m may be 0, 1, 2, 3, 4, 5, 6, 7 or 8; each of J" and J'" may independently be a moiety selected from TABLE 1; each $G^1$ $G^{1'}$ and $G^{1'''}$ may independently be linear or branched, or aromatic cyclic or non-aromatic cyclic, substituted or unsubstituted, saturated or unsaturated $C_1$-$C_{10}$ alkyl, wherein the optional substituent may be selected from the group consisting of oxo, OJ'", COOH, $R^4$, OH, $OR^4$, F, Cl, Br, I, $NH_2$, $NHR^4$, $NR^4_2$, CN, SH, $SR^4$, $SO_3H$, $SO_3R^4$, $SO_2R^4$, $OSO_3R^4$, $OR^5$, $CO_2R^4$, $CONH_2$, $CONHR^4$, $CONHR^5$, $CONR^4_2$, $NHR^5$, $OPO_3H_3$, $CONR^4R^5$, $NR^4R^5$, and $NO_2$; each $R^4$ may independently be unsubstituted $C_1$-$C_{10}$ alkyl; each $R^5$ may independently be $C_1$-$C_{10}$ acyl; R may be $C_1$-$C_{10}$ acyl; and wherein one or more of the OH groups may be optionally substituted to replace the H with a moiety selected from TABLE 1. In accordance with another embodiment, there is provided a use of a compound having a structure of Formula IX

IX wherein: X may be $CH_2$, $CHR^1$, or $CR^1R^2$; each of $R^1$ and $R^2$ may independently be linear or branched, substituted or unsubstituted, saturated or unsaturated $C_1$-$C_{10}$ alkyl, or $R^1$ and $R^2$ together form a substituted or unsubstituted, saturated or unsaturated cyclic $C_3$-$C_{10}$ alkyl, wherein the optional substituent may be selected from the group consisting of oxo, OJ''', COOH, $R^3$, OH, OR$^3$, F, Cl, Br, I, NH$_2$, NHR$^3$, NR$^3{}_2$, CN, SH, SR$^3$, SOR$^3$, SO$_3$H, SO$_3$R$^3$, SO$_2$R$^3$, OSO$_3$R$^3$, OR$^6$, CO$_2$R$^3$, CONH$_2$, CONHR$^3$, CONHR$^6$, CONR$^3{}_2$, NHR$^6$, OPO$_3$H$_3$, CONR$^3$R$^6$, NR$^3$R$^6$, and NO$_2$; each $R^3$ may independently be unsubstituted $C_1$-$C_{10}$ alkyl; each $R^6$ may independently be $C_1$-$C_{10}$ acyl; each remaining Z may independently be C-T, N, CH, CF, CCl, CBr, CI, COH, CG$^1$, COG$^1$, CNH$_2$, CNHG$^1$, CNG$^1{}_2$, COSO$_3$H, COPO$_3$H$_2$, CSG$^1$, CSOG$^1$, or CSO$_2$G$^1$; Q may be

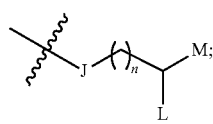

J may be G$^1$, O, CH$_2$, CHG$^1$, CG$^1{}_2$, S, NH, NG$^1$, SO, SO$_2$, or NR; M may be H, Cl, Br, CH$_2$Cl, CHCl$_2$, CCl$_3$, CH$_2$Br, CHBr$_2$, CBr$_3$, or C≡CH; L may be H or A-D; A may be O, S, NH, NG %, N$^+$H$_2$, or N$^+$HG$^1$; D may be H, G$^1$, R,

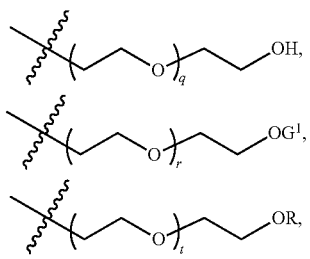

or a moiety selected from TABLE 1; each of q, r and t may independently be 0, 1, 2, 3, 4, 5, 6 or 7; n may be 0, 1, 2, 3, 4, 5, 6, 7 or 8; T may be

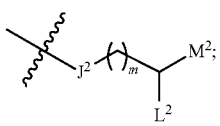

J$^2$ may be G$^1$, O, CH$_2$, CHG$^1$, CG$^1{}_2$, S, NH, NG %, SO, SO$_2$, or NR; M$^2$ may be H, CH$_3$, Cl, Br, CH$_2$Cl, CHCl$_2$, CCl$_3$, CH$_2$Br, CHBr$_2$, CBr$_3$, CH$_2$OH, CH$_2$OJ''', G$^1$, CH$_2$OG$^1$, CH$_2$OR, CH$_2$OG$^{1}$OG$^{1''}$, G$^1$OG$^{1''}$, G$^1$OG$^{1''}$OG$^{1'''}$, CH$_2$SG$^1$, CH$_2$NH$_2$, CH$_2$NHG$^1$, CH$_2$NG$^1{}_2$, or C≡CH; L$^2$ may be H or A$^2$-D$^2$; A$^2$ may be O, S, SO, SO$_2$, NH, NG$^1$, N$^+$H$_2$, or N$^+$HG$^1$; D$^2$ may be H, G$^1$, R,

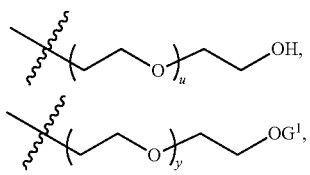

or a moiety selected from TABLE 1; each of u, y and j may independently be 0, 1, 2, 3, 4, 5, 6 or 7; m may be 0, 1, 2, 3, 4, 5, 6, 7 or 8; each of J'' and J''' may independently be a moiety selected from TABLE 1; each G$^1$ G$^{1''}$ and G$^{1'''}$ may independently be linear or branched, or aromatic cyclic or non-aromatic cyclic, substituted or unsubstituted, saturated or unsaturated $C_1$-$C_{10}$ alkyl, wherein the optional substituent may be selected from the group consisting of oxo, OJ''', COOH, $R^4$, OH, OR$^4$, F, Cl, Br, I, NH$_2$, NHR$^4$, NR$^4{}_2$, CN, SH, SR$^4$, SO$_3$H, SO$_3$R$^4$, SO$_2$R$^4$, OSO$_3$R$^4$, OR$^5$, CO$_2$R$^4$, CONH$_2$, CONHR$^4$, CONHR$^5$, CONR$^4{}_2$, NHR$^5$, OPO$_3$H$_3$, CONR$^4$R$^5$, NR$^4$R$^5$, and NO$_2$; each $R^4$ may independently be unsubstituted $C_1$-$C_{10}$ alkyl; each $R^5$ may independently be $C_1$-$C_{10}$ acyl; R may be $C_1$-$C_{10}$ acyl; and wherein one or more of the OH groups may be optionally substituted to replace the H with a moiety selected from TABLE 1.

J may be G$^1$, O, CH$_2$, CHG$^1$, CG$^1{}_2$, NH, SO, or NR. J may be G$^1$, O, CH$_2$, CHG$^1$, or CG$^1{}_2$. J may be O, NH, SO, or NR. J may be O.

M may be Cl, Br, CH$_2$Cl, CHCl$_2$, CCl$_3$, CH$_2$Br, CHBr$_2$, CBr$_3$, or C≡CH. M may be Cl, Br, CH$_2$Cl, CHCl$_2$, CCl$_3$, CH$_2$Br, CHBr$_2$, or CBr$_3$. M may be Br, CH$_2$Br, CHBr$_2$, or CBr$_3$. M may be Cl, CH$_2$Cl, CHCl$_2$, or CCl$_3$. M may be CH$_2$Cl, CH$_2$Br, or C≡CH. M may be CH$_2$Br or C≡CH. M may be CH$_2$Cl or C≡CH. M may be CH$_2$Br. M may be CH$_2$Cl. M may be C≡CH. M may be H.

L may be H. L may be A-D. A may be O or S. A may be O. D may be H, R, or a

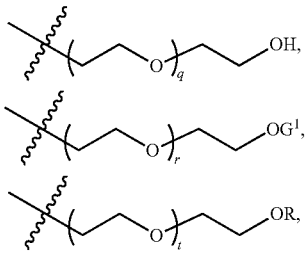

moiety selected from TABLE 1; and each of q, r and t may independently be 0, 1, 2, 3, 4, 5, 6 or 7. D may be H. D may be R. R may be $C_1$-$C_4$ acyl. R may be

D may be

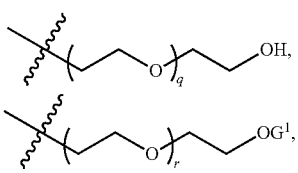

-continued

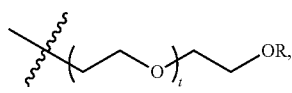

or a moiety selected from TABLE 1; and each of q, r and t may be independently 0, 1, 2, 3, 4, 5, 6 or 7. D may be

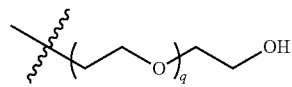

and q may be 0, 1, 2, 3, 4, 5, 6 or 7. q may be 1. D may be a moiety selected from TABLE 1. The moiety selected from TABLE 1 may be an amino acid based moiety selected from TABLE 1. The moiety selected from TABLE 1 may be

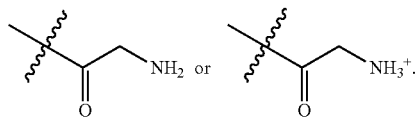

n may be 0, 1, 2, 3, 4, or 5. n may be 0. n may be 1, 2, 3, 4, or 5. n may be 1.

$J^2$ may be $G^1$, O, $CH_2$, $CHG^1$, $CG^1_2$, NH, SO, or NR. $J^2$ may be $G^1$, O, $CH_2$, $CHG^1$, or $CG^1_2$. $J^2$ may be O, NH, SO, or NR. $J^2$ may be O.

$M^2$ may be H, Cl, Br, $CH_2Cl$, $CHCl_2$, $CCl_3$, $CH_2Br$, $CHBr_2$, $CBr_3$, $CH_2OH$, $CH_2OJ''$, $CH_2OG^1$, $CH_2OR$, or C≡CH. $M^2$ may be H, $CH_2Cl$, $CH_2OH$, $CH_2OJ''$, $CH_2OG^1$, or C≡CH. $M^2$ may be H, $CH_2OH$, $CH_2OJ''$, $CH_2OG^1$, or C≡CH. $M^2$ may be H, $CH_2OH$, $CH_2OJ''$, or $CH_2OG^1$. $M^2$ may be $CH_2Cl$. $M^2$ may be $CH_2OG^1$. $M^2$ may be $CH_2OJ''$. $M^2$ may be $CH_2OH$. $M^2$ may be H. $M^2$ may be C≡CH.

$L^2$ may be H. $L^2$ may be $A^2$-$D^2$. $A^2$ may be O or S. $A^2$ may be O. $D^2$ may be H, R,

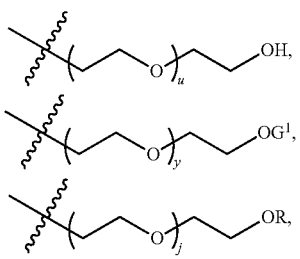

or a moiety selected from TABLE 1; and each of u, y and j may independently be 0, 1, 2, 3, 4, 5, 6 or 7. $D^2$ may be H. $D^2$ may be R. R may be $C_1$-$C_4$ acyl. R may be

$D^2$ may be

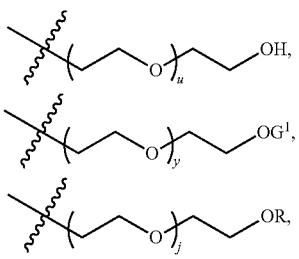

or a moiety selected from TABLE 1; and each of u, y and j may independently be 0, 1, 2, 3, 4, 5, 6 or 7. $D^2$ may be

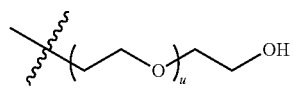

and u may be 0, 1, 2, 3, 4, 5, 6 or 7. u may be 1. $D^2$ may be a moiety selected from TABLE 1; and u may be 0, 1, 2, 3, 4, 5, 6 or 7. The moiety selected from TABLE 1 may be an amino acid based moiety selected from TABLE 1. The moiety selected from TABLE 1 may be

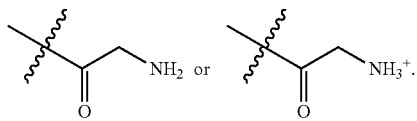

m may be 0, 1, 2, 3, 4, or 5. m may be 0. m may be 1, 2, 3, 4, or 5. m may be 1.

M may be C≡CH; $M^2$ may be $CH_2Cl$; and L may be H. $L^2$ may be H. $L^2$ may be $A^2$-$D^2$; $A^2$ may be O; and $D^2$ may be H. n may be 0. m may be 1, 2, 3, 4, or 5. J may be O and $J^2$ may be O. M may be $CH_2Cl$ and L may be H. $M^2$ may be H, $CH_2OH$, $CH_2OG^1$, or $CH_2Cl$. M may be $CH_2Cl$; L may be H; and $M^2$ may be H, $CH_2OH$, $CH_2OG^1$, or $CH_2Cl$. $L^2$ may be $A^2$-$D^2$; $A^2$ may be O; and $D^2$ may be H. $L^2$ may be $A^2$-$D^2$; $A^2$ may be O; and $D^2$ may be

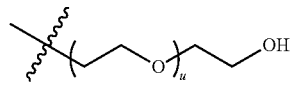

and u may be 0, 1, 2, 3, 4, 5, 6 or 7. n may be 1, 2, 3, 4, or 5. m may be 1, 2, 3, 4, or 5. J may be O and $J^2$ may be O. M may be $CH_2Cl$; L may be A-D; A may be O; D may be H; $M^2$ may be H; $L^2$ may be $A^2$-$D^2$; $A^2$ may be O; $D^2$ may be

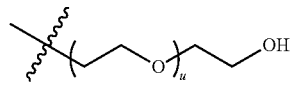

and u may be 0, 1, 2, 3, 4, 5, 6 or 7. n may be 1, 2, 3, 4, or 5. m may be 1, 2, 3, 4, or 5. J may be O and $J^2$ may be O.

Each J" and J''', when present, may independently be an amino acid based moiety selected from TABLE 1. Each J' and J''', when present, may independently be

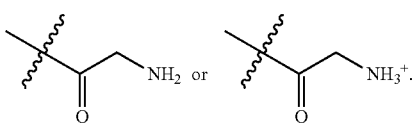

In accordance with another embodiment, there is provided a use of a compound having a structure of Formula III

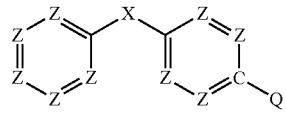

wherein: X may be $CH_2$, $CHR^1$, or $CR^1R^2$; each of $R^1$ and $R^2$ may independently be linear or branched, substituted or unsubstituted, saturated or unsaturated $C_1$-$C_{10}$ alkyl, or $R^1$ and $R^2$ may together form a substituted or unsubstituted, saturated or unsaturated cyclic $C_3$-$C_{10}$ alkyl, wherein the optional substituent may be selected from the group consisting of oxo, $OJ'''$, COOH, $R^3$, OH, $OR^3$, F, Cl, Br, I, $NH_2$, $NHR^3$, $NR^3{}_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3{}_2$, $NHR^6$, $OPO_3H_3$, $CONR^3R^6$, $NR^3R^6$, and $NO_2$; each $R^3$ may independently be unsubstituted $C_1$-$C_{10}$ alkyl; each $R^6$ may independently be $C_1$-$C_{10}$ acyl; wherein Q may be

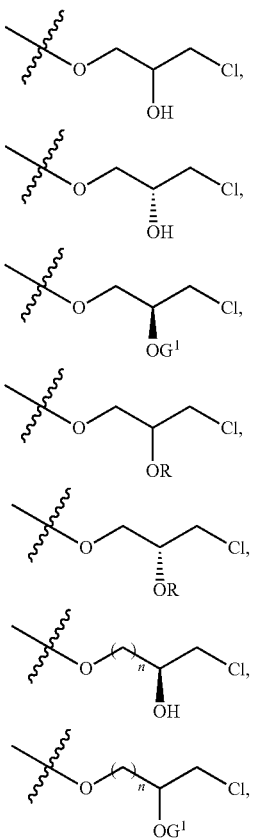
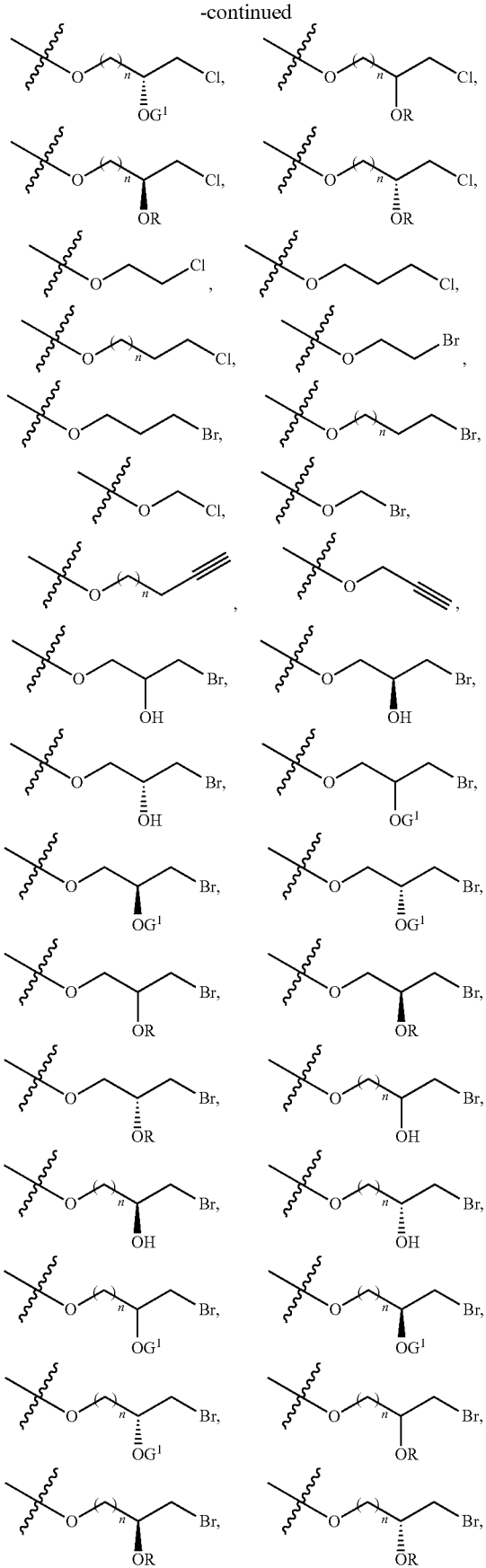

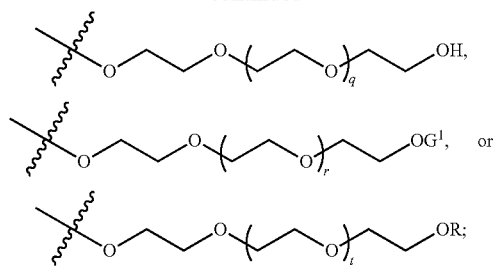
at least one Z of the other aromatic ring may independently be C-T, wherein T may be
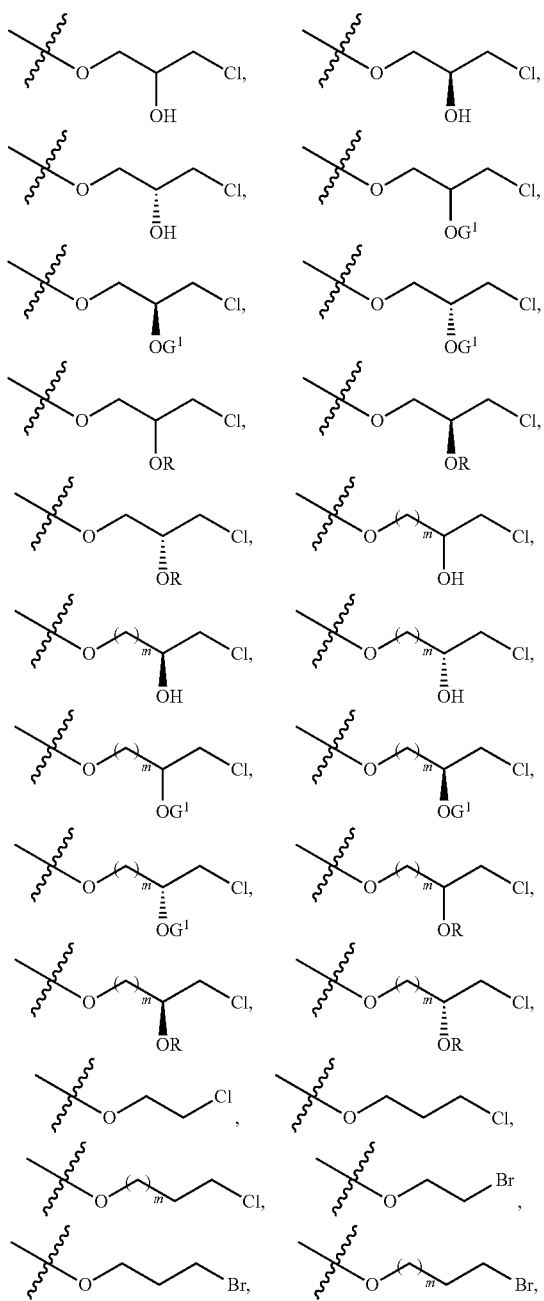
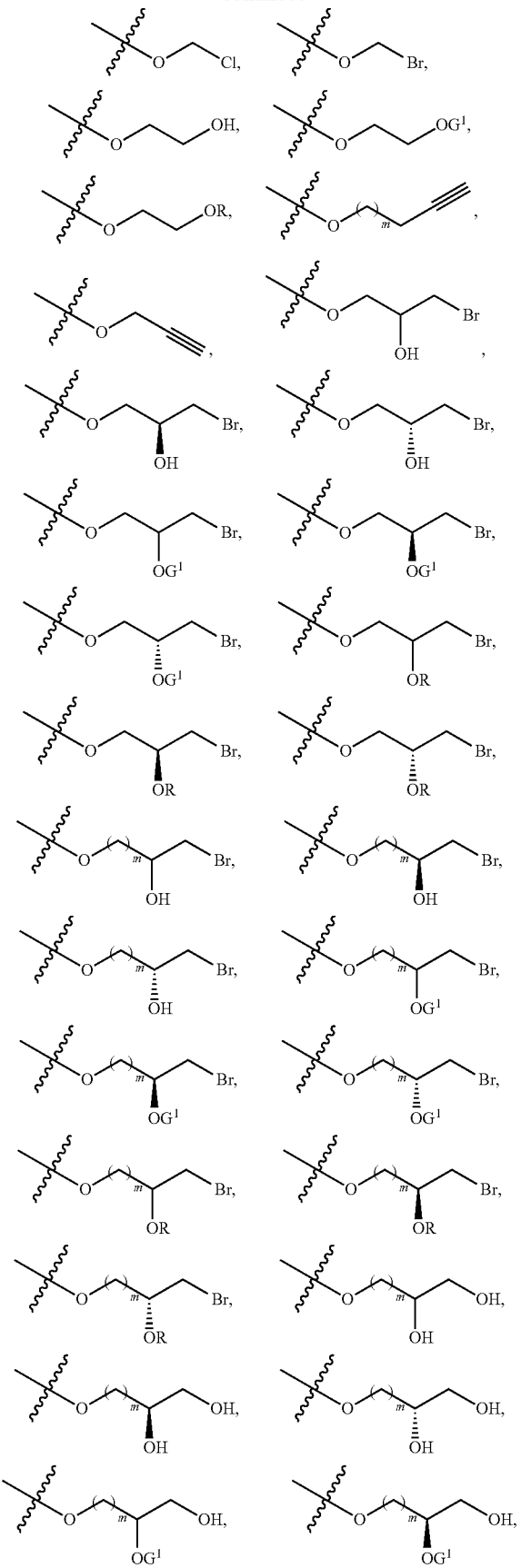

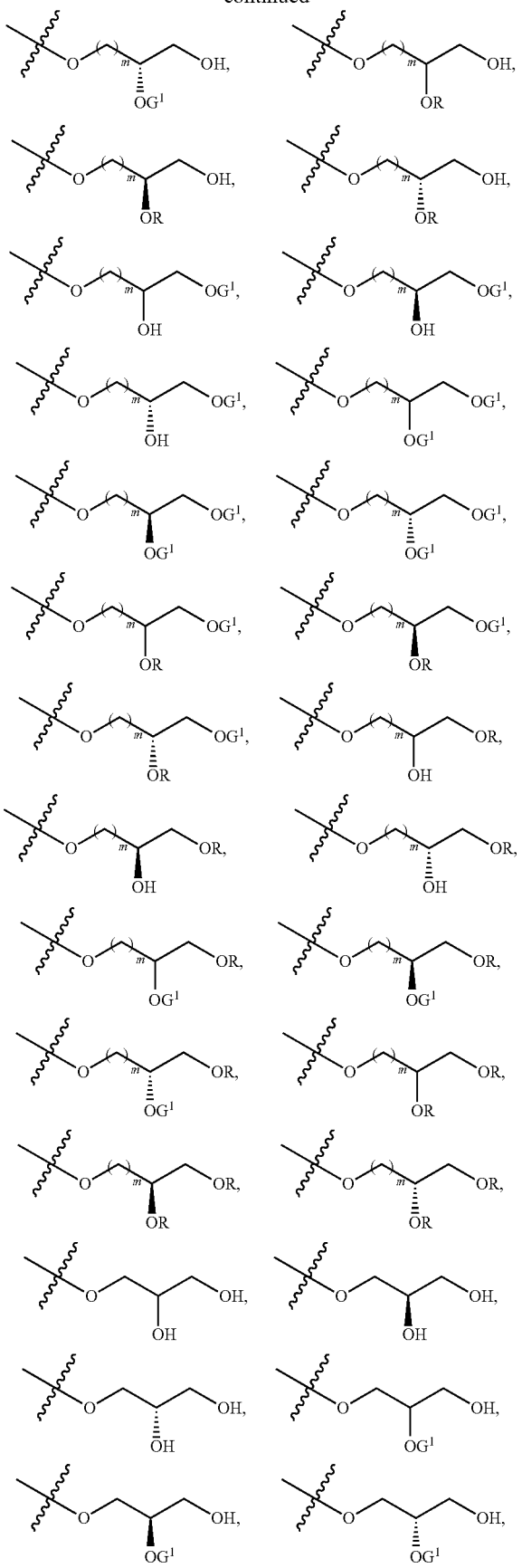
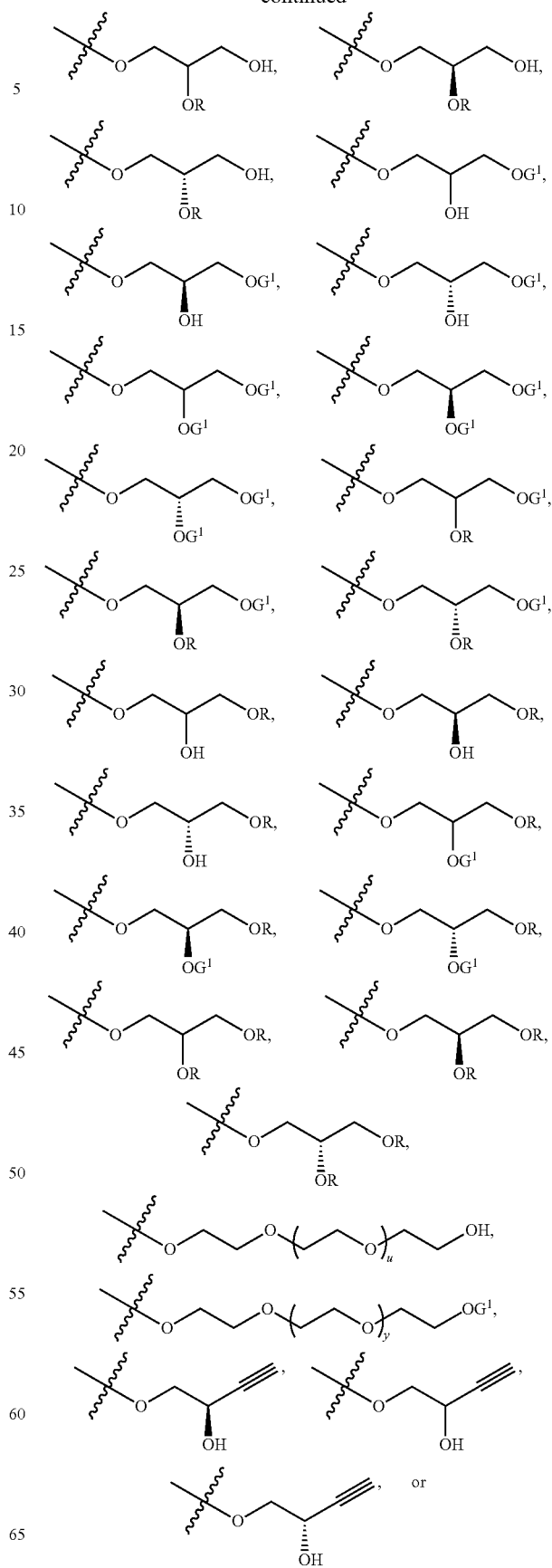

-continued

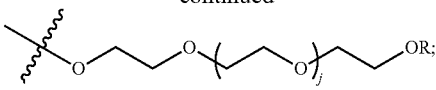

and each remaining Z may independently be C-T, N, CH, CF, CCl, CBr, CI, COH, $CG^1$, $COG^1$, $CNH_2$, $CNHG^1$, $CNG^1{}_2$, $COSO_3H$, $COPO_3H_2$, $CSG^1$, $CSOG^1$, or $CSO_2G^1$; n may be 0, 1, 2, 3, 4, 5, 6, 7 or 8; each q, r, and t may independently be 0, 1, 2, 3, 4, 5, 6 or 7; m may be 0, 1, 2, 3, 4, 5, 6, 7 or 8; each of u, j and y may independently be 0, 1, 2, 3, 4, 5, 6 or 7; each $G^1$ $G^{1\prime}$ and $G^{1\prime\prime\prime}$ may independently be linear or branched, or aromatic cyclic or non-aromatic cyclic, substituted or unsubstituted, saturated or unsaturated $C_1$-$C_{10}$ alkyl, wherein the optional substituent may be selected from the group consisting of oxo, $OJ^{\prime\prime\prime}$, COOH, $R^4$, OH, $OR^4$, F, Cl, Br, I, $NH_2$, $NHR^4$, $NR^4{}_2$, CN, SH, $SR^4$, $SO_3H$, $SO_3R^4$, $SO_2R^4$, $OSO_3R^4$, $OR^5$, $CO_2R^4$, $CONH_2$, $CONHR^4$, $CONHR^5$, $CONR^4{}_2$, $NHR^5$, $OPO_3H_3$, $CONR^4R^5$, $NR^4R^5$, and $NO_2$; each $R^4$ may independently be unsubstituted $C_1$-$C_{10}$ alkyl; each $R^5$ may independently be $C_1$-$C_{10}$ acyl; R may be $C_1$-$C_{10}$ acyl; and each of $J^{\prime\prime}$ and $J^{\prime\prime\prime}$ may independently be a moiety selected from TABLE 1; and wherein one or more of the OH groups may be optionally substituted to replace the H with a moiety selected from TABLE 1. Each of $R^1$ and $R^2$ may independently be linear or branched, substituted or unsubstituted, saturated or unsaturated $C_1$-$C_{10}$ alkyl, wherein the optional substituent may be selected from the group consisting of $OJ^{\prime\prime\prime}$, F, Cl, Br, I, or $NH_2$. Each remaining Z may independently be $CG^1$, N, CH, CF, CCl, CBr, CI, or COH. Each $G^1$ may independently be linear or branched, substituted or unsubstituted, saturated or unsaturated $C_1$-$C_{10}$ alkyl, wherein the optional substituent may be selected from the group consisting of oxo, $OJ^{\prime\prime\prime}$, COOH, OH, F, Cl, Br, I, $NH_2$, CN, SH, $SO_3H$, $CONH_2$, $OPO_3H_3$, and $NO_2$.

Q may be

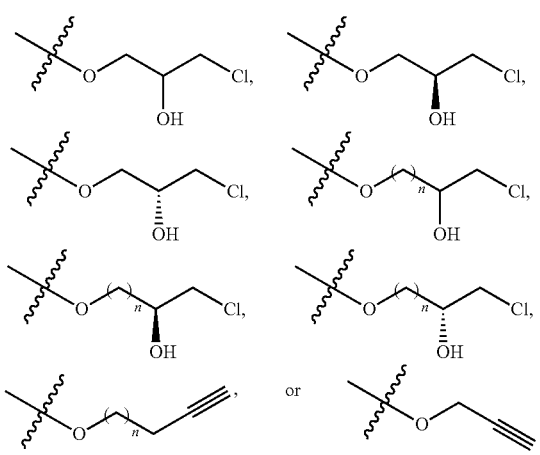

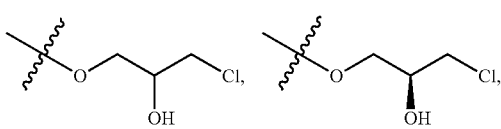

and n may be 0, 1, 2, 3, 4, 5, 6, 7 or 8. Q may be

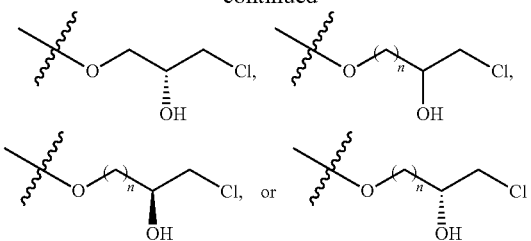

and n may be 0, 1, 2, 3, 4, 5, 6, 7 or 8. Q may be

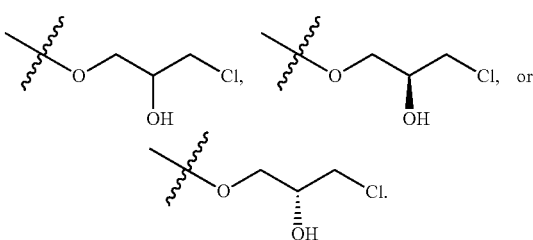

Q may be

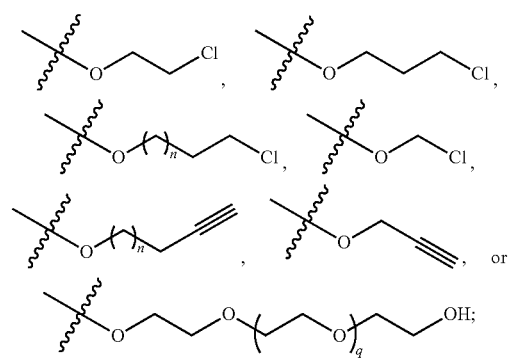

n may be 0, 1, 2, 3, 4, 5, 6, 7 or 8; and q may be 0, 1, 2, 3, 4, 5, 6 or 7. Q may be

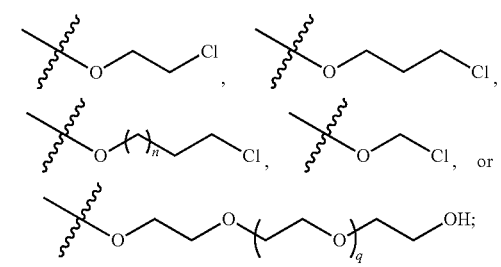

n may be 0, 1, 2, 3, 4, 5, 6, 7 or 8; and q may be 0, 1, 2, 3, 4, 5, 6 or 7. Q may be

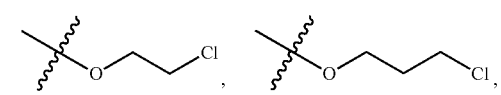

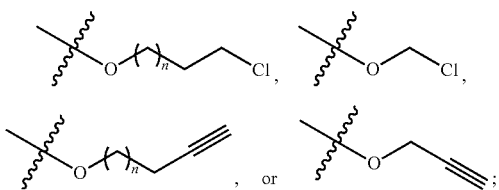
and n may be 0, 1, 2, 3, 4, 5, 6, 7 or 8. Q may be
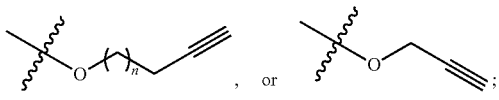
and n may be 0, 1, 2, 3, 4, 5, 6, 7 or 8. Q may be
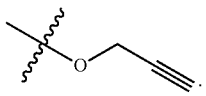 [SMILES: *OCC#C]
Q may be
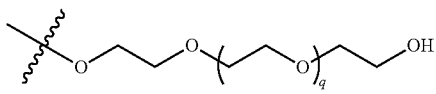
and q may be 0, 1, 2, 3, 4, 5, 6 or 7. q may be 1. Q may be
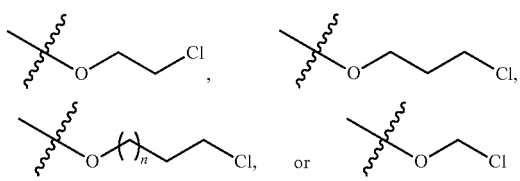
and n may be 0, 1, 2, 3, 4, 5, 6, 7 or 8. Q may be
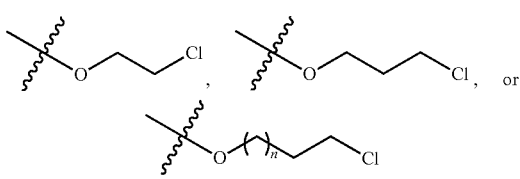
and n may be 0, 1, 2, 3, 4, 5, 6, 7 or 8. Q may be
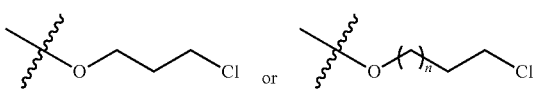
and n may be 0, 1, 2, 3, 4, 5, 6, 7 or 8. Q may be
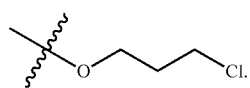 [SMILES: *OCCCCl]
T may be
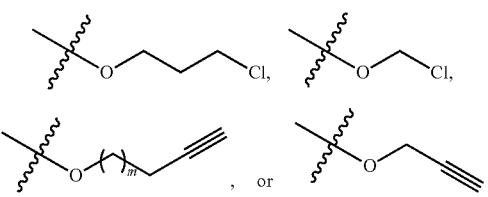
and m may be 0, 1, 2, 3, 4, 5, 6, 7 or 8. T may be
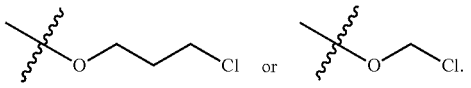
T may be
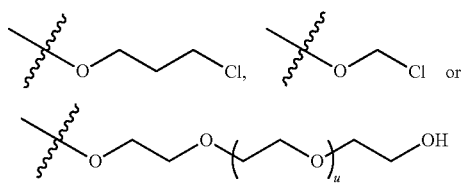
and u may be 0, 1, 2, 3, 4, 5, 6 or 7. T may be
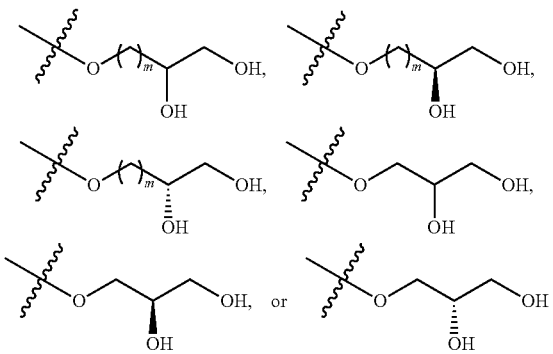
and m may be 0, 1, 2, 3, 4, 5, 6, 7 or 8. T may be
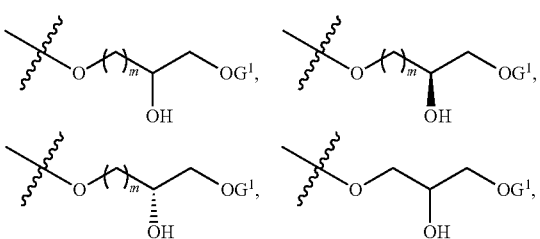

-continued

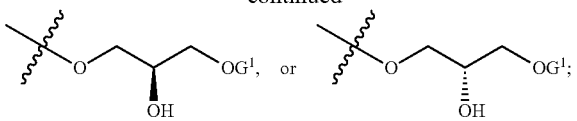

T may be

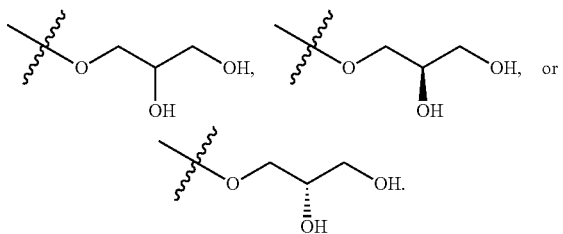

m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$. T may be

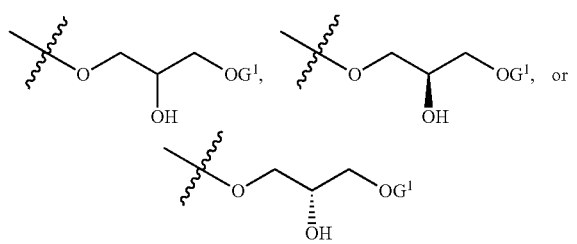

and each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$. T may be

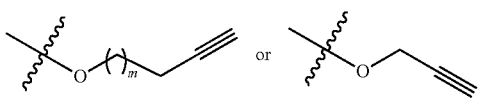

and m may be 0, 1, 2, 3, 4, 5, 6, 7 or 8. T may be

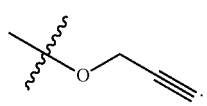 [SMILES: *OCC#C]

T may be

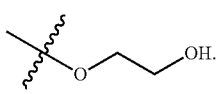 [SMILES: *OCCO]

T may be

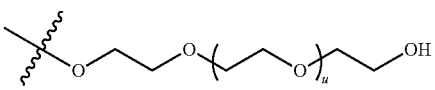

and u may be 0, 1, 2, 3, 4, 5, 6 or 7.

Q may be

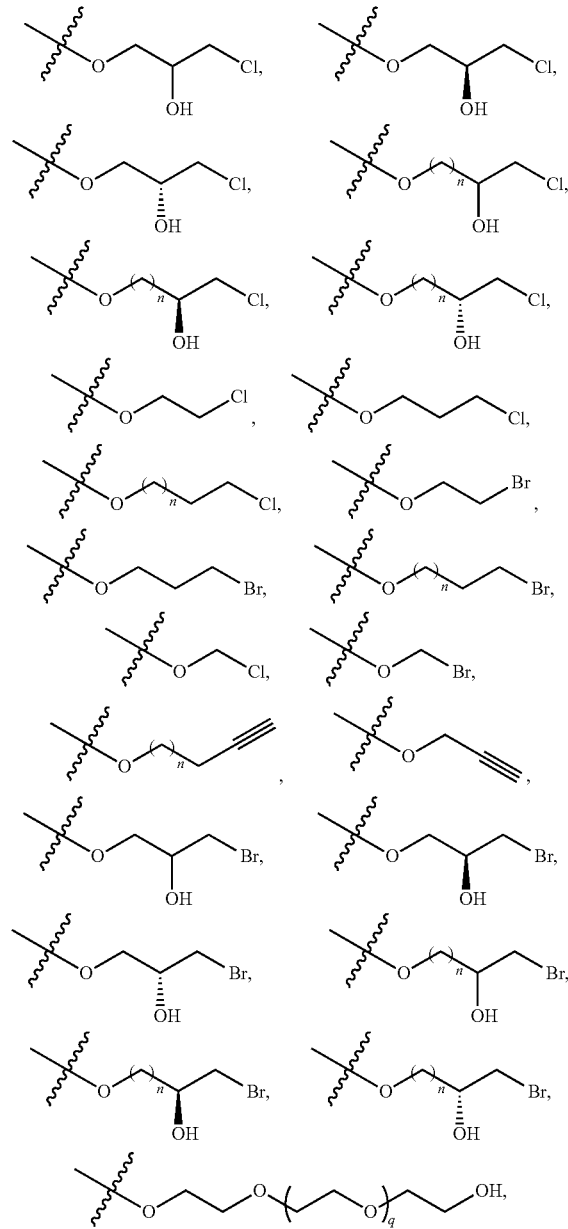

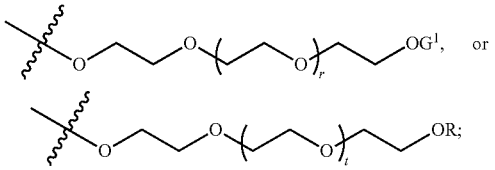

T may be

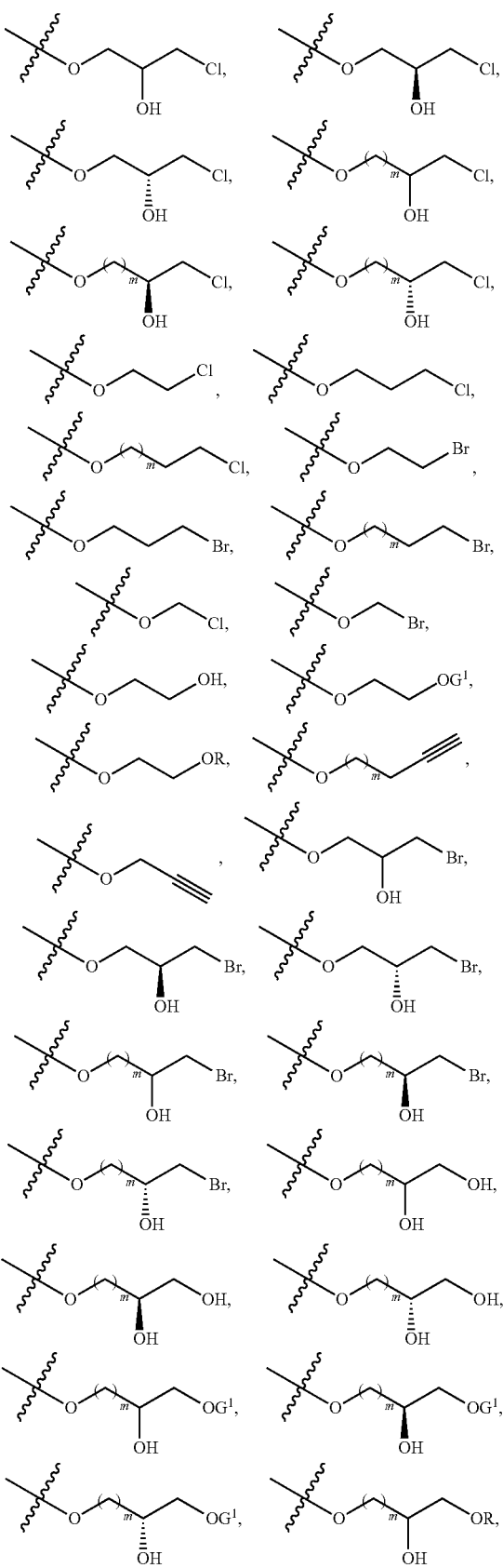

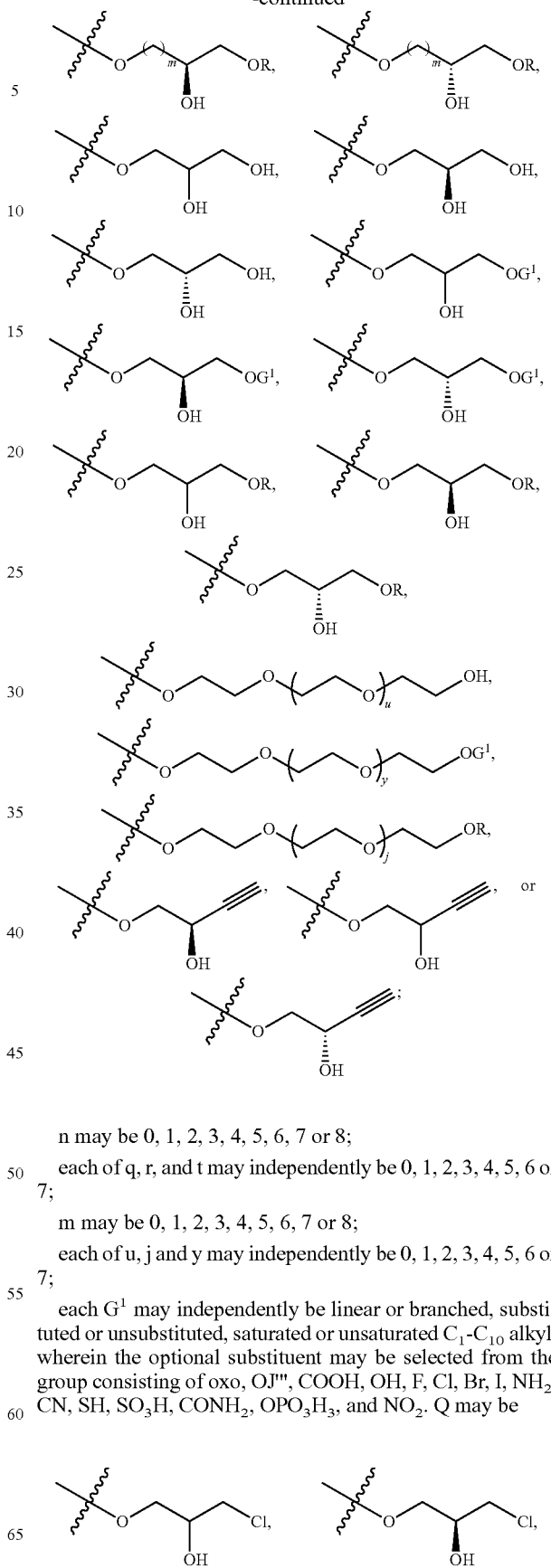

n may be 0, 1, 2, 3, 4, 5, 6, 7 or 8;

each of q, r, and t may independently be 0, 1, 2, 3, 4, 5, 6 or 7;

m may be 0, 1, 2, 3, 4, 5, 6, 7 or 8;

each of u, j and y may independently be 0, 1, 2, 3, 4, 5, 6 or 7;

each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be -continued

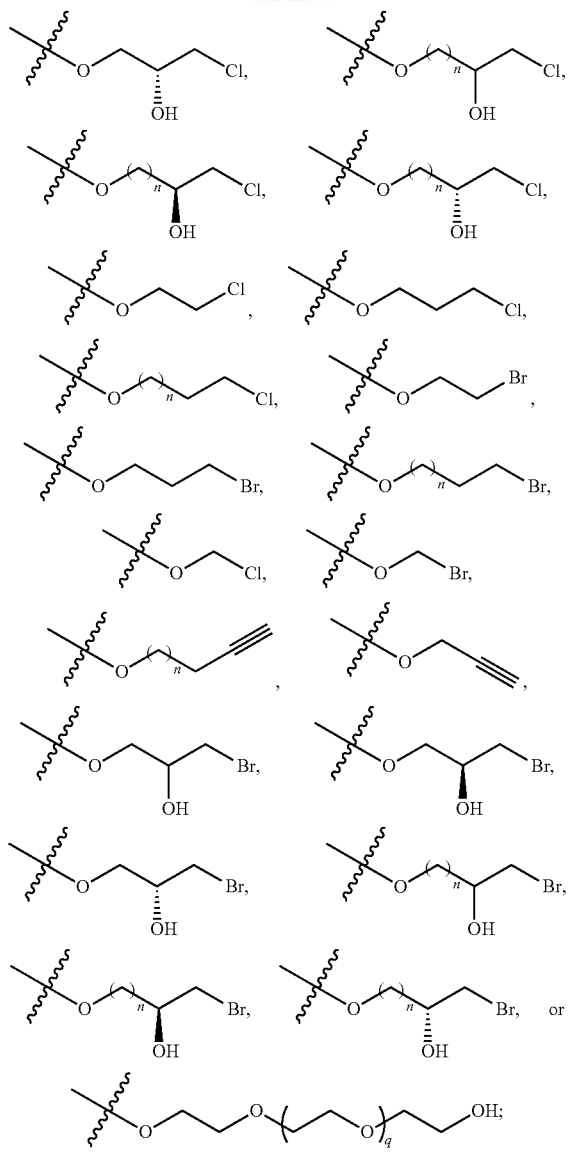

and T may be

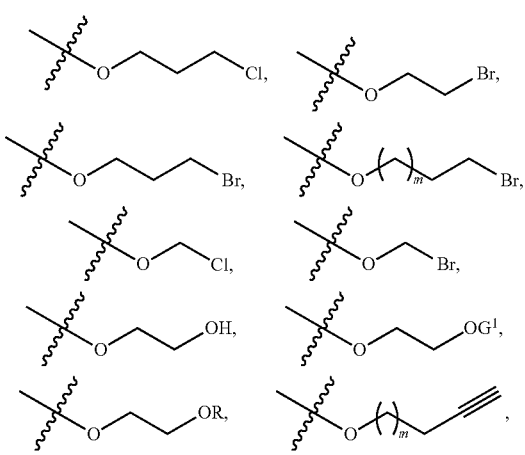

-continued

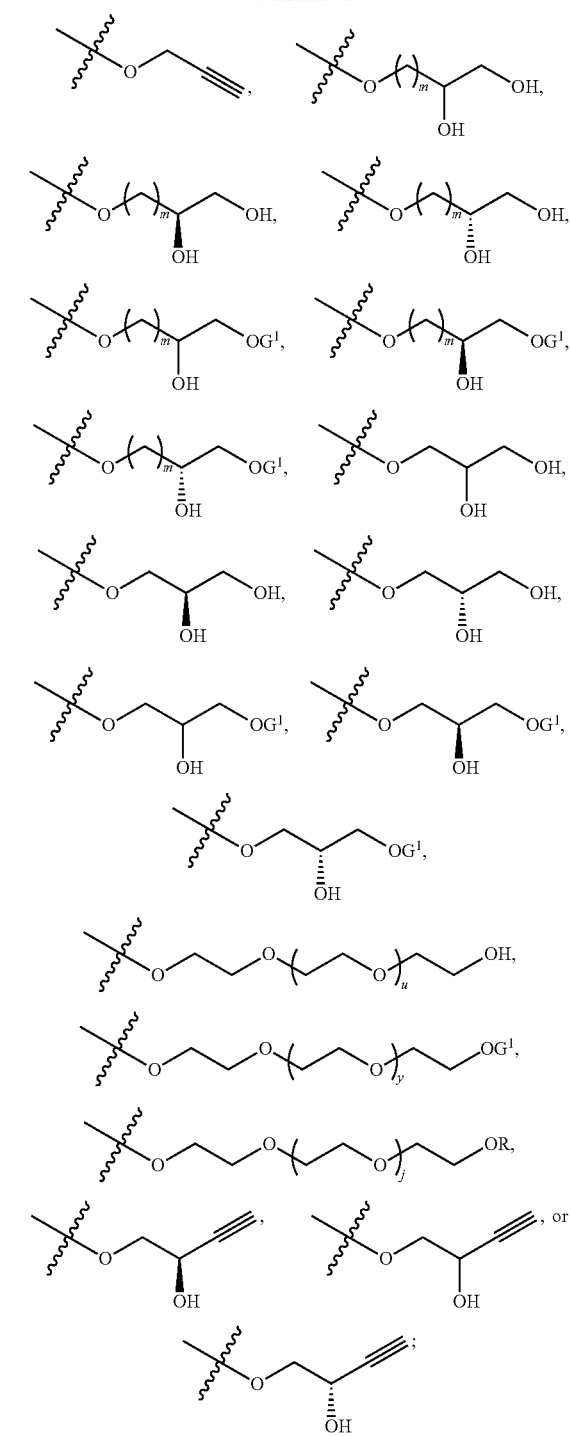

n may be 0, 1, 2, 3, 4, 5, 6, 7 or 8; q may be 0, 1, 2, 3, 4, 5, 6 or 7; m may be 0, 1, 2, 3, 4, 5, 6, 7 or 8; each of u, j and y may independently be 0, 1, 2, 3, 4, 5, 6 or 7; each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$; and each of J'' and J''' may independently be a moiety selected from TABLE 1.

Q may be
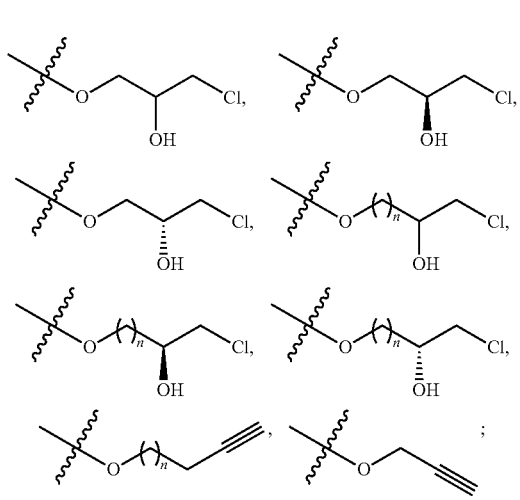
T may be
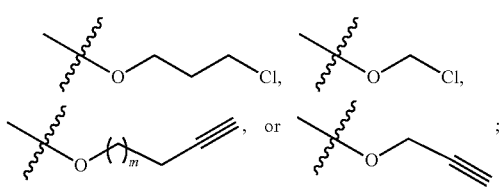
n may be 0, 1, 2, 3, 4, 5, 6, 7 or 8; and m may be 0, 1, 2, 3, 4, 5, 6, 7 or 8.
Q may be
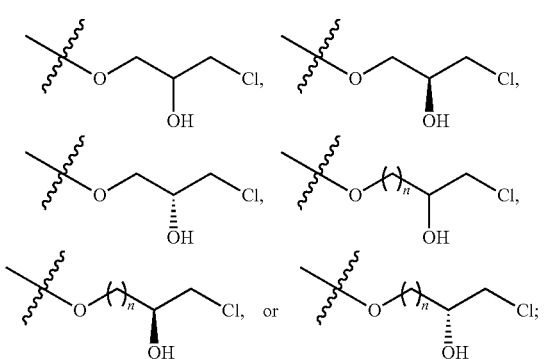
T may be
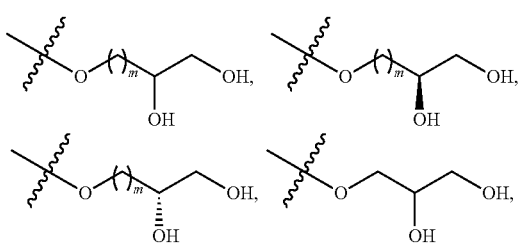
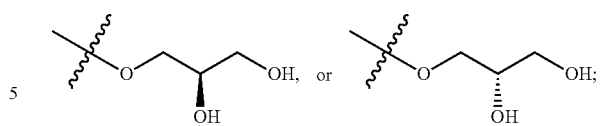
n may be 0, 1, 2, 3, 4, 5, 6, 7 or 8; and m may be 0, 1, 2, 3, 4, 5, 6, 7 or 8. Q may be
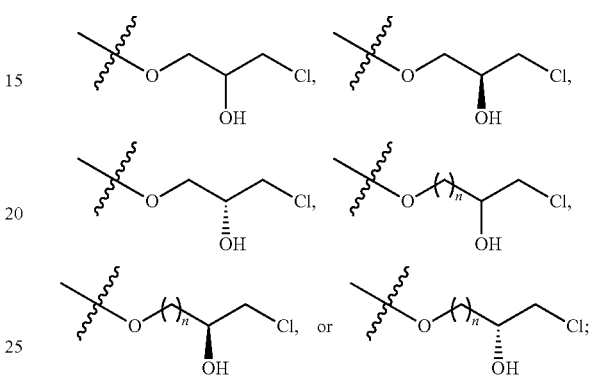
T may be
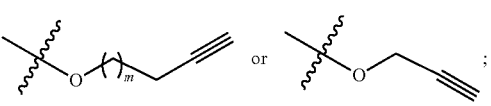
n may be 0, 1, 2, 3, 4, 5, 6, 7 or 8; and m may be 0, 1, 2, 3, 4, 5, 6, 7 or 8. Q may be
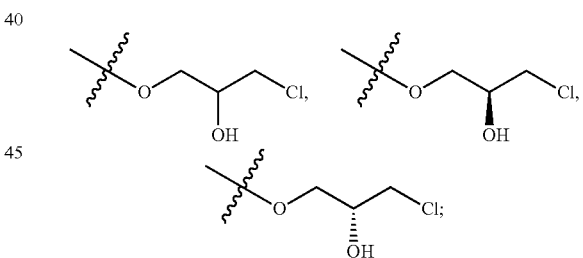
T may be
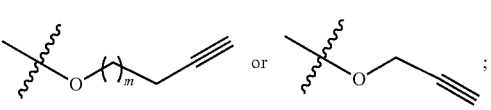
and m may be 0, 1, 2, 3, 4, 5, 6, 7 or 8. Q may be
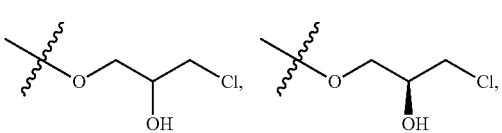

-continued
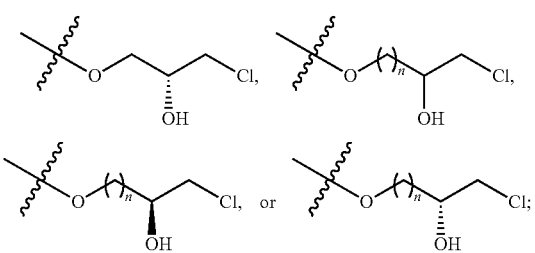
and T may be
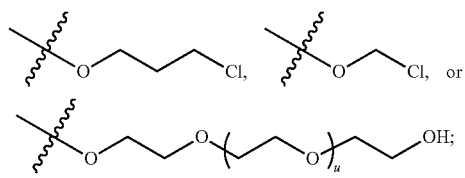
and u may be 0, 1, 2, 3, 4, 5, 6 or 7. Q may be
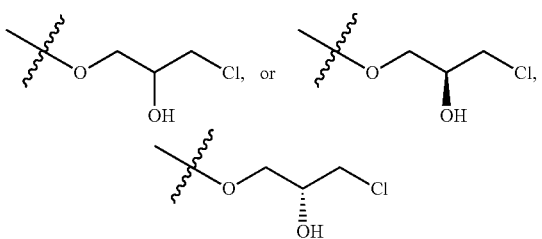
and T may be
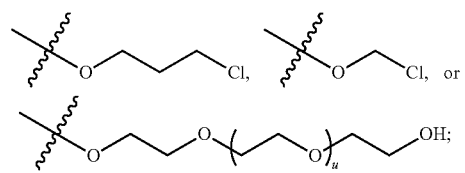
and u may be 0, 1, 2, 3, 4, 5, 6 or 7. Q may be
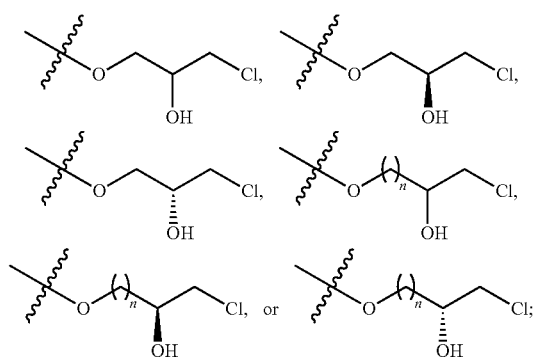
T may be
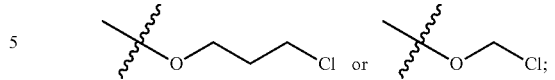
n may be 0, 1, 2, 3, 4, 5, 6, 7 or 8. Q may be
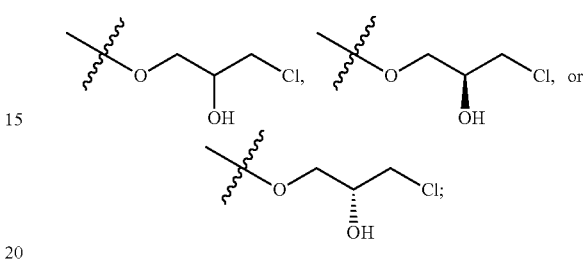
T may be
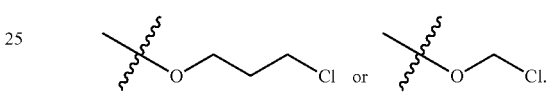
Q may be
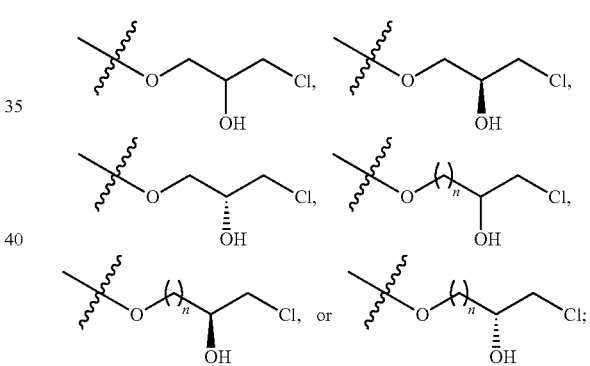
and T may be
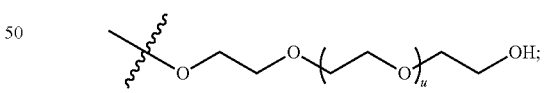
and u may be 0, 1, 2, 3, 4, 5, 6 or 7. Q may be
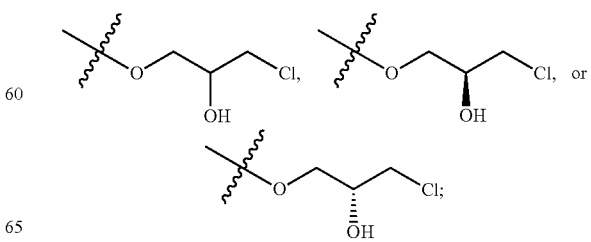

and T may be

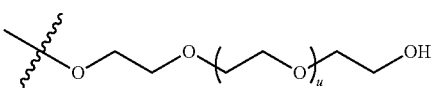

and u may be 0, 1, 2, 3, 4, 5, 6 or 7. Q may be

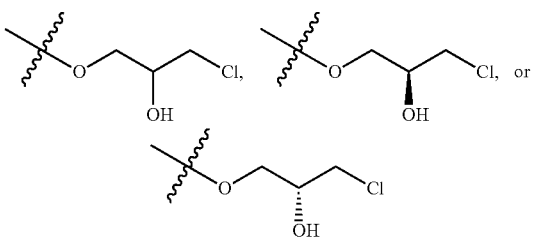

and T may be

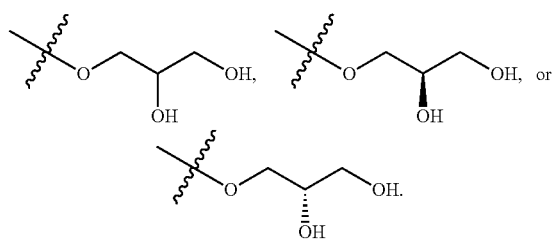

Q may be

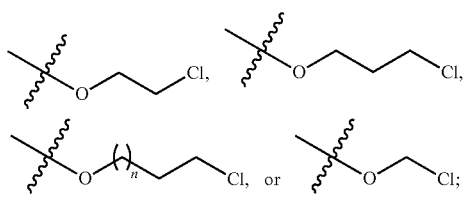

T may be

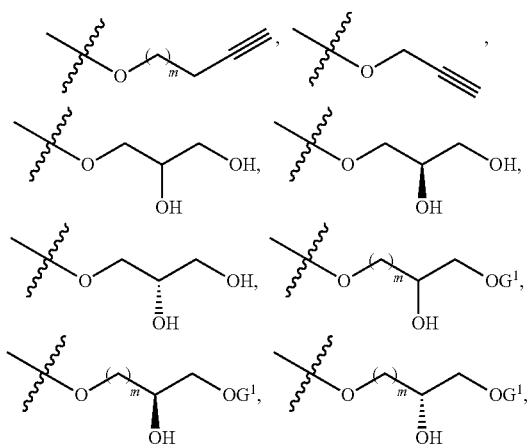

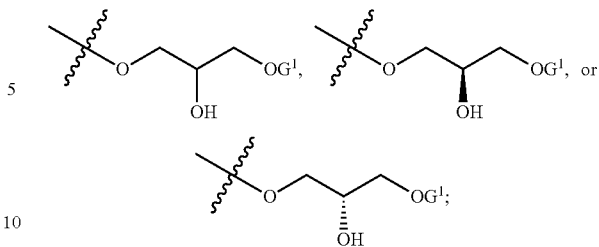

n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

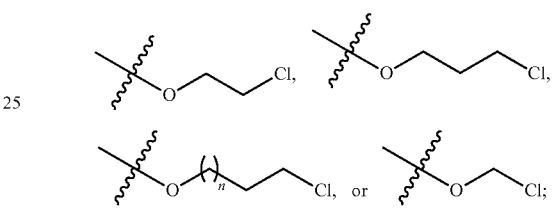

T may be

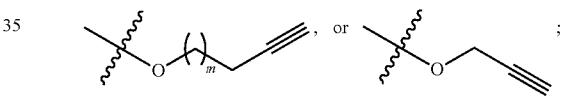

n may be 0, 1, 2, 3, 4, 5, 6, 7 or 8; and m may be 0, 1, 2, 3, 4, 5, 6, 7 or 8. Q may be

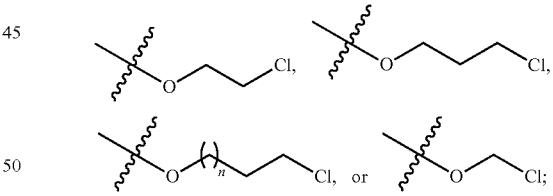

T may be

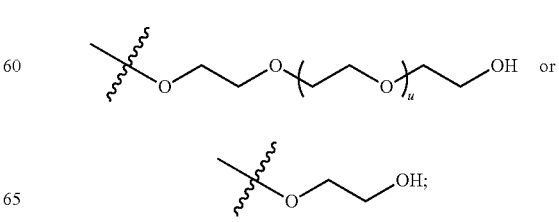

n may be 0, 1, 2, 3, 4, 5, 6, 7 or 8; and u may be 0, 1, 2, 3, 4, 5, 6 or 7. Q may be

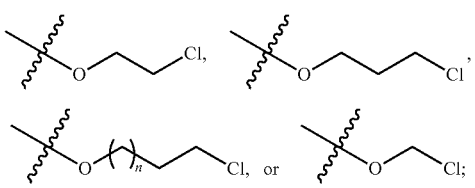

T may be

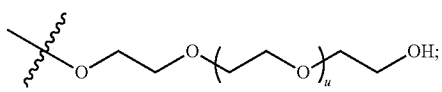

n may be 0, 1, 2, 3, 4, 5, 6, 7 or 8; and u may be 0, 1, 2, 3, 4, 5, 6 or 7. Q may be

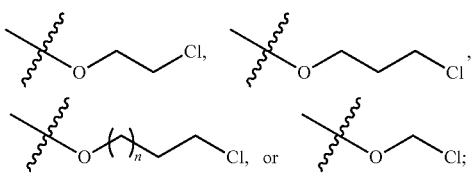

T may be

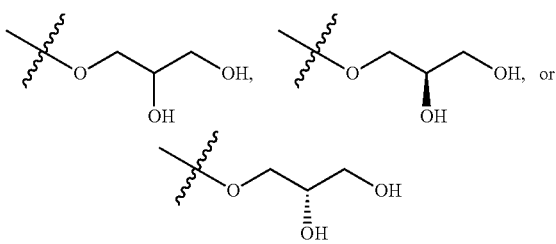

and n may be 0, 1, 2, 3, 4, 5, 6, 7 or 8. Q may be T

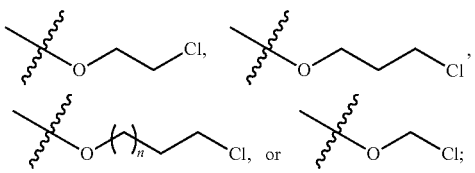

may be

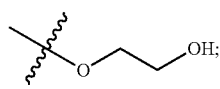 [SMILES: *OCCO]

and n may be 0, 1, 2, 3, 4, 5, 6, 7 or 8. Q may be

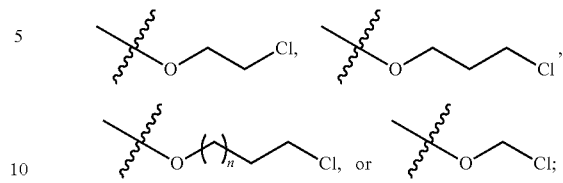

T may be

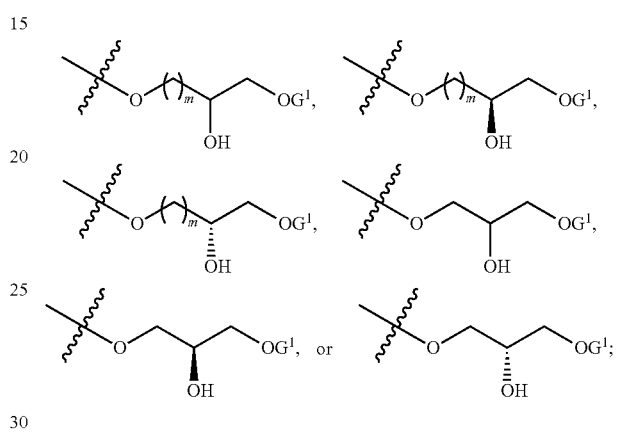

n may be 0, 1, 2, 3, 4, 5, 6, 7 or 8; m may be 0, 1, 2, 3, 4, 5, 6, 7 or 8; and each $G^1$ may be independently linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

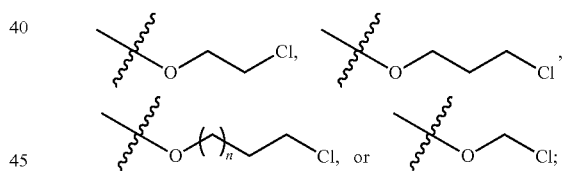

T may be

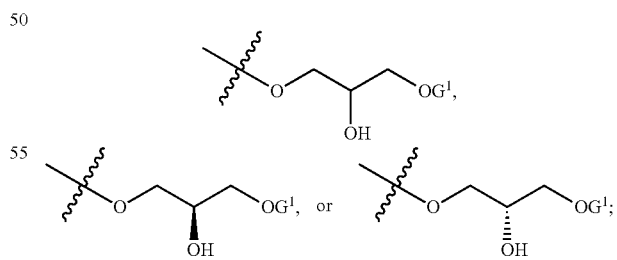

n may be 0, 1, 2, 3, 4, 5, 6, 7 or 8; and each $G^1$ may be independently linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$.

In accordance with another embodiment, there is provided a use of a compound having a structure of Formula IV

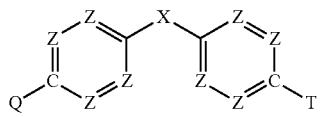

wherein: X may be $CH_2$, $CHR^1$, or $CR^1R^2$; each of $R^1$ and $R^2$ may independently be linear or branched, substituted or unsubstituted, saturated or unsaturated $C_1$-$C_{10}$ alkyl, or $R^1$ and $R^2$ may together form a substituted or unsubstituted, saturated or unsaturated cyclic $C_3$-$C_{10}$ alkyl, wherein the optional substituent may be selected from the group consisting of oxo, $OJ'''$, COOH, $R^3$, OH, $OR^3$, F, Cl, Br, I, $NH_2$, $NHR^3$, $NR^3_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3_2$, $NHR^6$, $OPO_3H_3$, $CONR^3R^6$, $NR^3R^6$, and $NO_2$; each $R^3$ may independently be unsubstituted $C_1$-$C_{10}$ alkyl; each $R^6$ may independently be $C_1$-$C_{10}$ acyl; each remaining Z may independently be C-T, N, CH, CF, CCl, CBr, CI, COH, $CG^1$, $COG^1$, $CNH_2$, $CNHG^1$, $CNG^1_2$, $COSO_3H$, $COPO_3H_2$, $CSG^1$, $CSOG^1$, or $CSO_2G^1$; wherein Q may be

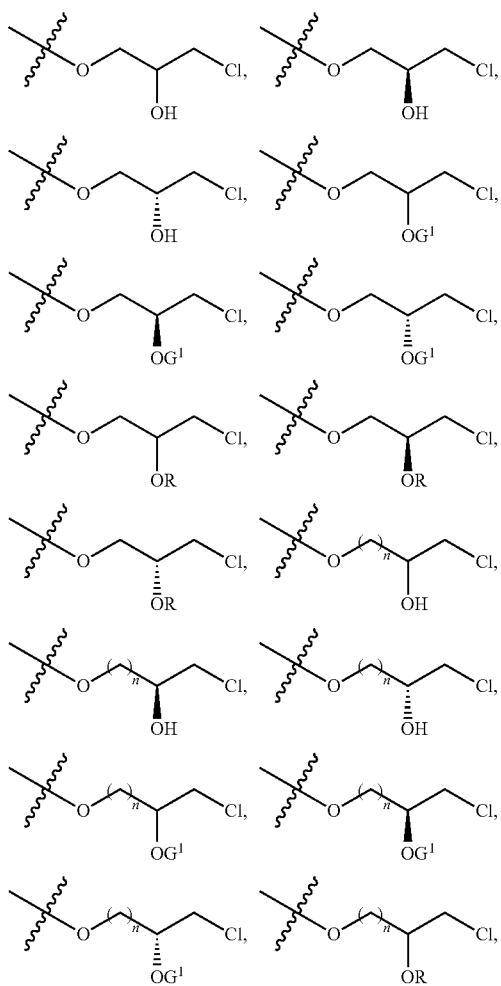

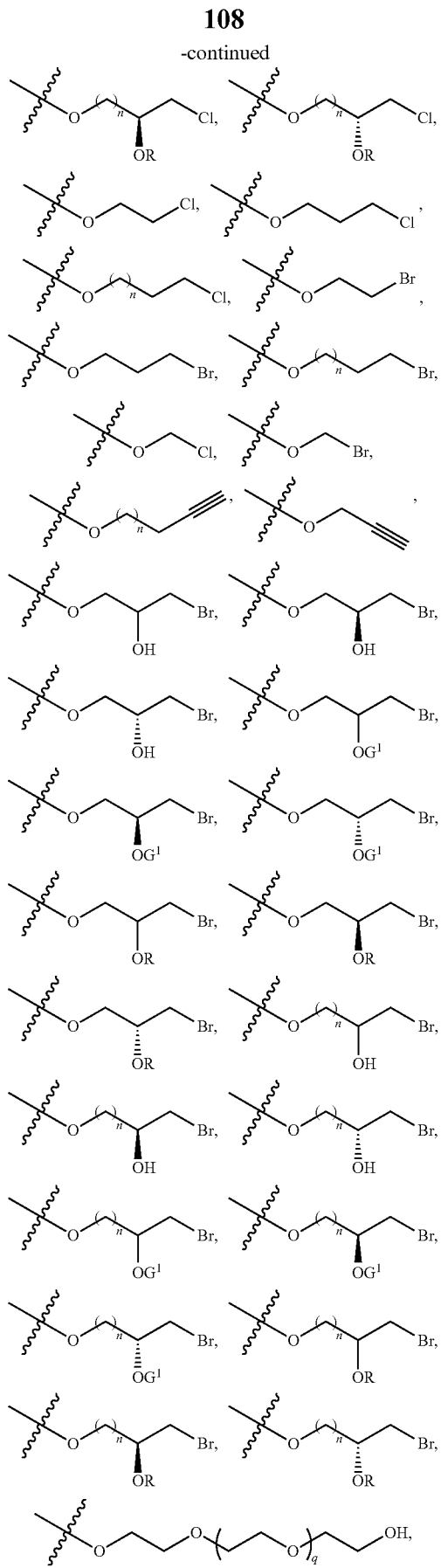

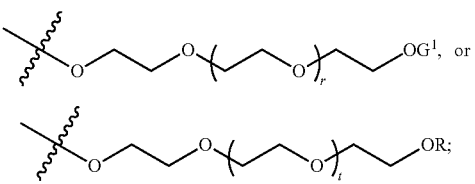
T may be
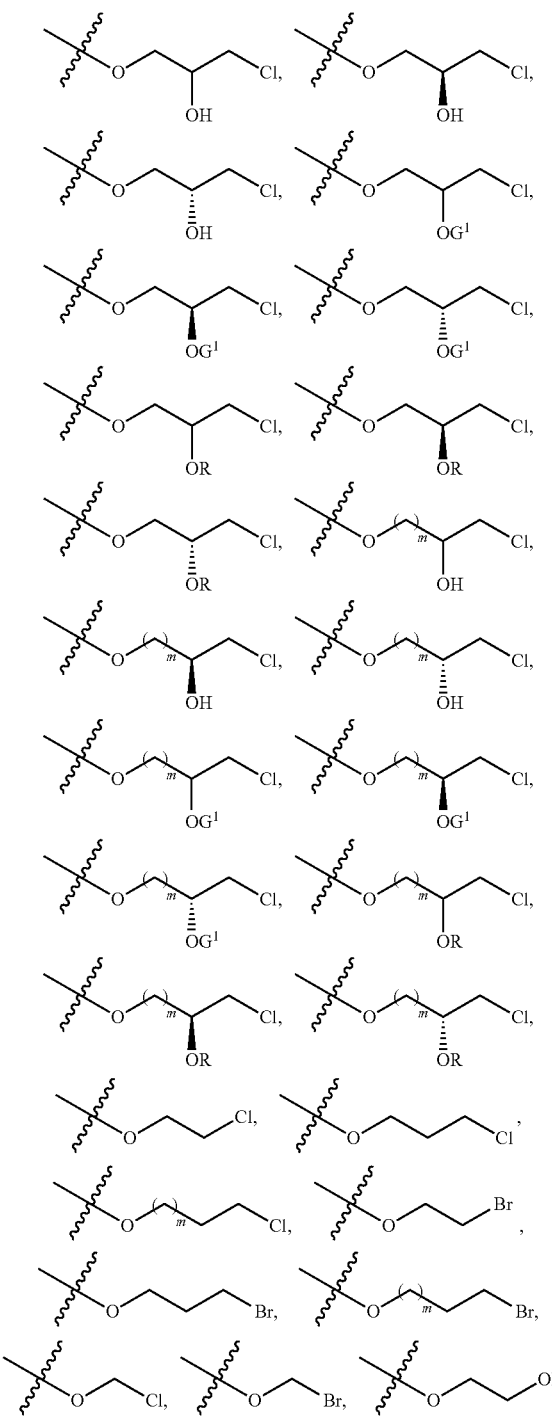
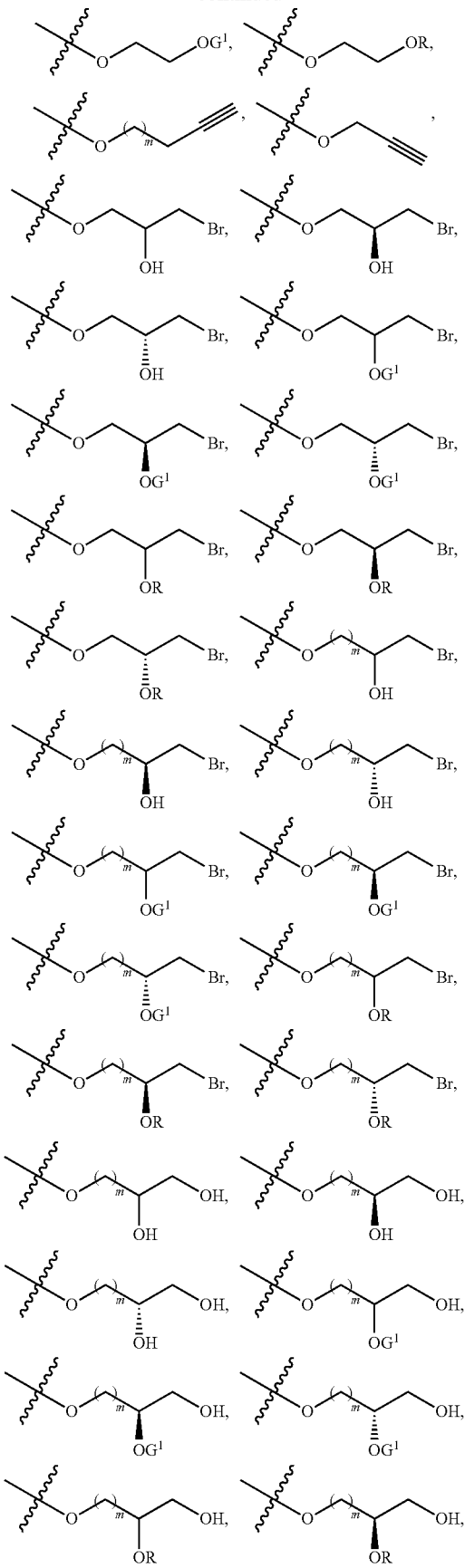

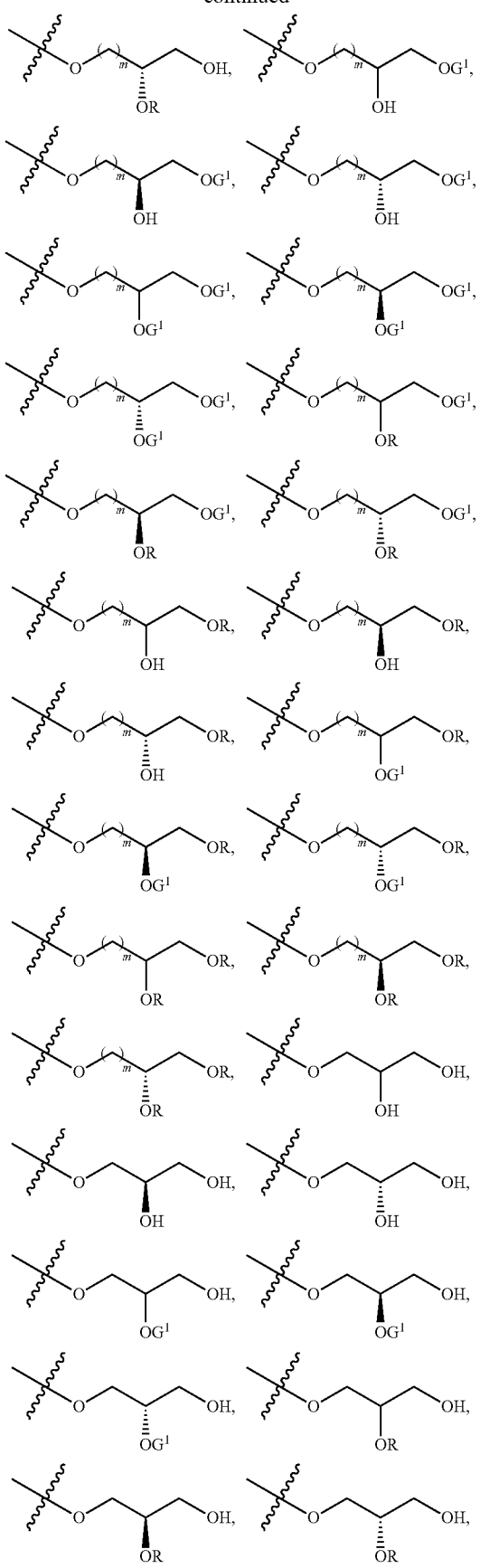
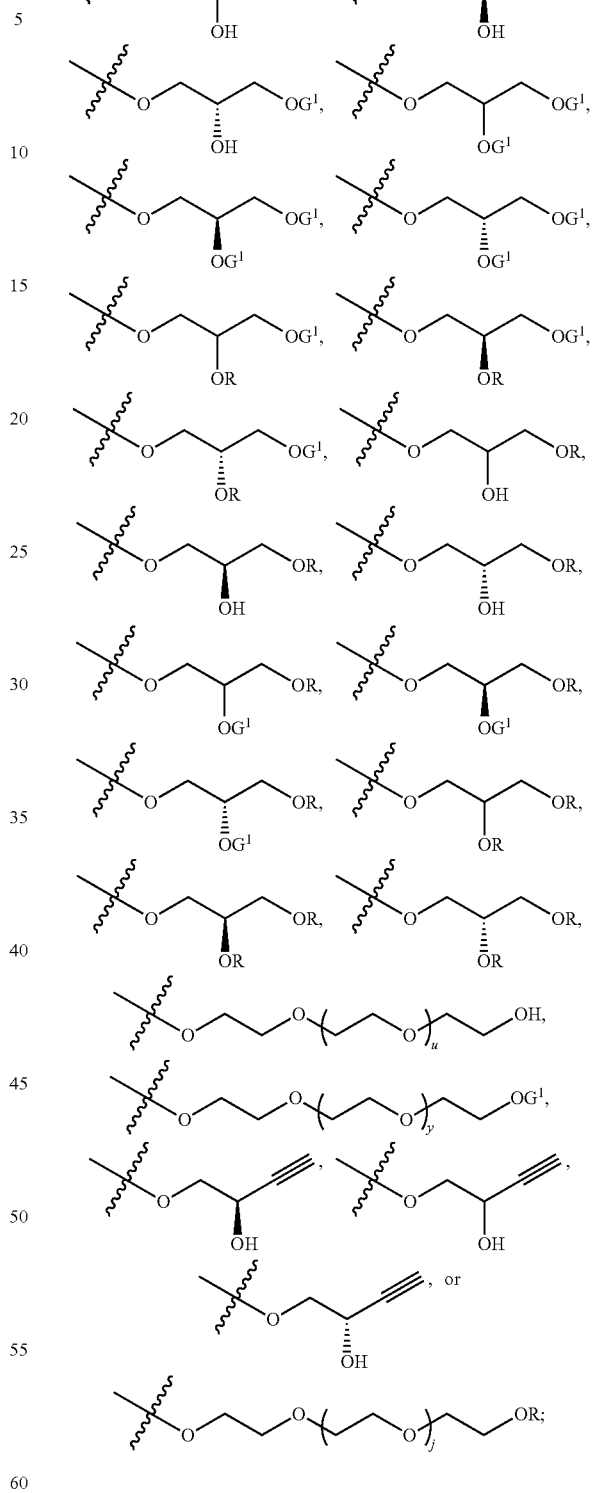
n may be 0, 1, 2, 3, 4, 5, 6, 7 or 8; each of q, r, and t may independently be 0, 1, 2, 3, 4, 5, 6 or 7; m may be 0, 1, 2, 3, 4, 5, 6, 7 or 8; each of u, j and y may independently be 0, 1, 2, 3, 4, 5, 6 or 7; each $G^1$ $G^{1\prime}$ and $G^{1\prime\prime}$ may independently be linear or branched, or aromatic cyclic or non-aromatic cyclic, substituted or unsubstituted, saturated or unsaturated $C_1$-$C_{10}$ alkyl, wherein the optional substituent may be selected from the group consisting of oxo, OJ''', COOH, $R^4$, OH, $OR^4$, F, Cl, Br, I, $NH_2$, $NHR^4$, $NR^4_2$, CN, SH, $SR^4$, $SO_3H$, $SO_3R^4$, $SO_2R^4$, $OSO_3R^4$, $OR^5$, $CO_2R^4$, $CONH_2$, $CONHR^4$, $CONHR^5$, $CONR^4_2$, $NHR^5$, $OPO_3H_3$, $CONR^4R^5$, $NR^4R^5$, and $NO_2$; each $R^4$ may independently be unsubstituted $C_1$-$C_{10}$ alkyl; each $R^5$ may independently be $C_1$-$C_{10}$ acyl; R may be $C_1$-$C_{10}$ acyl; and each of J'' and J''' may independently be a moiety selected from TABLE 1; and wherein one or more of the OH groups may be optionally substituted to replace the H with a moiety selected from TABLE 1. Each of $R^1$ and $R^2$ may be independently linear or branched, substituted or unsubstituted, saturated or unsaturated $C_1$-$C_{10}$ alkyl, wherein the optional substituent may be selected from the group consisting of OJ''', F, Cl, Br, I, or $NH_2$. Each Z may be independently $CG^1$, N, CH, CF, CCl, CBr, CI, or COH. Each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$.

Q may be

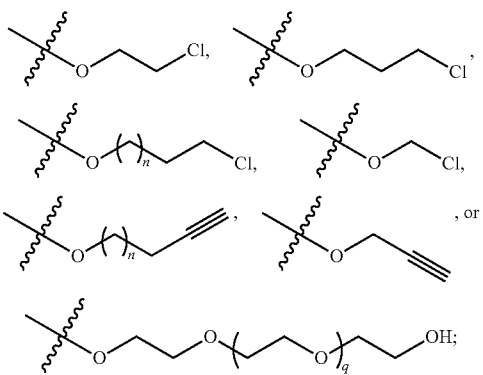

n may be 0, 1, 2, 3, 4, 5, 6, 7 or 8; and q may be 0, 1, 2, 3, 4, 5, 6 or 7. Q may be

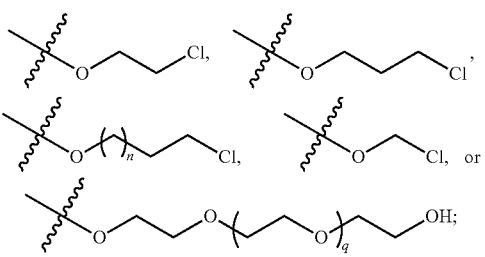

n may be 0, 1, 2, 3, 4, 5, 6, 7 or 8; and q may be 0, 1, 2, 3, 4, 5, 6 or 7. Q may be

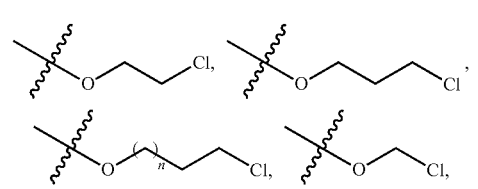

-continued

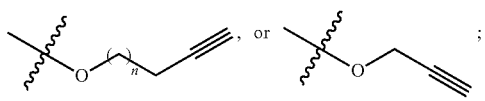

and n may be 0, 1, 2, 3, 4, 5, 6, 7 or 8. Q may be

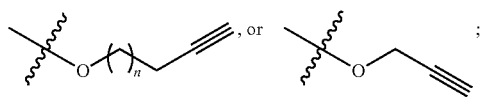

and n may be 0, 1, 2, 3, 4, 5, 6, 7 or 8. Q may be

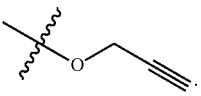 [SMILES: *OCC#C]

Q may be

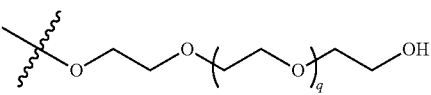

and q may be 0, 1, 2, 3, 4, 5, 6 or 7. q may be 1. Q may be

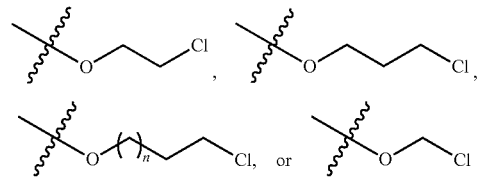

and n may be 0, 1, 2, 3, 4, 5, 6, 7 or 8. Q may be

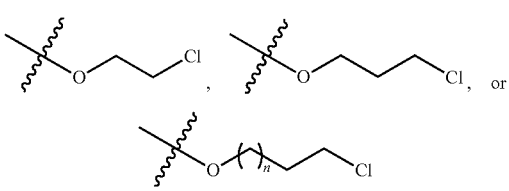

and n may be 0, 1, 2, 3, 4, 5, 6, 7 or 8. Q may be

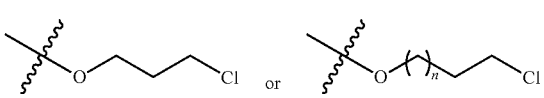

and n may be 0, 1, 2, 3, 4, 5, 6, 7 or 8. Q may be

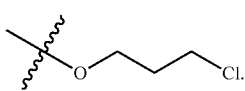 [SMILES: *OCCCCl]

T may be

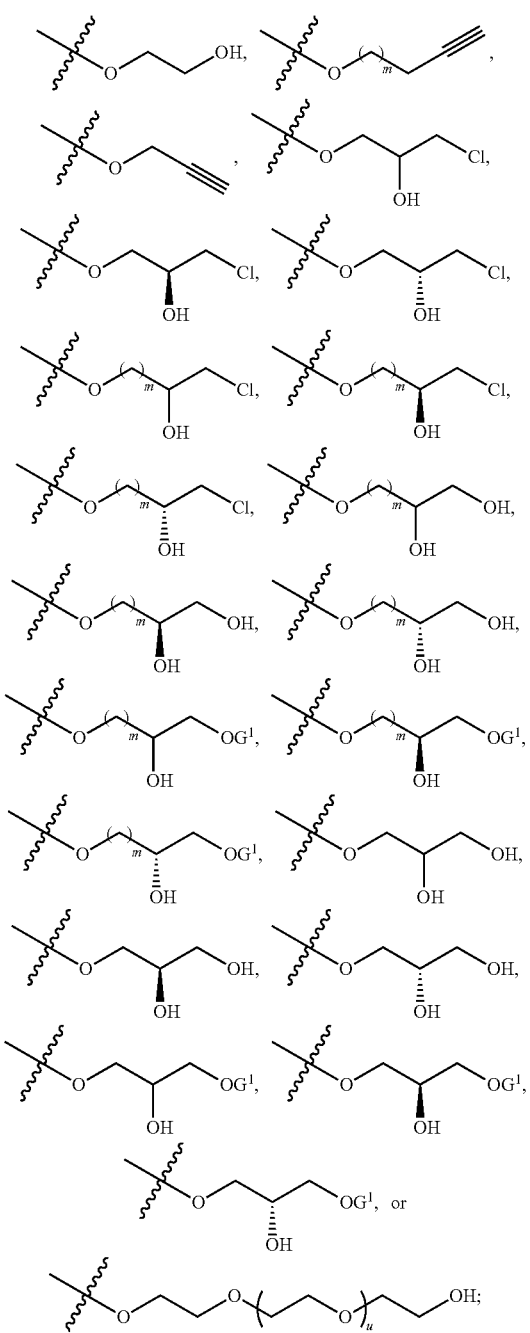

m may be 0, 1, 2, 3, 4, 5, 6, 7 or 8; u may be 0, 1, 2, 3, 4, 5, 6 or 7; and each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$. T may be

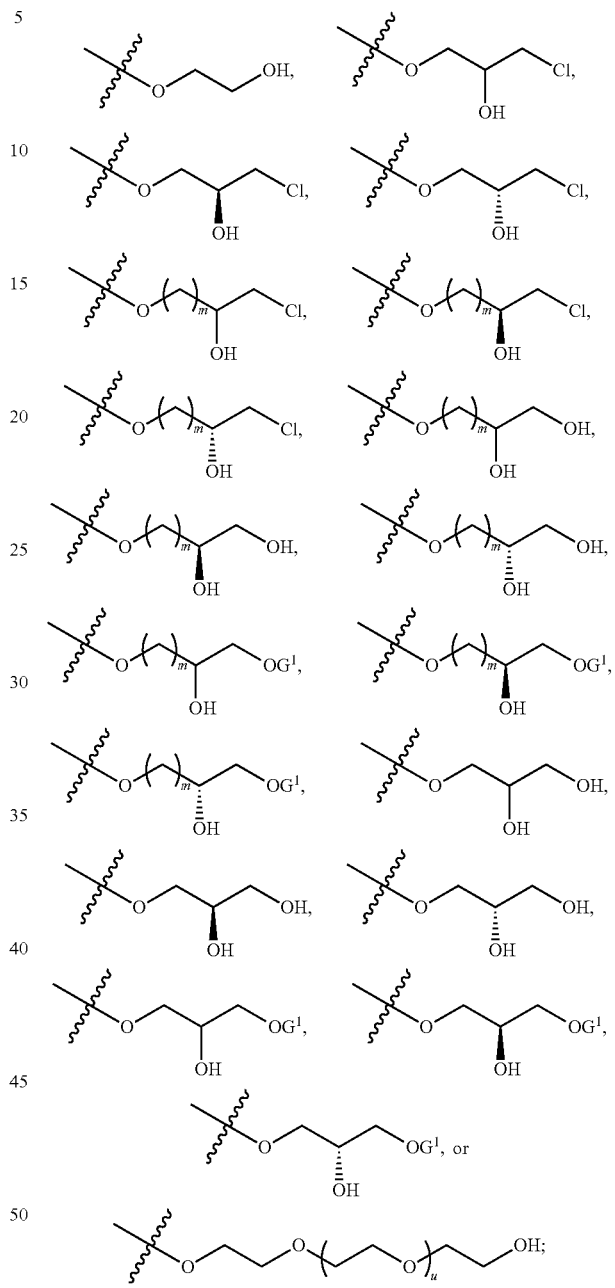

m may be 0, 1, 2, 3, 4, 5, 6, 7 or 8; u may be 0, 1, 2, 3, 4, 5, 6 or 7; and each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$. T may be

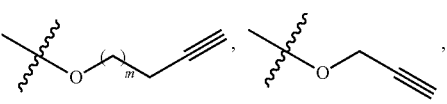

-continued

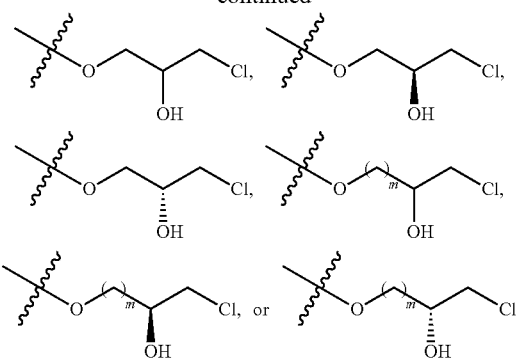

and m may be 0, 1, 2, 3, 4, 5, 6, 7 or 8. T may be

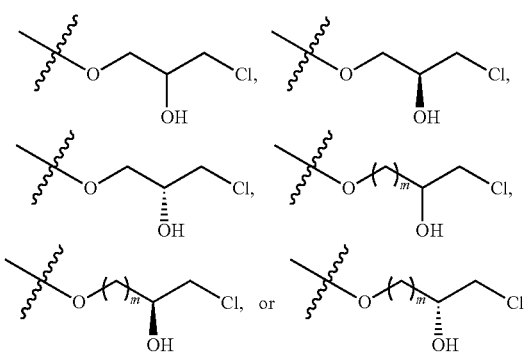

and m may be 0, 1, 2, 3, 4, 5, 6, 7 or 8. T may be

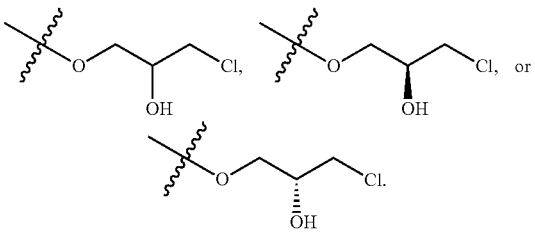

T may be

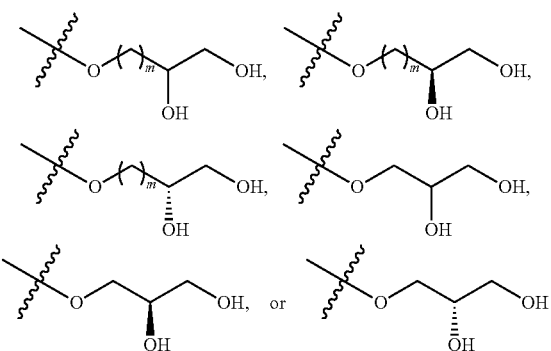

and m may be 0, 1, 2, 3, 4, 5, 6, 7 or 8. T may be

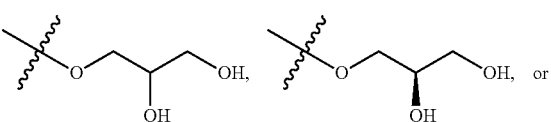

-continued

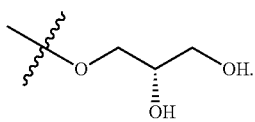

T may be

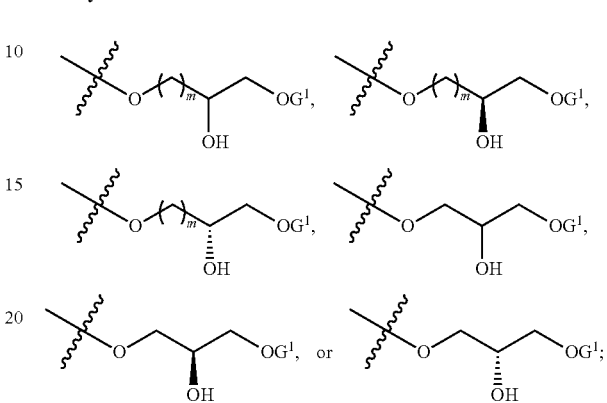

m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. T may be

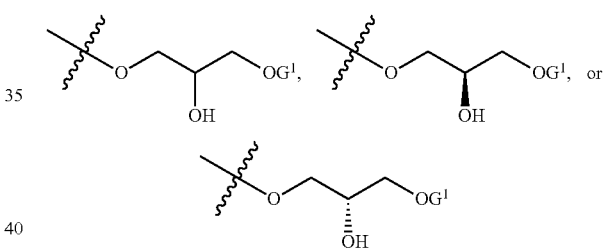

and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. T may be

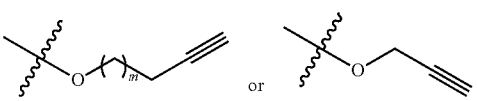

and m may be 0, 1, 2, 3, 4, 5, 6, 7 or 8. T may be

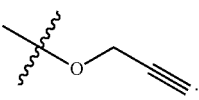

T may be

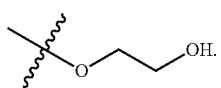 [SMILES: *OCCO]

T may be
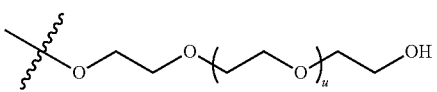
and u may be 0, 1, 2, 3, 4, 5, 6 or 7.
Q may be
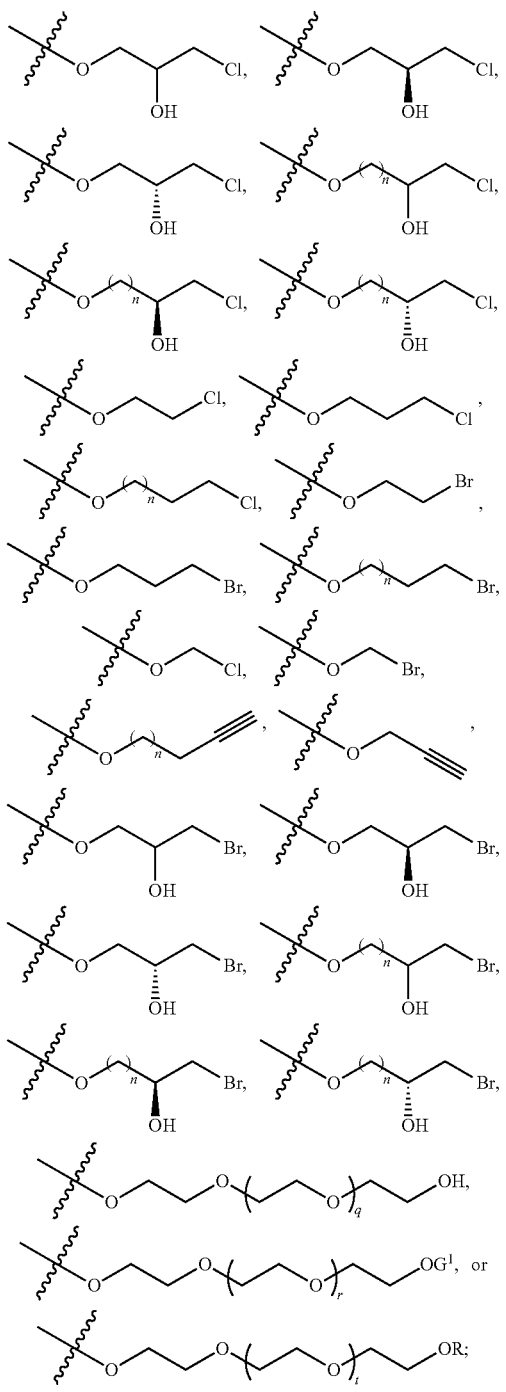
T may be
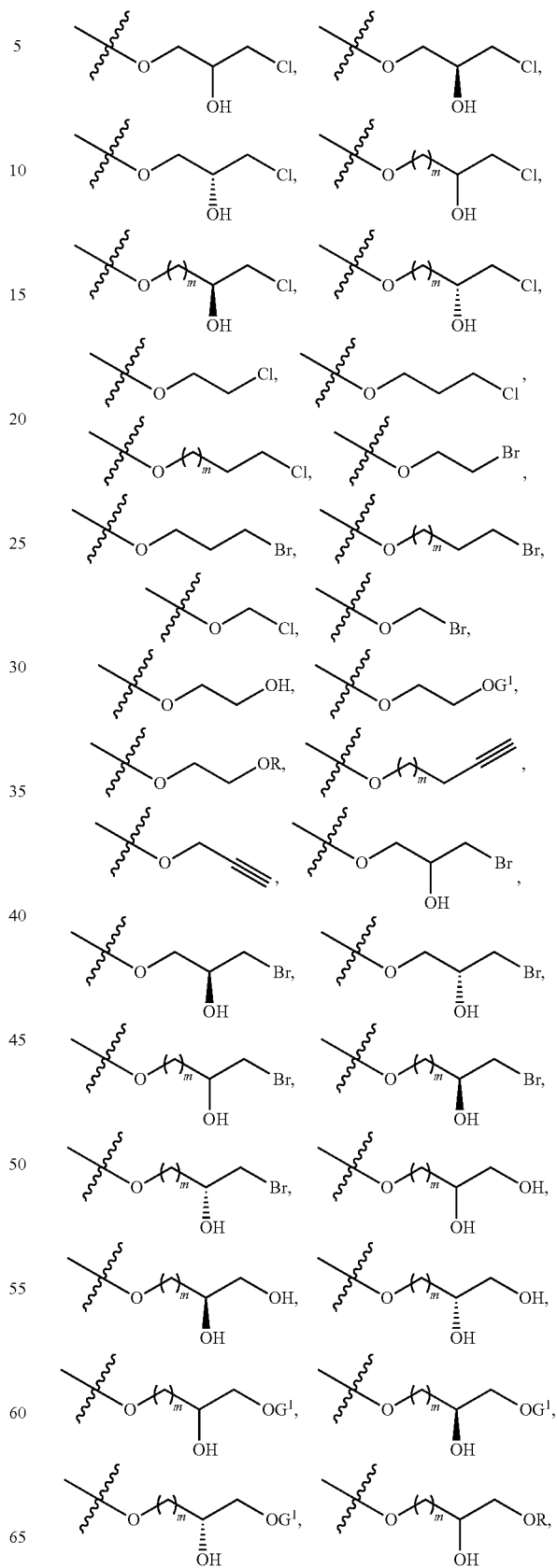

-continued

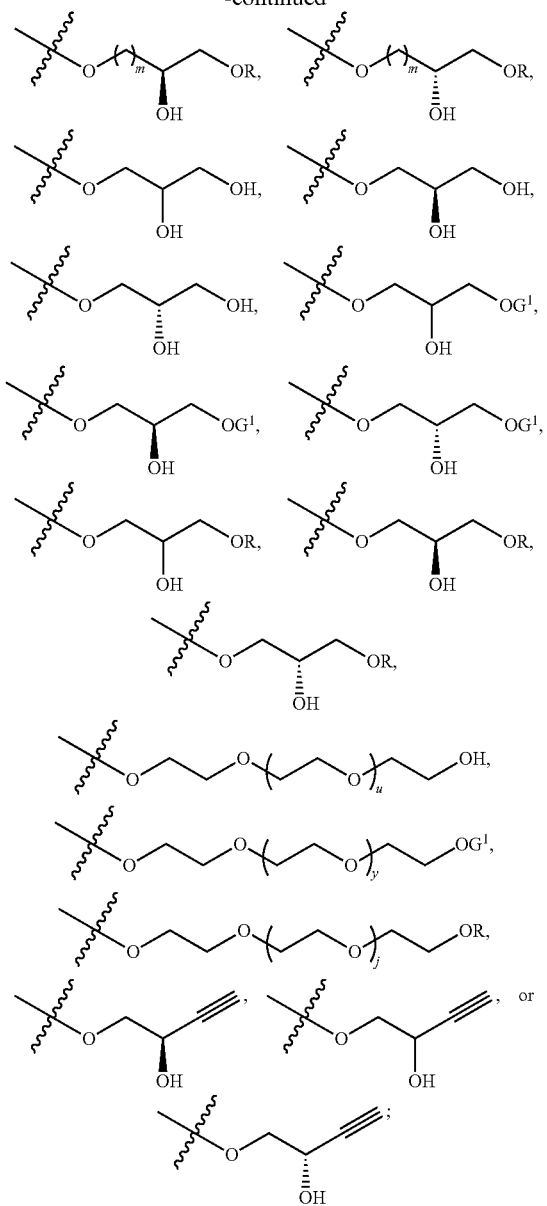

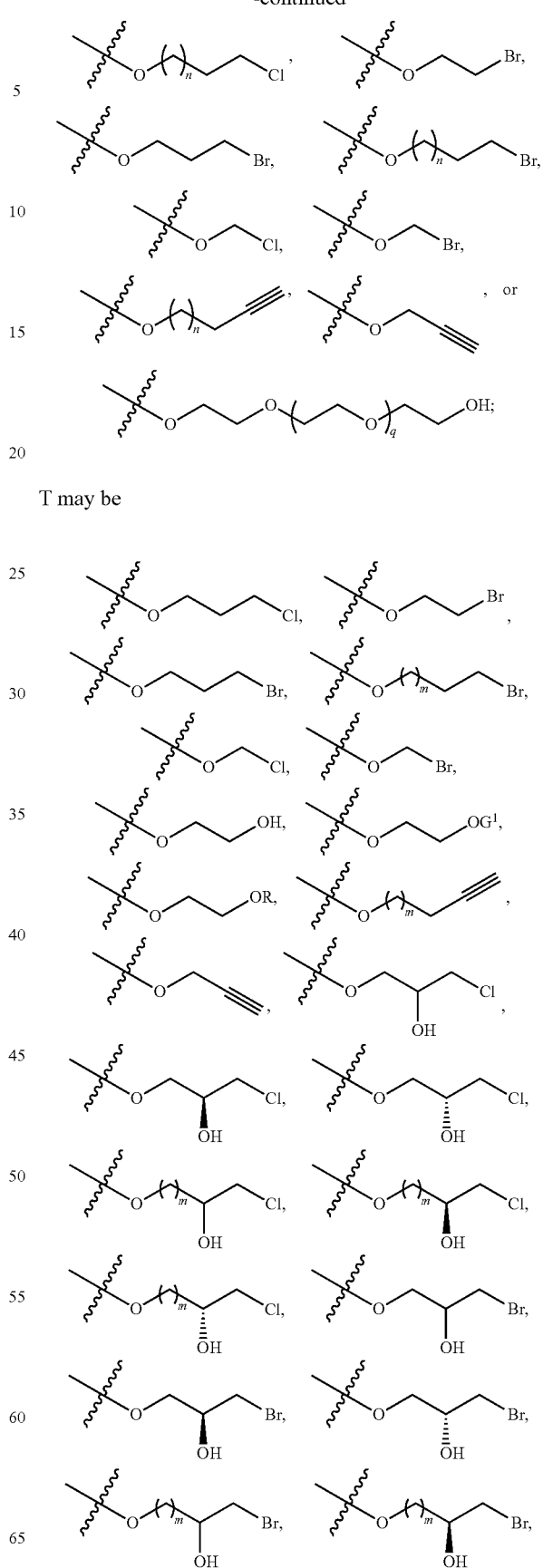

n may be 0, 1, 2, 3, 4, 5, 6, 7 or 8;

each of q, r, and t may independently be 0, 1, 2, 3, 4, 5, 6 or 7;

m may be 0, 1, 2, 3, 4, 5, 6, 7 or 8;

each of u, j and y may independently be 0, 1, 2, 3, 4, 5, 6 or 7;

each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

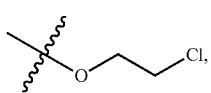 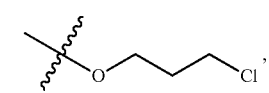

T may be

-continued

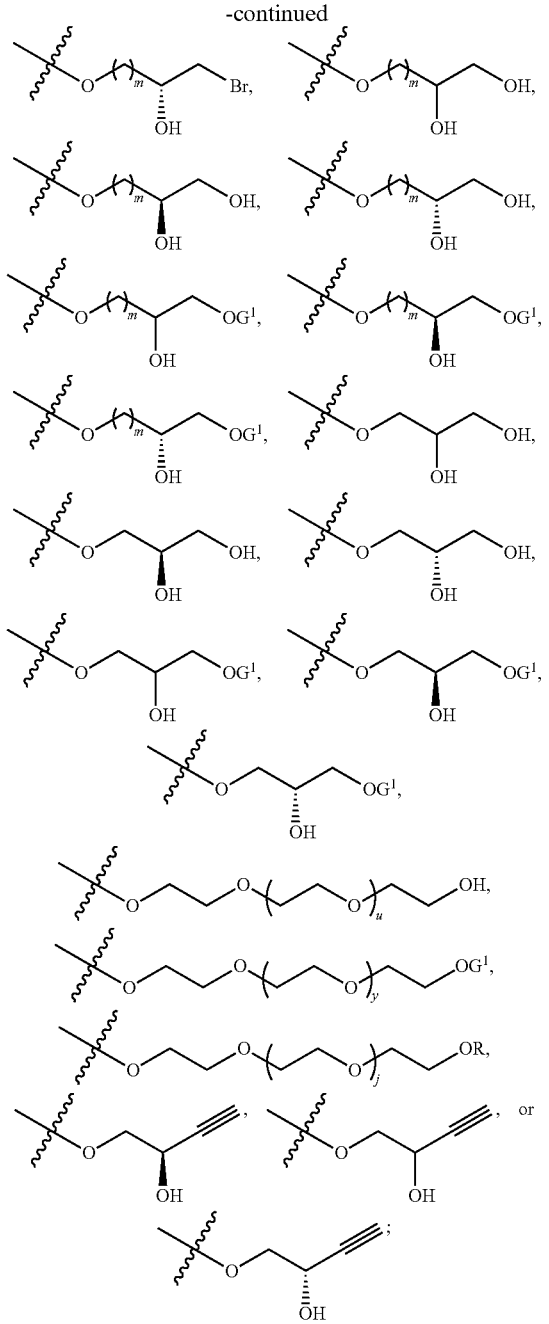

n may be 0, 1, 2, 3, 4, 5, 6, 7 or 8; q may be 0, 1, 2, 3, 4, 5, 6 or 7; m may be 0, 1, 2, 3, 4, 5, 6, 7 or 8; each of u, j and y may independently be 0, 1, 2, 3, 4, 5, 6 or 7; each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$; and each of J" and J''' may independently be a moiety selected from TABLE 1. Q may be -continued

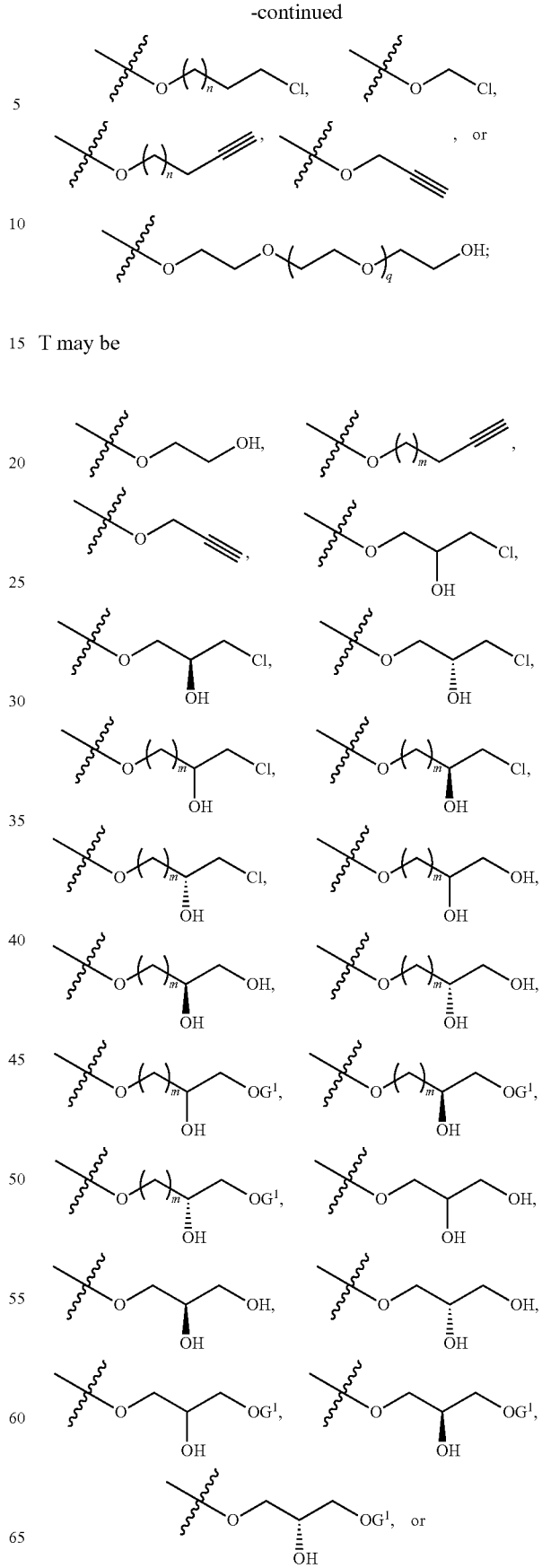

T may be

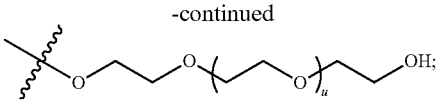

n may be 0, 1, 2, 3, 4, 5, 6, 7 or 8; q may be 0, 1, 2, 3, 4, 5, 6 or 7; m may be 0, 1, 2, 3, 4, 5, 6, 7 or 8; u may be 0, 1, 2, 3, 4, 5, 6 or 7; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

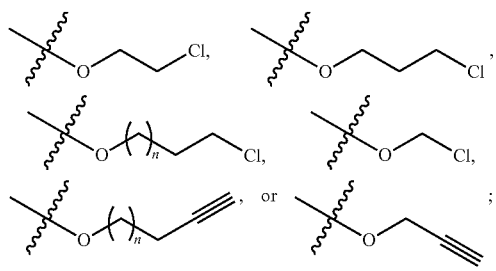

T may be

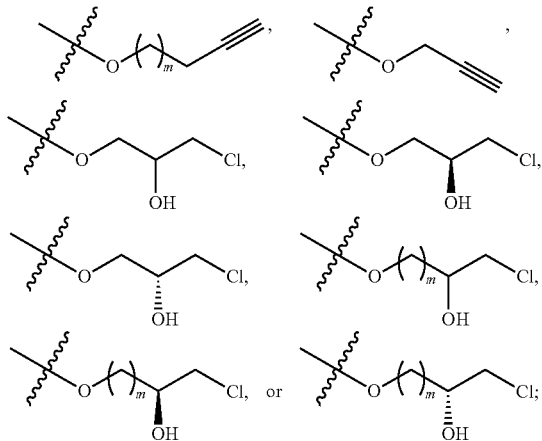

n may be 0, 1, 2, 3, 4, 5, 6, 7 or 8; and m may be 0, 1, 2, 3, 4, 5, 6, 7 or 8. Q may be

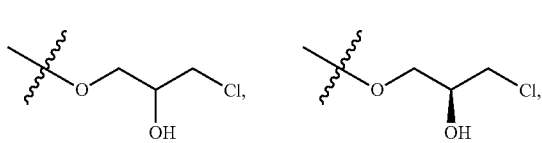

T may be

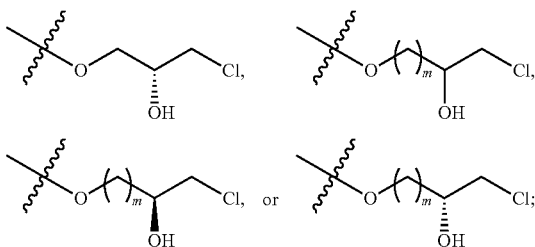

n may be 0, 1, 2, 3, 4, 5, 6, 7 or 8; and m may be 0, 1, 2, 3, 4, 5, 6, 7 or 8. Q may be

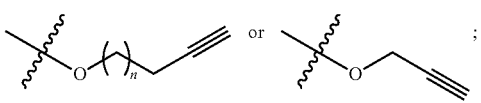

T may be

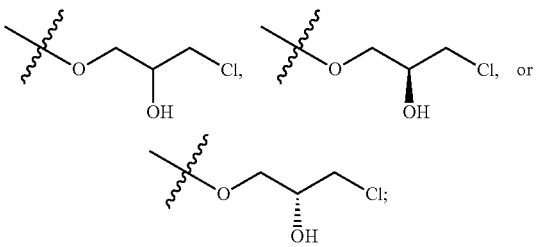

and n may be 0, 1, 2, 3, 4, 5, 6, 7. Q may be

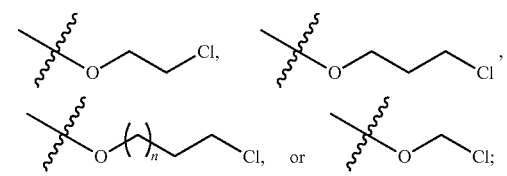

T may be

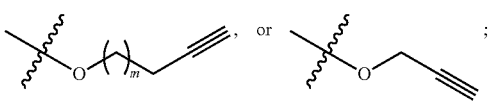

n may be 0, 1, 2, 3, 4, 5, 6, 7 or 8; and m may be 0, 1, 2, 3, 4, 5, 6, 7 or 8. Q may be

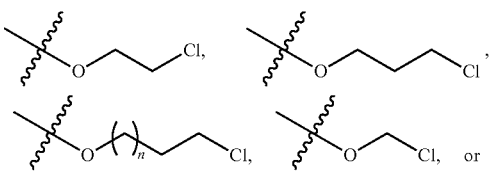

-continued

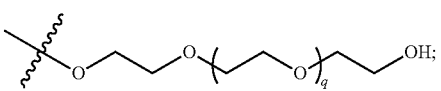

T may be

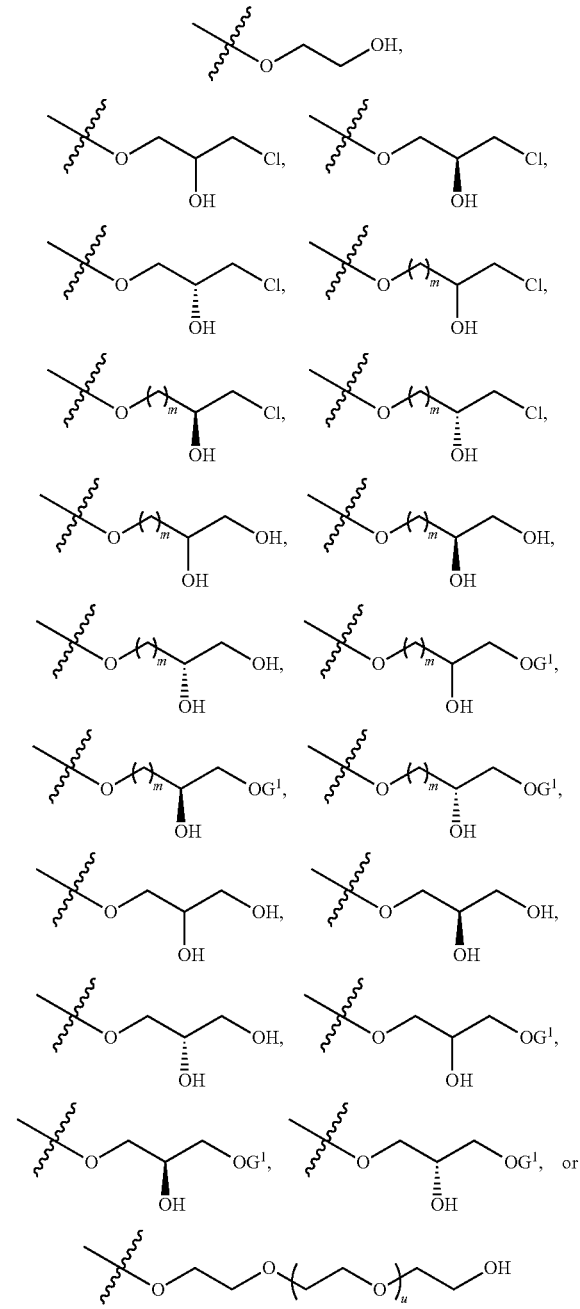

n may be 0, 1, 2, 3, 4, 5, 6, 7 or 8; q may be 0, 1, 2, 3, 4, 5, 6 or 7; m may be 0, 1, 2, 3, 4, 5, 6, 7 or 8; u may be 0, 1, 2, 3, 4, 5, 6 or 7; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

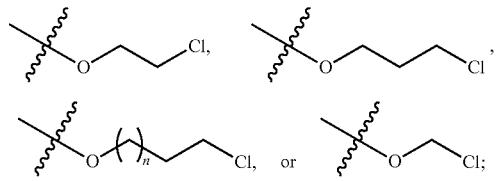

T may be

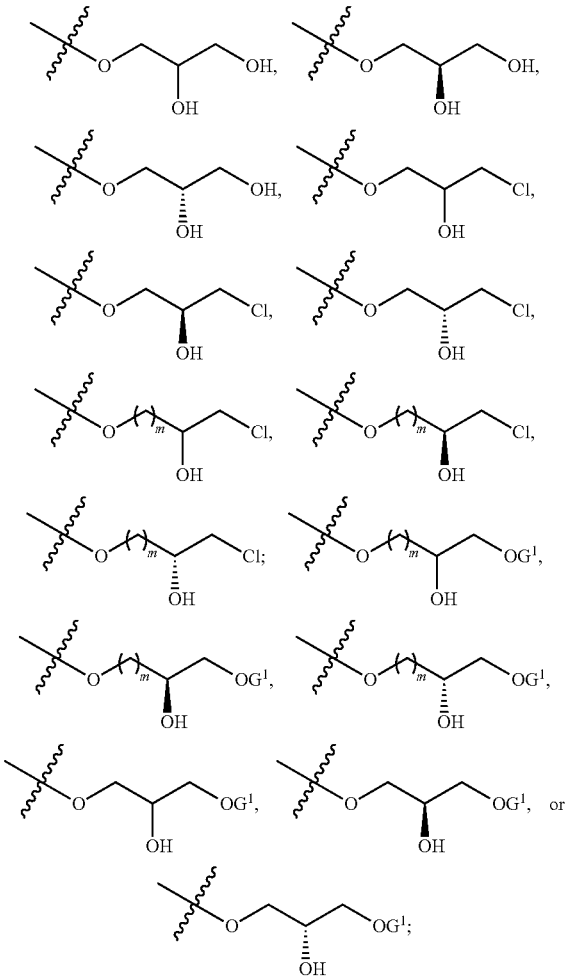

n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

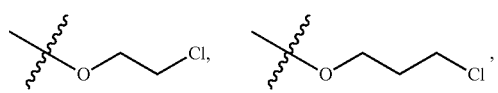

-continued
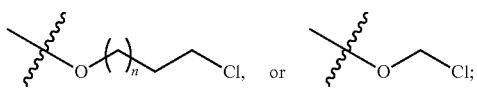
T may be
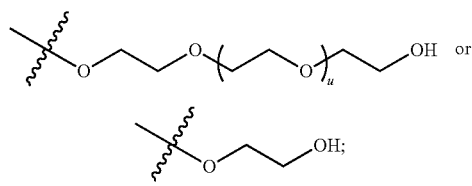
n may be 0, 1, 2, 3, 4, 5, 6, 7 or 8; and u may be 0, 1, 2, 3, 4, 5, 6 or 7. Q may be
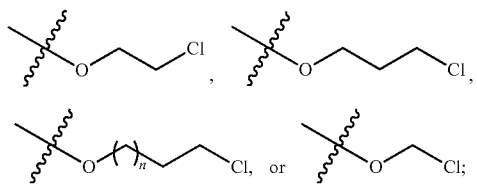
T may be
n may be 0, 1, 2, 3, 4, 5, 6, 7 or 8; and u may be 0, 1, 2, 3, 4, 5, 6 or 7. Q may be
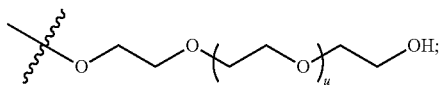
T may be
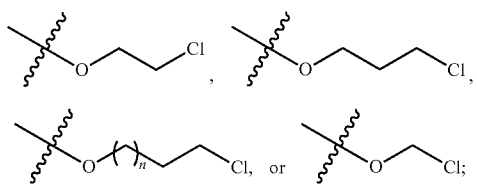
and n may be 0, 1, 2, 3, 4, 5, 6, 7 or 8. Q may be
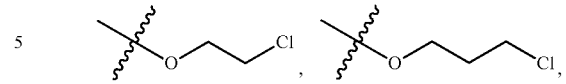
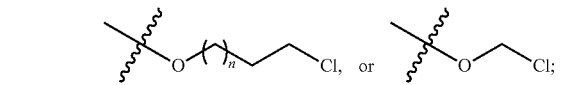
T may be
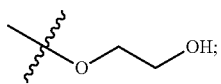 [SMILES: *OCCO]
and n may be 0, 1, 2, 3, 4, 5, 6, 7 or 8. Q may be
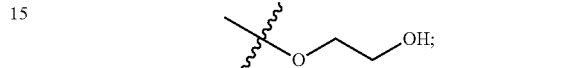
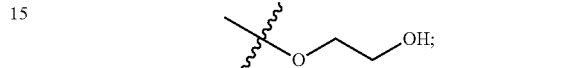
T may be
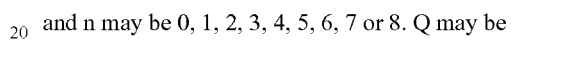
n may be 0, 1, 2, 3, 4, 5, 6, 7 or 8; and m may be 0, 1, 2, 3, 4, 5, 6, 7 or 8. Q may be
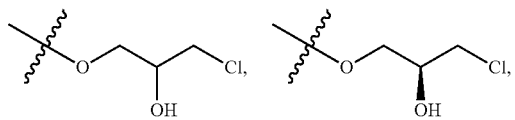
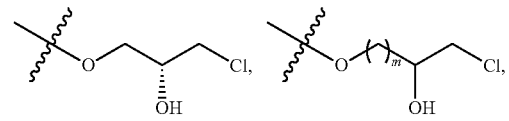
T may be
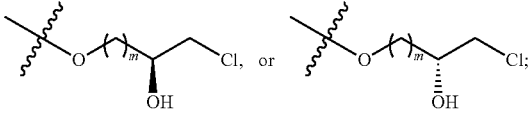

-continued

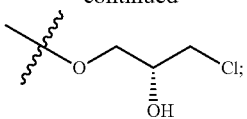

and n may be 0, 1, 2, 3, 4, 5, 6, 7 or 8. Q may be

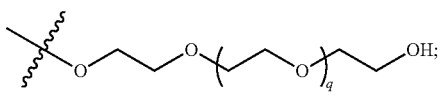

T may be

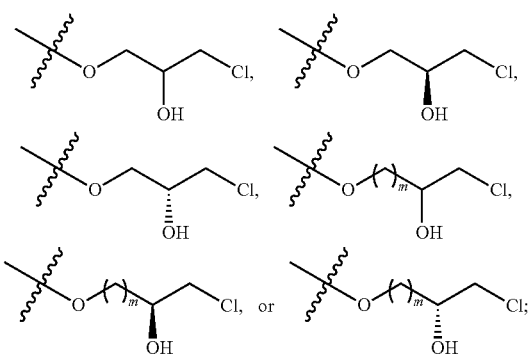

q may be 0, 1, 2, 3, 4, 5, 6 or 7; and m may be 0, 1, 2, 3, 4, 5, 6, 7 or 8. Q may be

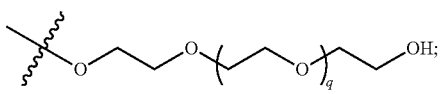

T may be

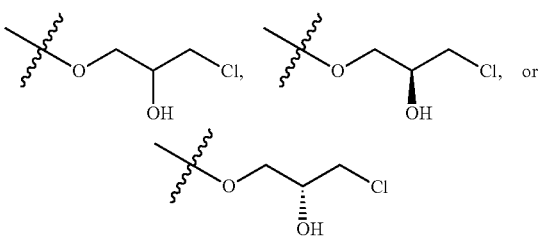

and q may be 0, 1, 2, 3, 4, 5, 6 or 7. Q may be

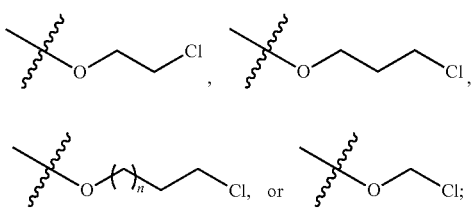

T may be

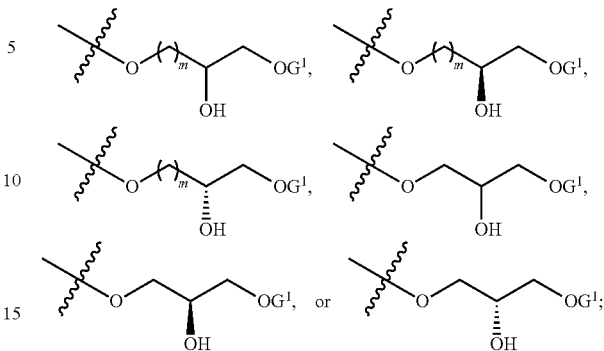

$n$ may be 0, 1, 2, 3, 4, 5, 6, 7 or 8; $m$ may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

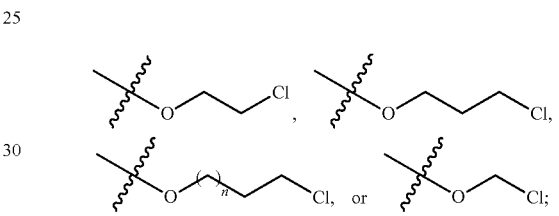

T may be

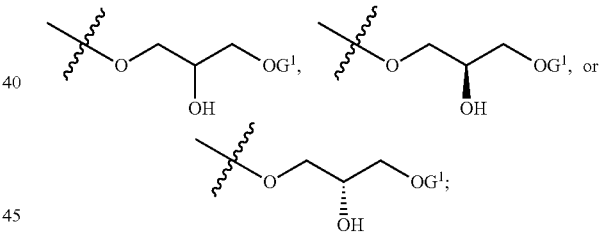

n may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$.

In accordance with another embodiment, there is provided a use of a compound having a structure of Formula IX

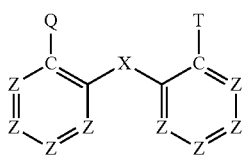

IX wherein: X may be $CH_2$, $CHR^1$, or $CR^1R^2$; each of $R^1$ and $R^2$ may independently be linear or branched, substituted or unsubstituted, saturated or unsaturated $C_1$-$C_{10}$ alkyl, or $R^1$ and $R^2$ may together form a substituted or unsubstituted, saturated or unsaturated cyclic $C_3$-$C_{10}$ alkyl, wherein the optional substituent may be selected from the group consisting of oxo, $OJ'''$, COOH, $R^3$, OH, $OR^3$, F, Cl, Br, I, $NH_2$, $NHR^3$, $NR^3_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3_2$, $NHR^6$, $OPO_3H_3$, $CONR^3R^6$, $NR^3R^6$, and $NO_2$; each $R^3$ may independently be unsubstituted $C_1$-$C_{10}$ alkyl; each $R^6$ may independently be $C_1$-$C_{10}$ acyl; each remaining Z may independently be C-T, N, CH, CF, CCl, CBr, CI, COH, $CG^1$, $COG^1$, $CNH_2$, $CNHG^1$, $CNG^1_2$, $COSO_3H$, $COPO_3H_2$, $CSG^1$, $CSOG^1$, or $CSO_2G^1$; wherein Q may be

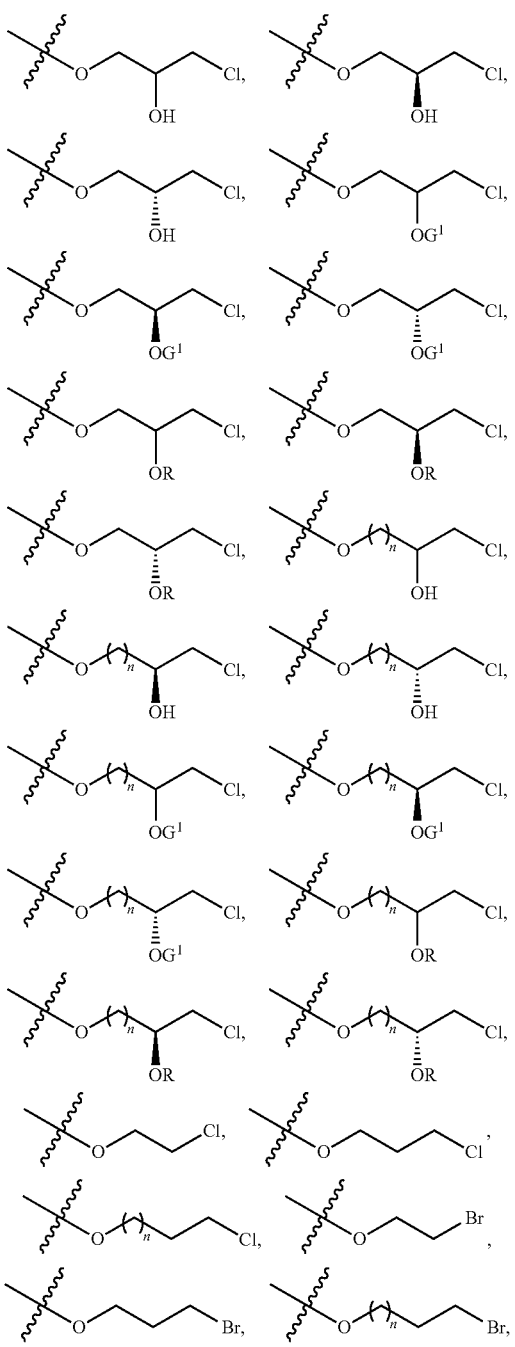

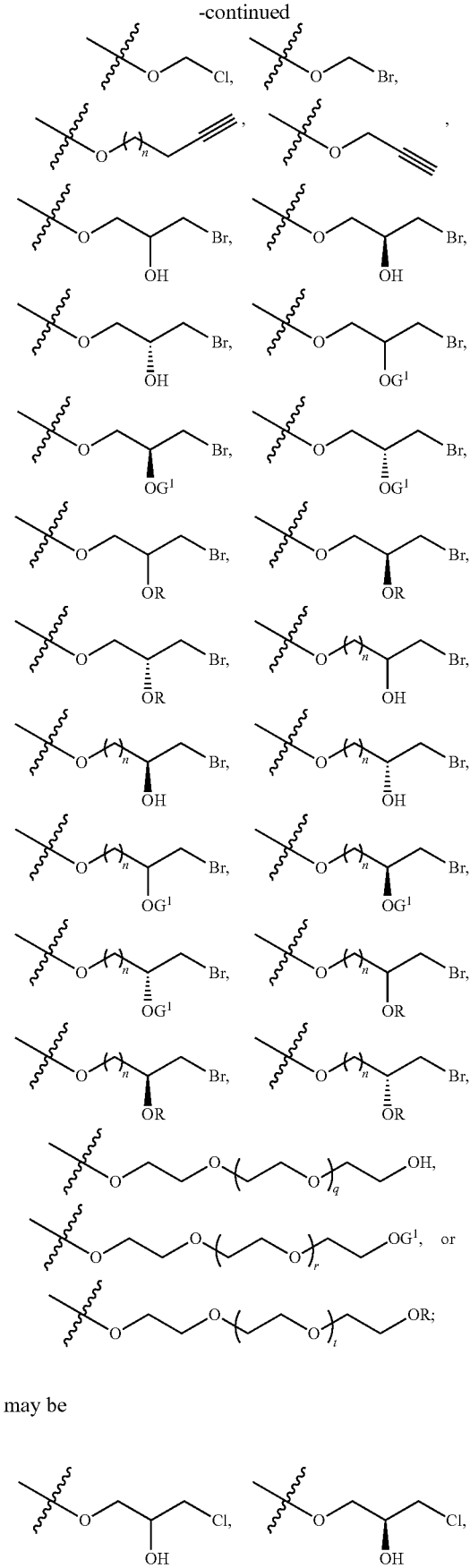

T may be

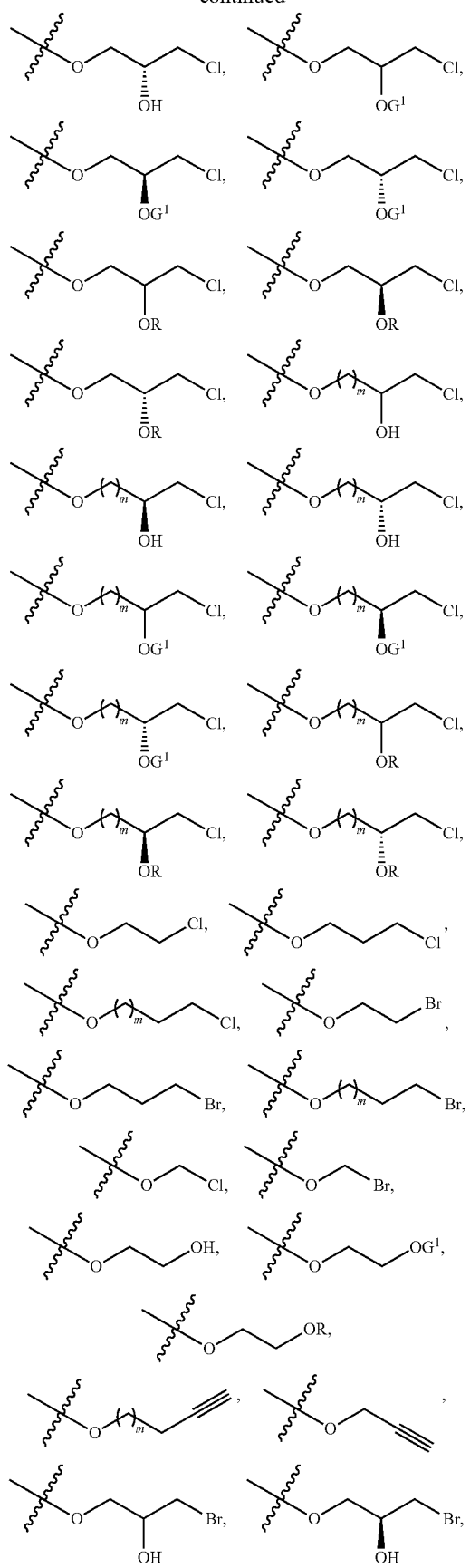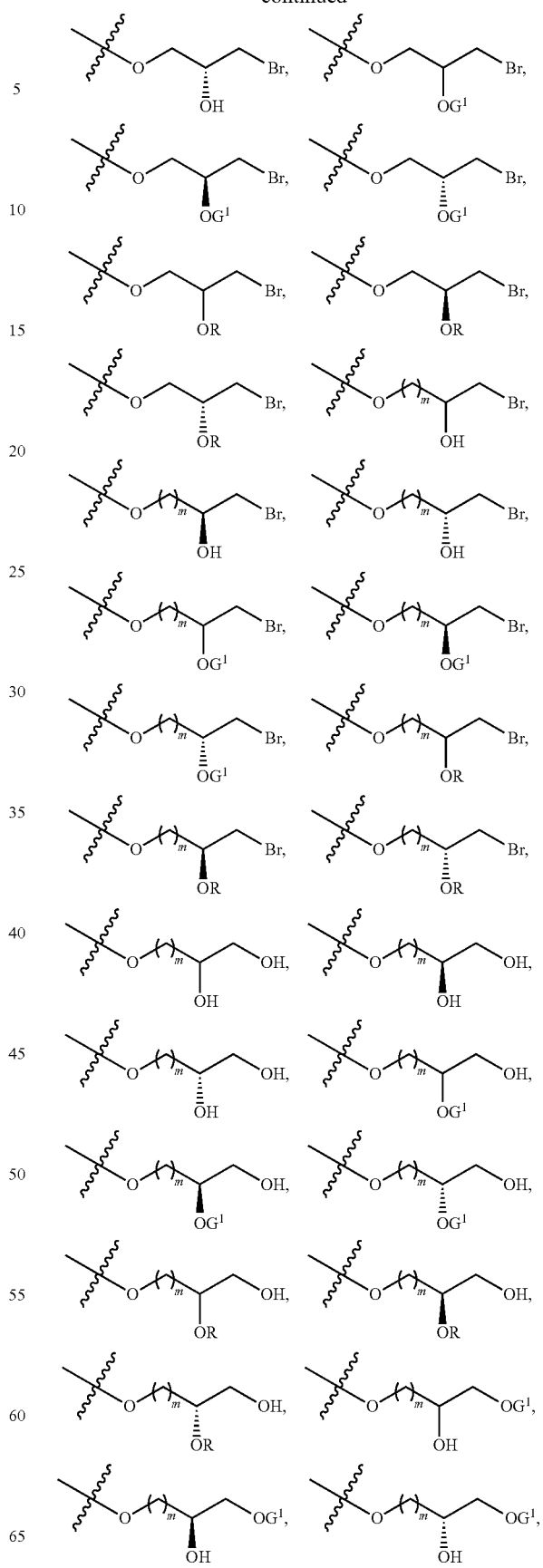

-continued

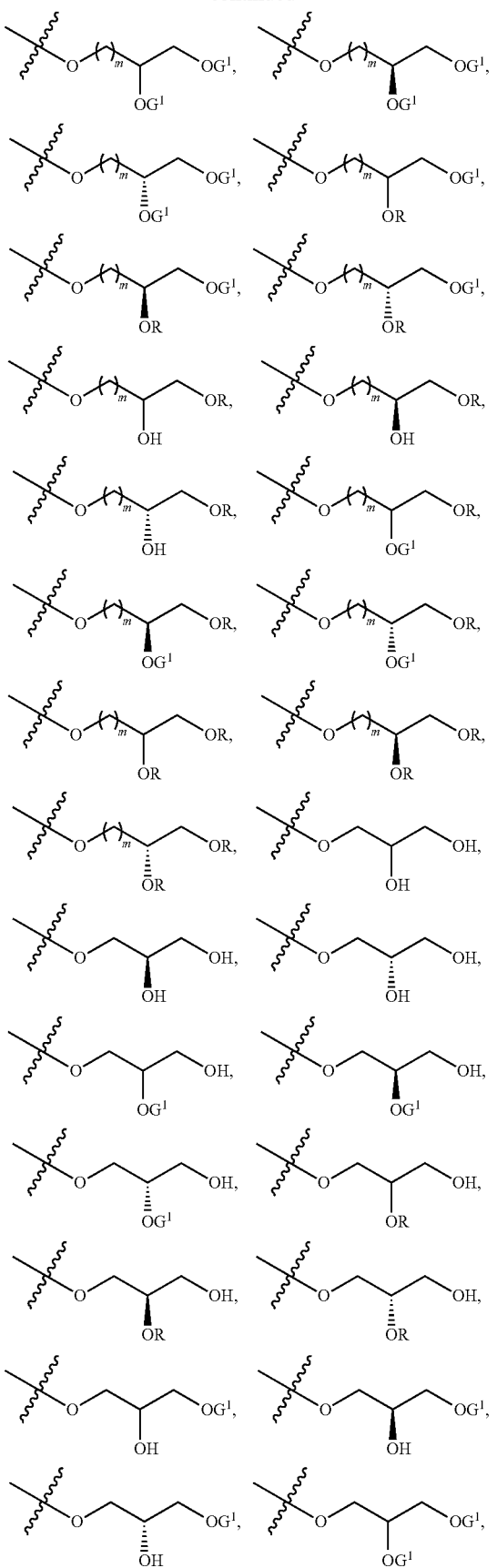
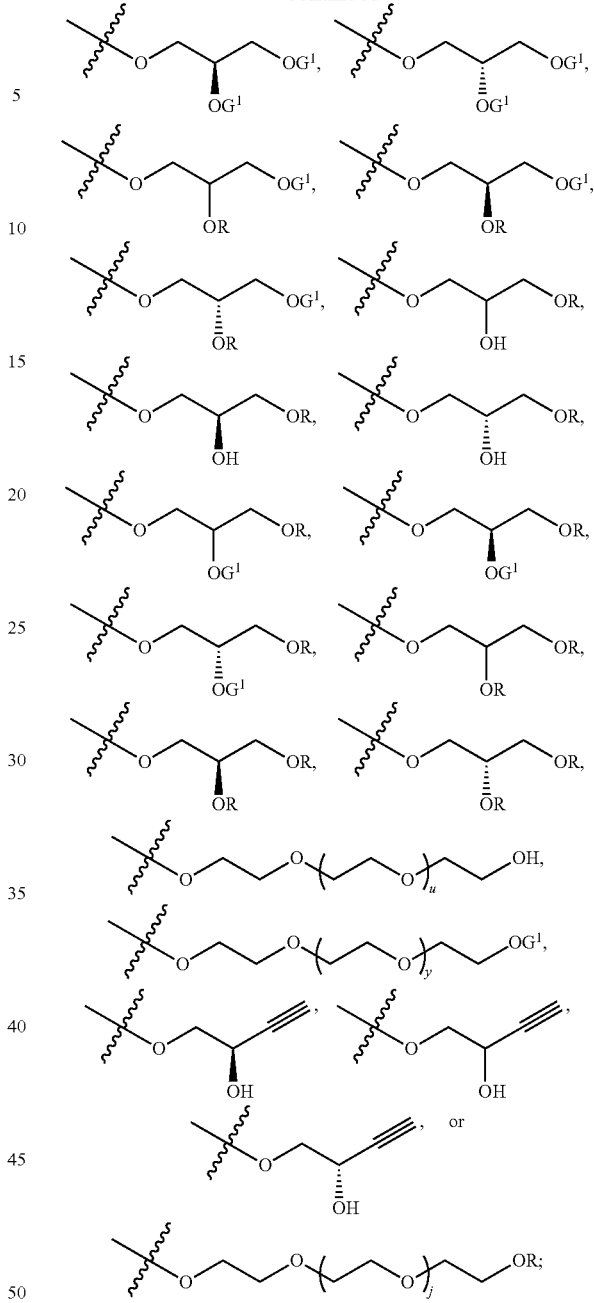

n may be 0, 1, 2, 3, 4, 5, 6, 7 or 8; each of q, r, and t may independently be 0, 1, 2, 3, 4, 5, 6 or 7; m may be 0, 1, 2, 3, 4, 5, 6, 7 or 8; each of u, j and y may independently be 0, 1, 2, 3, 4, 5, 6 or 7; each $G^1$ $G^{1\prime}$ and $G^{1\prime\prime\prime}$ may independently be linear or branched, or aromatic cyclic or non-aromatic cyclic, substituted or unsubstituted, saturated or unsaturated $C_1$-$C_{10}$ alkyl, wherein the optional substituent may be selected from the group consisting of oxo, $OJ^{\prime\prime\prime}$, COOH, $R^4$, OH, $OR^4$, F, Cl, Br, I, $NH_2$, $NHR^4$, $NR^4_2$, CN, SH, $SR^4$, $SO_3H$, $SO_3R^4$, $SO_2R^4$, $OSO_3R^4$, $OR^5$, $CO_2R^4$, $CONH_2$, $CONHR^4$, $CONHR^5$, $CONR^4_2$, $NHR^5$, $OPO_3H_3$, $CONR^4R^5$, $NR^4R^5$, and $NO_2$; each $R^4$ may independently be unsubstituted $C_1$-$C_{10}$ alkyl; each $R^5$ may independently be $C_1$-$C_{10}$ acyl; R may be $C_1$-$C_{10}$ acyl; and each of J″ and J‴ may independently be a moiety selected from TABLE 1; and wherein one or more of the OH groups may be optionally substituted to replace the H with a moiety selected from TABLE 1. Each of $R^1$ and $R^2$ may independently be linear or branched, substituted or unsubstituted, saturated or unsaturated $C_1$-$C_{10}$ alkyl, wherein the optional substituent may be selected from the group consisting of OJ''', F, Cl, Br, I, or $NH_2$. Each Z may independently be $CG^1$, N, CH, CF, CCl, CBr, CI, or COH. Each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$.

Q may be

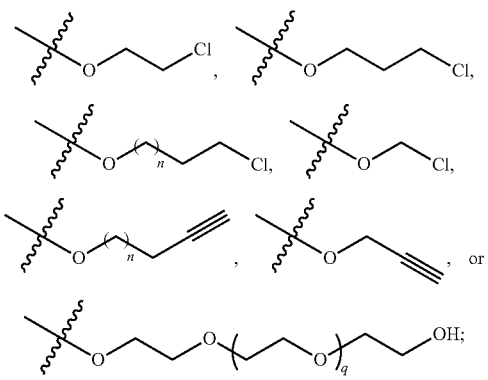

n may be 0, 1, 2, 3, 4, 5, 6, 7 or 8; and q may be 0, 1, 2, 3, 4, 5, 6 or 7. Q may be

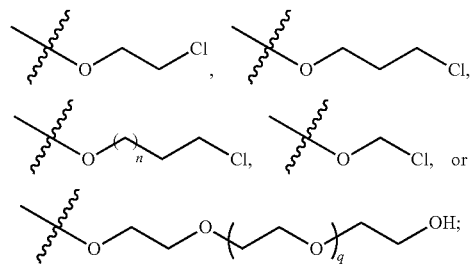

n may be 0, 1, 2, 3, 4, 5, 6, 7 or 8; and q may be 0, 1, 2, 3, 4, 5, 6 or 7. Q may be

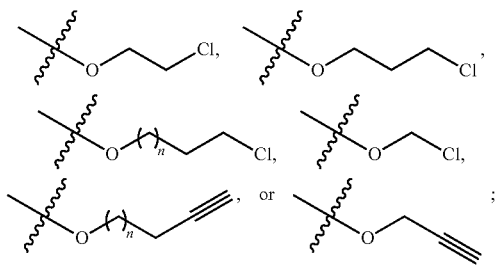

and n may be 0, 1, 2, 3, 4, 5, 6, 7 or 8. Q may be

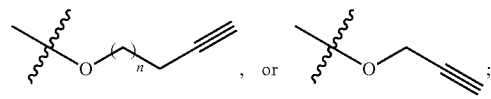

Q may be

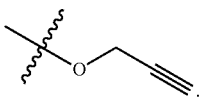 [SMILES: *OCC#C]

Q may be

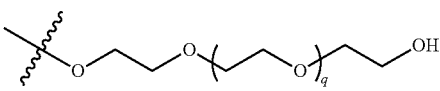

and q may be 0, 1, 2, 3, 4, 5, 6 or 7. q may be 1. Q may be

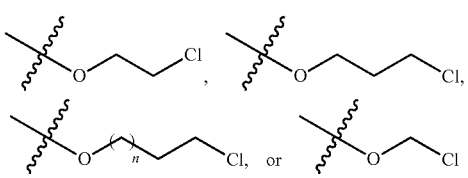

and n may be 0, 1, 2, 3, 4, 5, 6, 7 or 8. Q may be

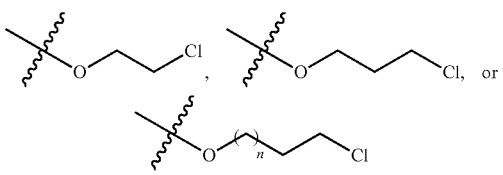

and n may be 0, 1, 2, 3, 4, 5, 6, 7 or 8. Q may be

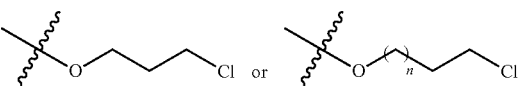

and n may be 0, 1, 2, 3, 4, 5, 6, 7 or 8. Q may be

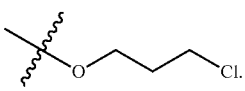 [SMILES: *OCCCCl]

Q may be

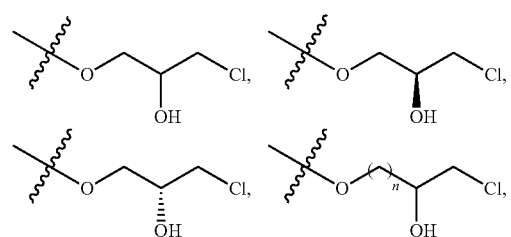

-continued

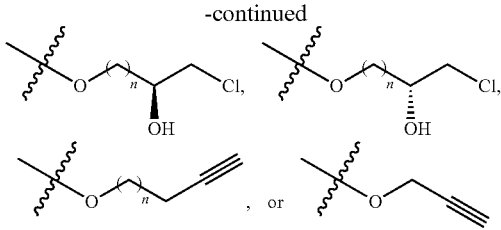

and n may be 0, 1, 2, 3, 4, 5, 6, 7 or 8. Q may be

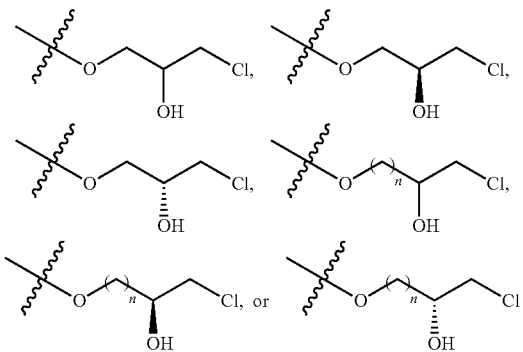

and n may be 0, 1, 2, 3, 4, 5, 6, 7 or 8. Q may be

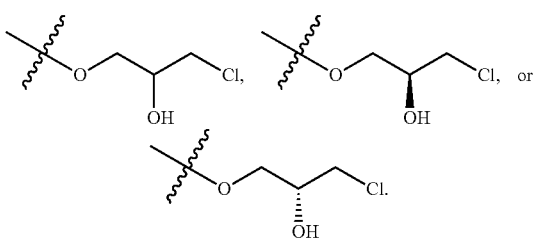

T may be

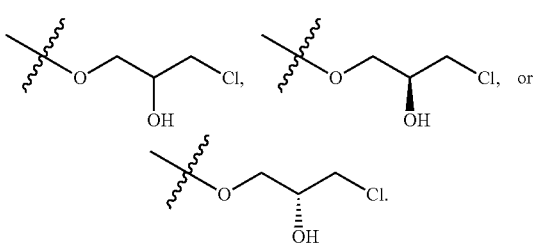

T may be

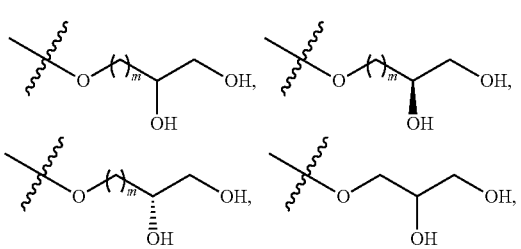

-continued

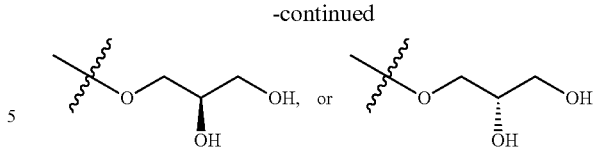

and m may be 0, 1, 2, 3, 4, 5, 6, 7 or 8. T may be

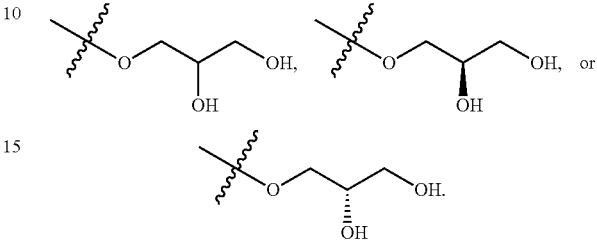

T may be

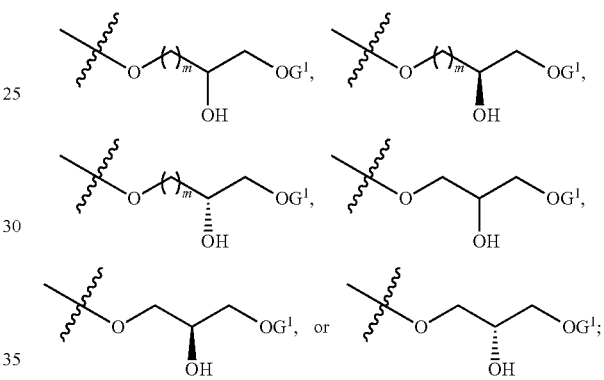

m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, NH$_2$, CN, SH, SO$_3$H, CONH$_2$, OPO$_3$H$_3$, and NO$_2$. T may be

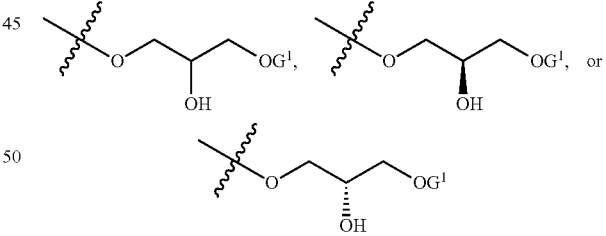

and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, NH$_2$, CN, SH, SO$_3$H, CONH$_2$, OPO$_3$H$_3$, and NO$_2$. T may be

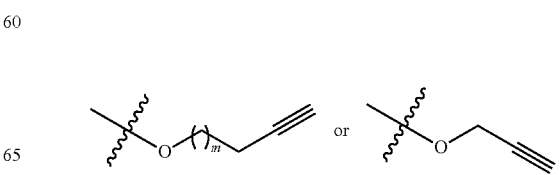

and m may be 0, 1, 2, 3, 4, 5, 6, 7 or 8. T may be

T may be

T may be and u may be 0, 1, 2, 3, 4, 5, 6 or 7. T may be and m may be 0, 1, 2, 3, 4, 5, 6, 7 or 8. T may be T may be and u may be 0, 1, 2, 3, 4, 5, 6 or 7.

Q may be

T may be

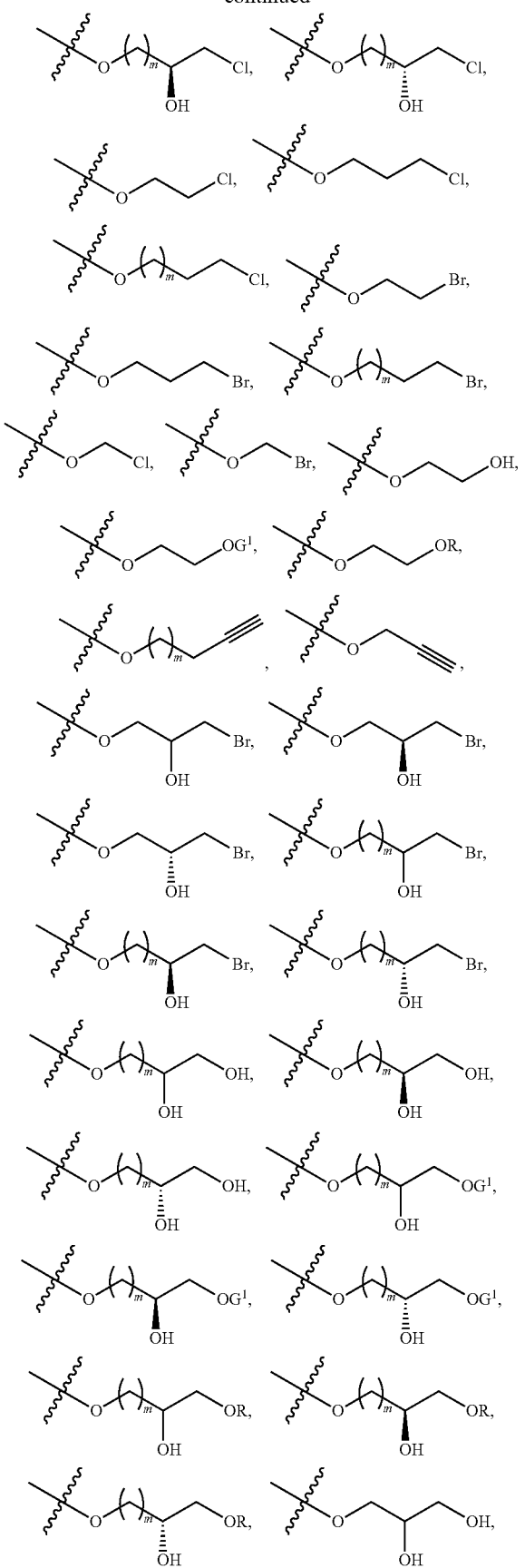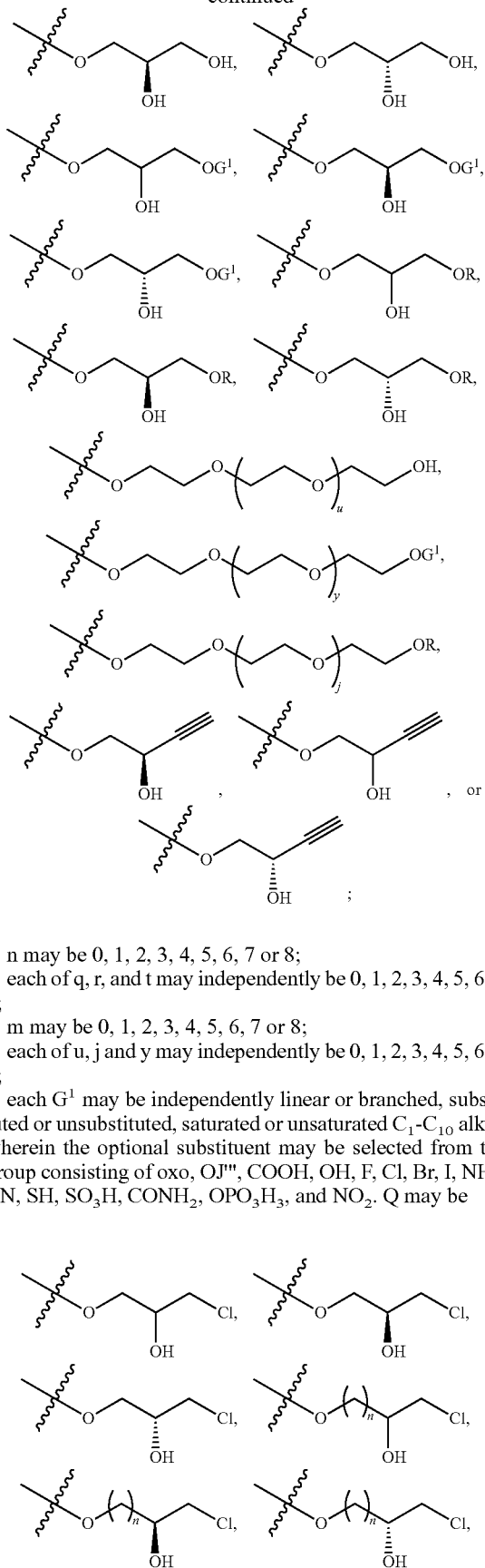

n may be 0, 1, 2, 3, 4, 5, 6, 7 or 8;
each of q, r, and t may independently be 0, 1, 2, 3, 4, 5, 6 or 7;
m may be 0, 1, 2, 3, 4, 5, 6, 7 or 8;
each of u, j and y may independently be 0, 1, 2, 3, 4, 5, 6 or 7;
each $G^1$ may be independently linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

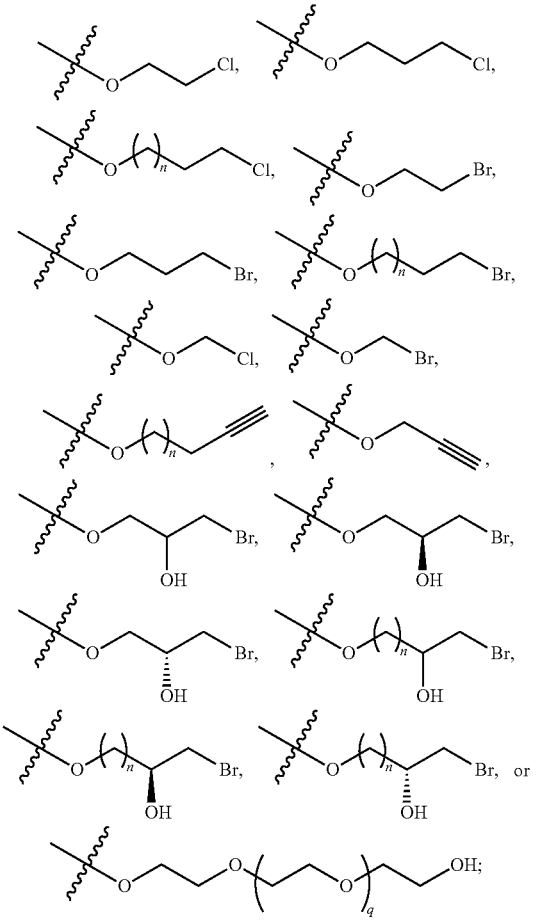

T may be

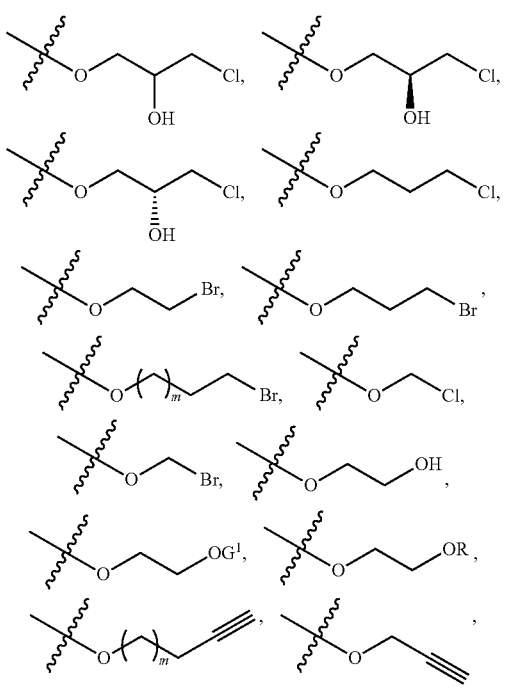

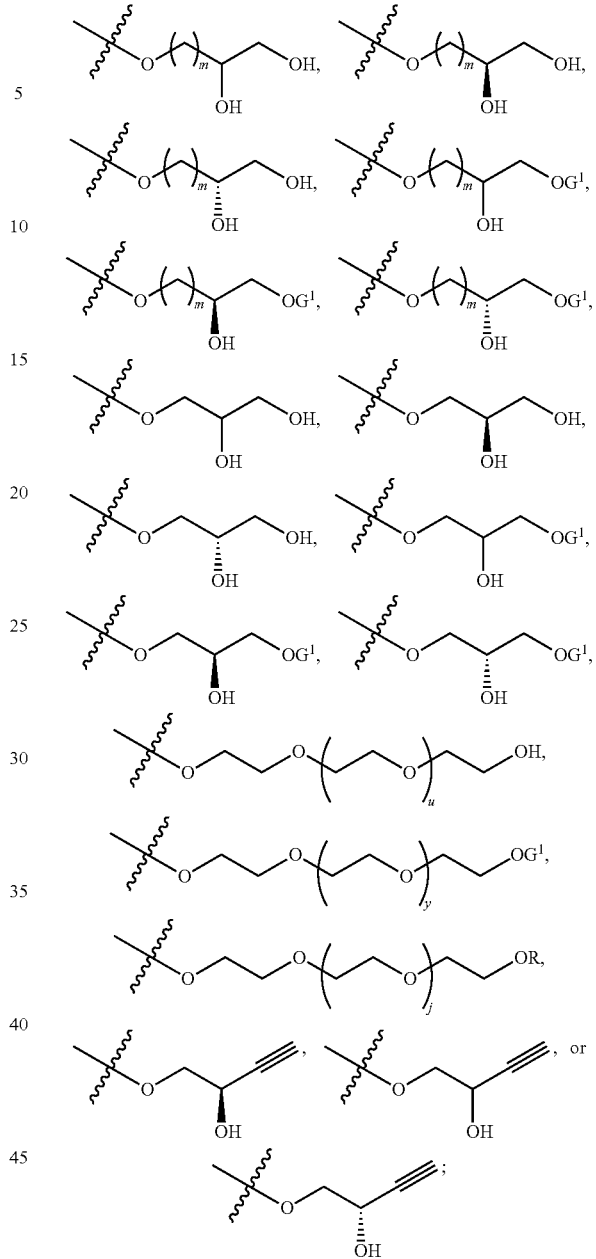

n may be 0, 1, 2, 3, 4, 5, 6, 7 or 8; q may be 0, 1, 2, 3, 4, 5, 6 or 7; m may be 0, 1, 2, 3, 4, 5, 6, 7 or 8; each of u, j and y may independently be 0, 1, 2, 3, 4, 5, 6 or 7; each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$; and each of J'' and J''' may independently be a moiety selected from TABLE 1. Q may be

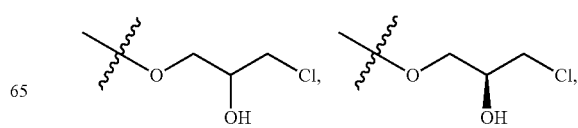

-continued

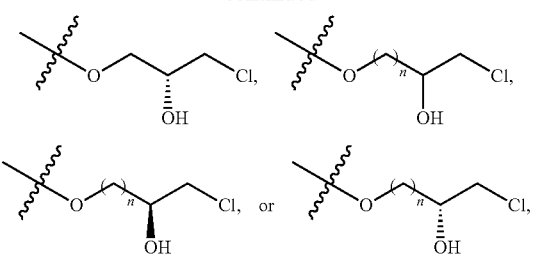

T may be

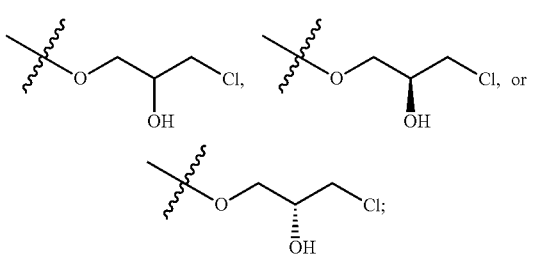

and n may be 0, 1, 2, 3, 4, 5, 6, 7 or 8. Q may be

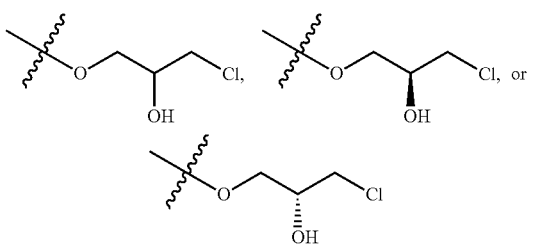

and T may be

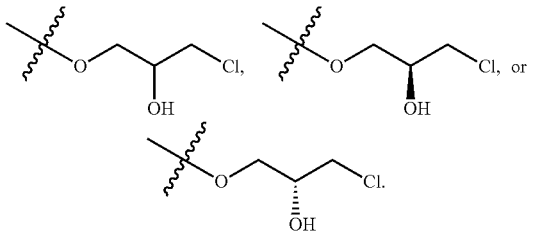

Q may be

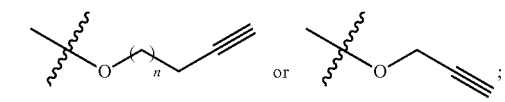

T may be

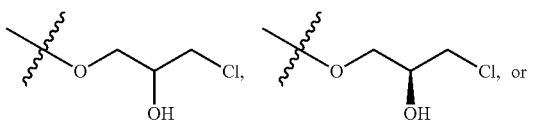

-continued

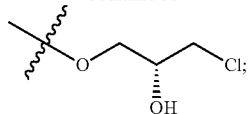

and n may be 0, 1, 2, 3, 4, 5, 6, 7. Q may be

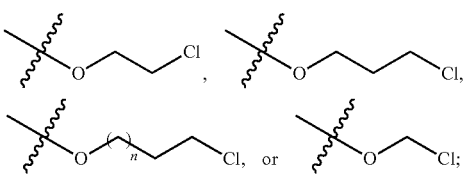

T may be

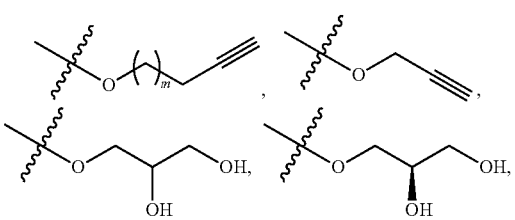

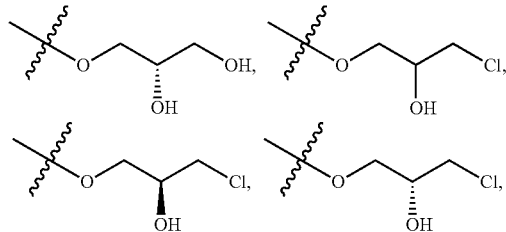

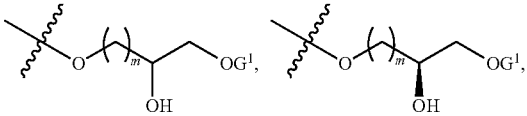

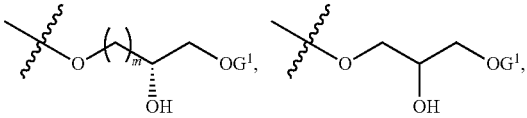

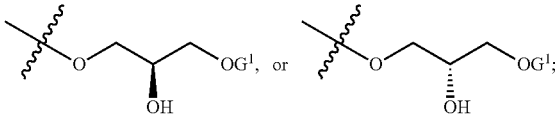

n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$. Q may be

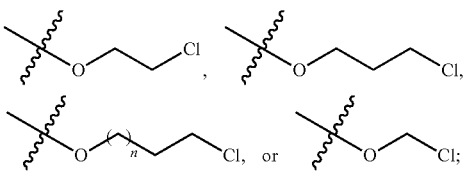

T may be
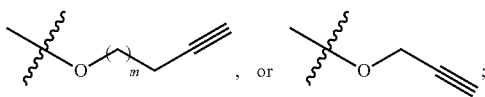
n may be 0, 1, 2, 3, 4, 5, 6, 7 or 8, and m may be 0, 1, 2, 3, 4, 5, 6, 7 or 8. Q may be
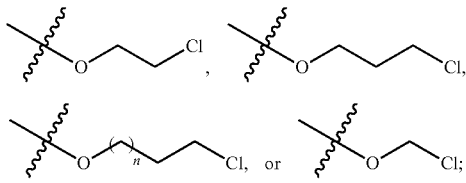
T may be
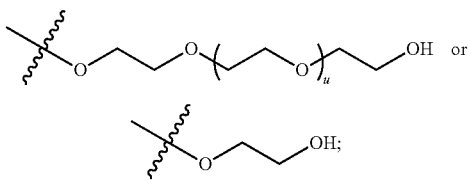
n may be 0, 1, 2, 3, 4, 5, 6, 7 or 8; and u may be 0, 1, 2, 3, 4, 5, 6 or 7. Q may be
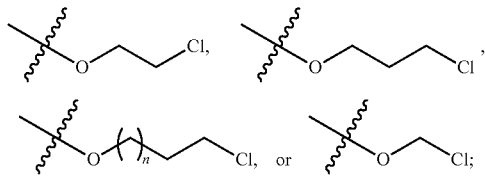
T may be
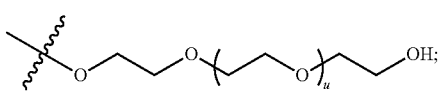
n may be 0, 1, 2, 3, 4, 5, 6, 7 or 8; and u may be 0, 1, 2, 3, 4, 5, 6 or 7. Q may be
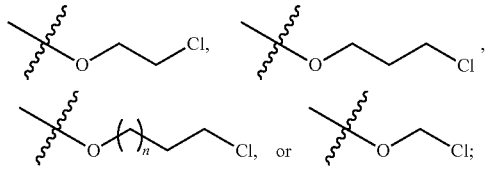
T may be
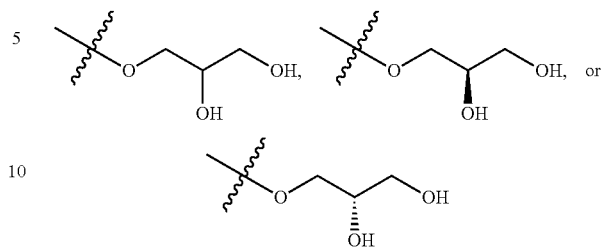
and n may be 0, 1, 2, 3, 4, 5, 6, 7 or 8. Q may be T
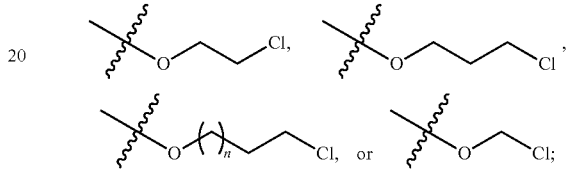
may be
and n may be 0, 1, 2, 3, 4, 5, 6, 7 or 8. Q may be
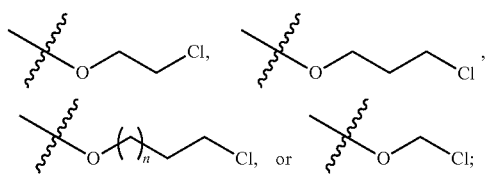
T may be
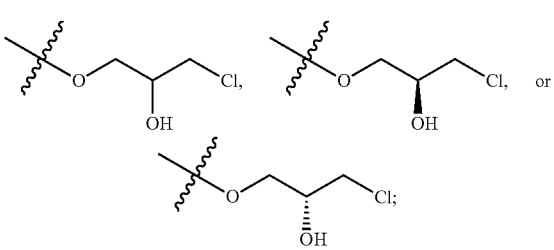
and n may be 0, 1, 2, 3, 4, 5, 6, 7 or 8. Q may be
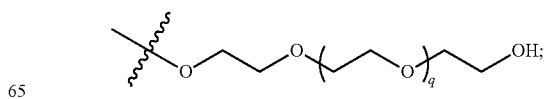

T may be

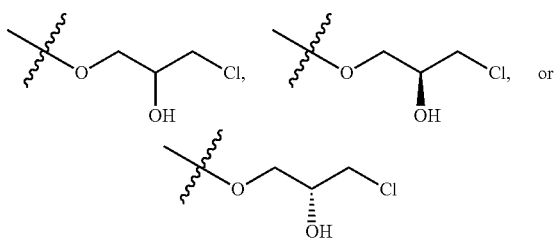

and q may be 0, 1, 2, 3, 4, 5, 6 or 7. Q may be

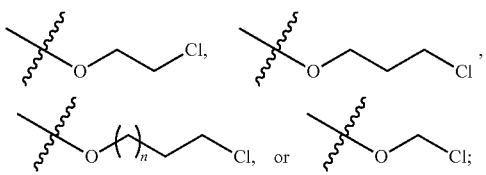

T may be

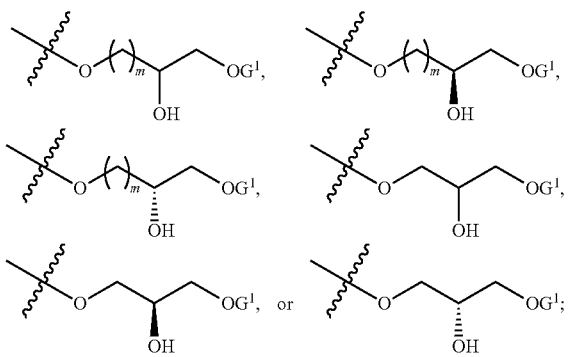

n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

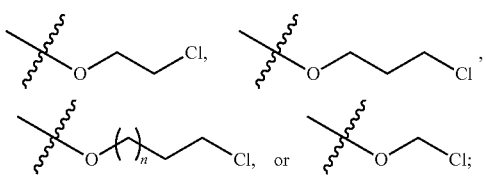

T may be

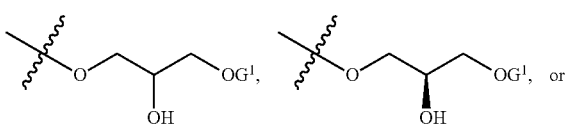

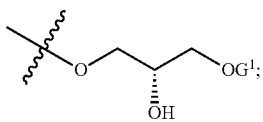

n may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

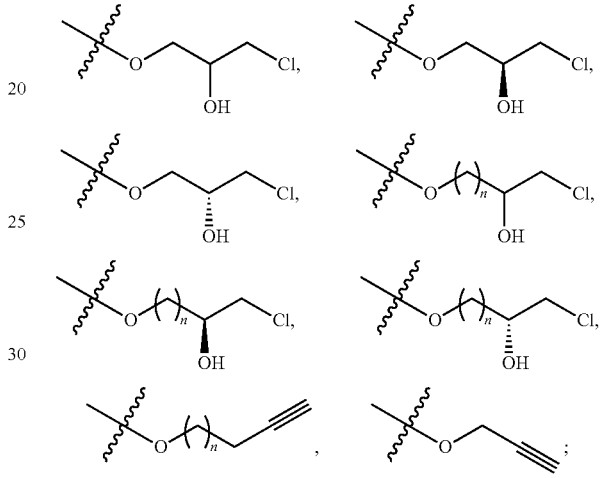

T may be

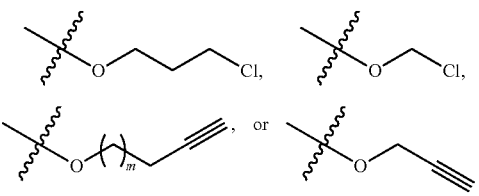

n may be 0, 1, 2, 3, 4, 5, 6, 7 or 8; and m may be 0, 1, 2, 3, 4, 5, 6, 7 or 8. Q may be

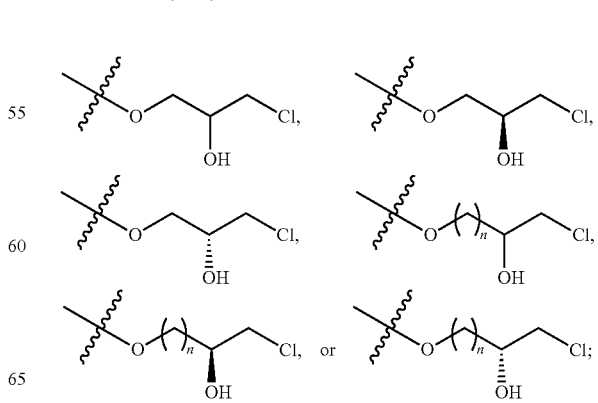

T may be
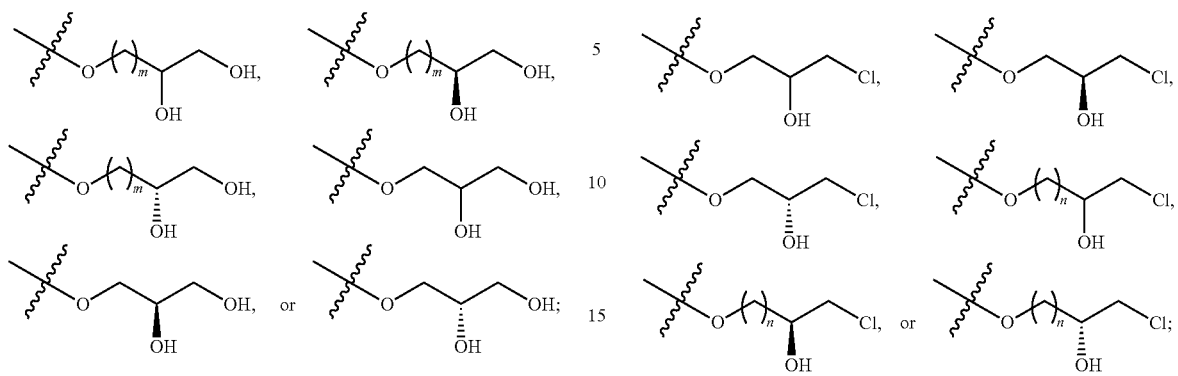
n may be 0, 1, 2, 3, 4, 5, 6, 7 or 8; and m may be 0, 1, 2, 3, 4, 5, 6, 7 or 8. Q may be
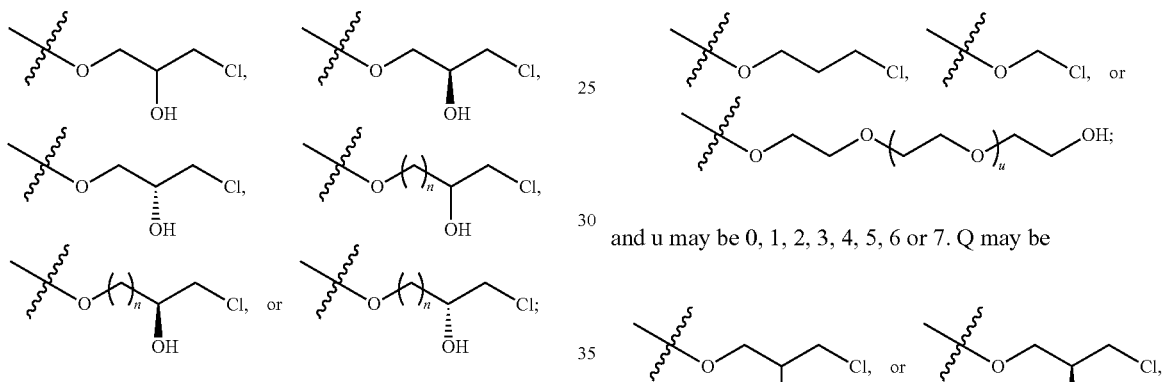
T may be
n may be 0, 1, 2, 3, 4, 5, 6, 7 or 8; and m may be 0, 1, 2, 3, 4, 5, 6, 7 or 8. Q may be
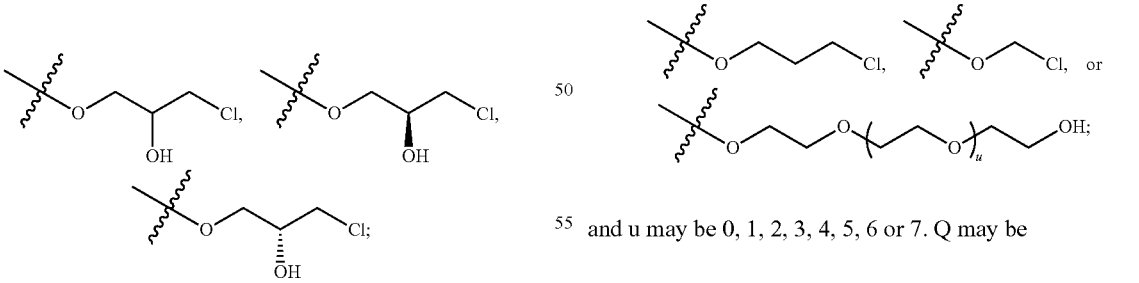
T may be
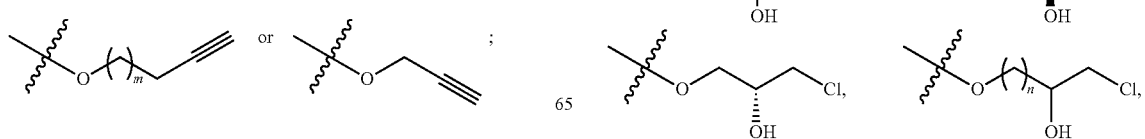
and m may be 0, 1, 2, 3, 4, 5, 6, 7 or 8. Q may be
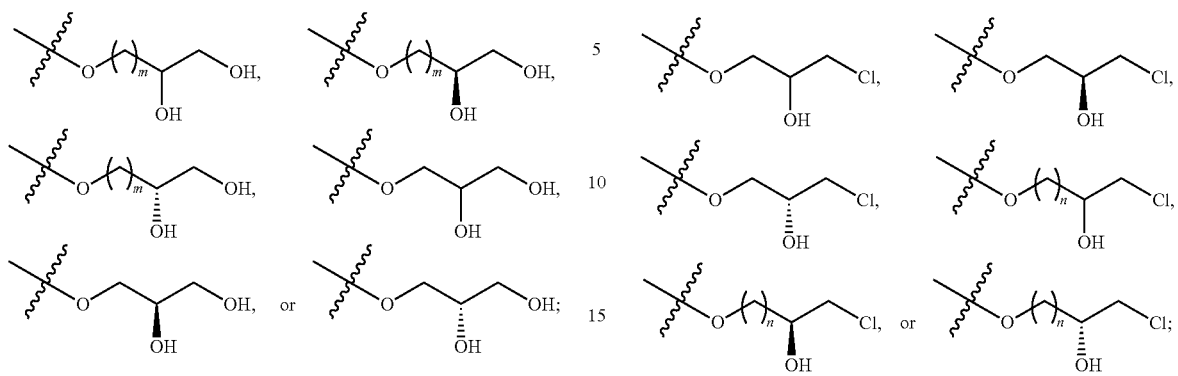
and T may be
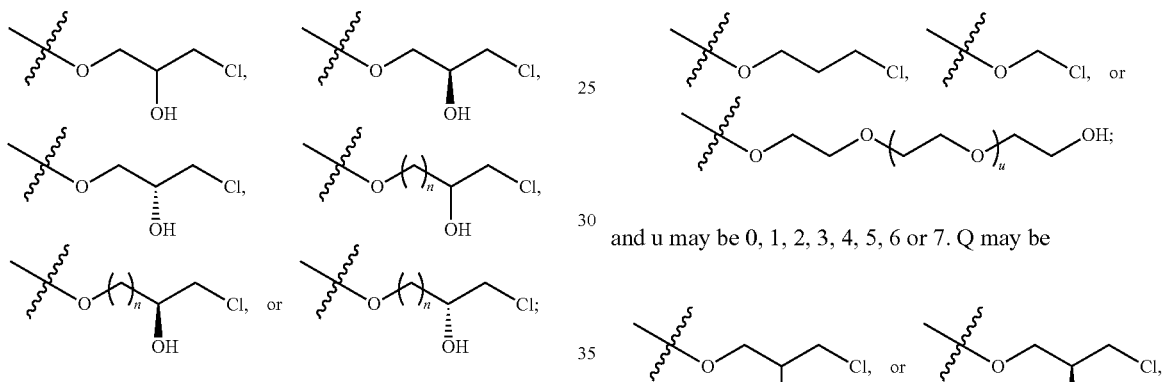
and u may be 0, 1, 2, 3, 4, 5, 6 or 7. Q may be
and T may be
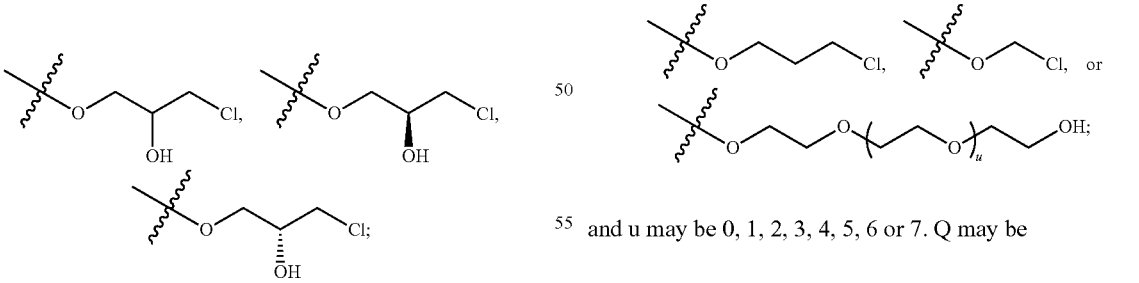
and u may be 0, 1, 2, 3, 4, 5, 6 or 7. Q may be
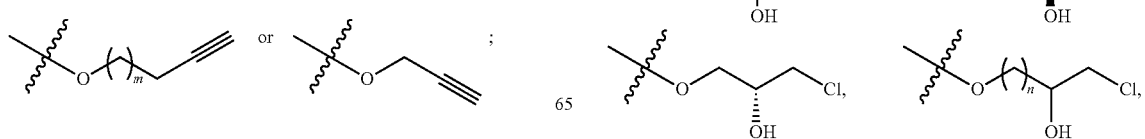

-continued
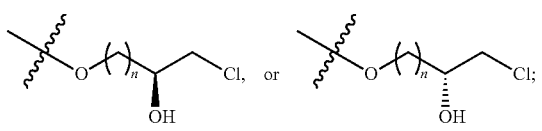
T may be
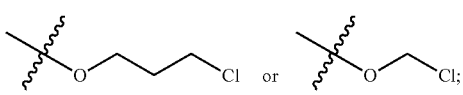
n may be 0, 1, 2, 3, 4, 5, 6, 7 or 8. Q may be
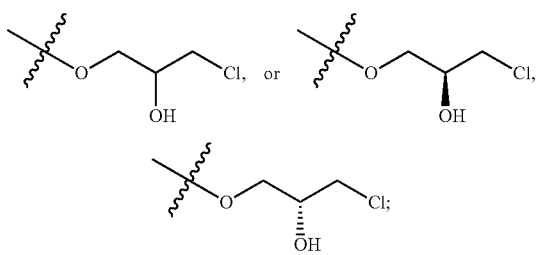 [SMILES: *OCC(O)CCl ; "or" ; *OC[C@H](O)CCl ; *OC[C@@H](O)CCl]
T may be
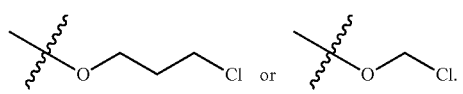
Q may be
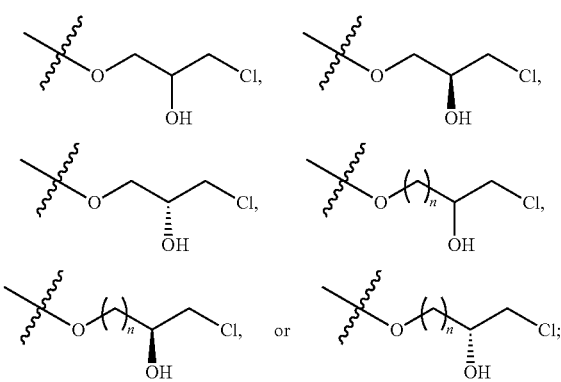
and T may be
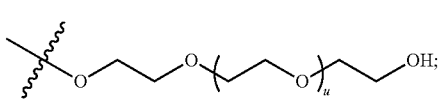
and u may be 0, 1, 2, 3, 4, 5, 6 or 7. Q may be
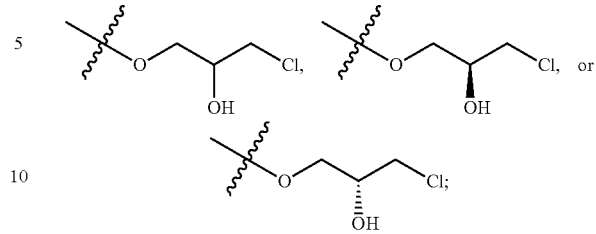
and T may be
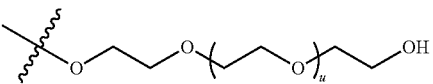
and u may be 0, 1, 2, 3, 4, 5, 6 or 7. Q may be
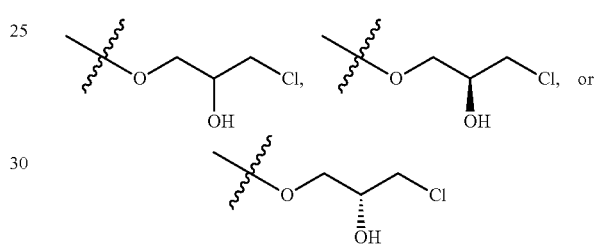
and T may be
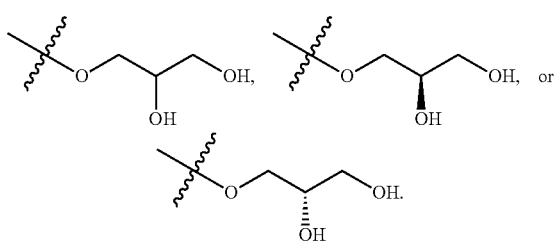
Q may be
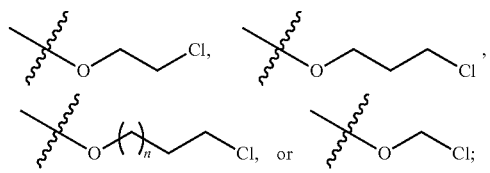
T may be
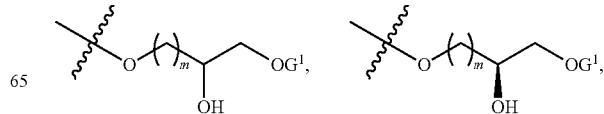

-continued

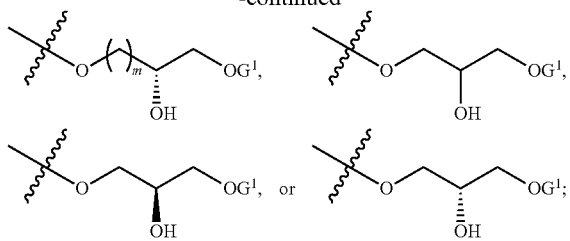

n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

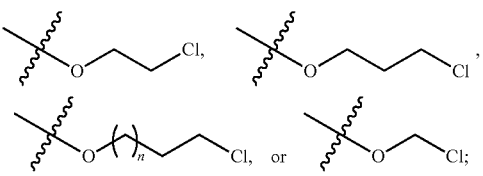

T may be

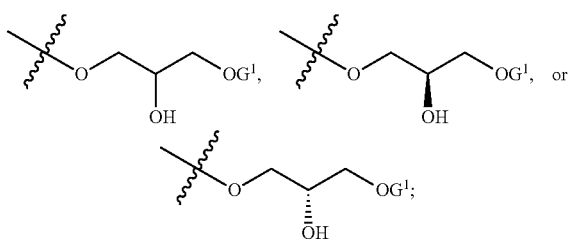

n may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$.

Each J'' and J''', when present, may independently be an amino acid based moiety selected from TABLE 1. Each J'' and J''', when present, may independently be

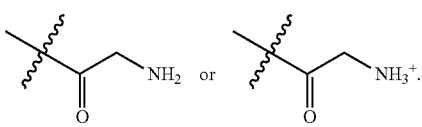

Each $G^1$ $G^{1'}$ and $G^{1'''}$, when present, is an independently linear or branched, substituted or unsubstituted, saturated or unsaturated $C_1$-$C_{10}$ alkyl. $G^1$, when present, may be cyclohexyl, $CH_2CH_2CH_2CH_3$, $CH_2C\equiv CH$ or $CH(CH_3)_2$. $G^1$, when present, may be $CH_2C\equiv CH$ or $CH(CH_3)_2$.

One or more of the OH groups of the compound may be optionally substituted to replace the H with a moiety selected from TABLE 1. The moiety selected from TABLE 1 may be an amino acid based moiety selected from TABLE 1. The moiety selected from TABLE 1 may be

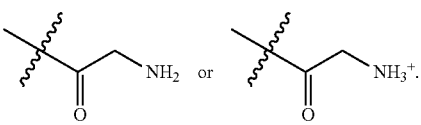

Each of the remaining Z may independently be selected from N; $CG^1$, CH; CF; CCl; CBr; and CI. Each remaining Z may independently be CH, CF, CCl, CBr, CI, or $CG^1$. Each of the remaining Z may independently be selected from $CG^1$; CH; CCl; and CBr. Each remaining Z may independently be CH, CBr, or $CG^1$. Each remaining Z may independently be CH, CBr, or $CCH_3$. Each remaining Z at the meta position to X may independently be CBr or $CG^1$. Each remaining Z at the meta position to X may independently be CBr or $CCH_3$. Each remaining Z at the ortho position to X may be CH. Each remaining Z at the meta position to X may independently be CBr or $CCH_3$ and each remaining Z at the ortho position to X may be CH. Each remaining Z may be CH.

X may be $CH_2$, $CHR^1$, or $CR^1R^2$; each of $R^1$ and $R^2$ may independently be linear or branched, substituted or unsubstituted, saturated or unsaturated $C_1$-$C_{10}$ alkyl, wherein the optional substituent may be selected from the group consisting of OJ''', $R^3$, $OR^3$, F, Cl, Br, I, $NH_2$, $NHR^3$, $NR^3_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3_2$, $NHR^6$, $OPO_3H_3$, $CONR^3R^6$, $NR^3R^6$, and $NO_2$; each $R^3$ may independently be unsubstituted $C_1$-$C_{10}$ alkyl; and each $R^6$ may independently be $C_1$-$C_{10}$ acyl. X may be $CH_2$. X may be $CHR^1$; $R^1$ may be linear or branched, substituted or unsubstituted, saturated or unsaturated $C_1$-$C_{10}$ alkyl, wherein the optional substituent may be selected from the group consisting of OJ''', $R^3$, $OR^3$, F, Cl, Br, I, $NH_2$, $NHR^3$, $NR^3_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3_2$, $NHR^6$, $OPO_3H_3$, $CONR^3R^6$, $NR^3R^6$, and $NO_2$; each $R^3$ may independently be unsubstituted $C_1$-$C_{10}$ alkyl; and each $R^6$ may independently be $C_1$-$C_{10}$ acyl. $R^1$ may be linear or branched, unsubstituted, saturated or unsaturated $C_1$-$C_{10}$ alkyl. $R^1$ may be linear or branched, unsubstituted, saturated $C_1$-$C_{10}$ alkyl. $R^1$ may be $CH_3$. X may be $CR^1R^2$; each of $R^1$ and $R^2$ may independently be linear or branched, substituted or unsubstituted, saturated or unsaturated $C_1$-$C_{10}$ alkyl, or $R^1$ and $R^2$ together form a substituted or unsubstituted, saturated or unsaturated cyclic $C_3$-$C_{10}$ alkyl, wherein the optional substituent may be selected from the group consisting of OJ''', $R^3$, $OR^3$, F, Cl, Br, I, $NH_2$, $NHR^3$, $NR^3_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3_2$, $NHR^6$, $OPO_3H_3$, $CONR^3R^6$, $NR^3R^6$, and $NO_2$; each $R^3$ may independently be unsubstituted $C_1$-$C_{10}$ alkyl; and each $R^6$ may independently be $C_1$-$C_{10}$ acyl. X may be $CR^1R^2$; each of $R^1$ and $R^2$ may independently be linear or branched, substituted or unsubstituted, saturated or unsaturated $C_1$-$C_{10}$ alkyl, wherein the optional substituent may be selected from the group consisting of OJ''', $R^3$, $OR^3$, F, Cl, Br, I, $NH_2$, $NHR^3$, $NR^3_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3_2$, $NHR^6$, $OPO_3H_3$, $CONR^3R^6$, $NR^3R^6$, and $NO_2$; each $R^3$ may independently be unsubstituted $C_1$-$C_{10}$ alkyl; and each $R^6$ may independently be $C_1$-$C_{10}$ acyl. X may be $CR^1R^2$; each of $R^1$ and $R^2$ may independently be linear or branched, unsubstituted, saturated or unsaturated $C_1$-$C_{10}$ alkyl. X may be $CR^1R^2$; each of $R^1$ and $R^2$ may independently be linear or branched, unsubstituted, saturated $C_1$-$C_{10}$ alkyl. X may be $CR^1R^2$; each of $R^1$ and $R^2$ may be $CH_3$. X may be $CR^1R^2$; $R^1$ and $R^2$ together form a substituted or unsubstituted, saturated or unsaturated cyclic $C_3$-$C_{10}$ alkyl, wherein the optional substituent may be selected from the group consisting of $OJ'''$, $R^3$, $OR^3$, F, Cl, Br, I, $NH_2$, $NHR^3$, $NR^3{}_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3{}_2$, $NHR^6$, $OPO_3H_3$, $CONR^3R^6$, $NR^3R^6$, and $NO_2$; each $R^3$ may independently be unsubstituted $C_1$-$C_{10}$ alkyl; and each $R^6$ may be independently $C_1$-$C_{10}$ acyl. X may be $CR^1R^2$; $R^1$ and $R^2$ together form a substituted or unsaturated, saturated cyclic $C_6$ alkyl, wherein the optional substituent may be selected from the group consisting of $OJ'''$, $R^3$, $OR^3$, F, Cl, Br, I, $NH_2$, $NHR^3$, $NR^3{}_2$, CN, SH, $SR^3$, $SOR^3$, $SO_3H$, $SO_3R^3$, $SO_2R^3$, $OSO_3R^3$, $OR^6$, $CO_2R^3$, $CONH_2$, $CONHR^3$, $CONHR^6$, $CONR^3{}_2$, $NHR^6$, $OPO_3H_3$, $CONR^3R^6$, $NR^3R^6$, and $NO_2$; each $R^3$ may independently be unsubstituted $C_1$-$C_{10}$ alkyl; and each $R^6$ may independently be $C_1$-$C_{10}$ acyl. X may be $CR^1R^2$; $R^1$ and $R^2$ together form an unsubstituted, saturated cyclic $C_6$ alkyl.

The compound may be selected from one or more of the following:

EPI-033

EPI-034

EPI-035

EPI-036

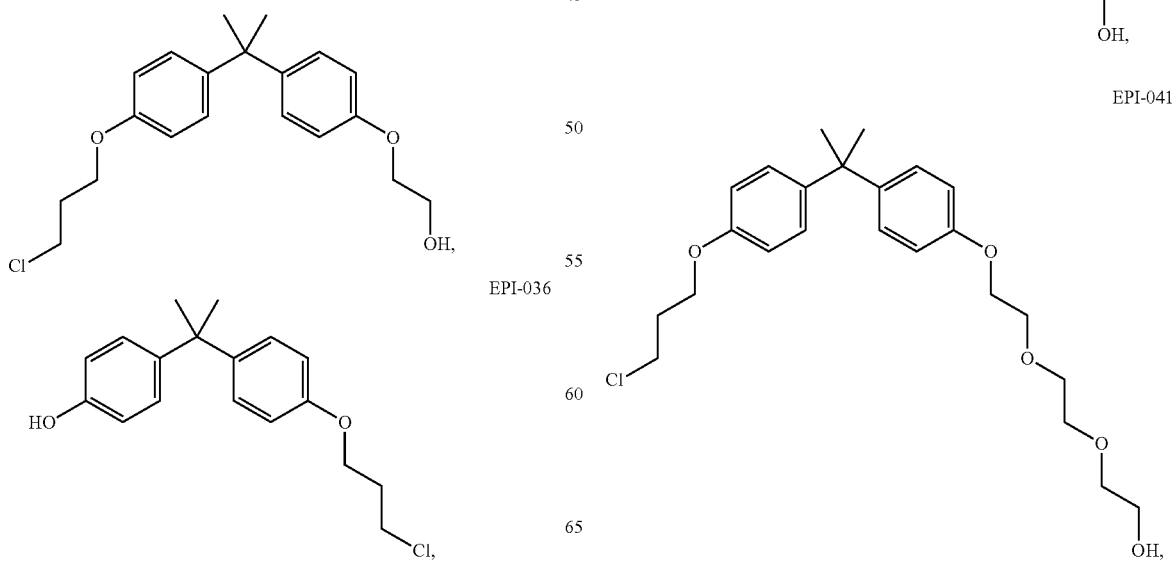

-continued

EPI-037

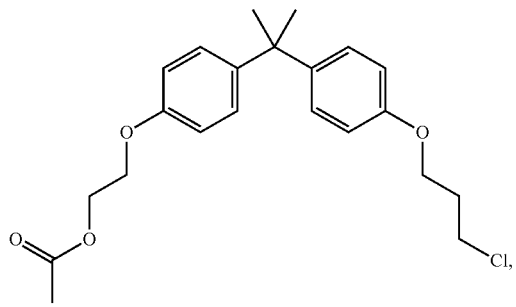

EPI-038

EPI-040

EPI-041

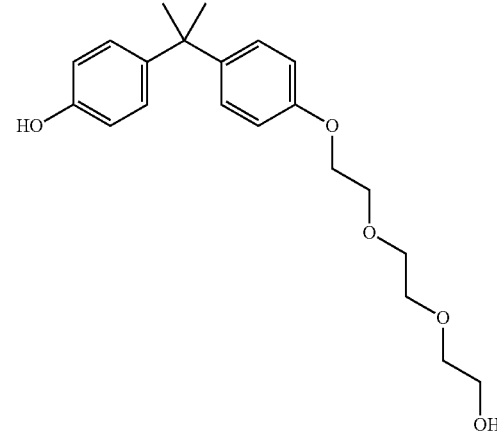

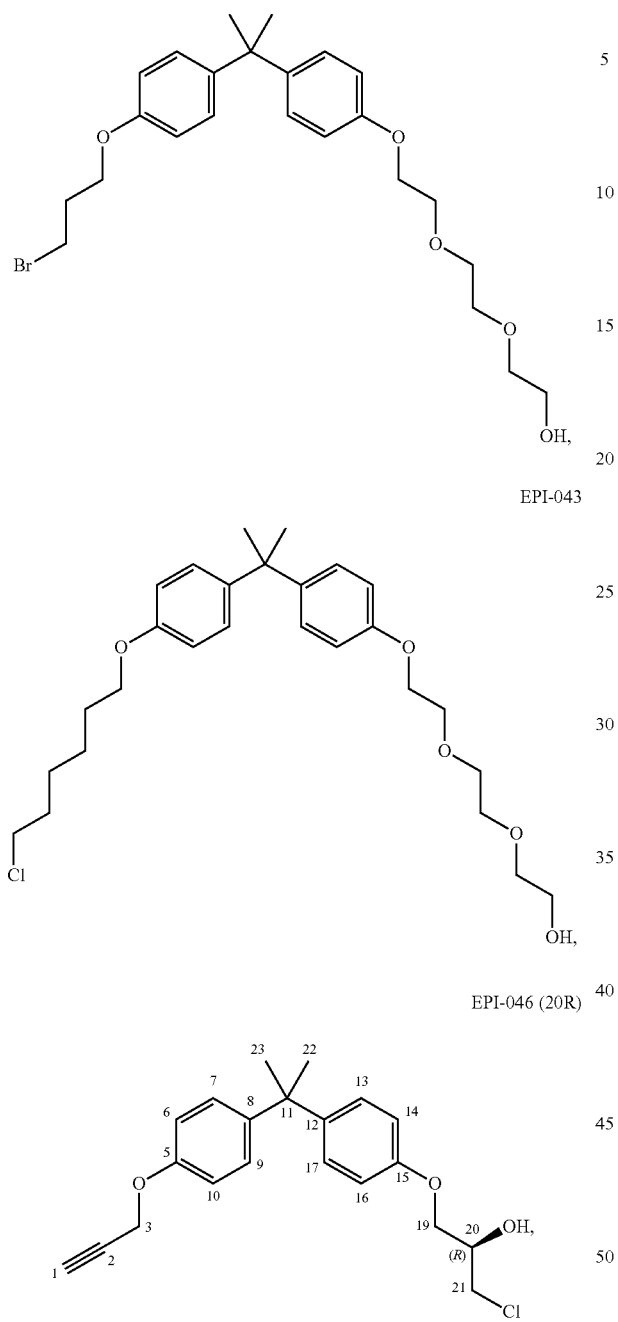
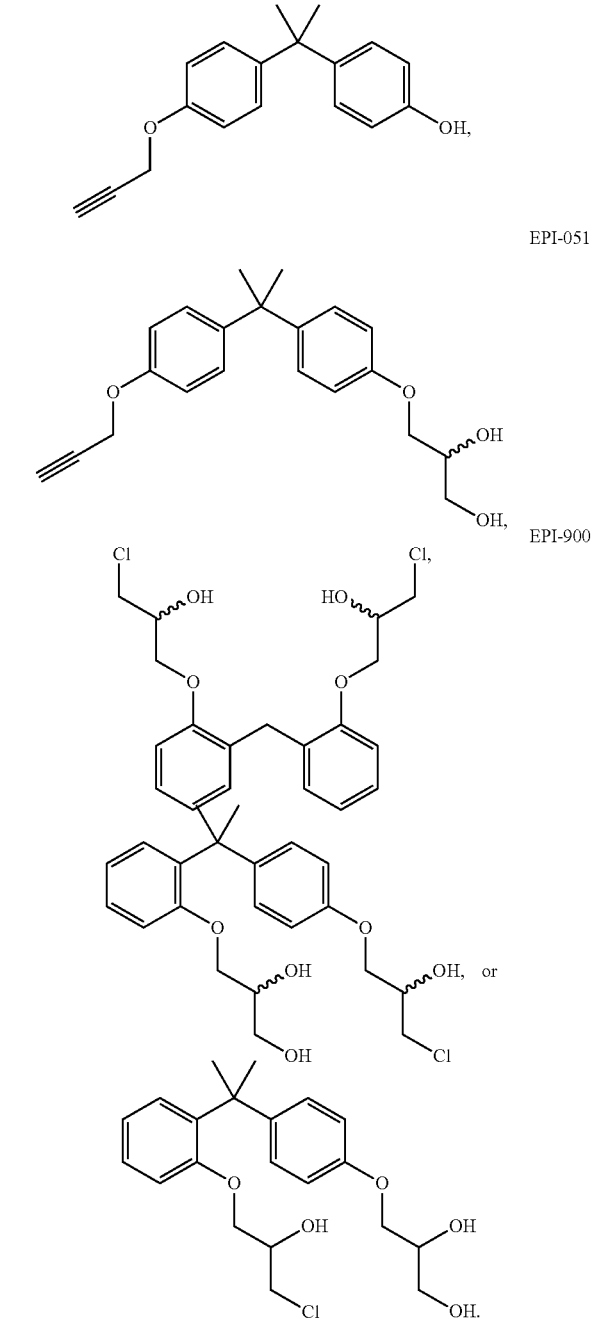
The compound may be selected from one or more of the following:
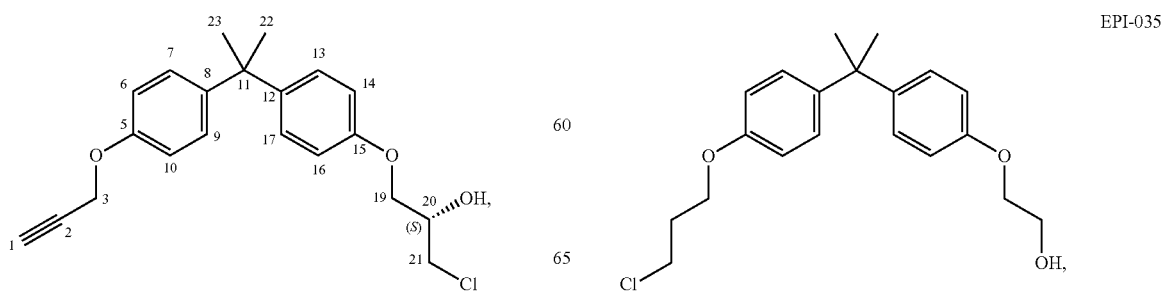

EPI-037
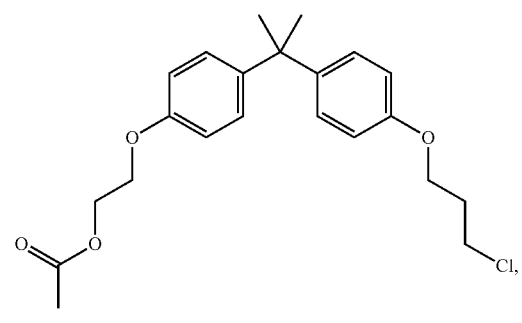
EPI-038
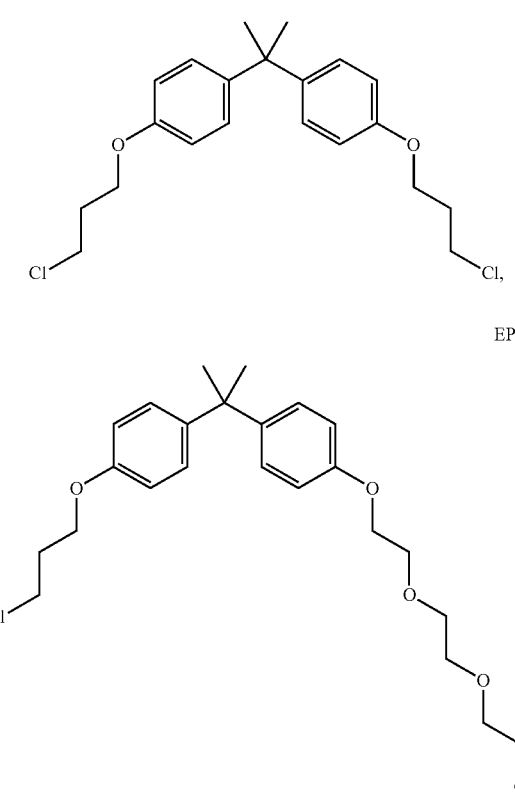
EPI-041
EPI-042
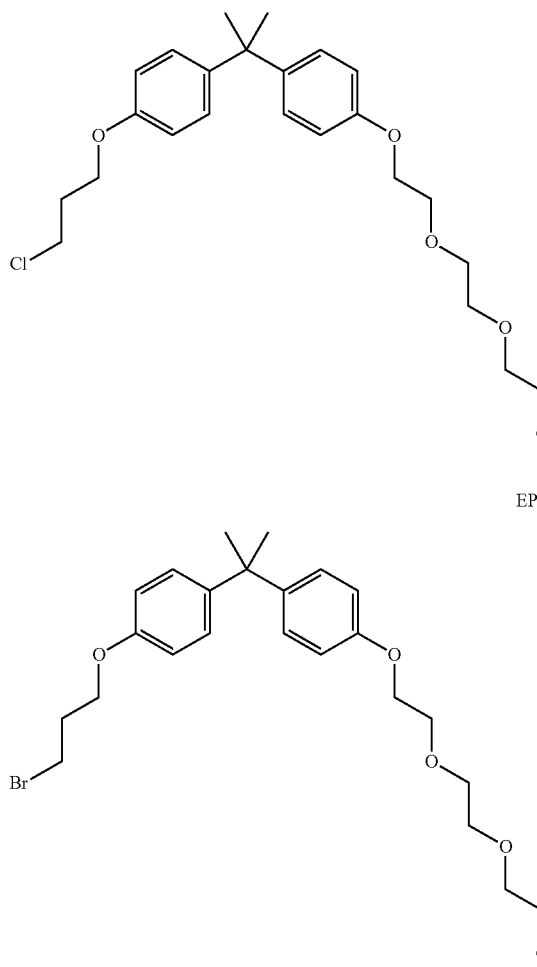
EPI-043
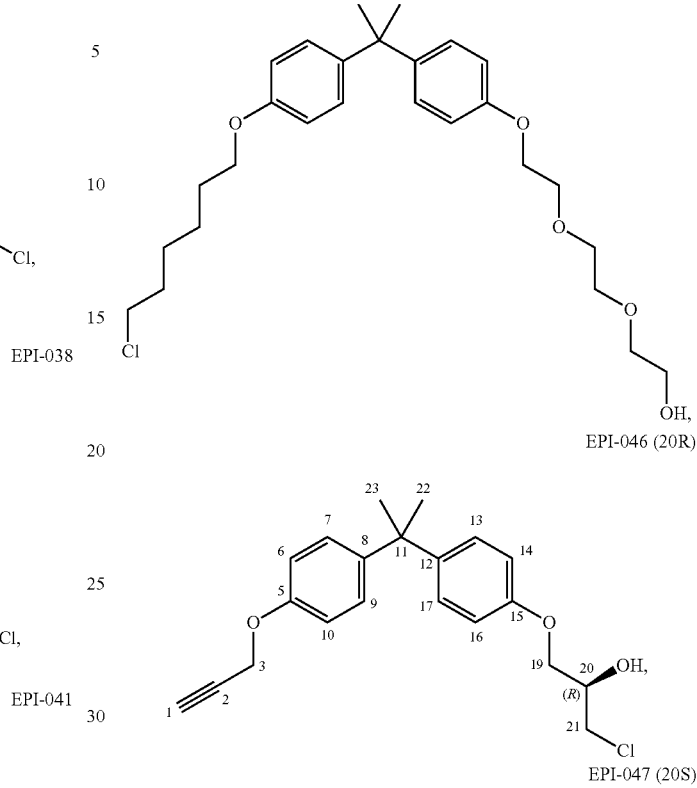
EPI-046 (20R)
EPI-047 (20S)
EPI-051
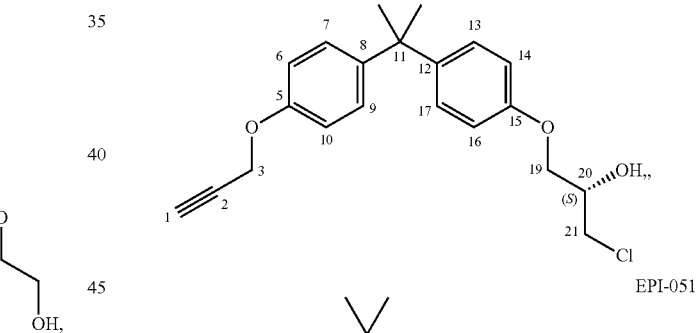
EPI-900
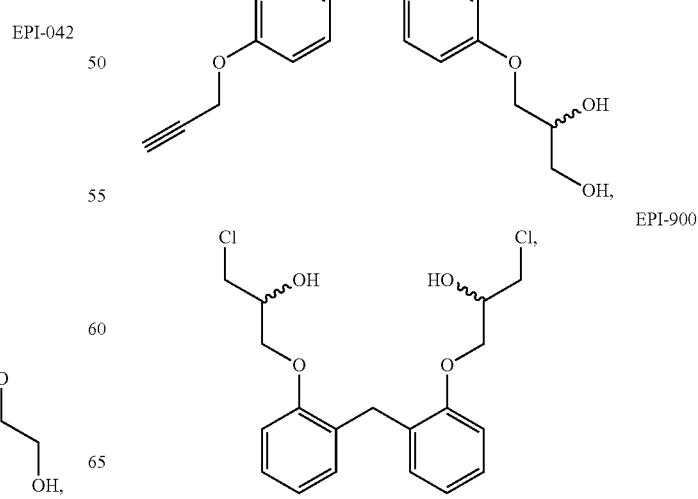

167

-continued

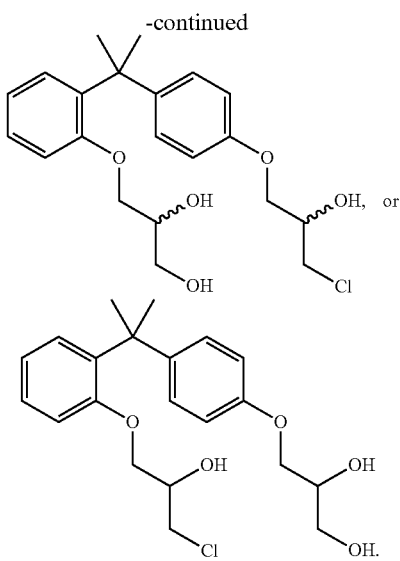

The compound may be selected from one or more of the compounds of TABLE 2.

The compounds described herein are meant to include all racemic mixtures and all individual enantiomers or combinations thereof, whether or not they are represented herein. Alternatively, one or more of the OH groups on the above compounds may be substituted to replace the H with a moiety selected from TABLE 1.

In accordance with another embodiment, there is provided a use of the compounds as described anywhere herein for preparation of a medicament for modulating androgen receptor (AR).

In accordance with another embodiment, there are provided the compounds having a structure of any one of the Formula I to XXI for modulating androgen receptor (AR).

In accordance with another embodiment, there is provided a pharmaceutical composition comprising a compound having a structure of any one of the Formula I to XXI set out above and a pharmaceutically acceptable excipient.

In accordance with another embodiment, there is provided a method for modulating AR activity, the method comprising administering to a mammalian cell a compound having a structure of any one of the Formula I to XXI set out above.

The modulating of the androgen receptor (AR) activity may be in a mammalian cell. The modulating of the androgen receptor (AR) activity may be in a mammal. The mammal may be a human.

Alternatively, the administering may be to a mammal. The administering may be to a mammal in need thereof and in an effective amount for the treatment of at least one indication selected from the group consisting of: prostate cancer, breast cancer, ovarian cancer, endometrial cancer, hair loss, acne, hirsutism, ovarian cysts, polycystic ovary disease, precocious puberty, and age-related macular degeneration.

The mammalian cell may be a human cell. The modulating AR activity may be for inhibiting AR N-terminal domain activity. The modulating AR activity may be for inhibiting AR activity. The modulating may be in vivo. The modulating AR activity may be for treatment of at least one indication selected from the group consisting of: prostate cancer, breast cancer, ovarian cancer, endometrial cancer, hair loss, acne, hirsutism, ovarian cysts, polycystic ovary disease, precocious puberty, and age-related macular degeneration. The indication may be prostate cancer. The prostate cancer may be androgen-independent prostate cancer. The prostate cancer may be androgen-dependent prostate cancer.

168

In accordance with another embodiment, there is provided a compound having a structure of Formula III

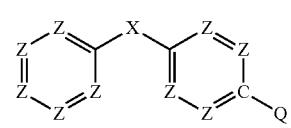

or a pharmaceutically acceptable salt thereof, wherein: X may be $CH_2$, $CHR^1$, or $CR^1R^2$; each of $R^1$ and $R^2$ may independently be linear or branched, substituted or unsubstituted, saturated or unsaturated $C_1$-$C_{10}$ alkyl, wherein the optional substituent may be selected from the group consisting of $OJ'''$, F, Cl, Br, I, or $NH_2$; wherein Q may be

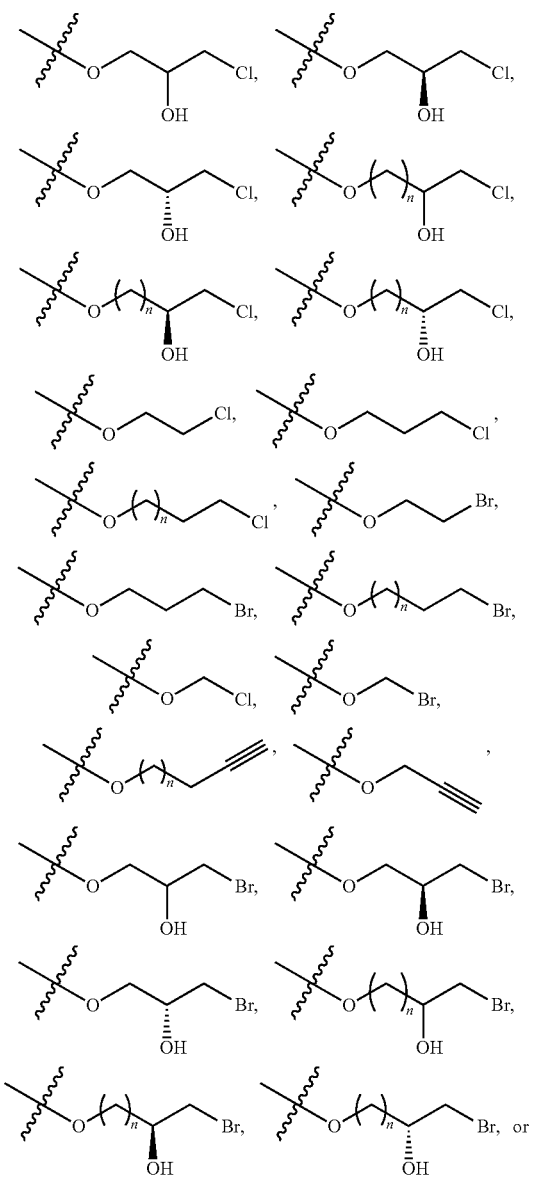

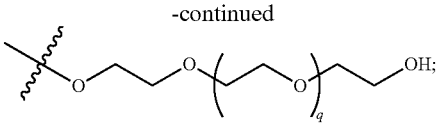

at least one Z of the other aromatic ring may independently be C-T, wherein T may be

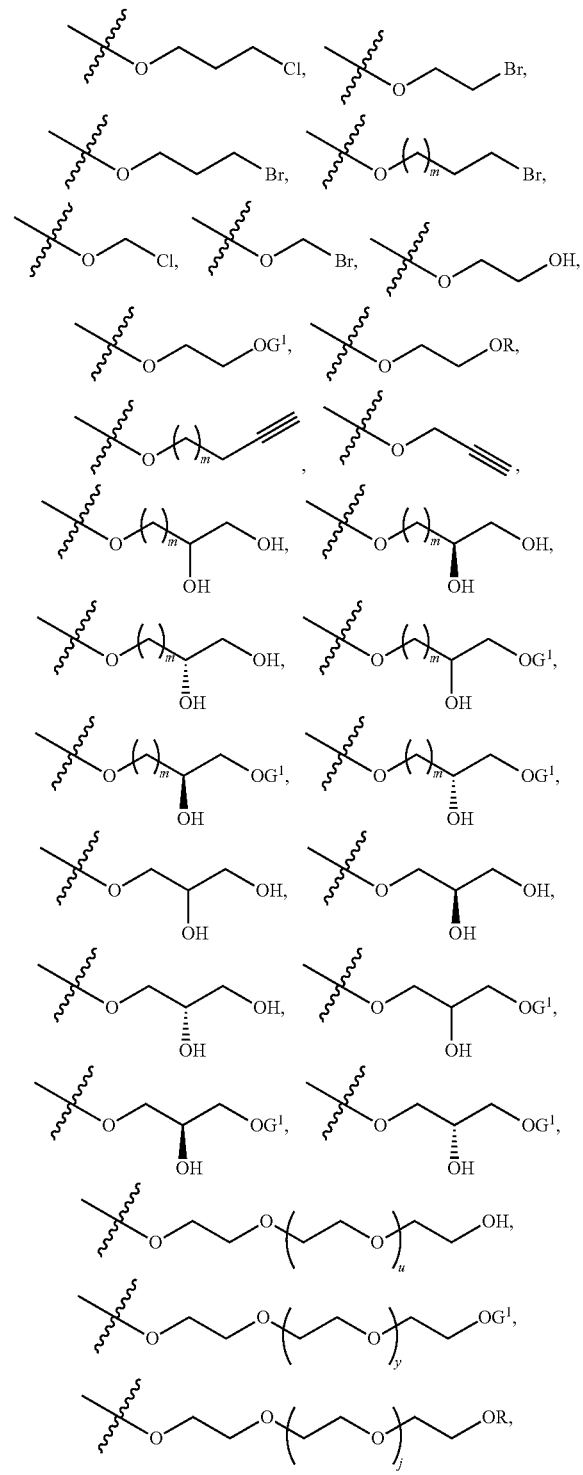

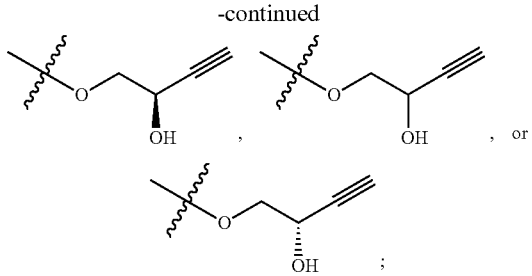

and each remaining Z may independently be $CG^1$, N, CH, CF, CCl, CBr, CI, or COH; n may be 0, 1, 2, 3, 4, 5, 6, 7 or 8; q may be 0, 1, 2, 3, 4, 5, 6 or 7; m may be 0, 1, 2, 3, 4, 5, 6, 7 or 8; each of u, j and y may independently be 0, 1, 2, 3, 4, 5, 6 or 7; each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$; and each of J'' and J''' may independently be a moiety selected from TABLE 1; and wherein one or more of the OH groups may be optionally substituted to replace the H with a moiety selected from TABLE 1.

Q may be

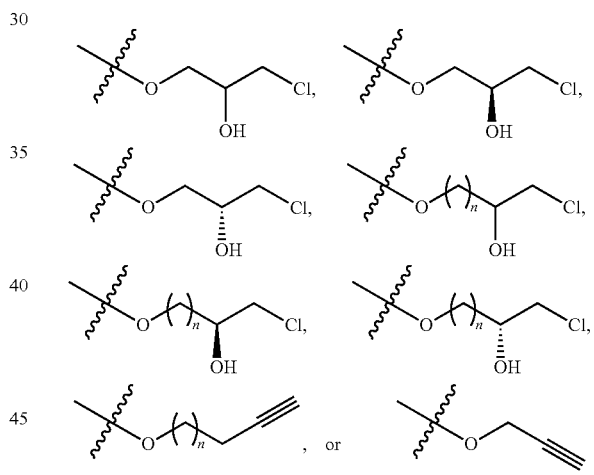

and n may be 0, 1, 2, 3, 4, 5, 6, 7 or 8. Q may be

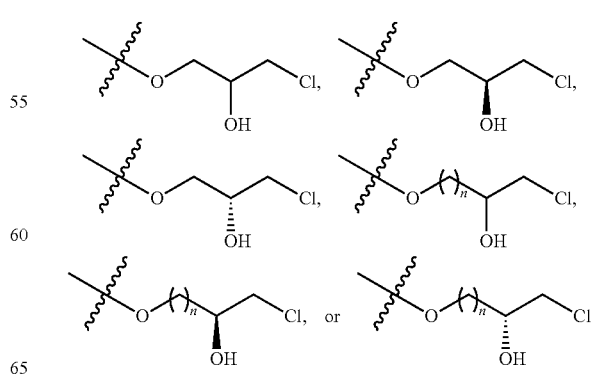

and n may be 0, 1, 2, 3, 4, 5, 6, 7 or 8. Q may be
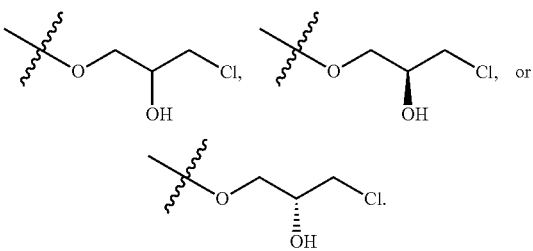 [SMILES: *OCC(O)CCl ; *OC[C@H](O)CCl ; "or" ; *OC[C@@H](O)CCl]
Q may be
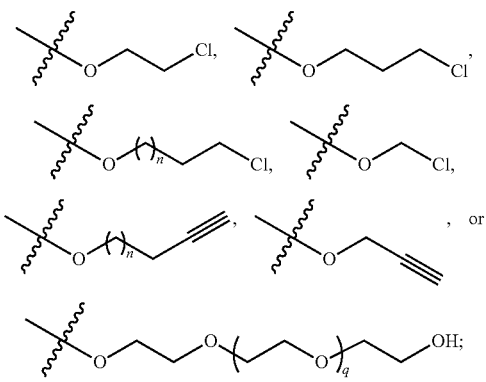
n may be 0, 1, 2, 3, 4, 5, 6, 7 or 8; and q may be 0, 1, 2, 3, 4, 5, 6 or 7. Q may be
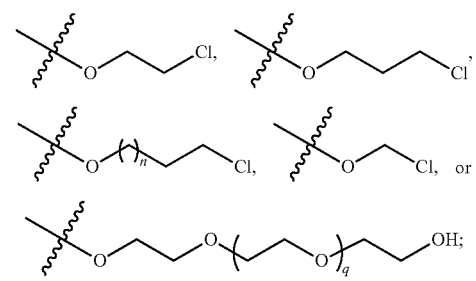
n may be 0, 1, 2, 3, 4, 5, 6, 7 or 8; and q may be 0, 1, 2, 3, 4, 5, 6 or 7. Q may be
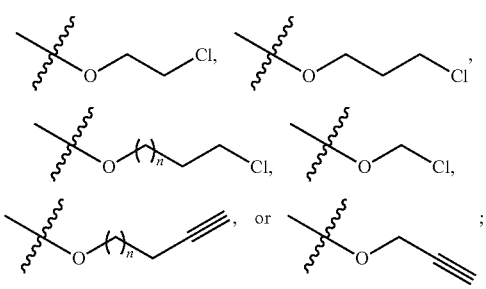
and n may be 0, 1, 2, 3, 4, 5, 6, 7 or 8. Q may be
and n may be 0, 1, 2, 3, 4, 5, 6, 7 or 8. Q may be
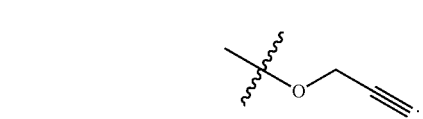
Q may be
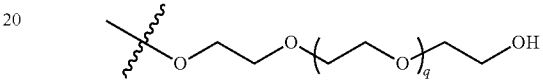
and q may be 0, 1, 2, 3, 4, 5, 6 or 7. q may be 1. Q may be
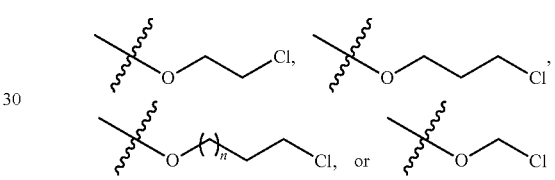
and n may be 0, 1, 2, 3, 4, 5, 6, 7 or 8. Q may be
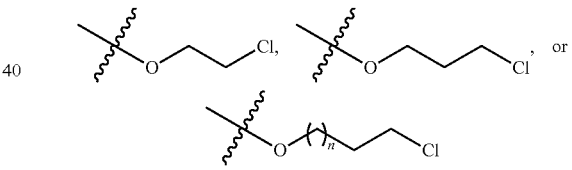
and n may be 0, 1, 2, 3, 4, 5, 6, 7 or 8. Q may be
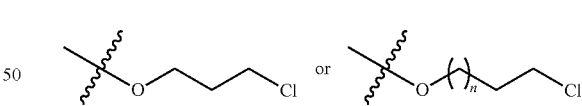
and n may be 0, 1, 2, 3, 4, 5, 6, 7 or 8. Q may be
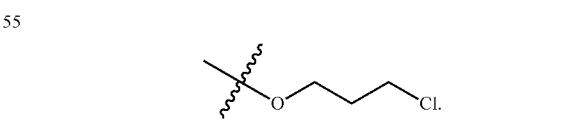
T may be
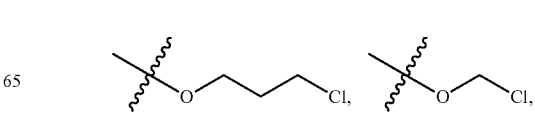

-continued

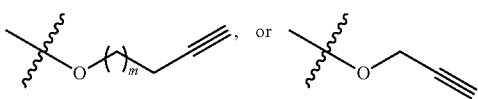

and m may be 0, 1, 2, 3, 4, 5, 6, 7 or 8. T may be

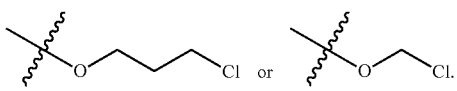

T may be

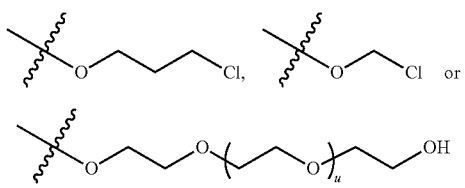

and u may be 0, 1, 2, 3, 4, 5, 6 or 7. T may be

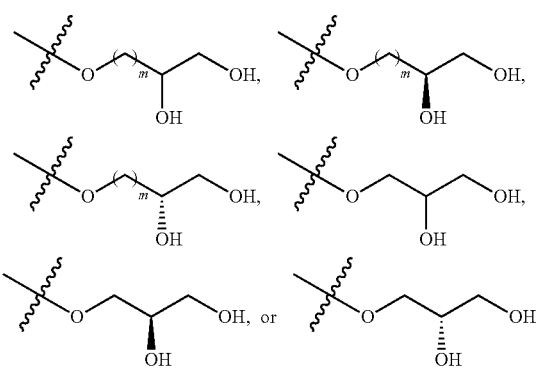

and m may be 0, 1, 2, 3, 4, 5, 6, 7 or 8. T may be

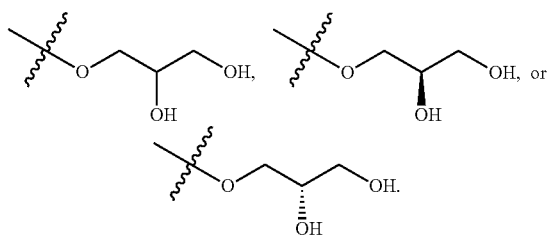

T may be

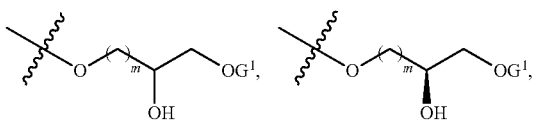

-continued

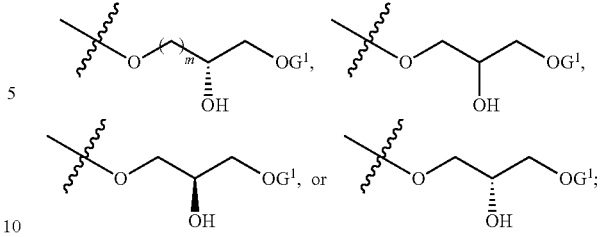

m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. T may be

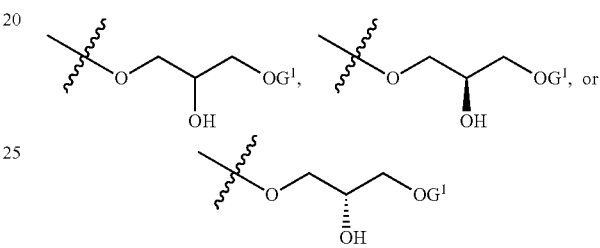

and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. T may be

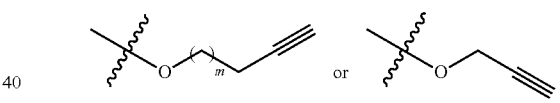

and m may be 0, 1, 2, 3, 4, 5, 6, 7 or 8. T may be

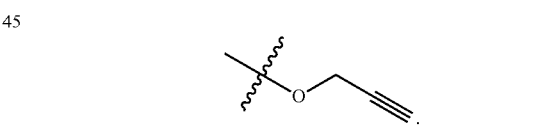

T may be

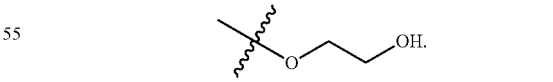

T may be

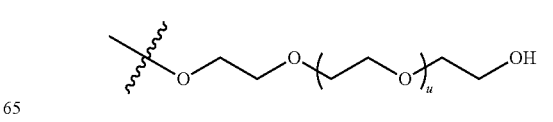

and u may be 0, 1, 2, 3, 4, 5, 6 or 7.

Q may be
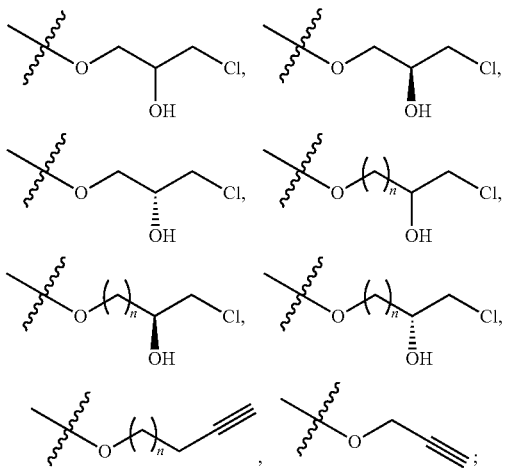
T may be
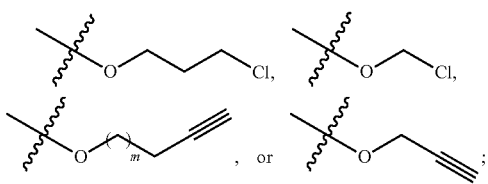
n may be 0, 1, 2, 3, 4, 5, 6, 7 or 8; and m may be 0, 1, 2, 3, 4, 5, 6, 7 or 8.
Q may be
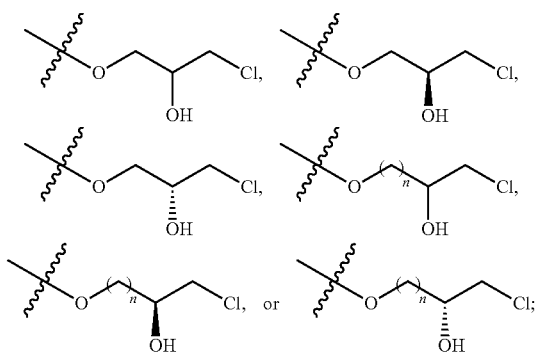
T may be
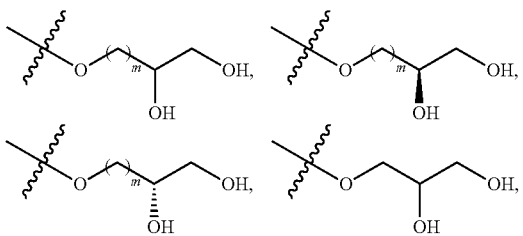
-continued
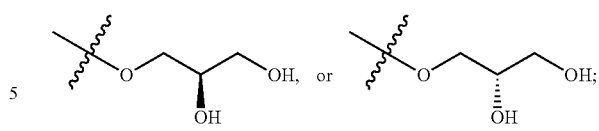
n may be 0, 1, 2, 3, 4, 5, 6, 7 or 8; and m may be 0, 1, 2, 3, 4, 5, 6, 7 or 8. Q may be
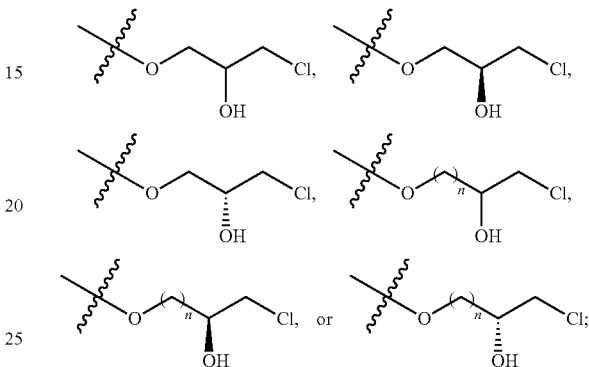
T may be
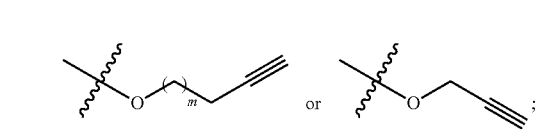
n may be 0, 1, 2, 3, 4, 5, 6, 7 or 8; and m may be 0, 1, 2, 3, 4, 5, 6, 7 or 8. Q may be
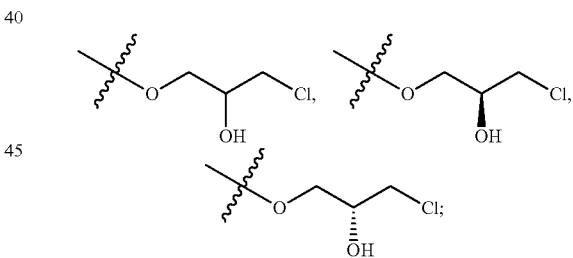
T may be
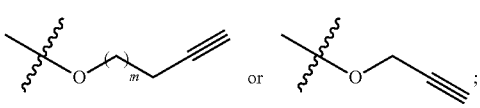
and m may be 0, 1, 2, 3, 4, 5, 6, 7 or 8. Q may be
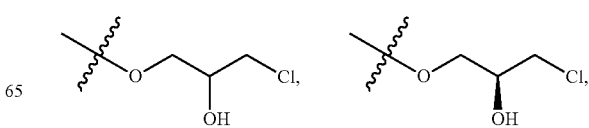

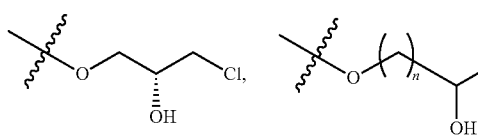 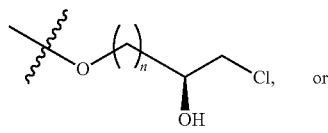
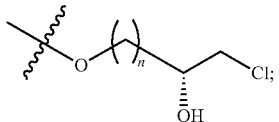
and T may be
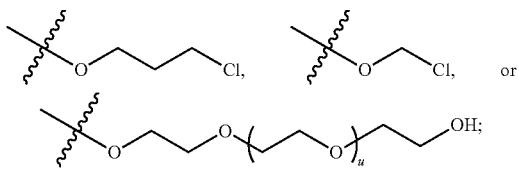
and u may be 0, 1, 2, 3, 4, 5, 6 or 7. Q may be
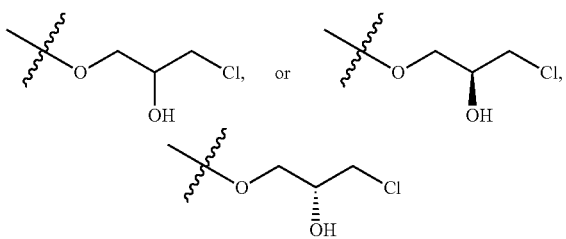
and T may be
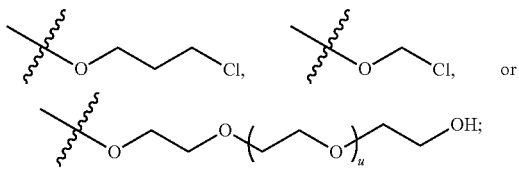
and u may be 0, 1, 2, 3, 4, 5, 6 or 7. Q may be
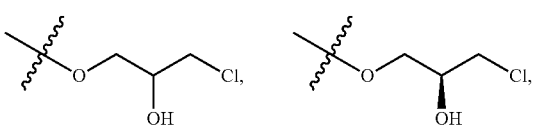
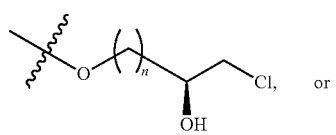
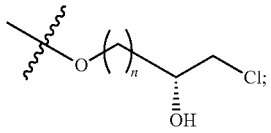
T may be
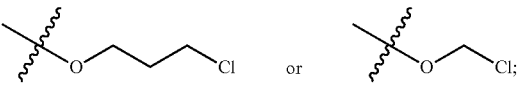
n may be 0, 1, 2, 3, 4, 5, 6, 7 or 8. Q may be
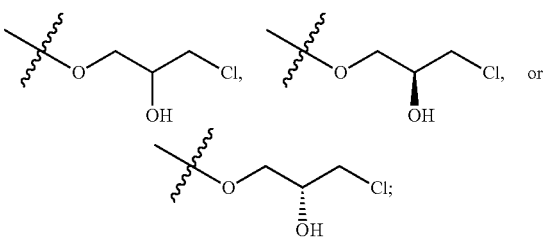
T may be
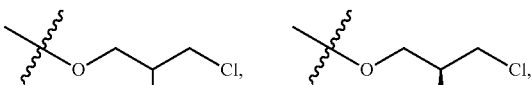
Q may be

and T may be

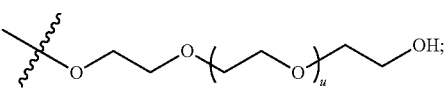

and u may be 0, 1, 2, 3, 4, 5, 6 or 7. Q may be

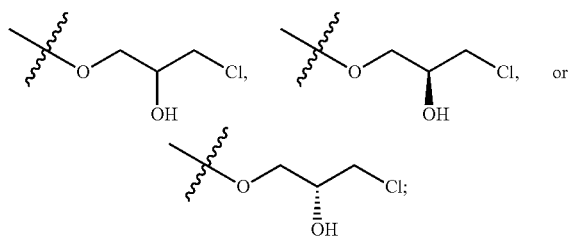

and T may be

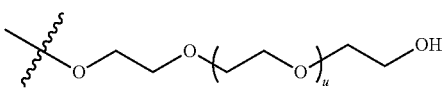

and u may be 0, 1, 2, 3, 4, 5, 6 or 7. Q may be

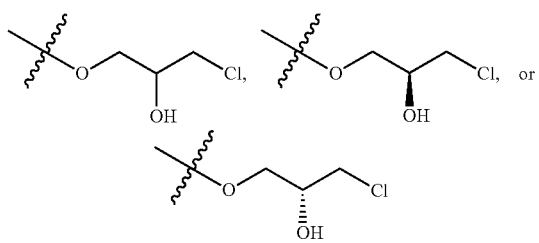

and T may be

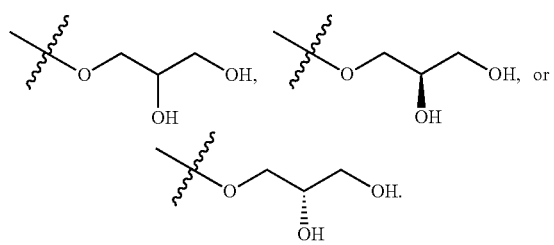

Q may be

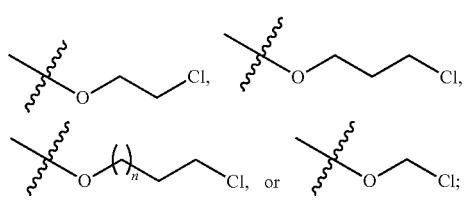

T may be

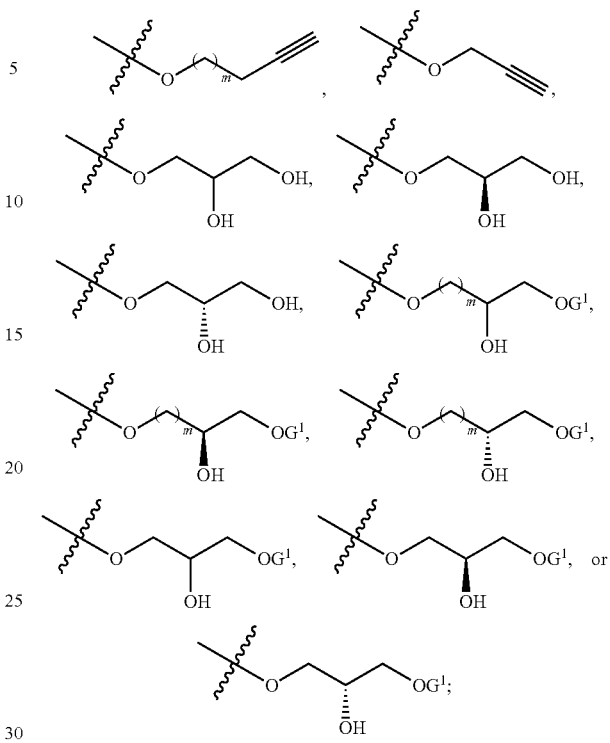

n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$. Q may be

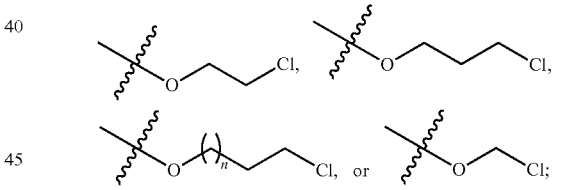

T may be

n may be 0, 1, 2, 3, 4, 5, 6, 7 or 8; and m may be 0, 1, 2, 3, 4, 5, 6, 7 or 8. Q may be

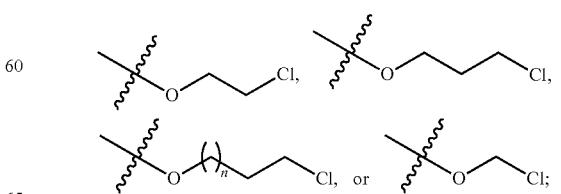

T may be

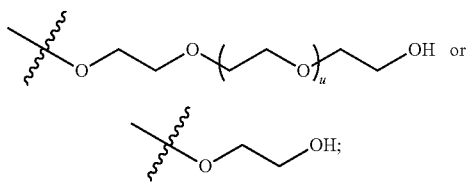

n may be 0, 1, 2, 3, 4, 5, 6, 7 or 8; and u may be 0, 1, 2, 3, 4, 5, 6 or 7. Q may be

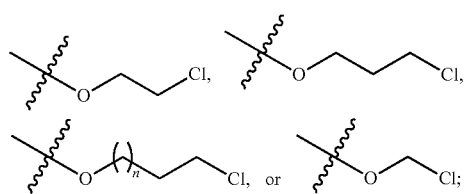

T may be

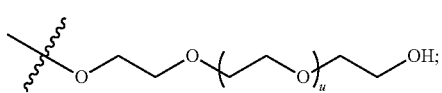

n may be 0, 1, 2, 3, 4, 5, 6, 7 or 8; and u may be 0, 1, 2, 3, 4, 5, 6 or 7. Q may be

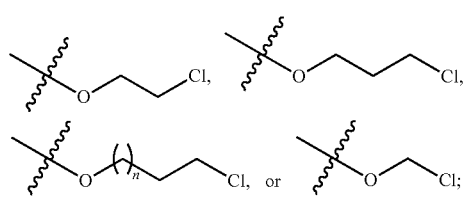

T may be

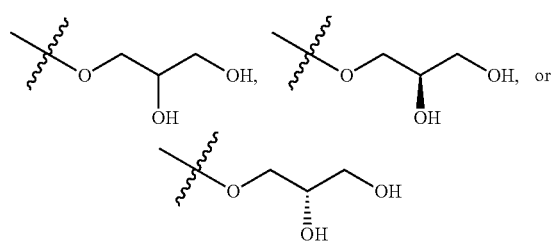

and n may be 0, 1, 2, 3, 4, 5, 6, 7 or 8. Q may be

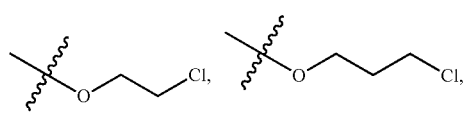

-continued

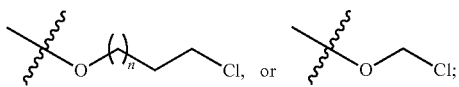

T may be

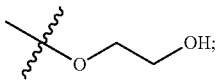

and n may be 0, 1, 2, 3, 4, 5, 6, 7 or 8. Q may be

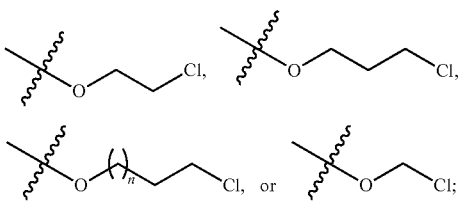

T may be

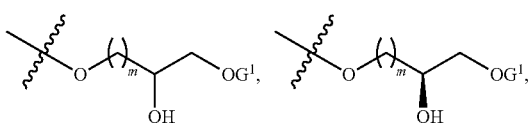
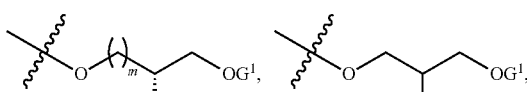
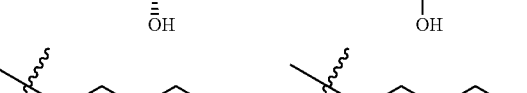
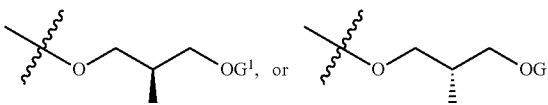

n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$. Q may be

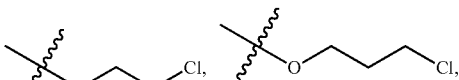
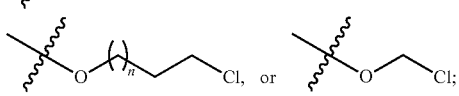

T may be

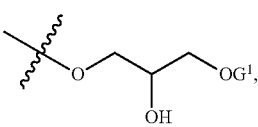

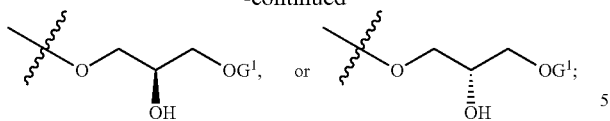

n may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$.

In accordance with another embodiment, there is provided a compound having the structure of Formula IV

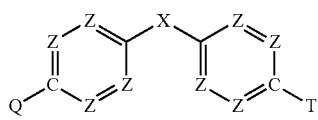

or a pharmaceutically acceptable salt thereof, wherein: X may be $CH_2$, $CHR^1$, or $CR^1R^2$; each of $R^1$ and $R^2$ may independently be linear or branched, substituted or unsubstituted, saturated or unsaturated $C_1$-$C_{10}$ alkyl, wherein the optional substituent may be selected from the group consisting of $OJ'''$, F, Cl, Br, I, or $NH_2$; each Z may independently be $CG^1$, N, CH, CF, CCl, CBr, CI, or COH; wherein Q may be

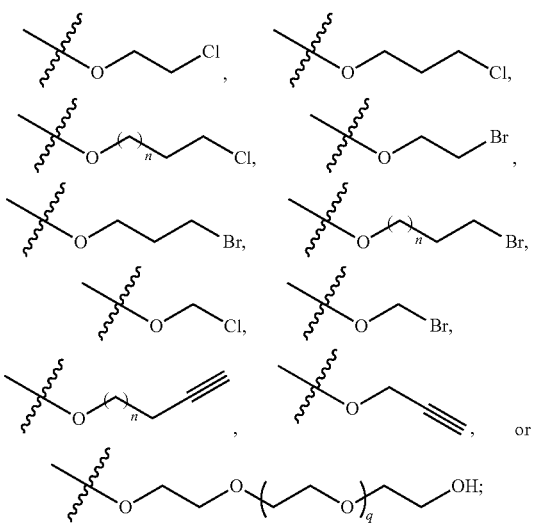

T may be

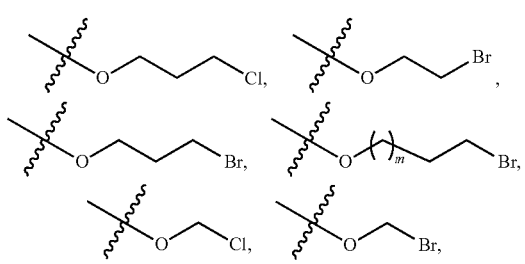

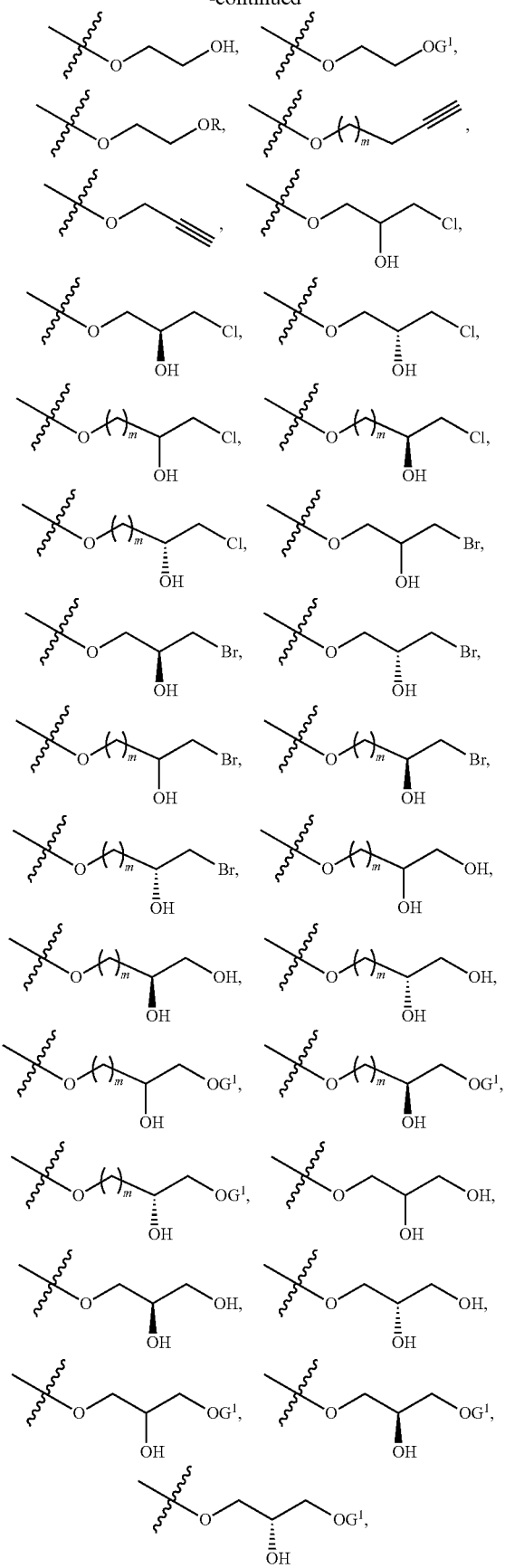

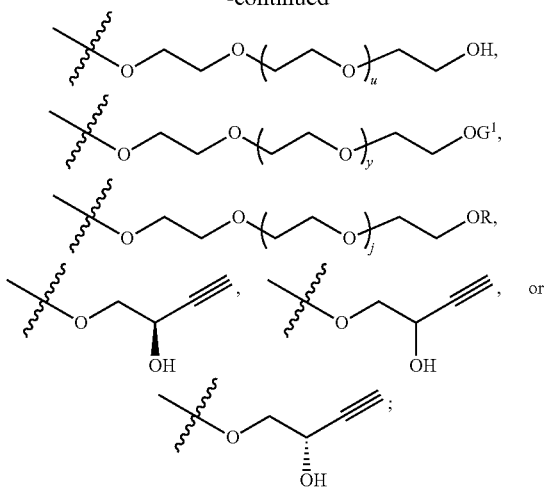

n may be 0, 1, 2, 3, 4, 5, 6, 7 or 8; q may be 0, 1, 2, 3, 4, 5, 6 or 7; m may be 0, 1, 2, 3, 4, 5, 6, 7 or 8; each of u, j and y may independently be 0, 1, 2, 3, 4, 5, 6 or 7; each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$; and each of J'' and J''' may independently be a moiety selected from TABLE 1; and wherein one or more of the OH groups may be optionally substituted to replace the H with a moiety selected from TABLE 1.

Q may be

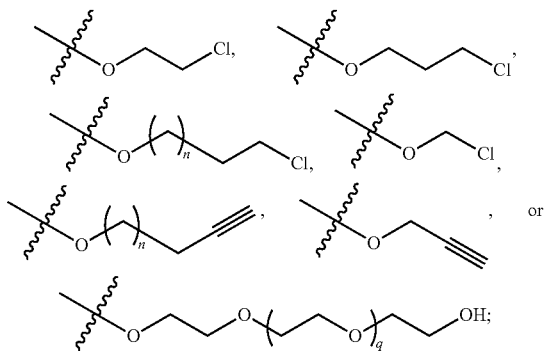

n may be 0, 1, 2, 3, 4, 5, 6, 7 or 8; and q may be 0, 1, 2, 3, 4, 5, 6 or 7. Q may be

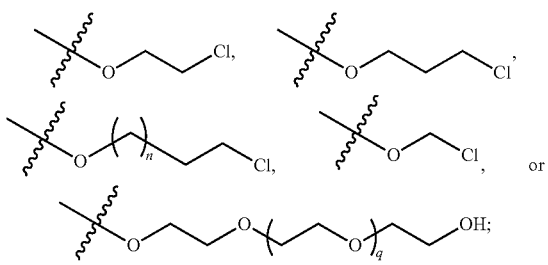

n may be 0, 1, 2, 3, 4, 5, 6, 7 or 8; and q may be 0, 1, 2, 3, 4, 5, 6 or 7. Q may be

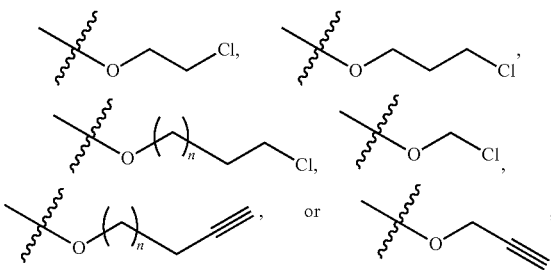

and n may be 0, 1, 2, 3, 4, 5, 6, 7 or 8. Q may be

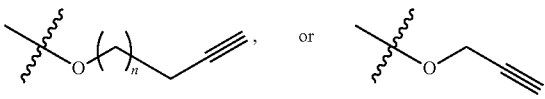

and n may be 0, 1, 2, 3, 4, 5, 6, 7 or 8. Q may be

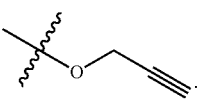 [SMILES: *OCC#C]

Q may be

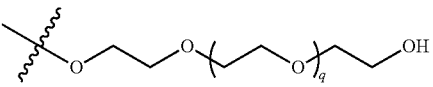

and q may be 0, 1, 2, 3, 4, 5, 6 or 7. q may be 1. Q may be

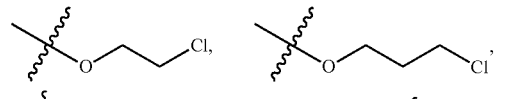

and n may be 0, 1, 2, 3, 4, 5, 6, 7 or 8. Q may be

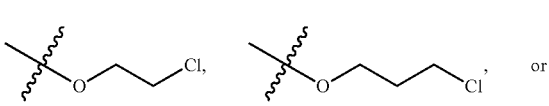

and n may be 0, 1, 2, 3, 4, 5, 6, 7 or 8. Q may be

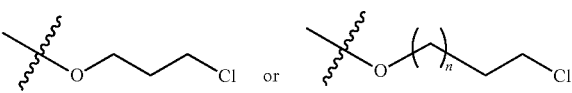

and n may be 0, 1, 2, 3, 4, 5, 6, 7 or 8. Q may be

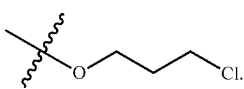

T may be

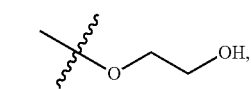 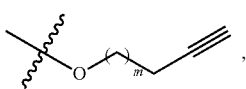

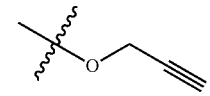 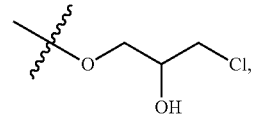

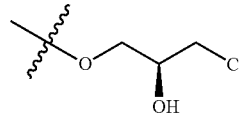 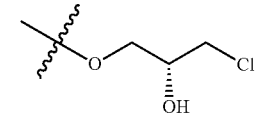

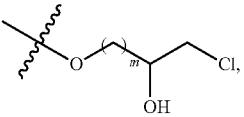 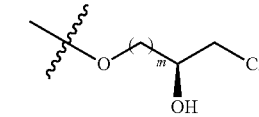

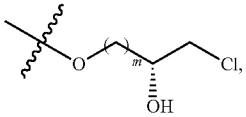 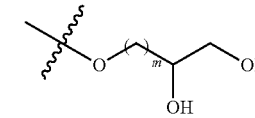

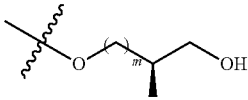 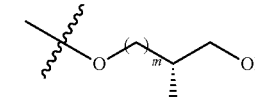

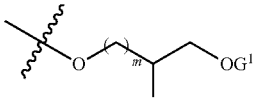 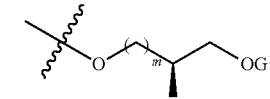

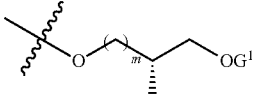 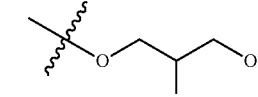

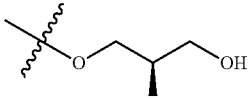 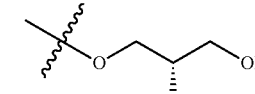

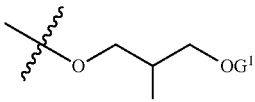 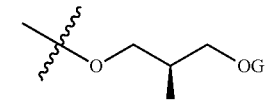

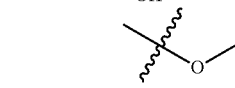 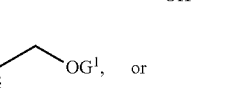

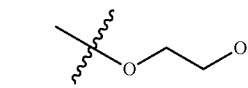 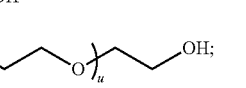

m may be 0, 1, 2, 3, 4, 5, 6, 7 or 8; u may be 0, 1, 2, 3, 4, 5, 6 or 7; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. T may be

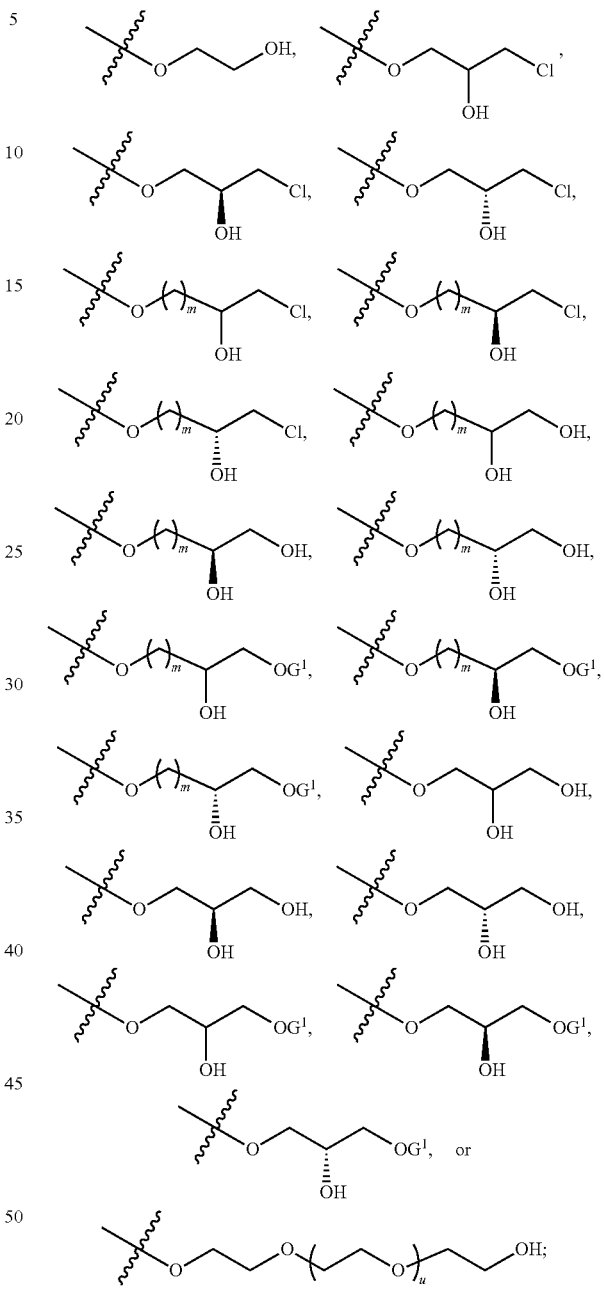

m may be 0, 1, 2, 3, 4, 5, 6, 7 or 8; u may be 0, 1, 2, 3, 4, 5, 6 or 7; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. T may be

-continued

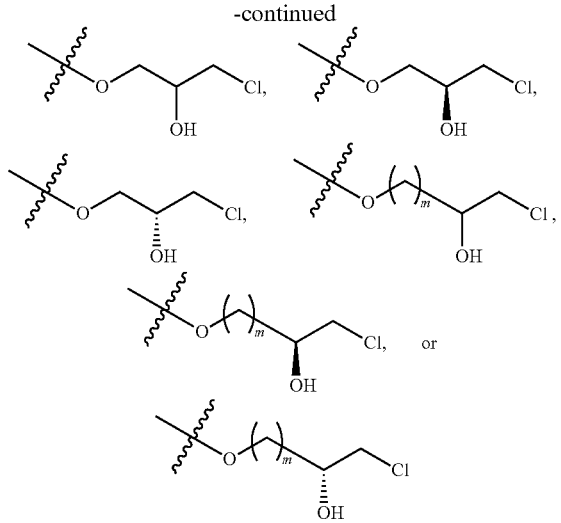

and m may be 0, 1, 2, 3, 4, 5, 6, 7 or 8. T may be

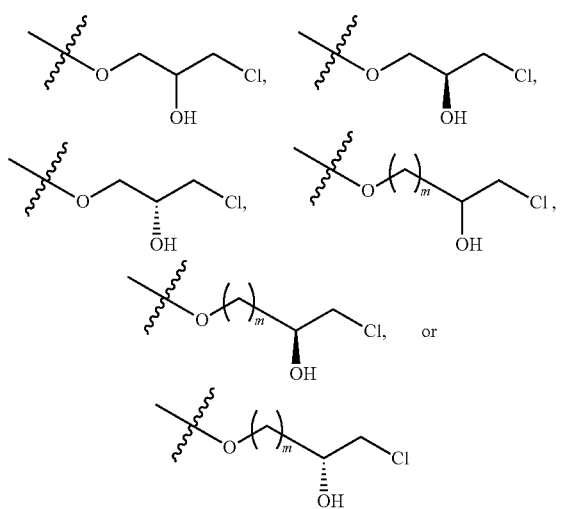

and m may be 0, 1, 2, 3, 4, 5, 6, 7 or 8. T may be

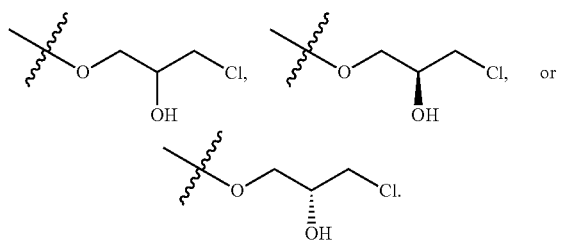

T may be

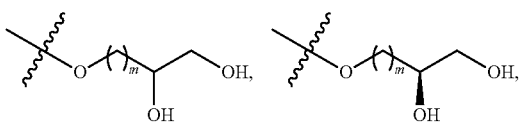

-continued

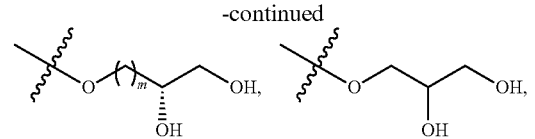

and m may be 0, 1, 2, 3, 4, 5, 6, 7 or 8. T may be

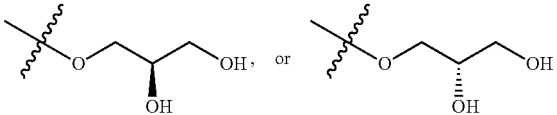

T may be

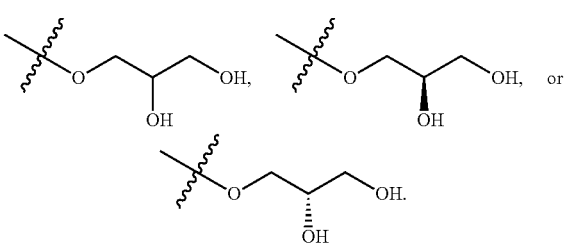

m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. T may be

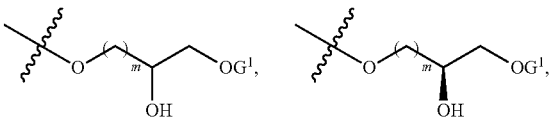

and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. T may be

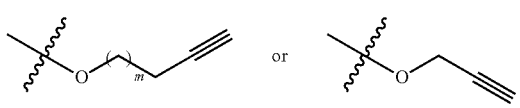

and m may be 0, 1, 2, 3, 4, 5, 6, 7 or 8. T may be

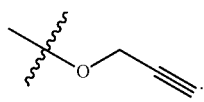 [SMILES: *OCC#C]

T may be

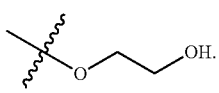

T may be

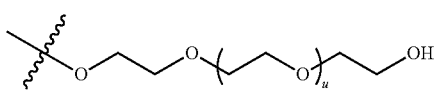

and u may be 0, 1, 2, 3, 4, 5, 6 or 7.

Q may be

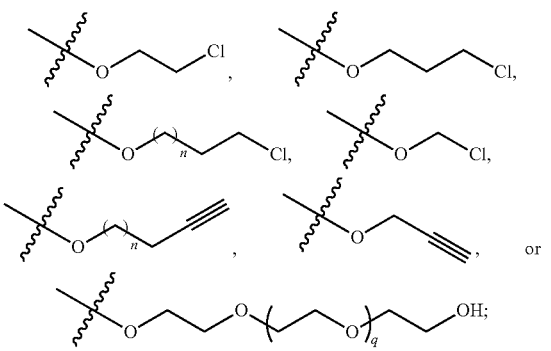

T may be

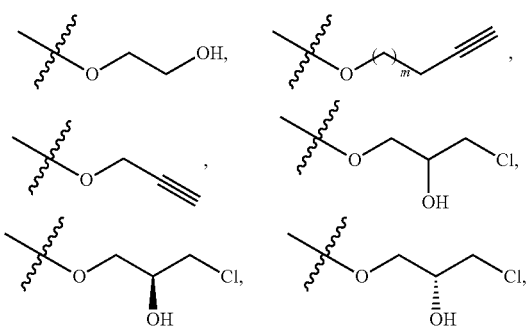

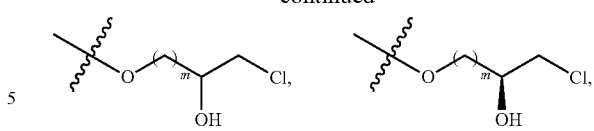

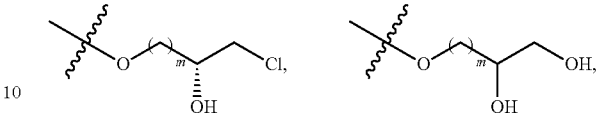

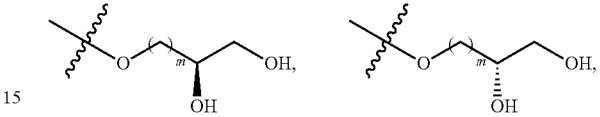

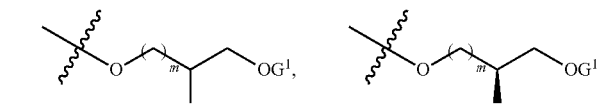

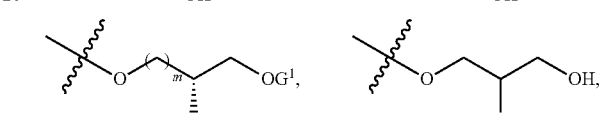

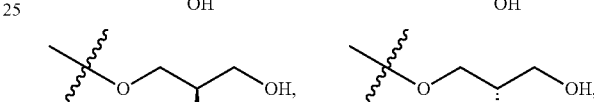

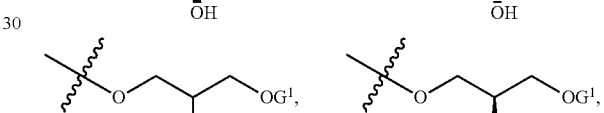

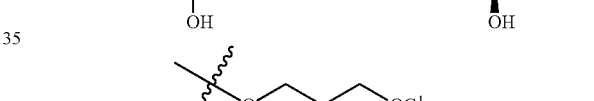

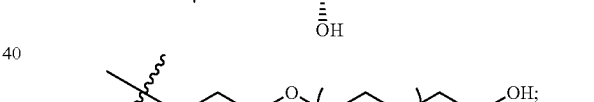

n may be 0, 1, 2, 3, 4, 5, 6, 7 or 8; q may be 0, 1, 2, 3, 4, 5, 6 or 7; m may be 0, 1, 2, 3, 4, 5, 6, 7 or 8; u may be 0, 1, 2, 3, 4, 5, 6 or 7; and each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$.

Q may be

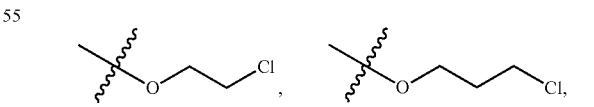

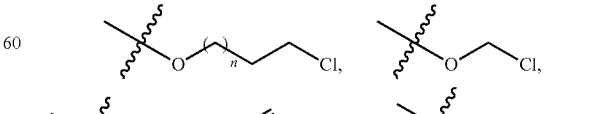

T may be
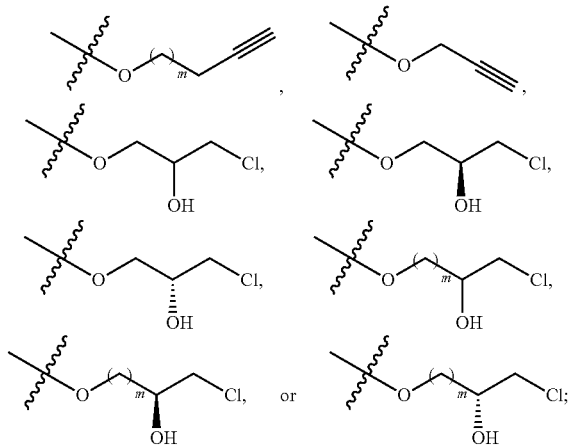
n may be 0, 1, 2, 3, 4, 5, 6, 7 or 8; and m may be 0, 1, 2, 3, 4, 5, 6, 7 or 8. Q may be
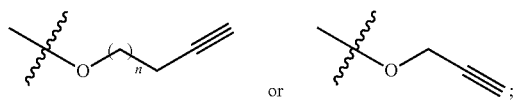
T may be
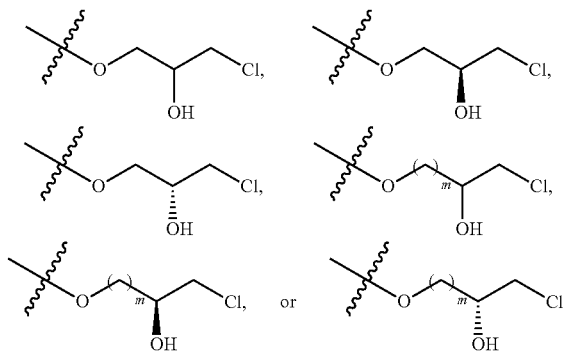
n may be 0, 1, 2, 3, 4, 5, 6, 7 or 8; and m may be 0, 1, 2, 3, 4, 5, 6, 7 or 8. Q may be
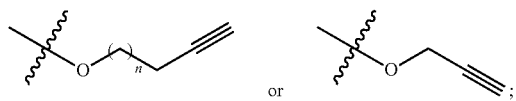
T may be
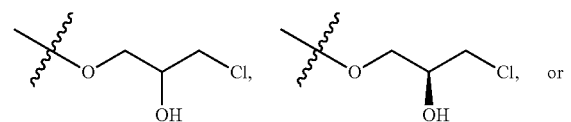
-continued
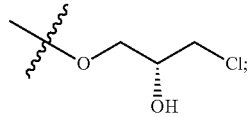
and n may be 0, 1, 2, 3, 4, 5, 6, 7. Q may be
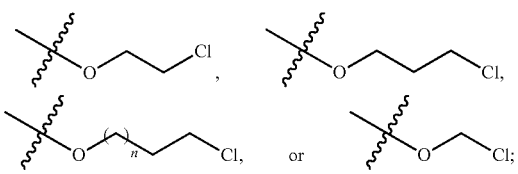
T may be
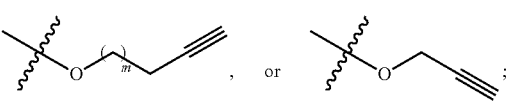
n may be 0, 1, 2, 3, 4, 5, 6, 7 or 8; and m may be 0, 1, 2, 3, 4, 5, 6, 7 or 8. Q may be
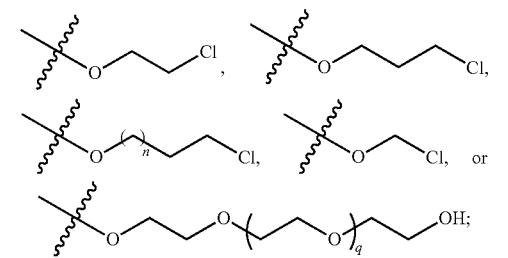
T may be
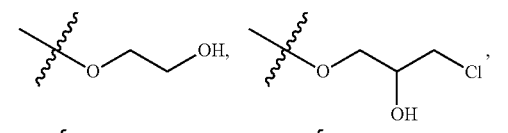
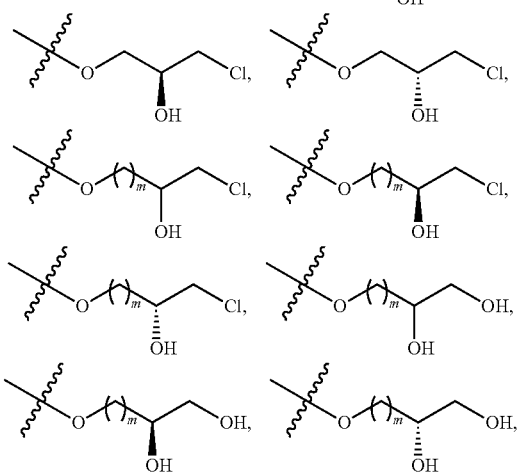

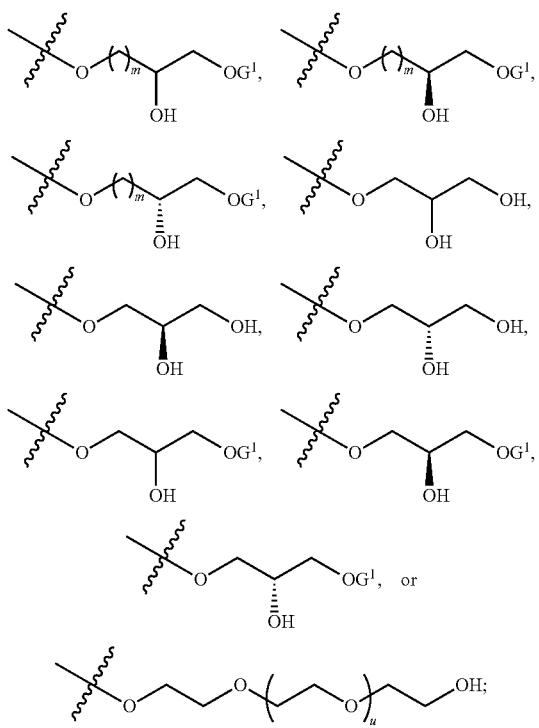

n may be 0, 1, 2, 3, 4, 5, 6, 7 or 8; q may be 0, 1, 2, 3, 4, 5, 6 or 7; m may be 0, 1, 2, 3, 4, 5, 6, 7 or 8; u may be 0, 1, 2, 3, 4, 5, 6 or 7; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be T may be n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be T may be n may be 0, 1, 2, 3, 4, 5, 6, 7 or 8; and u may be 0, 1, 2, 3, 4, 5, 6 or 7. Q may be

197
T may be
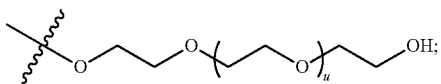
n may be 0, 1, 2, 3, 4, 5, 6, 7 or 8; and u may be 0, 1, 2, 3, 4, 5, 6 or 7. Q may be
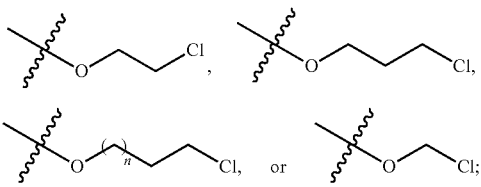
T may be
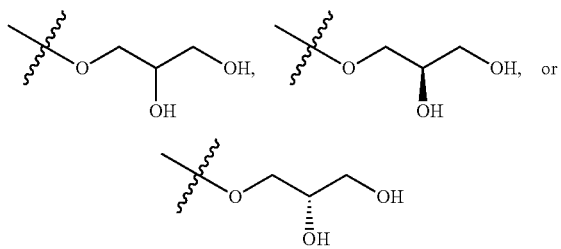
and n may be 0, 1, 2, 3, 4, 5, 6, 7 or 8. Q may be
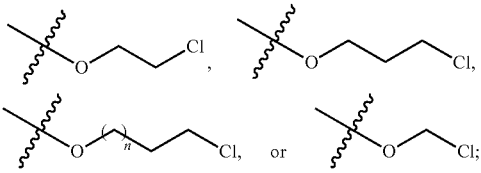
T may be
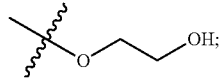 [SMILES: *OCCO]
and n may be 0, 1, 2, 3, 4, 5, 6, 7 or 8. Q may be
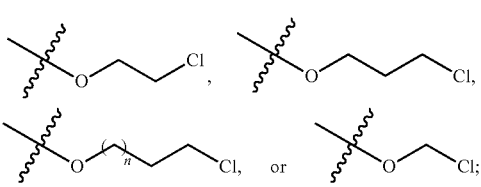
198
T may be
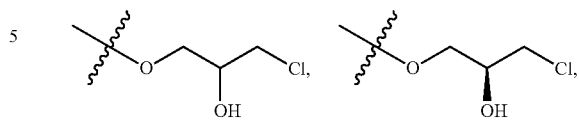
n may be 0, 1, 2, 3, 4, 5, 6, 7 or 8; and m may be 0, 1, 2, 3, 4, 5, 6, 7 or 8. Q may be
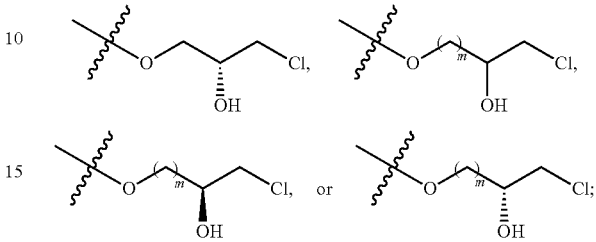
T may be
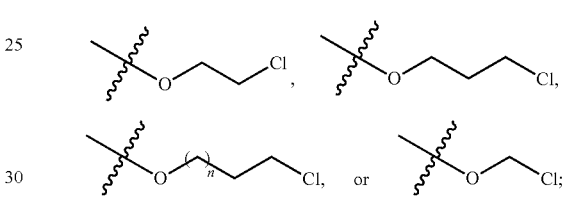
and n may be 0, 1, 2, 3, 4, 5, 6, 7 or 8. Q may be
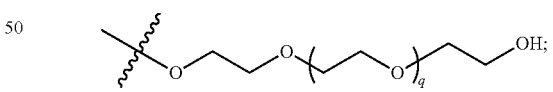
T may be
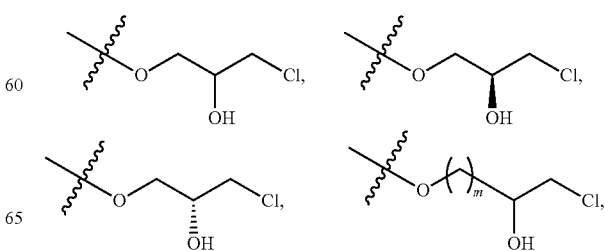

-continued

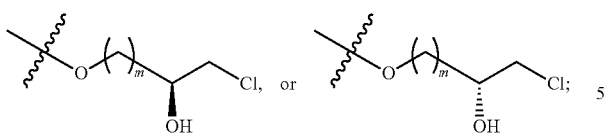

q may be 0, 1, 2, 3, 4, 5, 6 or 7; and m may be 0, 1, 2, 3, 4, 5, 6, 7 or 8. Q may be

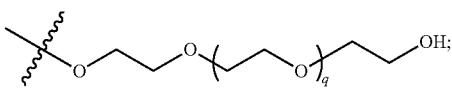

T may be

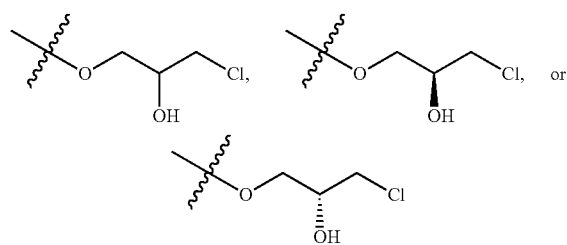

and q may be 0, 1, 2, 3, 4, 5, 6 or 7. Q may be

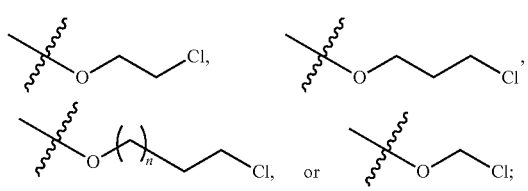

T may be

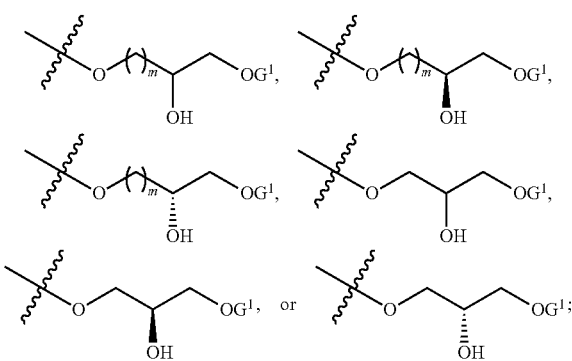

n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, NH$_2$, CN, SH, SO$_3$H, CONH$_2$, OPO$_3$H$_3$, and NO$_2$. Q may be

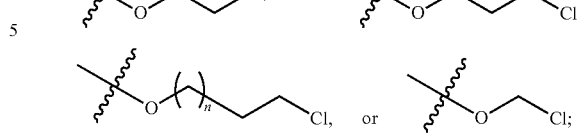

T may be

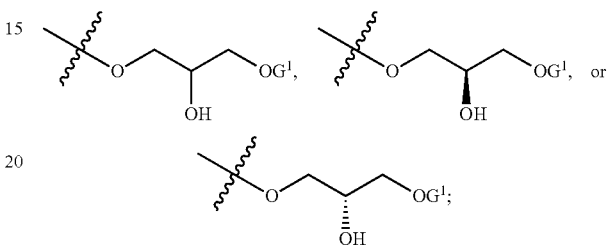

n may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, NH$_2$, CN, SH, SO$_3$H, CONH$_2$, OPO$_3$H$_3$, and NO$_2$.

In accordance with another embodiment, there is provided a compound having a structure of Formula IX

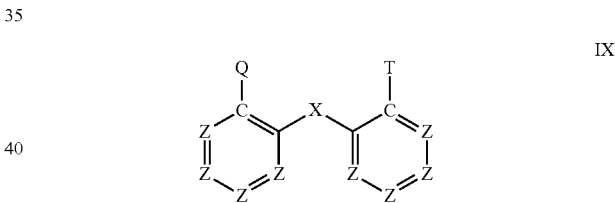

IX or a pharmaceutically acceptable salt thereof, wherein: X may be CH$_2$, CHR$^1$, or CR$^1$R$^2$; each of R$^1$ and R$^2$ may independently be linear or branched, substituted or unsubstituted, saturated or unsaturated $C_1$-$C_{10}$ alkyl, wherein the optional substituent may be selected from the group consisting of OJ''', F, Cl, Br, I, or NH$_2$; each Z may independently be CG$^1$, N, CH, CF, CCl, CBr, CI, or COH; wherein Q may be

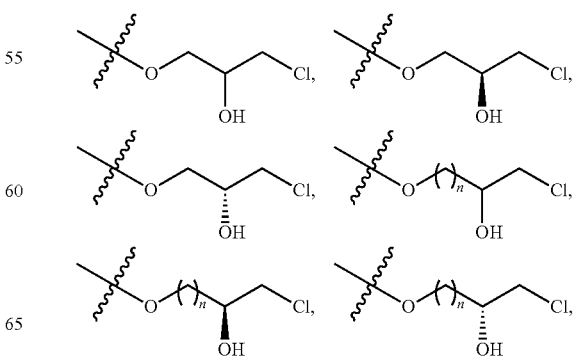

-continued

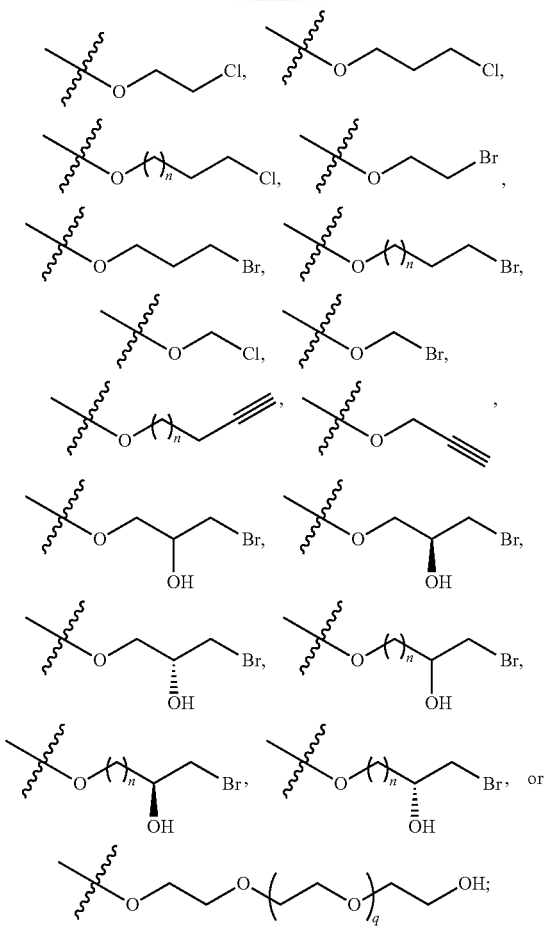

T may be

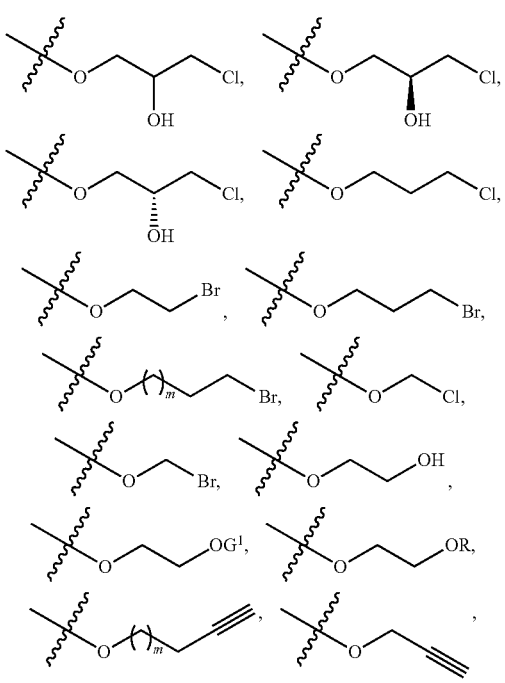

-continued

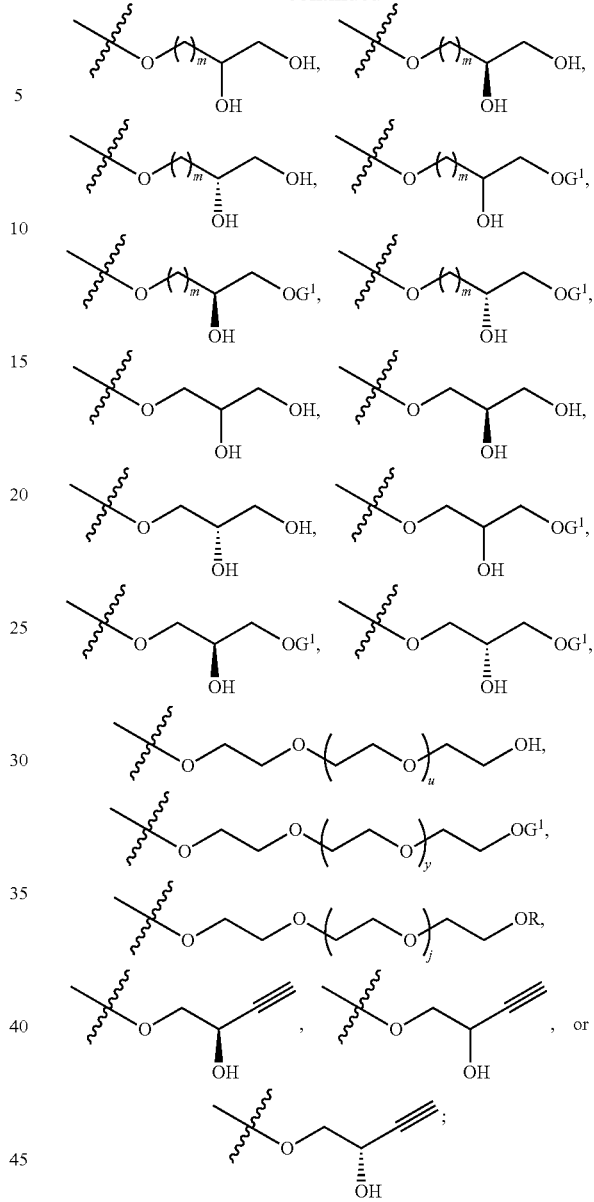

n may be 0, 1, 2, 3, 4, 5, 6, 7 or 8; q may be 0, 1, 2, 3, 4, 5, 6 or 7; m may be 0, 1, 2, 3, 4, 5, 6, 7 or 8; each of u, j and y may independently be 0, 1, 2, 3, 4, 5, 6 or 7; each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$; and each of J'' and J''' may independently be a moiety selected from TABLE 1; and wherein one or more of the OH groups may be optionally substituted to replace the H with a moiety selected from TABLE 1.

Q may be

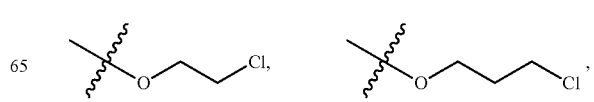

-continued
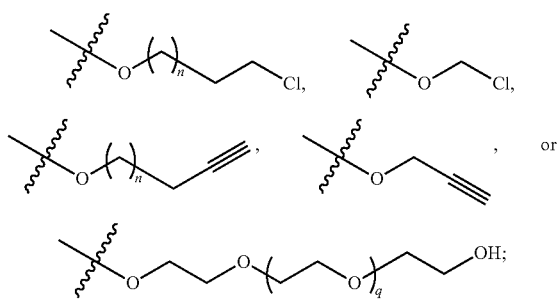
n may be 0, 1, 2, 3, 4, 5, 6, 7 or 8; and q may be 0, 1, 2, 3, 4, 5, 6 or 7. Q may be
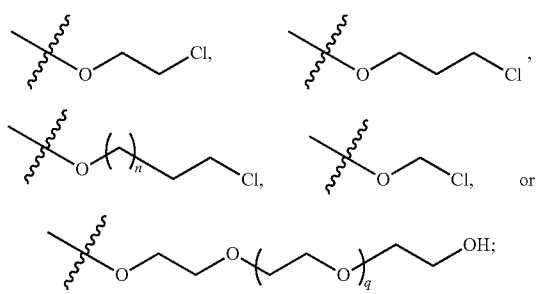
n may be 0, 1, 2, 3, 4, 5, 6, 7 or 8; and q may be 0, 1, 2, 3, 4, 5, 6 or 7. Q may be
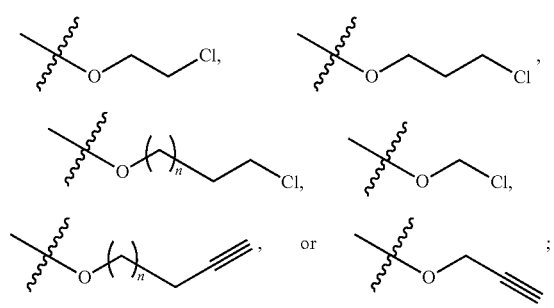
and n may be 0, 1, 2, 3, 4, 5, 6, 7 or 8. Q may be
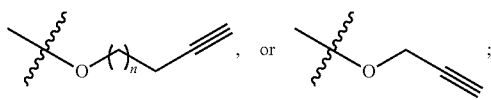
and n may be 0, 1, 2, 3, 4, 5, 6, 7 or 8. Q may be
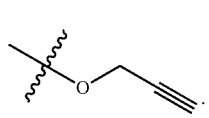 [SMILES: *OCC#C]
Q may be
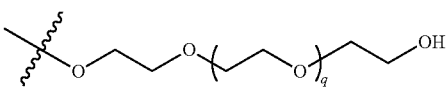
and q may be 0, 1, 2, 3, 4, 5, 6 or 7. q may be 1. Q may be
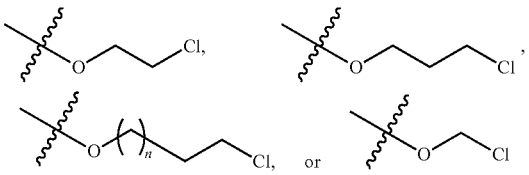
and n may be 0, 1, 2, 3, 4, 5, 6, 7 or 8. Q may be
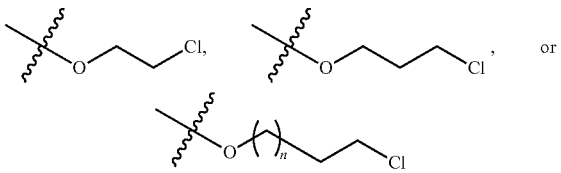
and n may be 0, 1, 2, 3, 4, 5, 6, 7 or 8. Q may be
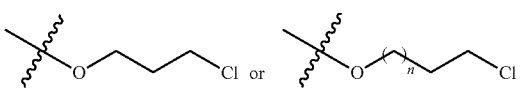
and n may be 0, 1, 2, 3, 4, 5, 6, 7 or 8. Q may be
Q may be
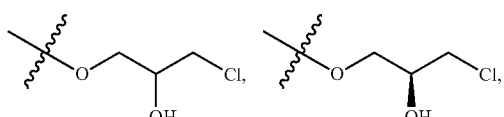
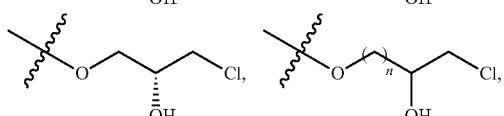
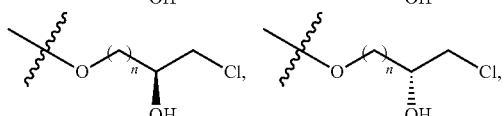
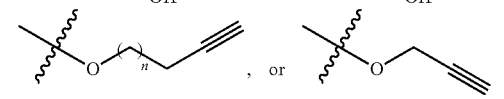

and n may be 0, 1, 2, 3, 4, 5, 6, 7 or 8. Q may be

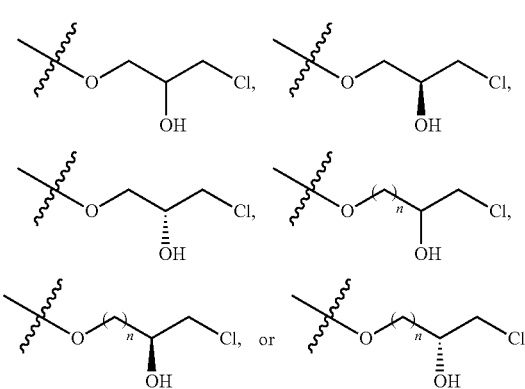

and n may be 0, 1, 2, 3, 4, 5, 6, 7 or 8. Q may be

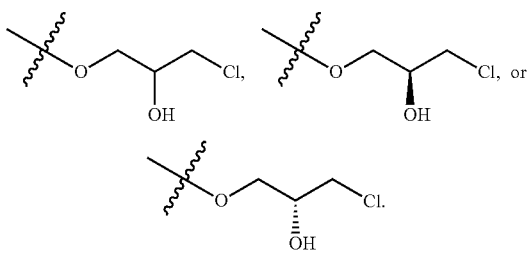

T may be

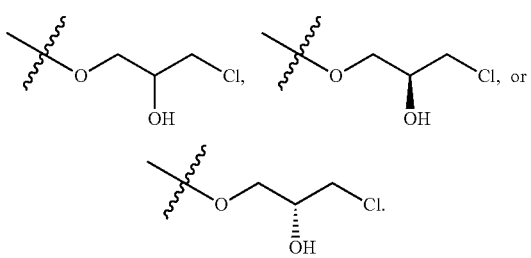

T may be

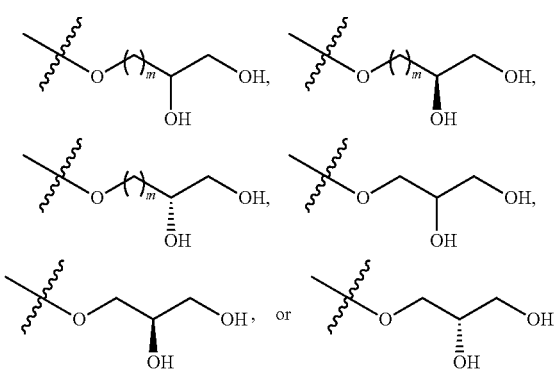

and m may be 0, 1, 2, 3, 4, 5, 6, 7 or 8. T may be

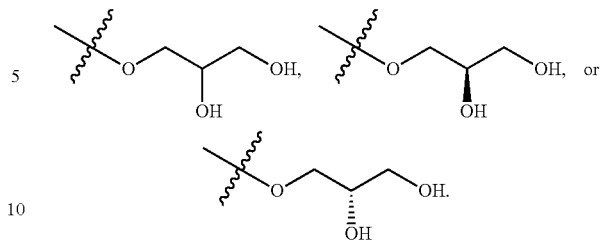

T may be

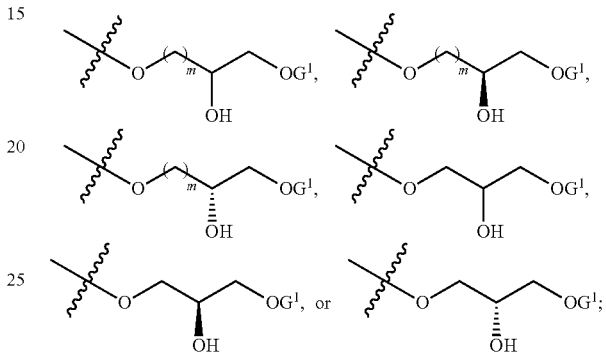

m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. T may be

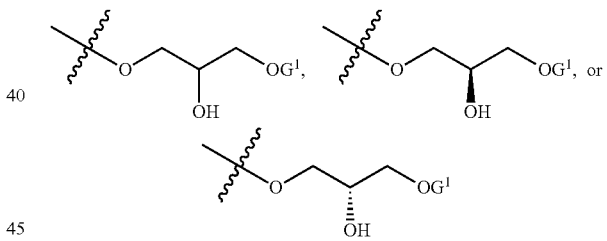

and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. T may be

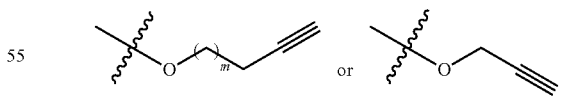

and m may be 0, 1, 2, 3, 4, 5, 6, 7 or 8. T may be

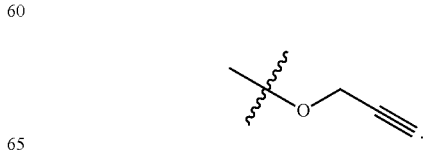

T may be
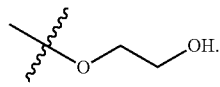 [SMILES: *OCCO]
T may be
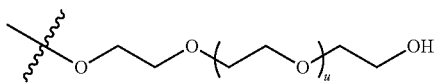
and u may be 0, 1, 2, 3, 4, 5, 6 or 7. T may be
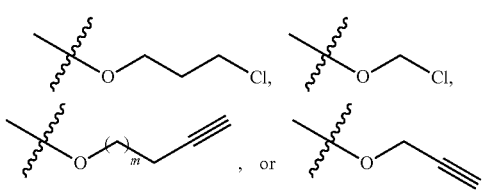
and m may be 0, 1, 2, 3, 4, 5, 6, 7 or 8. T may be
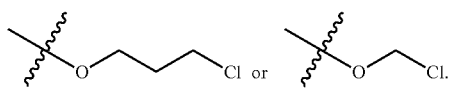
T may be
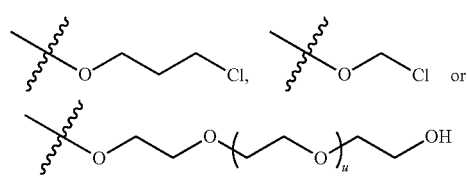
and u may be 0, 1, 2, 3, 4, 5, 6 or 7.
Q may be
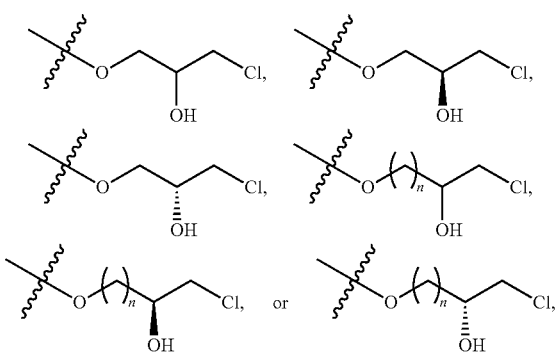
T may be
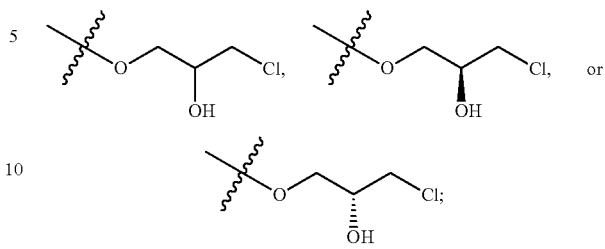
and n may be 0, 1, 2, 3, 4, 5, 6, 7 or 8. Q may be
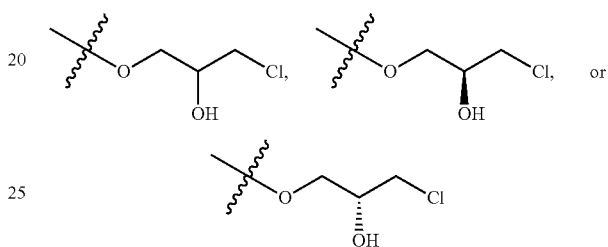
and T may be
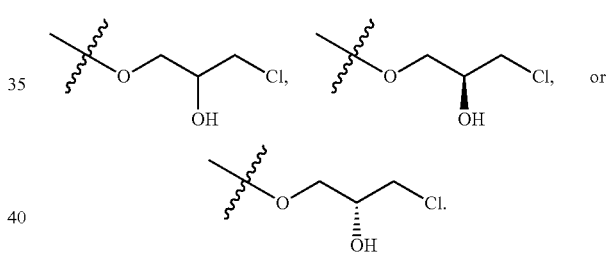
Q may be
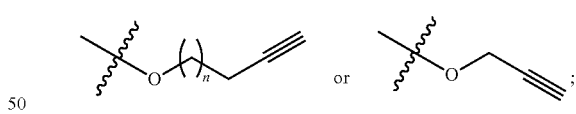
T may be
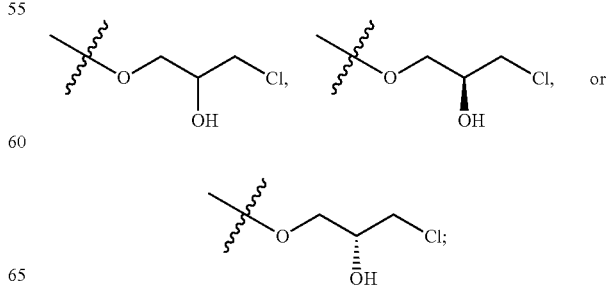

and n may be 0, 1, 2, 3, 4, 5, 6, 7. Q may be

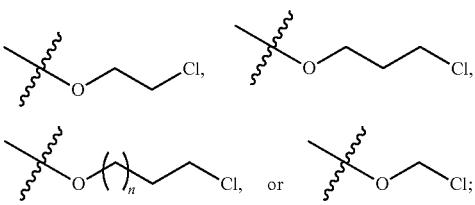

T may be

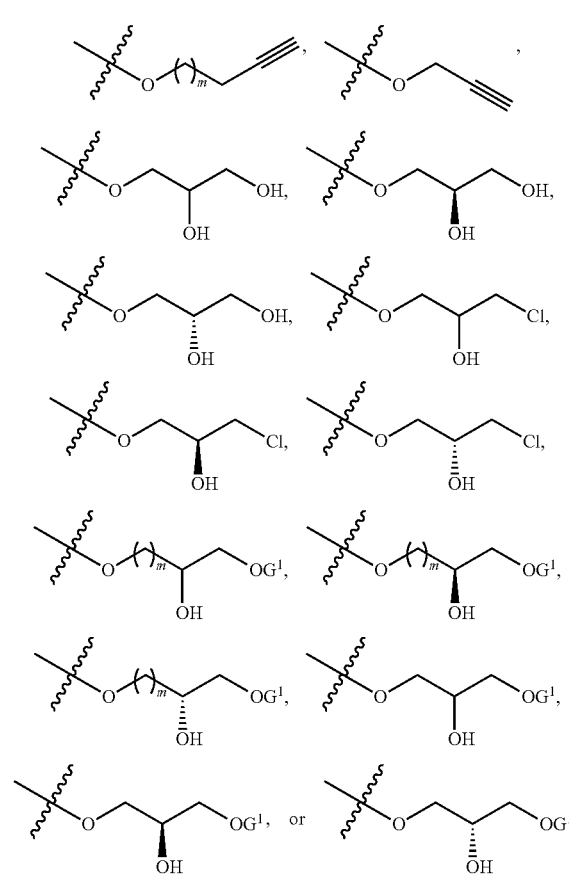

n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$. Q may be

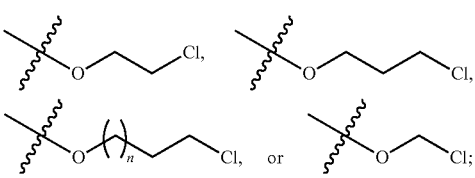

T may be

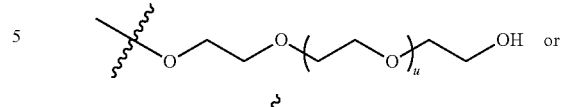

n may be 0, 1, 2, 3, 4, 5, 6, 7 or 8; and u may be 0, 1, 2, 3, 4, 5, 6 or 7. Q may be

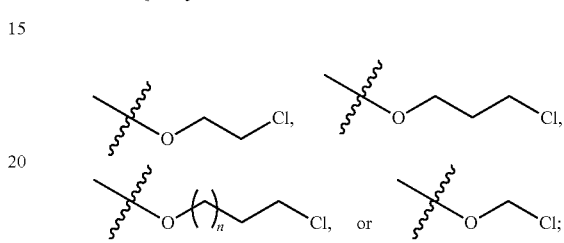

T may be

n may be 0, 1, 2, 3, 4, 5, 6, 7 or 8; and m may be 0, 1, 2, 3, 4, 5, 6, 7 or 8. Q may be

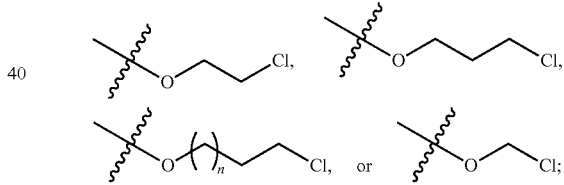

T may be

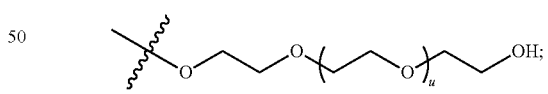

n may be 0, 1, 2, 3, 4, 5, 6, 7 or 8; and u may be 0, 1, 2, 3, 4, 5, 6 or 7. Q may be

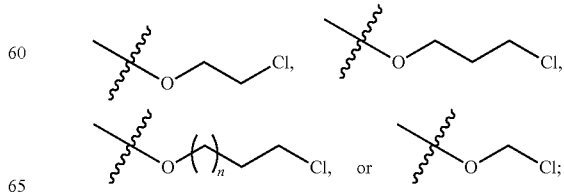

T may be

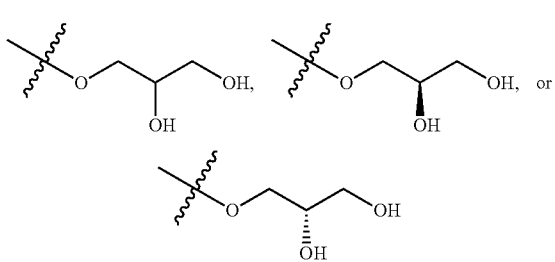

and n may be 0, 1, 2, 3, 4, 5, 6, 7 or 8. Q may be

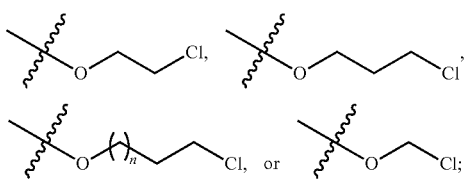

T may be

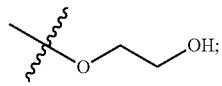 [SMILES: *OCCO]

and n may be 0, 1, 2, 3, 4, 5, 6, 7 or 8. Q may be

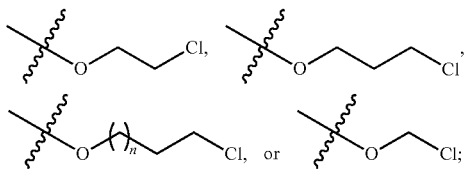

T may be

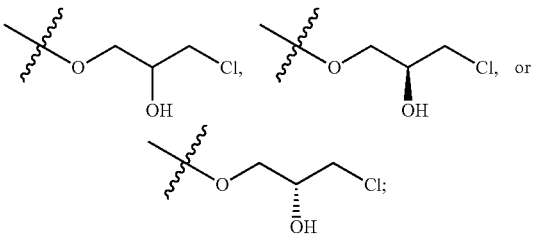

and n may be 0, 1, 2, 3, 4, 5, 6, 7 or 8. Q may be

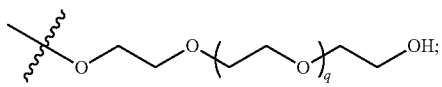

T may be

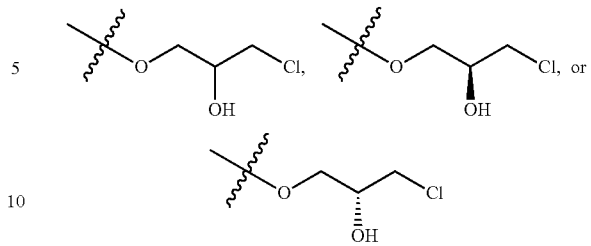

and q may be 0, 1, 2, 3, 4, 5, 6 or 7. Q may be

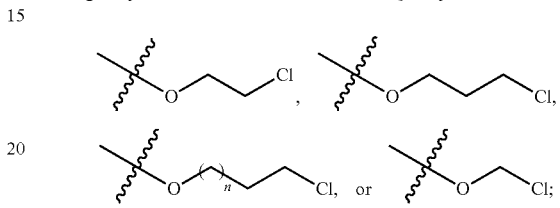

T may be

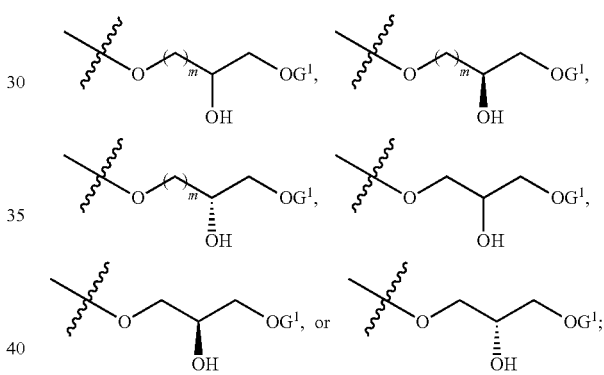

n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

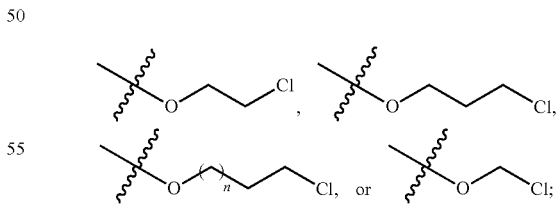

T may be

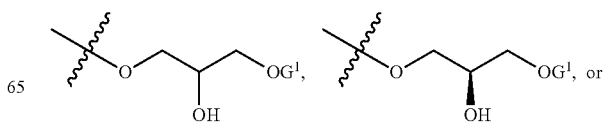

213

-continued

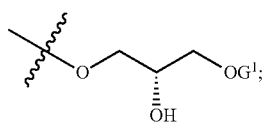

n may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, $OJ'''$, COOH, OH, F, Cl, Br, I, $NH_2$, CN, SH, $SO_3H$, $CONH_2$, $OPO_3H_3$, and $NO_2$. Q may be

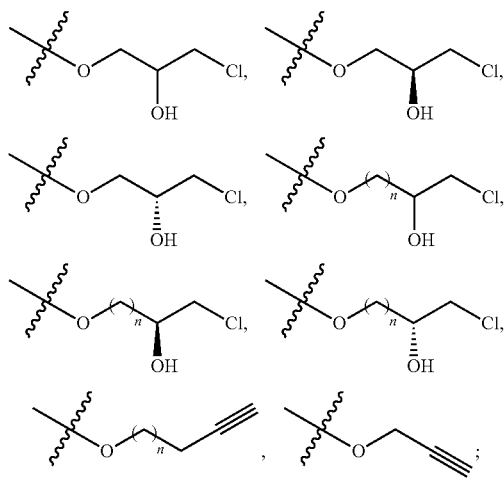

T may be

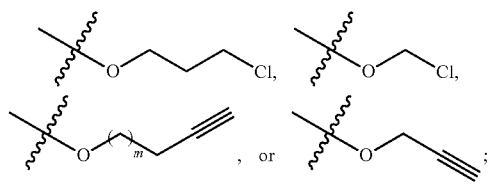

n may be 0, 1, 2, 3, 4, 5, 6, 7 or 8; and m may be 0, 1, 2, 3, 4, 5, 6, 7 or 8. Q may be

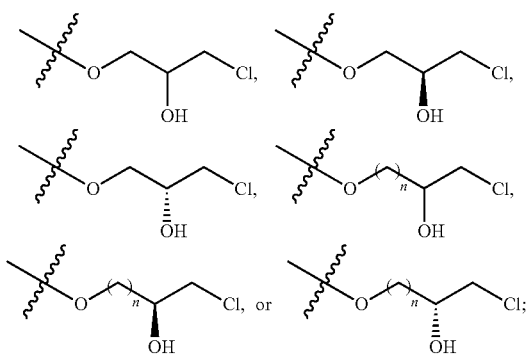

214

T may be

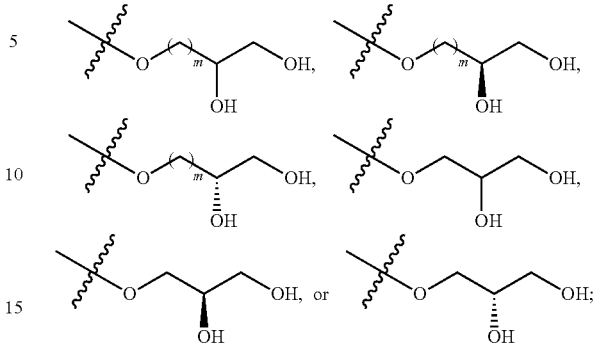

n may be 0, 1, 2, 3, 4, 5, 6, 7 or 8; and m may be 0, 1, 2, 3, 4, 5, 6, 7 or 8. Q may be

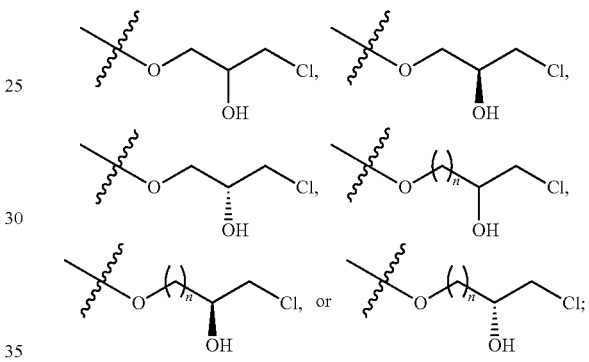

T may be

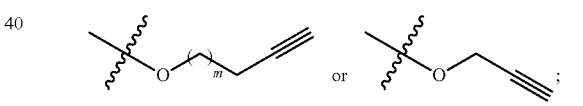

n may be 0, 1, 2, 3, 4, 5, 6, 7 or 8; and m may be 0, 1, 2, 3, 4, 5, 6, 7 or 8. Q may be

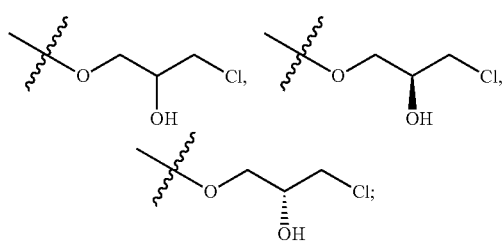

T may be

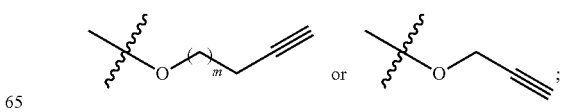

and m may be 0, 1, 2, 3, 4, 5, 6, 7 or 8. Q may be
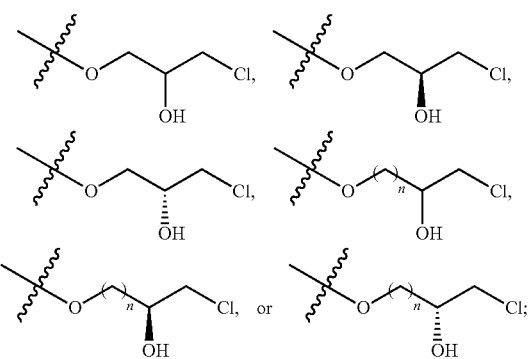
and T may be
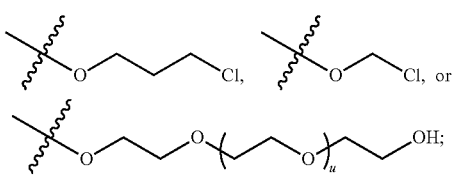
and u may be 0, 1, 2, 3, 4, 5, 6 or 7. Q may be
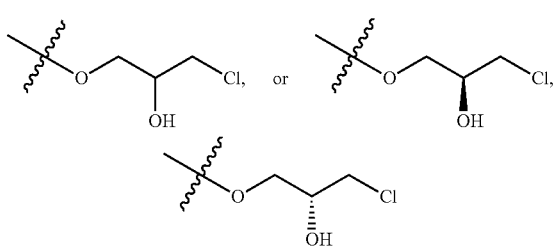
and T may be
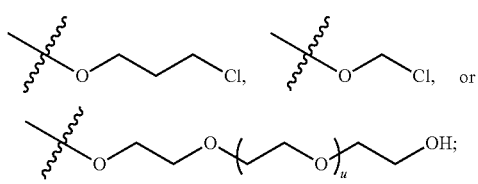
and u may be 0, 1, 2, 3, 4, 5, 6 or 7. Q may be
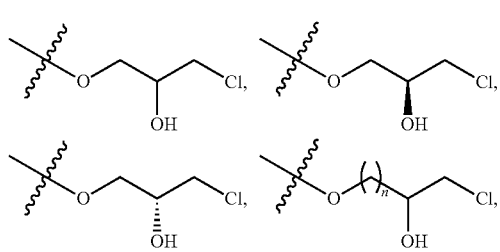
-continued
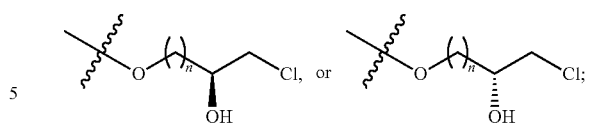
T may be
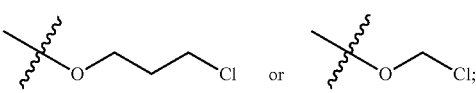
n may be 0, 1, 2, 3, 4, 5, 6, 7 or 8. Q may be
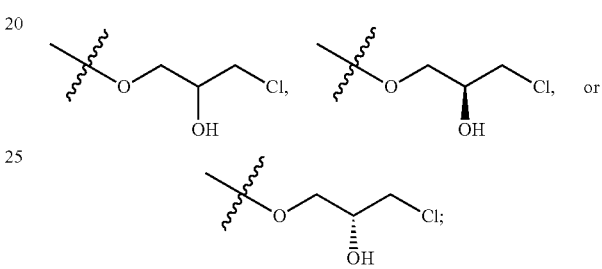
T may be
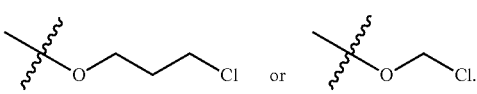
Q may be
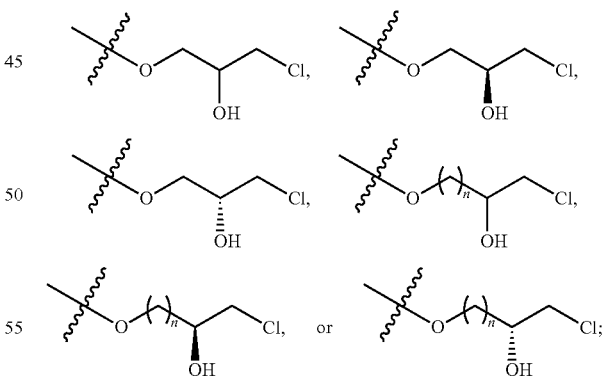
and T may be
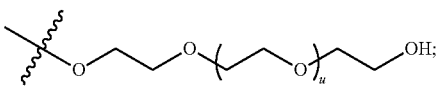

and u may be 0, 1, 2, 3, 4, 5, 6 or 7. Q may be

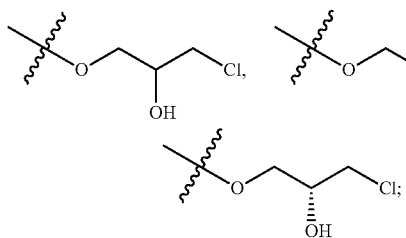

and T may be

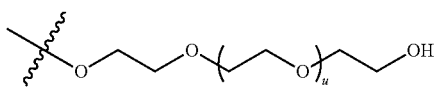

and u may be 0, 1, 2, 3, 4, 5, 6 or 7. Q may be

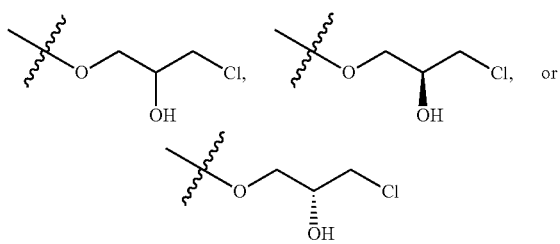

and T may be

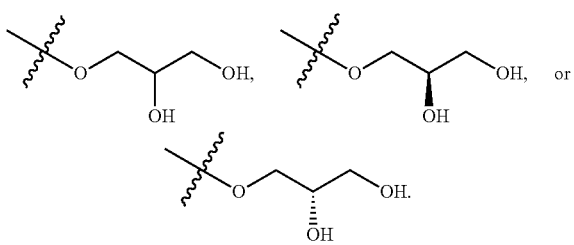

Q may be

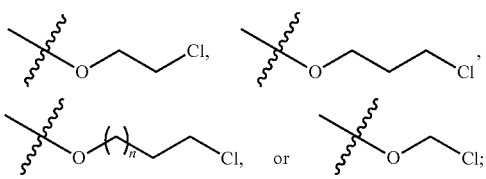

T may be

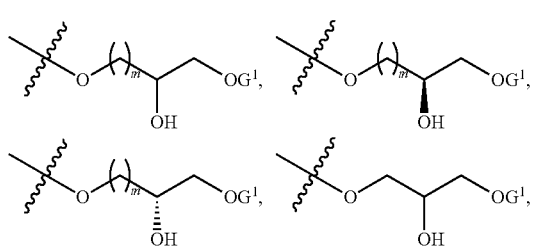

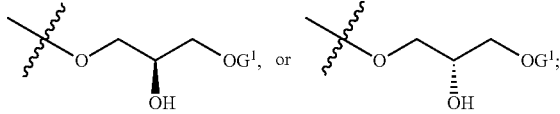

n may be 0, 1, 2, 3, 4, 5, 6, 7 or 8; m may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$. Q may be

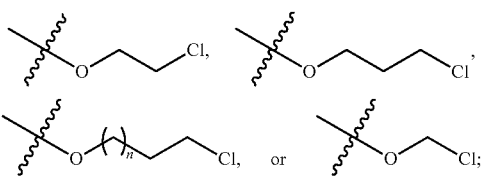

T may be

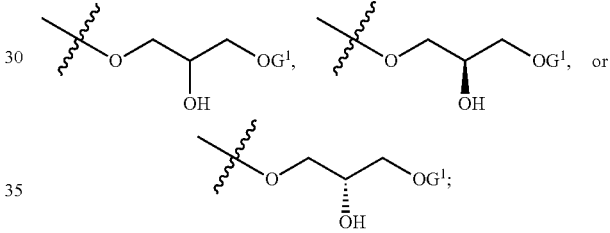

n may be 0, 1, 2, 3, 4, 5, 6, 7 or 8; and each $G^1$ may independently be linear or branched, substituted or unsubstituted, saturated or unsaturated $C_1$-$C_{10}$ alkyl, wherein the optional substituent may be selected from the group consisting of oxo, OJ''', COOH, OH, F, Cl, Br, I, $NH_2$, CN, SH, $SO_3H$, $CONH_2$, $OPO_3H_3$, and $NO_2$.

Each J'' and J''', when present, may independently be an amino acid based moiety selected from TABLE 1. Each J'' and J''', when present, may independently be

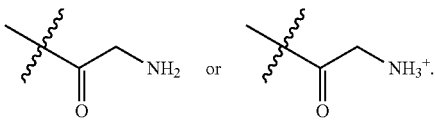

Each $G^1$ $G^{1\prime}$ and $G^{1\prime\prime\prime}$, when present, is an independently linear or branched, substituted or unsubstituted, saturated or unsaturated $C_1$-$C_{10}$ alkyl. $G^1$, when present, may be cyclohexyl, $CH_2CH_2CH_2CH_3$, $CH_2C\equiv CH$ or $CH(CH_3)_2$. $G^1$, when present, may be $CH_2C\equiv CH$ or $CH(CH_3)_2$.

One or more of the OH groups of the compound may be optionally substituted to replace the H with a moiety selected from TABLE 1. The moiety selected from TABLE 1 may be an amino acid based moiety selected from TABLE 1. The moiety selected from TABLE 1 may be

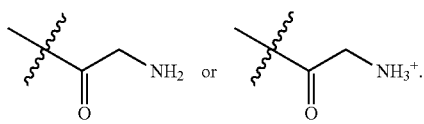

Each of the remaining Z may independently be selected from: N; $CG^1$; CH; CF; CCl; CBr; and CI. Each remaining Z may independently be CH, CF, CCl, CBr, CI, or $CG^1$. Each of the remaining Z may independently be selected from: $CG^1$; CH; CCl; and CBr. Each remaining Z may independently be CH, CBr, or $CG^1$. Each remaining Z may independently be CH, CBr, or $CCH_3$. Each remaining Z at the meta position to X may independently be CBr or $CG^1$. Each remaining Z at the meta position to X may independently be CBr or $CCH_3$. Each remaining Z at the ortho position to X may be CH. Each remaining Z at the meta position to X may independently be CBr or $CCH_3$ and each remaining Z at the ortho position to X may be CH. Each remaining Z may be CH.

X may be $CH_2$. X may be $CHR^1$ and $R^1$ may be linear or branched, unsubstituted, saturated or unsaturated $C_1$-$C_{10}$ alkyl. $R^1$ may be linear or branched, unsubstituted, saturated $C_1$-$C_{10}$ alkyl. $R^1$ may be $CH_3$. X may be $CR^1R^2$; each of $R^1$ and $R^2$ may independently be linear or branched, unsubstituted, saturated or unsaturated $C_1$-$C_{10}$ alkyl. Each of $R^1$ and $R^2$ may independently be linear or branched, unsubstituted, saturated $C_1$-$C_{10}$ alkyl. Each of $R^1$ and $R^2$ may be $CH_3$.

The compound may be selected from one or more of the following:

EPI-033

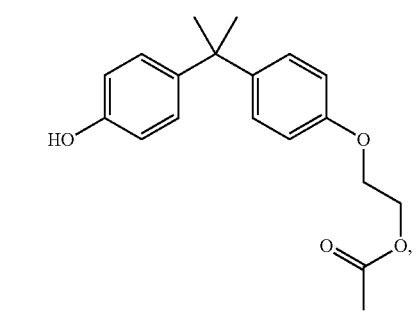

EPI-034

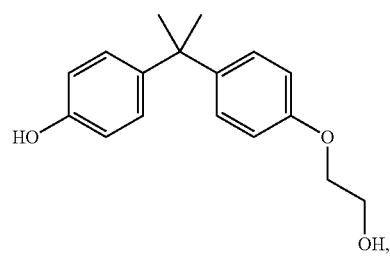

EPI-035

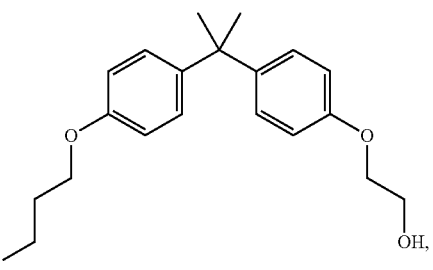

EPI-036

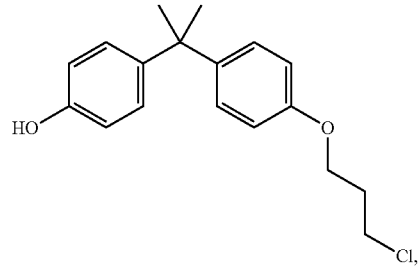

EPI-037

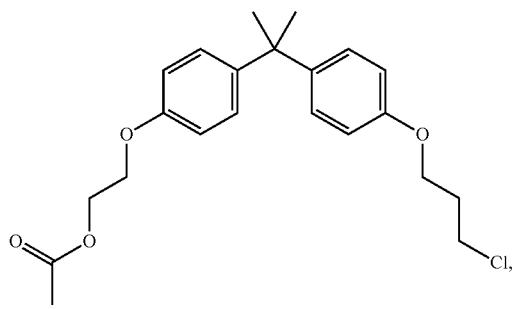

EPI-040

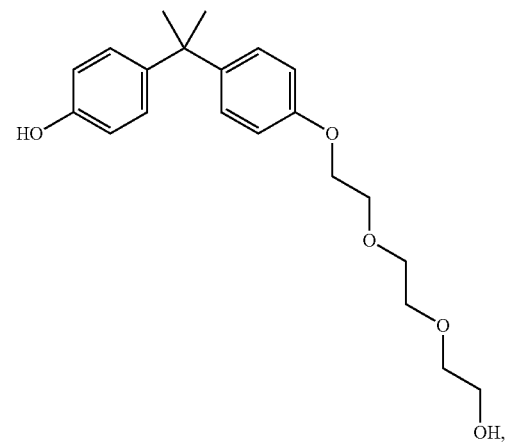

EPI-041

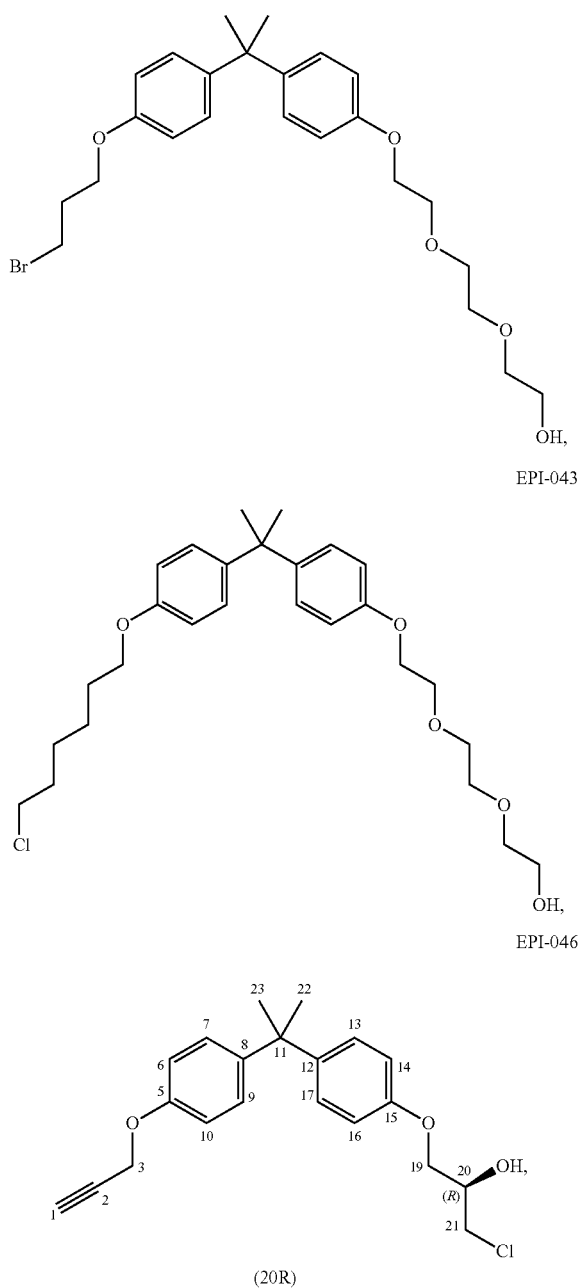
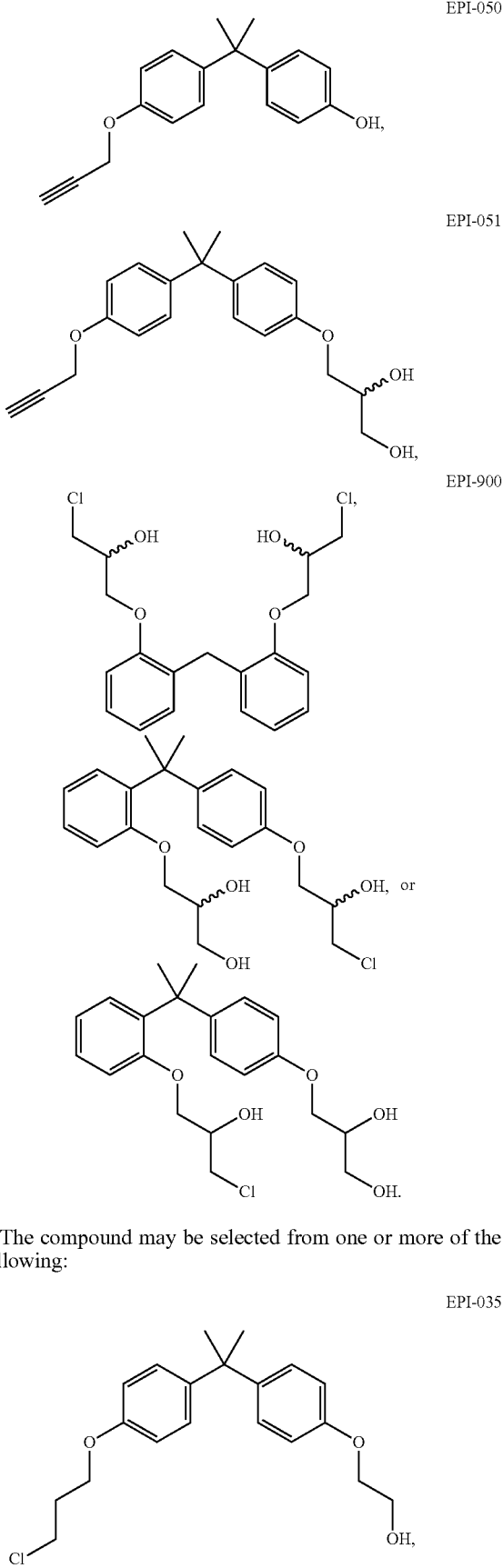
The compound may be selected from one or more of the following:

EPI-037
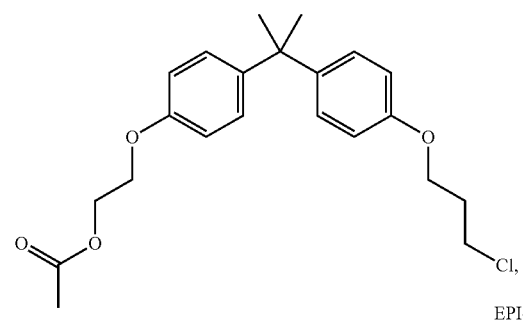
EPI-041
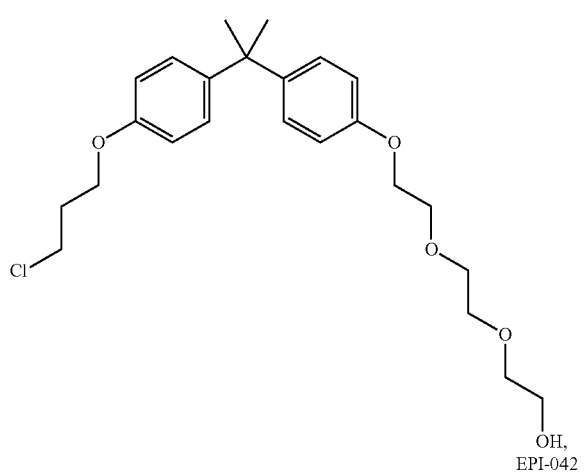
EPI-042
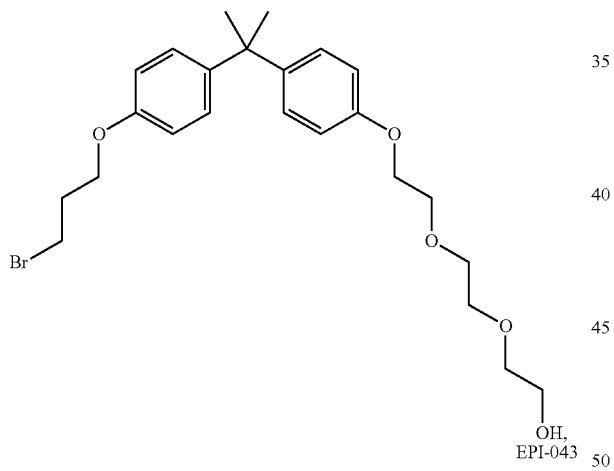
EPI-043
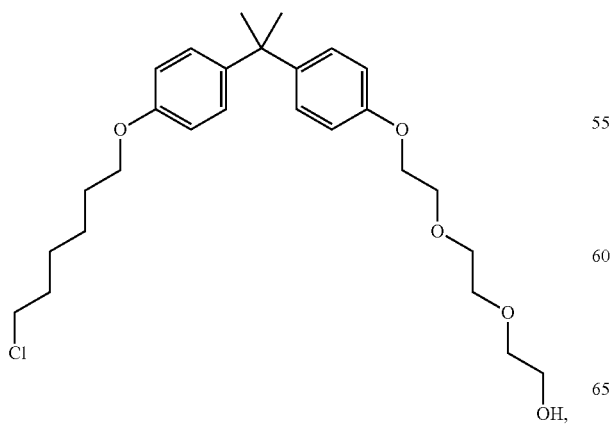
EPI-046
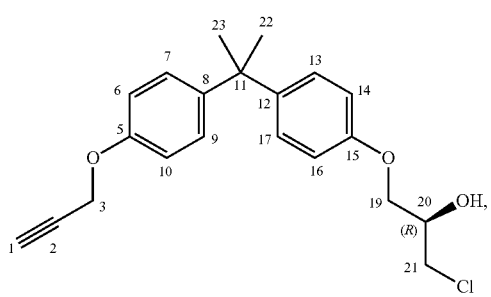
(20R)
EPI-047
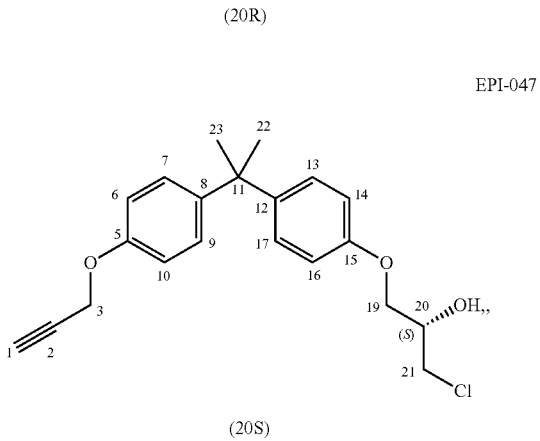
(20S)
EPI-051
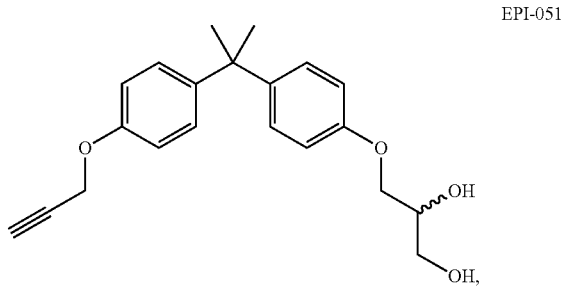
EPI-900
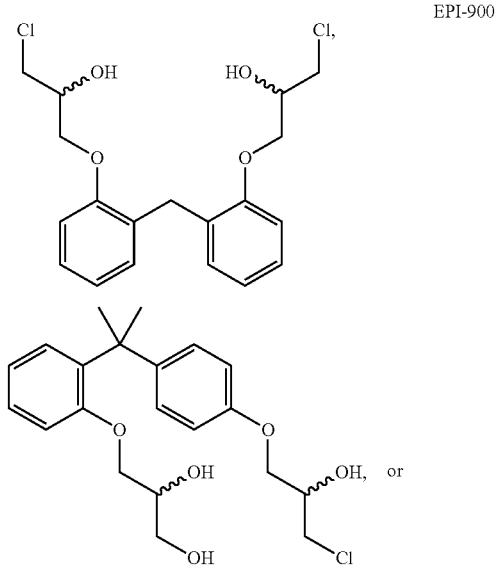
or

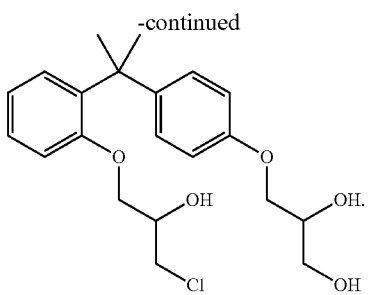

The compound may be selected from one or more of the compounds of TABLE 2.

The compounds described herein are meant to include all racemic mixtures and all individual enantiomers or combinations thereof, whether or not they are represented herein. Alternatively, one or more of the OH groups may be substituted to replace the H with a moiety selected from TABLE 1.

In accordance with another embodiment, there is provided a pharmaceutical composition comprising a compound according to any one of the above compounds and a pharmaceutically acceptable excipient. The pharmaceutical composition may be for treating one or more of the following: prostate cancer; breast cancer; ovarian cancer; endometrial cancer; hair loss; acne; hirsutism; ovarian cysts; polycystic ovary disease; precocious puberty; and age-related macular degeneration.

In accordance with a further embodiment, there is provided a method of screening for androgen receptor modulating compounds, wherein the compounds screened are selected from the compounds as described anywhere herein.

DETAILED DESCRIPTION

Figure 1:
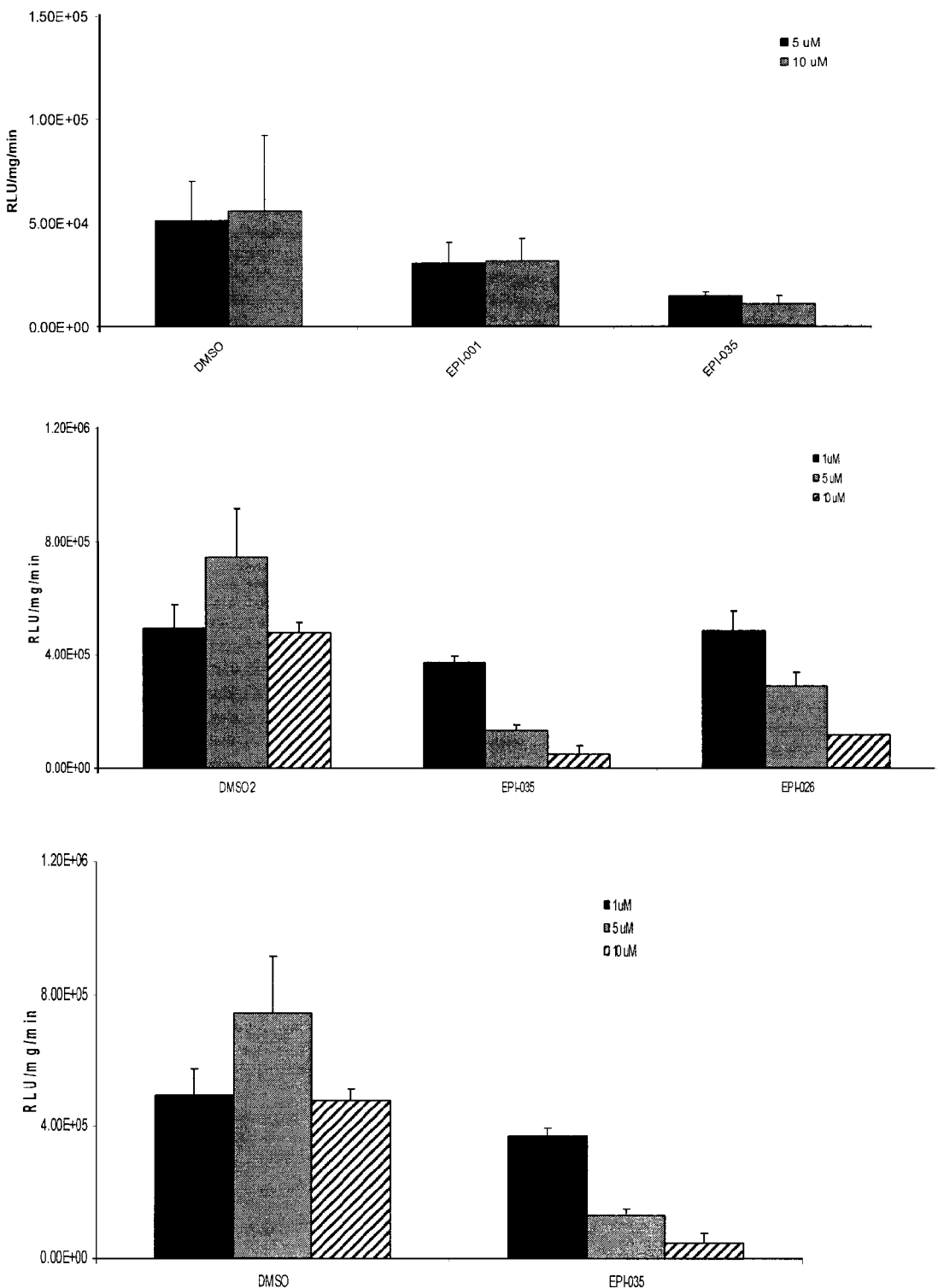
FIG. 1 shows a dose response for EPI-035 as compared to EPI-001 and EPI-026 in a LNCaP PSA (6.1 kb)-luciferase assay.

As used herein, the phrase "$C_x$—$C_y$ alkyl" is used as it is normally understood to a person of skill in the art and often refers to a chemical entity that has a carbon skeleton or main carbon chain comprising a number from x to y (with all individual integers within the range included, including integers x and y) of carbon atoms. For example a "$C_1$-$C_{10}$ alkyl" is a chemical entity that has 1, 2, 3, 4, 5, 6, 7, 8, 9 or 10 carbon atom(s) in its carbon skeleton or main chain.

As used herein, the term "cyclic $C_x$-$C_y$ alkyl" is used as it is normally understood to a person of skill in the art and often refers to a compound or a chemical entity in which at least a portion of the carbon skeleton or main chain of the chemical entity is bonded in such a way so as to form a 'loop', circle or ring of atoms that are bonded together. The atoms do not have to all be directly bonded to each other, but rather may be directly bonded to as few as two other atoms in the 'loop'. Non-limiting examples of cyclic alkyls include benzene, toluene, cyclopentane, bisphenol and 1-chloro-3-ethylcyclohexane.

As used herein, the term "branched" is used as it is normally understood to a person of skill in the art and often refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl are tert-butyl and isopropyl.

As used herein, the term "unbranched" is used as it is normally understood to a person of skill in the art and often refers to a chemical entity that comprises a skeleton or main chain that does not split off into more that one contiguous chain. Non-limiting examples of unbranched alkyls are methyl, ethyl, n-propyl, and n-butyl.

As used herein, the term "substituted" is used as it is normally understood to a person of skill in the art and often refers to a chemical entity that has one chemical group replaced with a different chemical group that contains one or more heteroatoms. Unless otherwise specified, a substituted alkyl is an alkyl in which one or more hydrogen atom(s) is/are replaced with one or more atom(s) that is/are not hydrogen(s). For example, chloromethyl is a non-limiting example of a substituted alkyl, more particularly an example of a substituted methyl. Aminoethyl is another non-limiting example of a substituted alkyl, more particularly it is a substituted ethyl.

As used herein, the term "unsubstituted" is used as it is normally understood to a person of skill in the art and often refers to a chemical entity that is a hydrocarbon and/or does not contain a heteroatom. Non-limiting examples of unsubstituted alkyls include methyl, ethyl, tert-butyl, and pentyl.

As used herein, the term "saturated" when referring to a chemical entity is used as it is normally understood to a person of skill in the art and often refers to a chemical entity that comprises only single bonds. Non-limiting examples of saturated chemical entities include ethane, tert-butyl, and $N^+H_3$.

As used herein, $C_1$-$C_{10}$ alkyl may include, for example, and without limitation, saturated $C_1$-$C_{10}$ alkyl, $C_2$-$C_{10}$ alkenyl and $C_2$-$C_{10}$ alkynyl. Non-limiting examples of saturated $C_1$-$C_{10}$ alkyl may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl and t-decyl. Non-limiting examples of $C_2$-$C_{10}$ alkenyl may include vinyl, allyl, isopropenyl, 1-propene-2-yl, 1-butene-1-yl, 1-butene-2-yl, 1-butene-3-yl, 2-butene-1-yl, 2-butene-2-yl, octenyl and decenyl. Non-limiting examples of $C_2$-$C_{10}$ alkynyl may include ethynyl, propynyl, butynyl, pentynyl, hexynyl, heptynyl, octynyl, nonynyl and decynyl. Saturated $C_1$-$C_{10}$ alkyl, $C_2$-$C_{10}$ alkenyl or $C_2$-$C_{10}$ alkynyl may be, for example, and without limitation, interrupted by one or more heteroatoms which are independently nitrogen, sulfur or oxygen.

As used herein, cyclic $C_3$-$C_{10}$ alkyl may include, for example, and without limitation, saturated $C_3$-$C_{10}$ cycloalkyl, $C_3$-$C_{10}$ cycloalkenyl, $C_3$-$C_{10}$ cycloalkynyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently nitrogen, sulfur or oxygen, and a 5- to 10-membered aromatic heterocyclic group containing one or more heteroatoms which are independently nitrogen, sulfur or oxygen. Non-limiting examples of the saturated $C_3$-$C_{10}$ cycloalkyl group may include cyclopropanyl, cyclobutanyl, cyclopentanyl, cyclohexanyl, cycloheptanyl, cyclooctanyl, cyclononanyl and cyclodecanyl. Non-limiting examples of the $C_3$-$C_{10}$ cycloalkenyl group may include cyclopropenyl, cyclobutenyl, cyclopentenyl, cyclohexenyl, cycloheptenyl, cyclooctenyl, cyclononanenyl and cyclodecanenyl. Non-limiting examples of the $C_6$-$C_{10}$ aryl group may include phenyl (Ph), pentalenyl, indenyl, naphthyl, and azulenyl. The $C_{6-9}$ aryl-$C_{1-4}$ alkyl group may be, for example, and without limitation, a $C_{1-4}$ alkyl group as defined anywhere above having a $C_{6-9}$ aryl group as defined anywhere above as a substituent. The $C_{6-8}$ aryl-$C_{2-4}$ alkenyl group may be, for example, and without limitation, a $C_{2-4}$ alkenyl as defined anywhere above having a $C_{6-8}$ aryl group as defined anywhere above as a substituent. The $C_{6-8}$ aryl-$C_{2-4}$ alkynyl group may be, for example, and without limitation, a $C_{2-4}$ alkynyl group as defined anywhere above having a $C_{6-8}$ aryl group as defined anywhere above as a substituent. Non-limiting examples of the 4- to 10-membered non-aromatic heterocyclic group containing one or more heteroatoms which are independently nitrogen, sulfur or oxygen may include pyrrolidinyl, pyrrolinyl, piperidinyl, piperazinyl, imidazolinyl, pyrazolidinyl, imidazolydinyl, morpholinyl, tetrahydropyranyl, azetidinyl, oxetanyl, oxathiolanyl, phthalimide and succinimide. Non-limiting examples of the 5- to 10-membered aromatic heterocyclic group containing one or more heteroatoms which are independently nitrogen, sulfur or oxygen may include pyrrolyl, pyridinyl, pyridazinyl, pyrimidinyl, pirazinyl, imidazolyl, thiazolyl and oxazolyl.

Non-limiting examples of one to ten carbon substituted or unsubstituted acyl include acetyl, propionyl, butanoyl and pentanoyl. Non-limiting examples of $C_1$-$C_{10}$ alkoxy include methoxy, ethoxy, propoxy and butoxy.

As used herein, the symbol

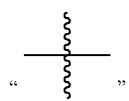

(hereinafter may be referred to as "a point of attachment bond") denotes a bond that is a point of attachment between two chemical entities, one of which is depicted as being attached to the point of attachment bond and the other of which is not depicted as being attached to the point of attachment bond. For example,

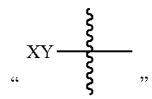

indicates that the chemical entity "XY" is bonded to another chemical entity via the point of attachment bond. Furthermore, the specific point of attachment to the non-depicted chemical entity may be specified by inference. For example The compound $CH_3$—$R^3$, wherein $R^3$ is H or

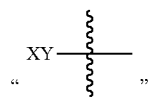

infers that when $R^3$ is "XY", the point of attachment bond is the same bond as the bond by which $R^3$ is depicted as being bonded to $CH_3$.

As used herein, the term "moiety" refers to a moiety set out in the following Table 1.

TABLE 1

| MOIETIES |
|---|
| Amino Acid Based Moieties |

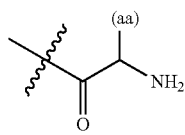

(aa)

(aa) = any naturally occurring amino acid side chain

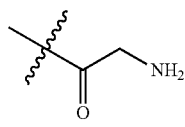

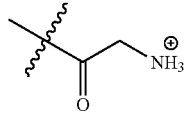 [SMILES: *C(=O)C[NH3+]]

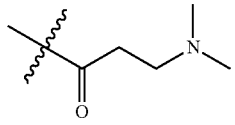 [SMILES: *C(=O)CCN(C)C]

| Polyethylene Glycol Based Moieties |
|---|

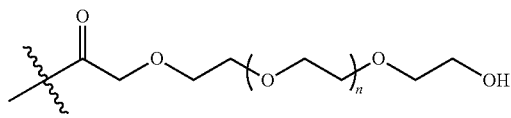

n = 1-200

TABLE 1-continued
MOIETIES
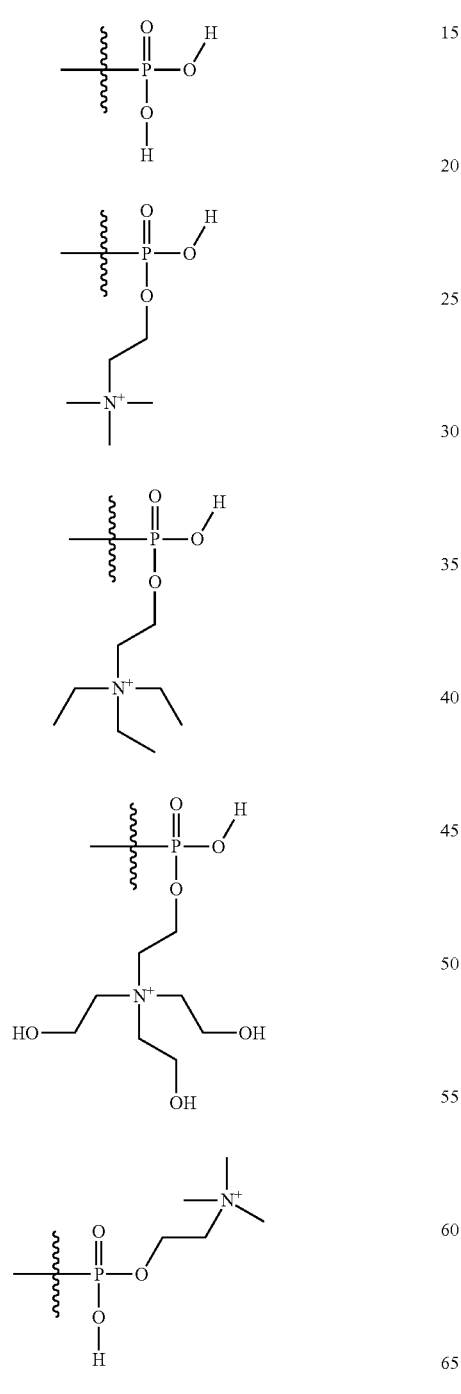
Phosphate Based Moieties
TABLE 1-continued
MOIETIES
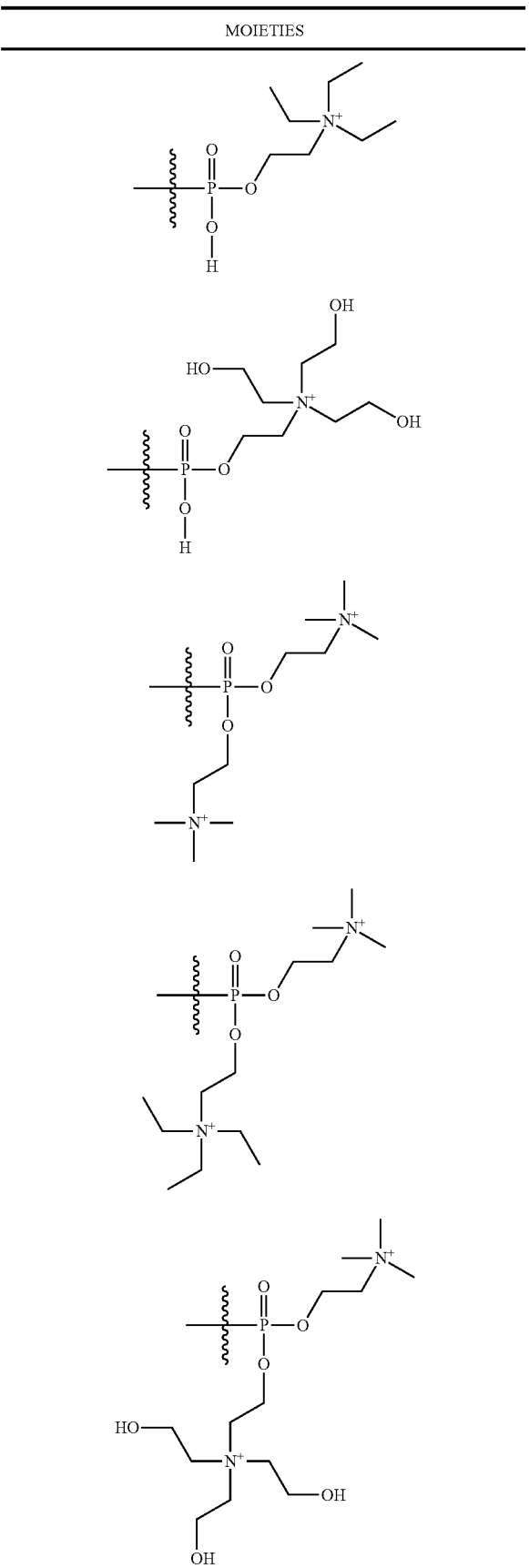

TABLE 1-continued

MOIETIES

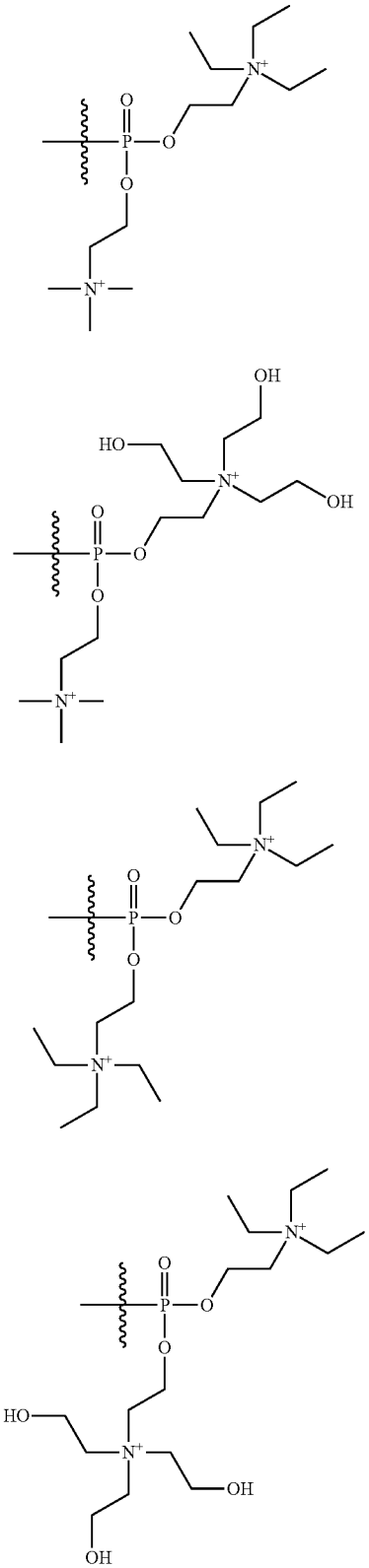
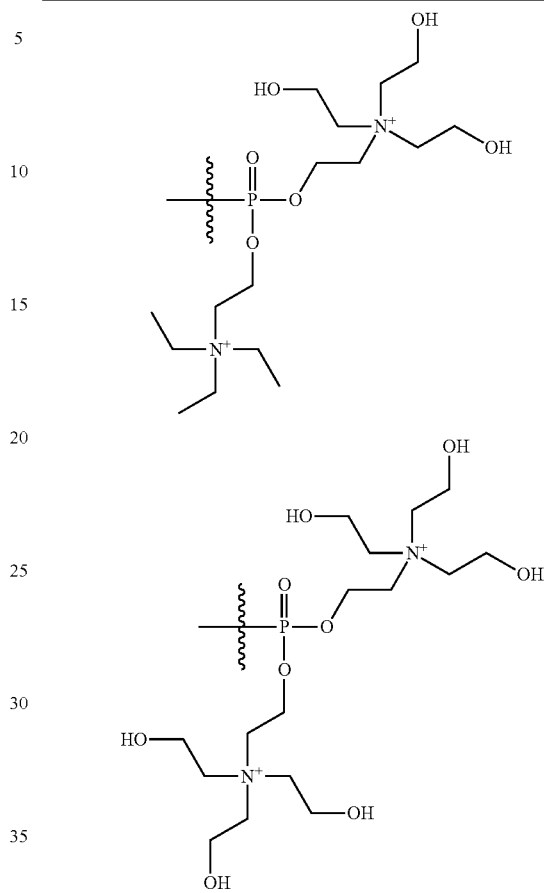

Moieties may be, for example, and without limitation, subdivided into three groups: 1) amino acid based moieties; 2) polyethylene glycol based moieties; and 3) phosphate based moieties. In the Moieties Table 1 above, the first four moieties are amino acid based moieties, the fifth and sixth are polyethylene glycol based moieties and the remaining moieties are phosphate based moieties.

The amino acid side chains of naturally occurring amino acids (as often denoted herein using "(aa)") are well known to a person of skill in the art and may be found in a variety of text books such as "Molecular Cell Biology" by James Darnell et al. Third Edition, published by Scientific American Books in 1995. Often the naturally occurring amino acids are represented by the formula $(NH_2)C(COOH)(H)(R)$, where the chemical groups in brackets are each bonded to the carbon not in brackets. R represents the side chains in this particular formula.

Those skilled in the art will appreciate that the point of covalent attachment of the moiety to the compounds as described herein may be, for example, and without limitation, cleaved under specified conditions. Specified conditions may include, for example, and without limitation, in vivo enzymatic or non-enzymatic means. Cleavage of the moiety may occur, for example, and without limitation, spontaneously, or it may be catalyzed, induced by another agent, or a change in a physical parameter or environmental parameter, for example, an enzyme, light, acid, temperature or pH. The moiety may be, for example, and without limitation, a protecting group that acts to mask a functional group, a group that acts as a substrate for one or more active or passive transport mechanisms, or a group that acts to impart or enhance a property of the compound, for example, solubility, bioavailability or localization.
In other particular embodiments of the compounds as described anywhere herein, the following compounds in Table 2 are provided.
TABLE 2
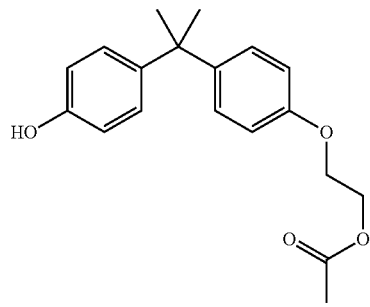 [SMILES: CC(=O)OCCOc1ccc(C(C)(C)c2ccc(O)cc2)cc1]
EPI-033
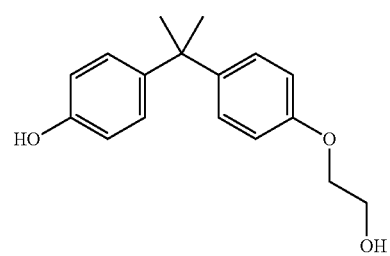 [SMILES: CC(C)(c1ccc(O)cc1)c1ccc(OCCO)cc1]
EPI-034
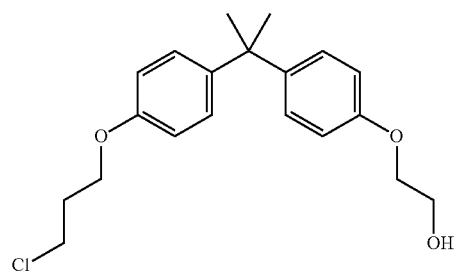
EPI-035
(JG-101, JG-133)
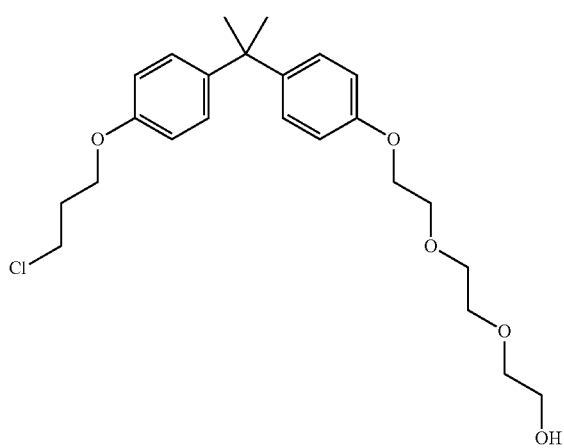
EPI-041
(JG-140A)

TABLE 2-continued
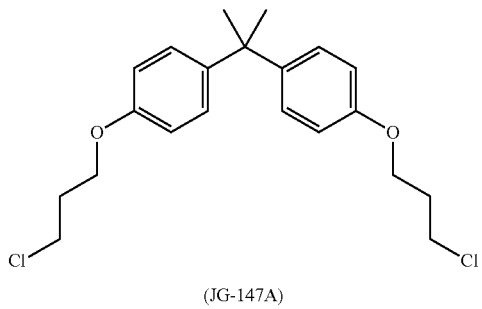 [SMILES: CC(C)(c1ccc(OCCCCl)cc1)c1ccc(OCCCCl)cc1]
(JG-147A) EPI-038
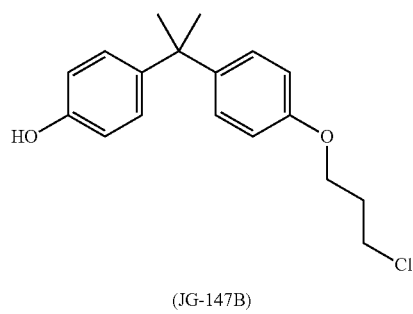 [SMILES: CC(C)(c1ccc(O)cc1)c1ccc(OCCCCl)cc1]
(JG-147B) EPI-036
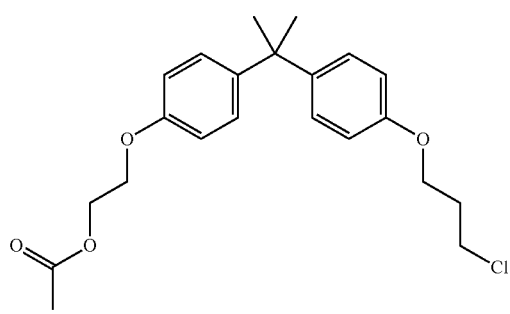
(JG-148A) EPI-037
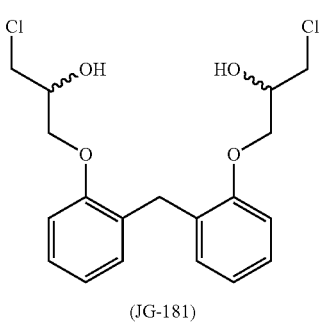 [SMILES: OC(CCl)COc1ccccc1Cc1ccccc1OCC(O)CCl]
(JG-181) EPI-900

TABLE 2-continued
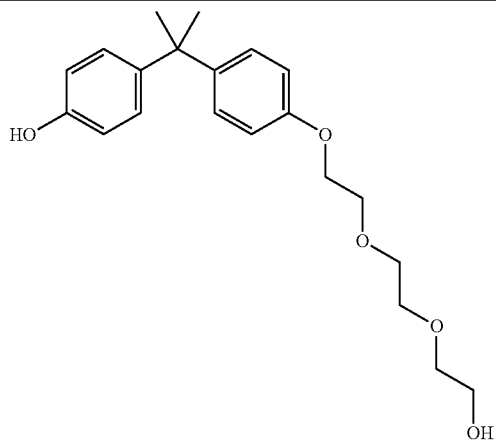
(JG-122B)
EPI-040
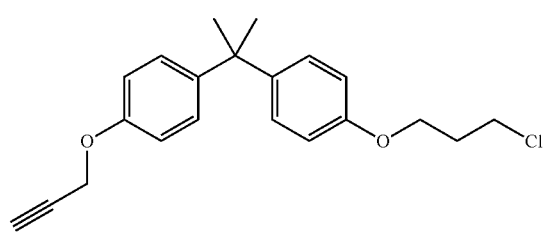 [SMILES: C#CCOc1ccc(C(C)(C)c2ccc(OCCCCl)cc2)cc1]
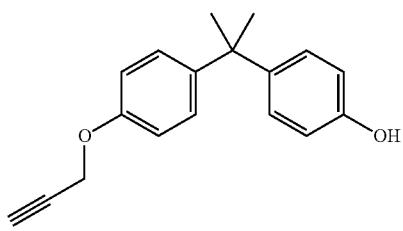 [SMILES: C#CCOc1ccc(C(C)(C)c2ccc(O)cc2)cc1]
EPI-050
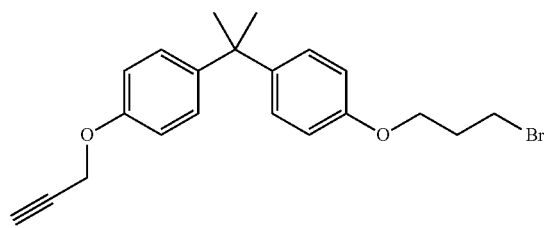 [SMILES: C#CCOc1ccc(C(C)(C)c2ccc(OCCCBr)cc2)cc1]
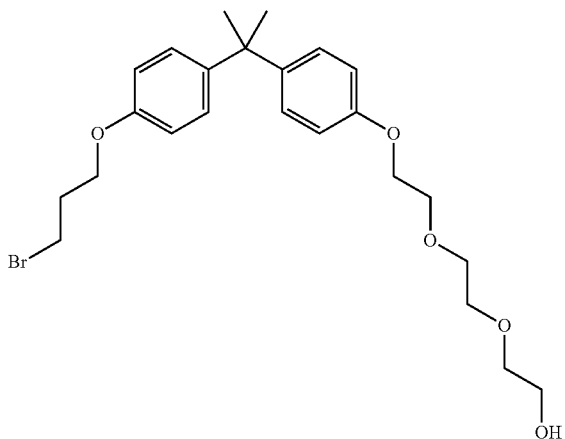
(JG-202)
EPI-042

TABLE 2-continued
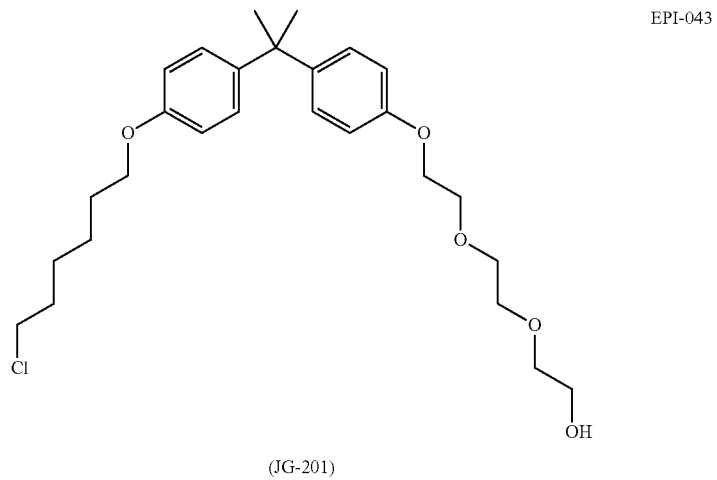
(JG-201) EPI-043
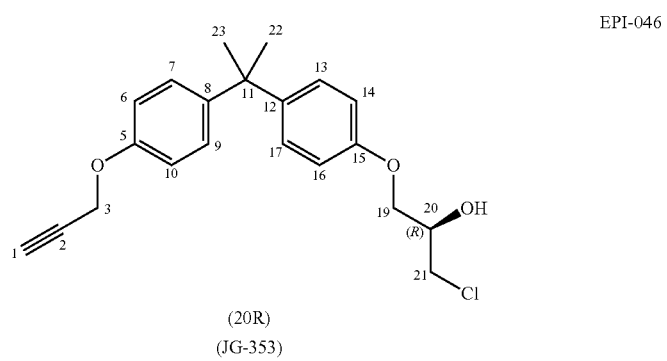
(20R)
(JG-353) EPI-046
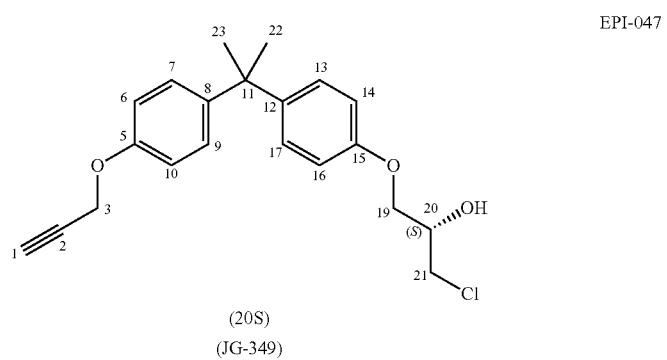
(20S)
(JG-349) EPI-047
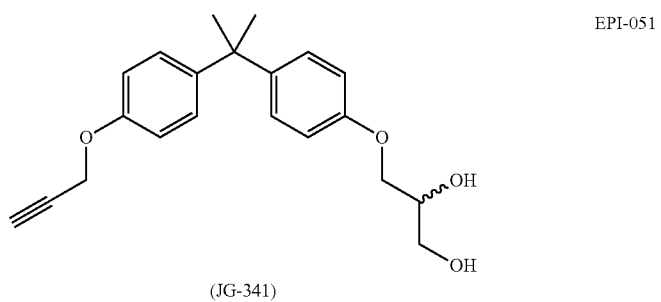
(JG-341) EPI-051

TABLE 2-continued

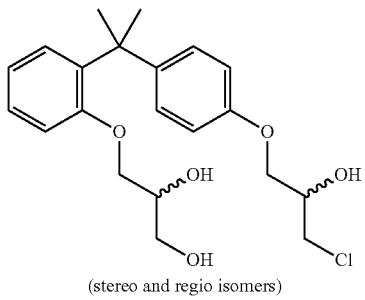 [SMILES: CC(C)(c1ccc(OCC(O)CCl)cc1)c1ccccc1OCC(O)CO]

EPI-6000, EPI-6001, EPI-6002, and EPI-6003

(stereo and regio isomers)

In some embodiments, the compounds as described herein or acceptable salts thereof above may be used for systemic treatment of at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. In some embodiments, the compounds as described herein or acceptable salts thereof above may be used in the preparation of a medicament or a composition for systemic treatment of an indication described herein. In some embodiments, methods of systemically treating any of the indications described herein are also provided. Some aspects of this invention, make use of compositions comprising a compound described herein and a pharmaceutically acceptable excipients or carrier. In some embodiments, the prostate cancer is androgen-independent prostate cancer (also referred to as hormone refractory, castration resistant, androgen deprivation resistant, androgen ablation resistant, androgen depletion-independent, castration-recurrent, anti-androgen-recurrent). In some embodiments the prostate cancer is androgen-dependent or androgen-sensitive. Methods of treating any of the indications described herein are also provided. Such methods may include administering a compound as described herein or a composition of a compound as described herein, or an effective amount of a compound as described herein or composition of a compound as described herein to a subject in need thereof.

Compounds as described herein may be in the free form or in the form of a salt thereof. In some embodiments, compounds as described herein may be in the form of a pharmaceutically acceptable salt, which are known in the art (Berge et al., *J. Pharm. Sci.* 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, pharmaceutical compositions in accordance with this invention may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy by Alfonso Gennaro*, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition according to the invention includes a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen-independent form. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods for at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. For example, compounds and all their different forms as described herein may be used as neoadjuvant (prior), adjunctive (during), and/or adjuvant (after) therapy with surgery, radiation (brachytherapy or external beam), or other therapies (eg. HIFU).

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions. Some compounds of this invention may be toxic at some concentrations. Titration studies may be used to determine toxic and non-toxic concentrations. Toxicity may be evaluated by examining a particular compound's or composition's specificity across cell lines using PC3 cells as a negative control that do not express AR. Animal studies may be used to provide an indication if the compound has any effects on other tissues. Systemic therapy that targets the AR will not likely cause major problems to other tissues since antiandrogens and androgen insensitivity syndrome are not fatal.

Compounds as described herein may be administered to a subject. As used herein, a "subject" may be a human, non-human primate, rat, mouse, cow, horse, pig, sheep, goat, dog, cat, etc. The subject may be suspected of having or at risk for having a cancer, such as prostate cancer, breast cancer, ovarian cancer or endometrial cancer, or suspected of having or at risk for having acne, hirsutism, alopecia, benign prostatic hyperplasia, ovarian cysts, polycystic ovary disease, precocious puberty, or age-related macular degeneration. Diagnostic methods for various cancers, such as prostate cancer, breast cancer, ovarian cancer or endometrial cancer, and diagnostic methods for acne, hirsutism, alopecia, benign prostatic hyperplasia, ovarian cysts, polycystic ovary disease, precocious puberty, or age-related macular degeneration and the clinical delineation of cancer, such as prostate cancer, breast cancer, ovarian cancer or endometrial cancer, diagnoses and the clinical delineation of acne, hirsutism, alopecia, benign prostatic hyperplasia, ovarian cysts, polycystic ovary disease, precocious puberty, or age-related macular degeneration are known to those of ordinary skill in the art.

Compounds described herein may be used for treatment of at least one indication selected from the group consisting of prostate cancer, breast cancer, ovarian cancer, endometrial cancer, hair loss, acne, hirsutism, ovarian cysts, polycystic ovary disease, precocious puberty and age-related macular degeneration. Compounds described herein may be used for treatment of prostate cancer. Compounds described herein may be used for treatment of androgen-independent prostate cancer. Compounds described herein may be used for treatment of androgen-dependent prostate cancer. Compounds described herein may be used for preparation of a medicament for treatment of at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. Compounds described herein may be used for the preparation of a medicament for treatment of prostate cancer. Compounds described herein may be used for the preparation of a medicament for treatment of androgen-independent prostate cancer. Compounds described herein may be used for the preparation of a medicament for treatment of androgen-dependent prostate cancer. Compounds described herein may be used in a method for treatment of at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. The method may comprise administering to a subject in need thereof an effective amount of a compound described herein. Compounds described herein may be used in a method of treatment of prostate cancer, the method comprising administering to a subject in need thereof an effective amount of a compound described herein. Compounds described herein may be used in a method of treatment of androgen-independent prostate cancer, the method comprising administering to a subject in need thereof an effective amount of a compound described herein. Compounds described herein may be used in a method of treatment of androgen-dependent prostate cancer, the method comprising administering to a subject in need thereof an effective amount of a compound described herein.

Compounds described herein may also be used in assays and for research purposes. Definitions used include ligand-dependent activation of the androgen receptor (AR) by androgens such as dihydrotestosterone (DHT) or the synthetic androgen (R1881) used for research purposes. Ligand-independent activation of the AR refers to transactivation of the AR in the absence of androgen (ligand) by, for example, stimulation of the cAMP-dependent protein kinase (PICA) pathway with forskolin (FSK). Some compounds and compositions of this invention may inhibit both FSK and androgen (e.g. R1881) induction of ARE-luciferase (ARE-luc). Such compounds may block a mechanism that is common to both ligand-dependent and ligand-independent activation of the AR. This could involve any step in activation of the AR including dissociation of heatshock proteins, essential post-translational modifications (e.g., acetylation, phosphorylation), nuclear translocation, protein-protein interactions, formation of the transcriptional complex, release of co-repressors, and/or increased degradation. Some compounds and compositions of this invention may inhibit R1881 only and may interfere with a mechanism specific to ligand-dependent activation (e.g., accessibility of the ligand binding domain (LBD) to androgen). Numerous disorders in addition to prostate cancer involve the androgen axis (e.g., acne, hirsutism, alopecia, benign prostatic hyperplasia) and compounds interfering with this mechanism may be used to treat such conditions. Some compounds and compositions of this invention may only inhibit FSK induction and may be specific inhibitors to ligand-independent activation of the AR. These compounds and compositions may interfere with the cascade of events that normally occur with FSK and/or PKA activity or any downstream effects that may play a role on the AR (e.g. FSK increases MAPK activity which has a potent effect on AR activity). Examples may include an inhibitor of cAMP and or PKA or other kinases. Some compounds and compositions of this invention may induce basal levels of activity of the AR (no androgen or stimulation of the PKA pathway). Some compounds and compositions of this invention may increase induction by R1881 or FSK. Such compounds and compositions may stimulate transcription or transactivation of the AR. Some compounds and compositions of this invention may inhibit activity of the androgen receptor. Interleukin-6 (IL-6) also causes ligand-independent activation of the AR in LNCaP cells and can be used in addition to FSK.

Compounds for use in the present invention may be obtained from medical sources or modified using known methodologies from naturally occurring compounds. In addition, methods of preparing or synthesizing compounds of the present invention will be understood by a person of skill in the art having reference to known chemical synthesis principles. For example, Auzou et al 1974 *European Journal of Medicinal Chemistry* 9(5), 548-554 describes suitable synthetic procedures that may be considered and suitably adapted for preparing compounds of any one of the Formula I to XXI as set out above. Other references that may be helpful include: Debasish Das, Jyh-Fu Lee and Soofin Cheng "Sulfonic acid functionalized mesoporous MCM-41 silica as a convenient catalyst for Bisphenol-A synthesis" *Chemical Communications*, (2001) 2178-2179; U.S. Pat. No. 2,571,217 Davis, Orris L.; Knight, Horace S.; Skinner, John R. (Shell Development Co.) "Halohydrin ethers of phenols." (1951); and Rokicki, G.; Pawlicki, J.; Kuran, W. "Reactions of 4-chloromethyl-1,3-dioxolan-2-one with phenols as a new route to polyols and cyclic carbonates." Journal fuer Praktische Chemie (Leipzig) (1985) 327, 718-722.

For example, compounds of the present invention which contain an ether moiety may be obtained with reference to the following general chemical synthetic scheme I:

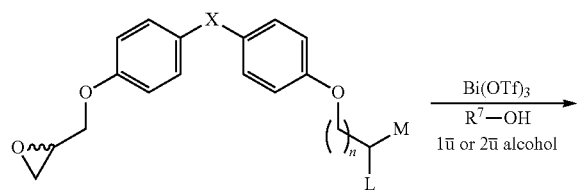

A

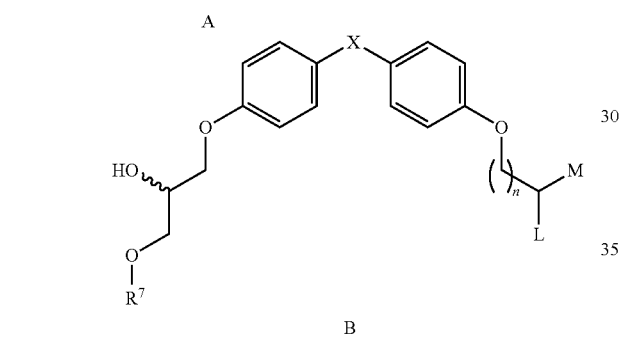

B wherein $R^7$—OH represents an alcohol and X, M, L, and n are as defined anywhere herein. Bismuth triflate may be added in portions to a solution of racemic derivative A in an alcohol $R^7$—OH over the course of the reaction. The mixture may be stirred under suitable conditions (for example, rt for 24 h). The resulting suspension may be quenched by a suitable reagent (for example, by addition of sodium bicarbonate), extracted (for example, with ethyl acetate), dried (for example, over anhydrous magnesium sulphate), and concentrated (for example, under vacuum). The resulting residue may be purified by a suitable method (for example, flash column chromatography on silica gel-eluent: 90% hexane in ethyl acetate) to provide B. A person of skill in the art will understand that the above general scheme I may be suitably adapted to prepare compounds of the present invention which contain a propargyl ether moiety, for example, based on the following general chemical synthetic scheme II:

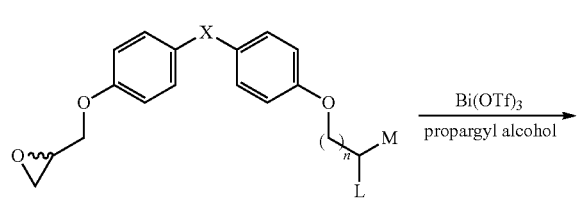

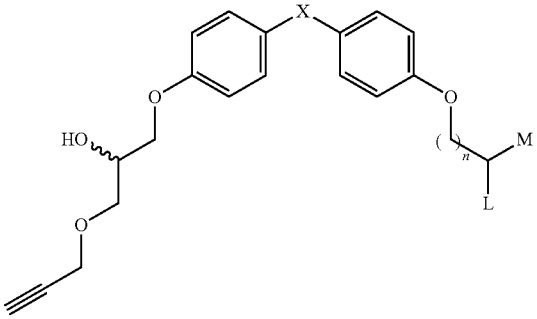

wherein X, M, L, and n are as defined anywhere herein. The general scheme I may be suitably adapted to prepare compounds of the present invention which contain an isopropyl ether moiety, for example, based on the following general chemical synthetic scheme III:

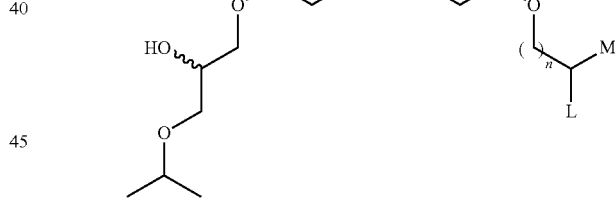

wherein X, M, L, and n are as defined anywhere herein. The general scheme I may be suitably adapted to prepare compounds of the present invention which contain an n-butyl ether moiety, for example, based on the following general chemical synthetic scheme IV:

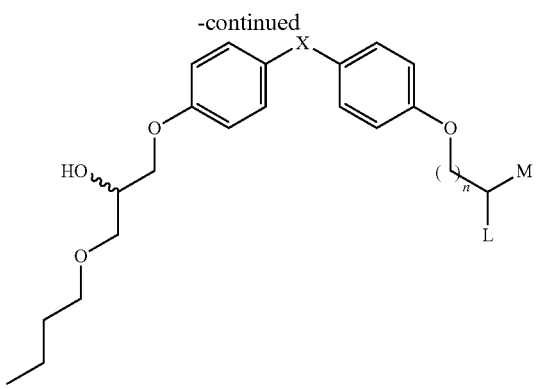

wherein X, M, L, and n are as defined anywhere herein. The general scheme I may be suitably adapted to prepare compounds of the present invention which contain a cyclohexyl ether moiety, for example, based on the following general chemical synthetic scheme V:

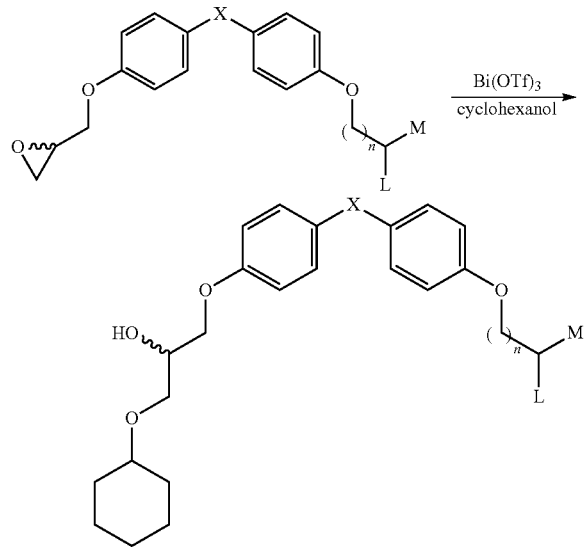

wherein X, M, L, and n are as defined anywhere herein.

General methodologies for chemical preparation of compounds of any one of the Formula I to XXI are described in the following non-limiting exemplary schemes.

Various alternative embodiments and examples of the invention are described herein. These embodiments and examples are illustrative and should not be construed as limiting the scope of the invention.

EXAMPLES

General Methodologies

Chemical Synthesis

All reactions were performed in flame-dried round bottomed flasks. The flasks were fitted with rubber septa and reactions were conducted under a positive pressure of argon unless otherwise specified. Stainless steel syringes were used to transfer air- and moisture-sensitive liquids. Flash column chromatography was performed as described by Still et al. (Still, W. C., Kahn, M., Mitra, A., *J. Org. Chem.* 1978, 43, 2923) using 230-400 mesh silica gel. Thin-layer chromatography was performed using aluminium plates pre-coated with 0.25 mm 230-400 mesh silica gel impregnated with a fluorescent indicator (254 nm). Thin-layer chromatography plates were visualized by exposure to ultraviolet light and a solution of p-anisaldehyde (1% p-anisaldehyde, 2% $H_2SO_4$, 20% acetic acid and 77% ethanol) followed by heating (~1 min) with a heating gun (~250° C.). Alternatively, a "Seebach staining solution" may be used (700 mL water, 10.5 g Cerium (IV) sulphate tetrahydrate, 15.0 g molybdato phosphoric acid, 17.5 mL sulphuric acid). Organic solutions were concentrated on Büchi R-114 rotatory evaporators at 25 torr at 25-30° C.

Commercial regents and solvents were used as received. All solvents used for extraction and chromatography were HPLC grade. Normal-phase Si gel Sep Paks™ were purchased from Waters, Inc. Thin-layer chromatography plates were Kieselgel $60F_{254}$. All synthetic reagents were purchased from Sigma Aldrich and Fisher Scientific Canada.

Proton nuclear magnetic resonance ($^1$H NMR) spectra were recorded at 25° C. using a Bruker 400 with inverse probe and Bruker 400 spectrometers, are reported in parts per million on the δ scale, and are referenced from the residual protium in the NMR solvent (DMSO-$d_6$: δ 2.50 (DMSO-$d_5$)). Data is reported as follows: chemical shift [multiplicity (s=singlet, d=doublet, dd=doublet of doublets, in =multiplet, q=quintuplet, t=triplet), coupling constant(s) in Hertz, integration]. Carbon-13 nuclear magnetic resonance ($^{13}$C NMR) spectra were recorded with a Bruker 400 spectrometer, are reported in parts per million on the δ scale, and are referenced from the carbon resonances of the solvent (DMSO-$d_6$: δ 39.51). Data is reported as follows: chemical shift. Fluorine nuclear magnetic resonance ($^{19}$F NMR) spectra were recorded at 25° C. using a Bruker 300 spectrometer, are reported in parts per million on the δ scale.

Cell Lines, Androgen and Reporters

LNCaP cells were employed initially for all experiments because they are well-differentiated human prostate cancer cells in which ligand-independent activation of the AR by FSK has been characterized (Nazareth et al 1996 *J. Biol. Chem.* 271, 19900-19907; and Sadar 1999 *J. Biol. Chem.* 274, 7777-7783). LNCaP cells express endogenous AR and secrete prostate-specific antigen (PSA) (Horoszewicz et al 1983 *Cancer Res.* 43, 1809-1818). LNCaP cells can be grown either as monolayers in cell culture or as tumors in the well-characterized xenograft model that progresses to androgen independence in castrated hosts (Sato et al 1996 *J. Steroid Biochem. Mol. Biol.* 58, 139-146; Gleave et al 1991 *Cancer Res.* 51, 3753-3761; Sato et al 1997 *Cancer Res.* 57, 1584-1589; and Sadar et al 2002 *Mol. Cancer Ther.* 1(8), 629-637). PC3 human prostate cancer cells do not express functional AR (Kaighn et al 1978 *Natl. Cancer Inst. Monogr.* 49, 17-21) and were used to test specificity of compound for the AR. Small molecules that specifically target the AR-NTD should have no effect on PC3 cells. This means that they should not alter the proliferation of PC3 cells if they specifically block the AR to mediate their inhibitory effects. R1881 was employed since it is stable and avoids problems associated with the labile physiological ligand dihydrotestosterone (DHT). Reporter specificity may be determined using several alternative reporter gene constructs. Some well characterized ARE-driven reporter gene constructs that have been used extensively are the PSA (6.1 kb) enhance/promoter which contains several AREs and is highly inducible by androgens as well as by FSK (Ueda et al 2002 A *J. Biol. Chem.* 277, 7076-7085) and the ARR3-thymidine kinase (tk)-luciferase, which is an artificial reporter construct that contains three tandem repeats of the rat probasin ARE1 and ARE2 regions upstream of a luciferase reporter (Snoek et al 1996 *J. Steroid Biochem. Mol. Biol.* 59, 243-250). CMV-luc (no AREs and is constitutively active) was employed to determine that a compound does not have a general inhibitory effect on transcription.

Example 1

EPI-035 (JG-133)

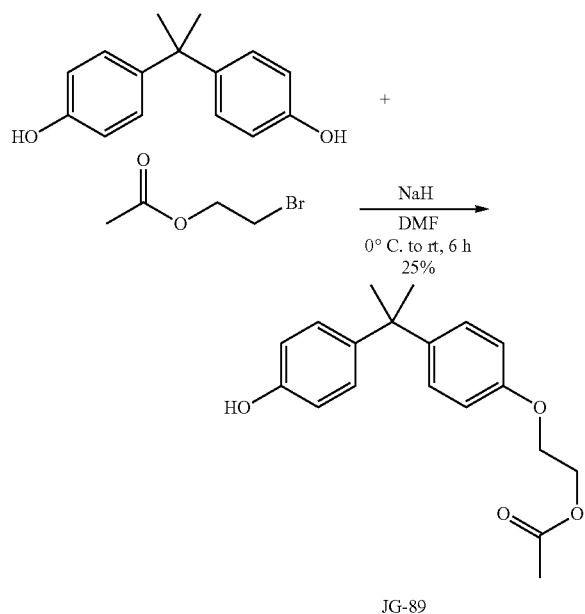

EPI-033 (JG-89).

NaH as a 60% dispersion in mineral oil (44 mg, 1.09 mmol, 1.0 equiv) was suspended in anhydrous dimethyl formamide (5 mL) under argon atmosphere. The mixture was cooled to 0° C. and bisphenol A (250 mg, 1.09 mmol, 1.0 equiv) was added. After 5 min, 2-bromoethylacetate (120 μL, 1.09 mmol, 1.0 equiv) was added via syringe and the mixture was allowed to react at room temperature for 6 h. Then, the solution was quenched with deionized water (~3 mL) and the mixture was extracted with ethyl acetate (3×3 mL). The organic layer was washed with deionized water (2 mL), was dried over anhydrous magnesium sulfate, was filtered, and was concentrated under reduced pressure. The resulting residue was purified by flash column chromatography on silica gel (eluent: dichloromethane and 5% ethylacetate in dichloromethane) to provide JG-89 (74 mg, 25%) colourless foam.

$^1$H NMR (400 MHz, DMSO-$d_6$): δ 9.12 (s, 1H), 7.09 (d, J=8.4, 2H), 6.97 (d, J=8.8, 2H), 6.81 (d, J=8.4, 2H), 6.63 (d, J=8.4, 2H), 4.30 (d, J=3.6, 2H), 4.12 (d, J=4.4, 2H), 2.02 (s, 3H), 1.54 (s, 6H).

$^{13}$C NMR (100 MHz, DMSO-$d_6$): δ 170.9, 156.5, 155.6, 143.8, 141.3, 128.0, 127.9, 115.2, 114.4, 66.2, 63.2, 41.7, 31.4, 21.3.

HRMS (ESI) (m/z): na

TLC (5% methanol in dichloromethane), Rf: 0.63 (UV, p-anisaldehyde).

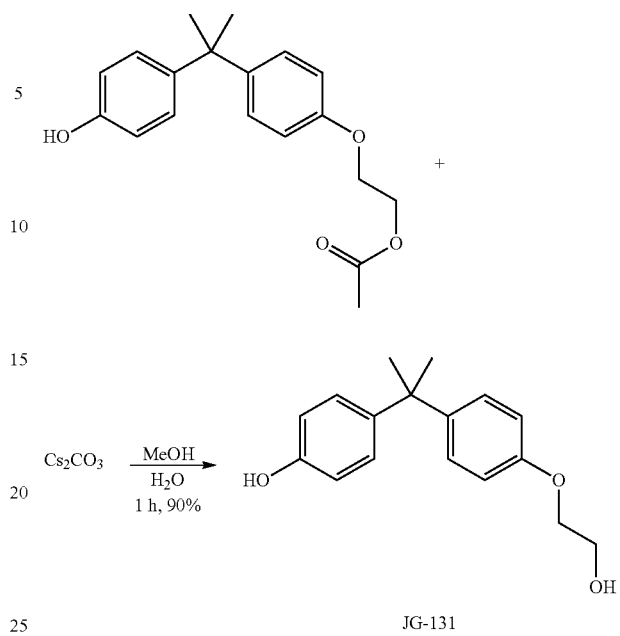

EPI-034 (JG-131).

Bisphenol A derivative JG-89 (74 mg, 0.23 mmol, 1.0 equiv) was dissolved in methanol (1 mL), and $Cs_2CO_3$ (260 mg, 0.79 mmol, 3.5 equiv) in $H_2O$ (0.5 mL) was added. The mixture was allowed to react at room temperature for 1.0 h. Then, the solution was quenched with deionized water (~1 mL) and the mixture was extracted with ethyl acetate (3×1 mL). The organic layer was dried over anhydrous magnesium sulfate, was filtered, and was concentrated under reduced pressure to provide JG-131 (58 mg, 90%) as a white solid.

$^1$H NMR (400 MHz, DMSO-$d_6$): δ 9.12 (s, 1H), 7.07 (d, J=8.4, 2H), 6.97 (d, J=8.4, 2H), 6.80 (d, J=8.8, 2H), 6.63 (d, J=8.4, 2H), 4.81 (t, J=5.2, 1H), 3.92 (t, J=4.8, 2H), 3.68 (m, 2H), 1.54 (s, 6H).

$^{13}$C NMR (100 MHz, DMSO-$d_6$): δ 156.9, 155.6, 143.4, 141.4, 128.0, 127.9, 115.2, 114.4, 70.0, 60.2, 41.6, 31.4.

HRMS (ESI) (m/z): calc'd for $C_{17}H_{20}O_3Na$ [M+Na]$^+$: 295.1310. found: 295.1304.

TLC (5% methanol in dichloromethane), Rf: 0.45 (UV, p-anisaldehyde).

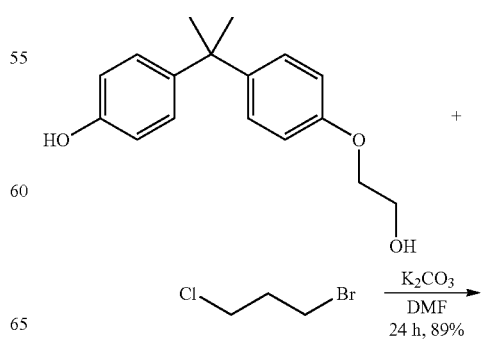

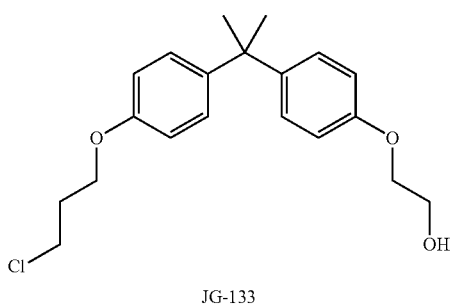

JG-133

EPI-035 (JG-133).

To a stirred solution of bisphenol A derivative JG-131 (20 mg, 0.073 mmol, 1 equiv) in anhydrous dimethyl formamide (0.3 mL) at rt was added $K_2CO_3$ (15 mg, 0.109 mmol, 1 equiv) and the mixture was stirred for 5 min under argon atmosphere. 1-Bromo-3-chloropropane (22 μL, 0.22 mmol, 3 equiv) was added and the mixture was stirred for 18 h at rt when 22 μL of 1-Bromo-3-chloropropane were added and the mixture was stirred for further 2 h. Deionized water (0.2 mL) was added and the mixture was extracted with ethyl acetate (3×1 mL). The organic layer was washed with deionized water (2 mL), was dried over anhydrous magnesium sulfate, was filtered, and was concentrated under reduced pressure. The resulting residue was purified by flash column chromatography on silica gel (eluent: dichloromethane and 5% methanol in dichloromethane) to provide JG-133 (23 mg, 89%) as a colourless foam.

$^1$H NMR (400 MHz, DMSO-$d_6$): δ 7.09 (m, 4H), 6.81 (m, 4H), 4.80 (t, J=5.2, 1H), 4.03 (t, J=6.0, 2H), 3.92 (t, J=5.2, 2H), 3.76 (t, J=6.4, 2H), 3.67 (m, 2H), 2.13 (m 2H), 1.56 (s, 6H).

$^{13}$C NMR (100 MHz, DMSO-$d_6$): δ 157.0, 156.7, 143.4, 143.1, 128.0, 127.9, 114.5, 69.9, 64.7, 60.2, 42.6, 41.8, 32.4, 31.3.

HRMS (ESI) (m/z): calc'd for $C_{20}H_{25}O_3NaCl$ [M+Na]$^+$: 371.1390. found: 371.1387.

TLC (5% methanol in dichloromethane), RJ: 0.68 (UV, p-anisaldehyde).

Example 2

EPI-038 (JG-147 A), EPI-037 (JG-148 A)

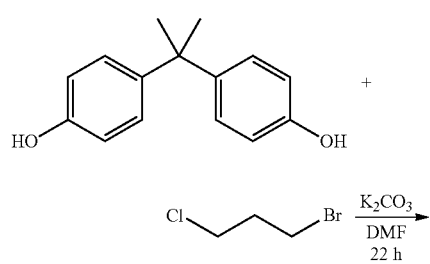

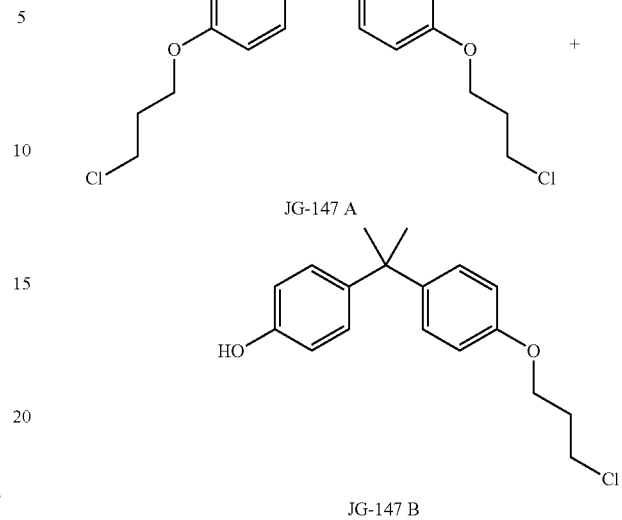

JG-147 A

JG-147 B

EPI-038 (JG-147 A), EPI-036 (JG-147 B).

To a stirred solution of Bisphenol A (200 mg, 0.87 mmol, 1 equiv) in anhydrous dimethyl formamide (2.0 mL) at rt was added $K_2CO_3$ (363 mg, 2.63 mmol, 3 equiv) and the mixture was stirred for 20 min under argon atmosphere. 1-Bromo-3-chloropropane (342 μL, 3.48 mmol, 4 equiv) was added and the mixture was stirred for 22 h at rt. Deionized water (1.0 mL) was added and the mixture was extracted with ethyl acetate (3×2 mL). The organic layer was washed with deionized water (2 mL), was dried over anhydrous magnesium sulfate, was filtered, and was concentrated under reduced pressure. The resulting residue was purified by flash column chromatography on silica gel (eluent: dichloromethane) to provide JG-147 A (261 mg, 78%) as a yellow oil and JG-147 B (139 mg, 52%) as a white solid.

JG-147 A $^1$H NMR (400 MHz, DMSO-$d_6$): δ 7.09 (d, J=8.4, 4H), 6.82 (d, J=8.4, 4H), 4.03 (t, J=6.0, 4H), 3.76 (t, J=6.4, 4H), 2.13 (q, 4H), 1.56 (s, 6H).

$^{13}$C NMR (100 MHz, DMSO-$d_6$): δ 156.7, 143.4, 141.4, 128.0, 114.5, 64.7, 42.6, 41.8, 32.4, 31.4.

HRMS (ESI) (m/z): calc'd for $C_{21}H_{26}O_2NaCl_2$ [M+Na]$^+$: 403.1208. found: 403.1208.

TLC (5% methanol in dichloromethane), Rf: 0.87 (UV, p-anisaldehyde).

JG-147 B $^1$H NMR (400 MHz, DMSO-$d_6$): δ 9.12 (s, 1H), 7.08 (d, J=8.8, 2H), 6.97 (d, J=8.4, 2H), 6.81 (d, J=8.8, 2H), 6.63 (d, J=8.8, 2H), 4.02 (t, J=6.0, 2H), 3.76 (t, J=6.4, 2H), 2.13 (q, 2H), 1.54 (s, 6H).

$^{13}$C NMR (100 MHz, DMSO-$d_6$): δ 156.7, 155.6, 143.7, 141.4, 128.0, 127.9, 115.2, 114.4, 64.7, 42.6, 41.6, 32.4, 31.4.

HRMS (ESI) (m/z): na

TLC (5% methanol in dichloromethane), Rf: 0.65 (UV, p-anisaldehyde).

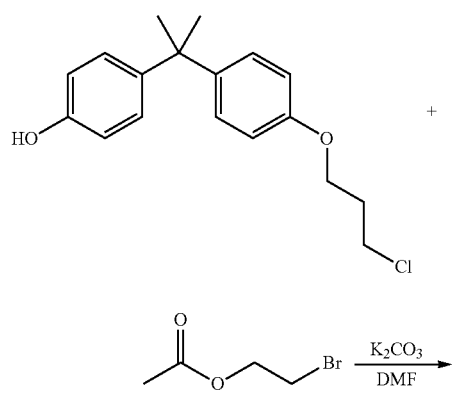

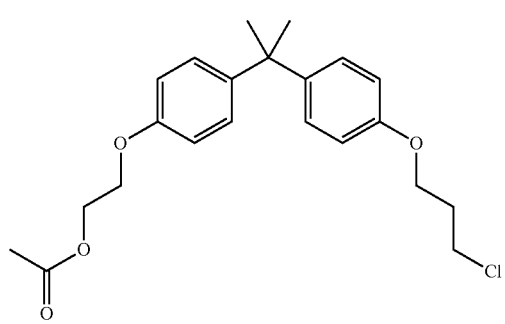

JG-148 A

EPI-037 (JG-148 A).

To a stirred solution of bisphenol A derivative JG-147 B (1040 mg, 3.41 mmol, 1.0 equiv) in anhydrous dimethyl formamide (10.0 mL) at rt was added $K_2CO_3$ (1400 mg, 10.25 mmol, 3.0 equiv) and the mixture was stirred for 10 min under argon atmosphere. 2-Bromoethylacetate (750 µL, 6.82 mmol, 2.0 equiv) was added via syringe and the mixture was allowed to react at room temperature for 44 h, when 1.0 equiv of 2-bromoethylacetate were added and the mixture was stirred for further 46 h. Then, the solution was quenched with deionized water (~5 mL) and the mixture was extracted with ethyl acetate (3×5 mL). The organic layer was washed with deionized water (4 mL), was dried over anhydrous magnesium sulfate, was filtered, and was concentrated under reduced pressure. The resulting residue was purified by flash column chromatography on silica gel (eluent: dichloromethane) to provide JG-148 A (1.2 g, 92%) as an oily product.

$^1$H NMR (400 MHz, DMSO-$d_6$): δ 7.08 (dd, J=8.8, 1.2, 4H), 6.82 (dd, J=8.8, 1.6, 2H), 4.29 (t, J=4.0, 2H), 4.12 (t, J=4.4, 2H), 4.03 (t, J=6.0, 2H), 3.76 (t, J=6.8, 2H), 2.13 (q, 2H), 2.02 (s, 3H), 1.57 (s, 6H).

$^{13}$C NMR (100 MHz, DMSO-$d_6$): δ170.9, 156.7, 156.5, 143.5, 143.3, 128.1, 114.5, 114.4, 66.2, 64.7, 63.2, 42.6, 41.8, 32.3, 31.3, 21.3.

HRMS (ESI) (m/z): na

TLC (5% methanol in dichloromethane), Rf: 0.87 (UV, p-anisaldehyde).

Example 3

JG-177

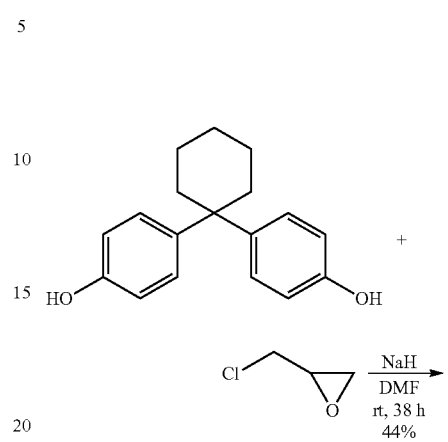

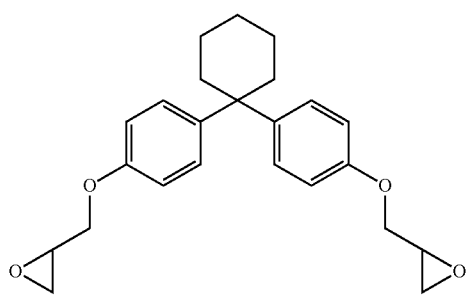

JG-168

(JG-168).

A round-bottomed flask was charged sequentially with NaH (223 mg, 5.58 mmol, 3 equiv), anhydrous dimethyl formamide (5 mL), and 4,4'-cyclohexylidenebisphenol (500 mg, 1.86 mmol, 1 equiv) and the contents were stirred under an atmosphere of argon for 20 min. Racemic epichlorohydrin (437 µL, 5.58 mmol, 3 equiv) was added via syringe and the mixture was allowed to react at room temperature for 38 h. Then, the solution was quenched with deionized water (~2 mL) and the mixture was extracted with ethyl acetate (3×4 mL). The organic layer was washed with deionized water (2 mL), was dried over anhydrous magnesium sulfate, was filtered, and was concentrated under reduced pressure. The resulting residue was purified by flash column chromatography on silica gel (eluent: 10% ethyl acetate in dichloromethane) to provide JG-168 (312 mg, 44%) as a white foam.

$^1$H NMR (400 MHz, DMSO-$d_6$): δ 7.16 (d, J=8.0, 4H), 6.83 (d, J=8.0, 4H), 4.23 (d, J=11.2, 2H), 3.76 (dd, J=10.8, 6.4, 2H), 3.28 (m, 2H), 2.80 (t, J=4.0, 2H), 2.66 (m, 2H), 2.17 (m, 4H), 1.42 (m, 6H).

$^{13}$C NMR (100 MHz, DMSO-$d_6$): δ 156.3, 141.5, 128.4, 114.7, 69.4, 50.3, 44.9, 44.4, 37.0, 26.4, 23.1.

HRMS (ESI) (m/z): na

TLC (5% methanol in dichloromethane), Rf: 0.80 (UV, p-anisaldehyde).

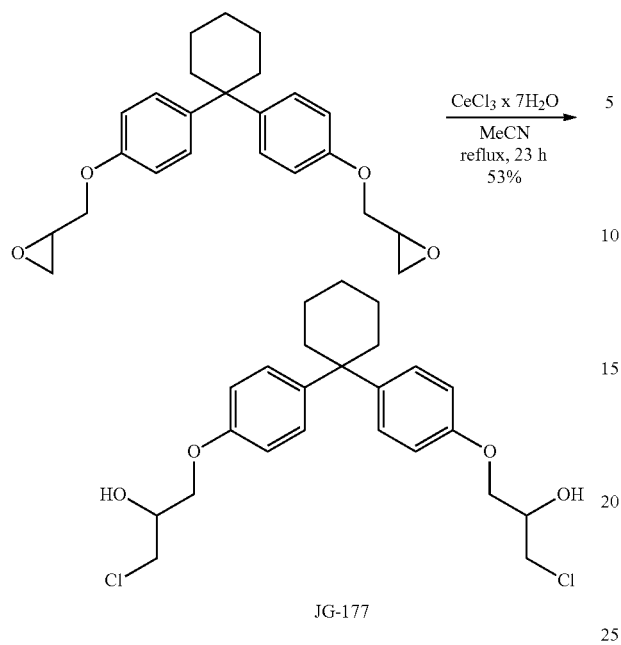

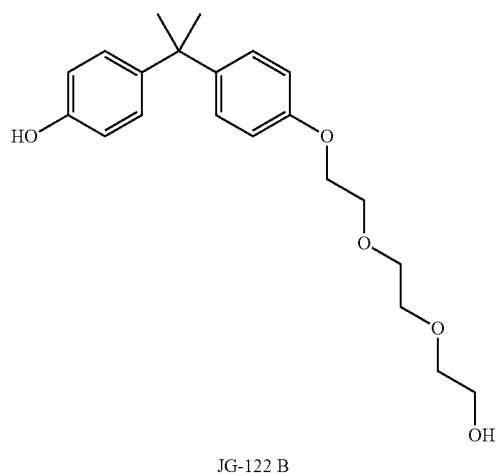

(JG-177).

To a solution of racemic 4,4'-cyclohexylidenebisphenol diglycidyl ether JG-168 (100 mg, 0.26 mmol, 1 equiv) in acetonitrile (4.0 mL) was added $CeCl_3 \cdot 7H_2O$ (294 mg, 0.78 mmol, 3 equiv) and the mixture was refluxed for 23 h. The resulting white paste was filtered with dichloromethane and the clear suspension was concentrated under reduced pressure. The resulting residue was purified by flash column chromatography on silica gel (eluent: dichloromethane and 10% methanol in dichloromethane) to provide JG-177 (63 mg, 53%) as a colourless oil.

$^1$H NMR (400 MHz, DMSO-$d_6$): δ 7.15 (d, J=8.8, 4H), 6.82 (d, J=8.8, 4H), 5.49 (d, J=5.2, 2H), 3.99 (m, 2H), 3.91 (d, J=5.2, 4H), 3.72 (dd, J=11.2, 4.4, 2H), 3.63 (dd, J=11.2, 5.2, 2H), 2.17 (m, 4H), 1.42 (m, 6H).

$^{13}$C NMR (100 MHz, DMSO-$d_6$): δ 156.5, 141.4, 128.4, 114.7, 69.4, 69.3, 47.4, 45.0, 37.1, 26.4, 23.1.

HRMS (ESI) (m/z): calc'd for $C_{24}H_{30}O_4NaCl_2$ [M+Na]$^+$: 475.1419. found: 475.1424.

TLC (5% methanol in dichloromethane), Rf: 0.59 (UV, p-anisaldehyde).

Example 4

EPI-041 (JG-140 A)

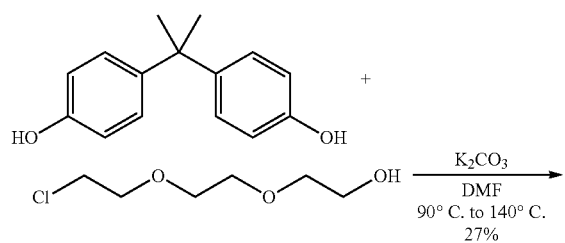

EPI-040 (JG-122 B).

To a stirred solution of bisphenol A (500 mg, 2.19 mmol, 1.0 equiv) in anhydrous dimethyl formamide (5.0 mL) at rt was added $K_2CO_3$ (604 mg, 4.38 mmol, 2.0 equiv) and the mixture was stirred for 60 min at 90° C. 2-[2-(2-Chloroethoxy)ethoxy]ethanol (636 µL, 4.38 mmol, 2.0 equiv) was added via syringe and the mixture was allowed to react at reflux for 6 days. Then, the solution was allowed to cool and quenched with deionized water (~2 mL) and the mixture was extracted with ethyl acetate (3×3 mL). The organic layer was washed with deionized water (4 mL), was dried over anhydrous magnesium sulfate, was filtered, and was concentrated under reduced pressure. The resulting residue was purified by flash column chromatography on silica gel (eluent: dichloromethane) to provide JG-122 B (212 g, 27%) as a yellow oily product.

$^1$H NMR (400 MHz, DMSO-$d_6$): δ 9.12 (s, 1H), 7.08 (d, J=8.8, 2H), 6.97 (d, J=8.4, 2H), 6.81 (d, J=8.8, 2H), 6.63 (d, J=8.4, 2H), 4.55 (t, J=5.6, 1H), 4.03 (t, J=4.0, 2H), 3.71 (t, J=4.8, 2H), 3.56 (m, 2H), 3.52 (m, 2H), 3.47 (m, 2H), 3.41 (m, 2H), 1.57 (s, 6H).

$^{13}$C NMR (100 MHz, DMSO-$d_6$): δ 156.7, 155.6, 143.5, 141.4, 128.0, 127.9, 115.2, 114.4, 73.0, 70.5, 70.4, 69.6, 67.6, 60.8, 41.6, 31.4.

HRMS (ESI) (m/z): calc'd for $C_{21}H_{28}O_5Na$ [M+Na]$^+$: 383.1834. found: 383.1823.

TLC (5% methanol in dichloromethane), Rf: 0.44 (UV, p-anisaldehyde).

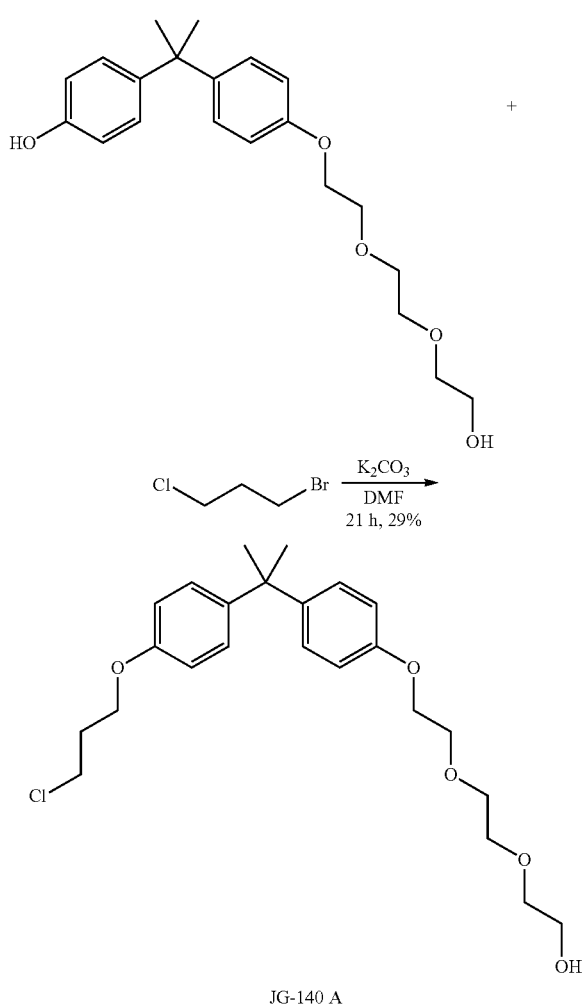

JG-140 A

EPI-041 (JG-140 A).

To a stirred solution of bisphenol A derivative JG-122 B (100 mg, 0.277 mmol, 1 equiv) in anhydrous dimethyl formamide (1.5 mL) at rt was added $K_2CO_3$ (77 mg, 0.55 mmol, 2 equiv) and the mixture was stirred for 20 min under argon atmosphere. 1-Bromo-3-chloropropane (54 µL, 0.55 mmol, 2 equiv) was added and the mixture was stirred for 21 h at rt. Deionized water (0.5 mL) was added and the mixture was extracted with ethyl acetate (3×2 mL). The organic layer was washed with deionized water (2 mL), was dried over anhydrous magnesium sulfate, was filtered, and was concentrated under reduced pressure. The resulting residue was purified by flash column chromatography on silica gel (eluent: dichloromethane and 5% methanol in dichloromethane) to provide JG-140 A (35 mg, 29%) as a colourless oil.

$^1$H NMR (400 MHz, DMSO-$d_6$): δ 7.09 (dd, J=8.8, 2.4, 4H), 6.82 (dd, J=8.8, 2.4, 4H), 4.55 (t, J=5.6, 1H), 4.03 (m, 4H), 3.77 (t, J=6.8, 2H), 3.71 (t, J=4.8, 2H), 3.56 (m, 2H), 3.52 (m, 2H), 3.47 (m, 2H), 3.41 (m, 2H), 2.14, (q, 2H), 1.57 (s, 6H).

$^{13}$C NMR (100 MHz, DMSO-$d_6$): δ 156.8, 156.7, 143.4, 143.2, 128.0, 128.0, 114.5, 73.0, 70.5, 70.4, 69.6, 67.6, 64.7, 60.8, 42.6, 41.8, 32.4, 31.3.

HRMS (ESI) (m/z): na

TLC (5% methanol in dichloromethane), Rf: 0.51 (UV, p-anisaldehyde).

Example 5

EPI-900 (JG-181)

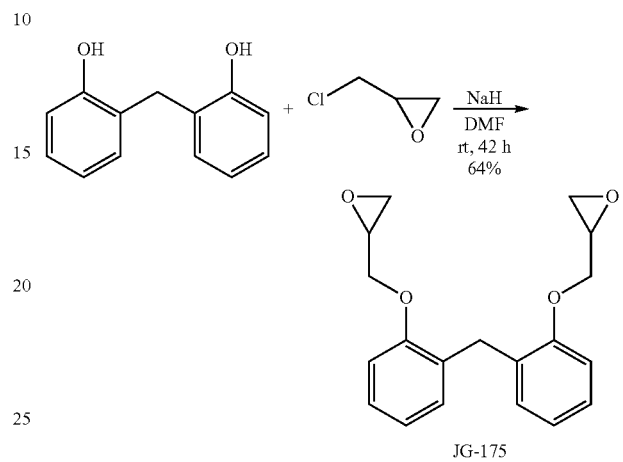

JG-175

(JG-175).

A round-bottomed flask was charged sequentially with NaH (150 mg, 3.74 mmol, 3 equiv), anhydrous dimethyl formamide (3 mL), and bis(2-hydroxyphenyl)methane (250 mg, 1.24 mmol, 1 equiv) and the contents were stirred under an atmosphere of argon for 30 min. Racemic epichlorohydrin (293 µL, 3.74 mmol, 3 equiv) was added via syringe and the mixture was allowed to react at room temperature for 42 h. Then, the solution was quenched with deionized water (1 mL) and the mixture was extracted with ethyl acetate (3×3 mL). The organic layer was washed with deionized water (2 mL), was dried over anhydrous magnesium sulfate, was filtered, and was concentrated under reduced pressure. The resulting residue was purified by flash column chromatography on silica gel (eluent: 40% ethyl acetate in hexane) to provide JG-175 (250 mg, 64%) as a white solid.

$^1$H NMR (400 MHz, DMSO-$d_6$): δ 7.15 (m, 2H), 7.05 (m, 2H) 6.95 (m, 2H), 6.85 (m, 2H), 4.29 (m, 2H), 3.87 (m, 4H), 3.30 (m, 2H), 2.81 (t, J=4.8, 2H), 2.67 (dd, J=4.8, 2.4, 2H).

$^{13}$C NMR (100 MHz, DMSO-$d_6$): δ 156.7, 130.8, 129.3, 127.9, 121.2, 112.5, 69.5, 50.4, 44.3, 29.9.

HRMS (ESI) (m/z): na

TLC (5% methanol in dichloromethane), Rf: 0.88 (UV, p-anisaldehyde).

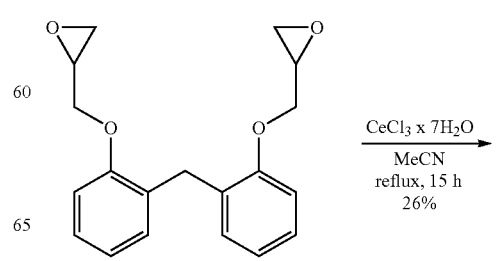

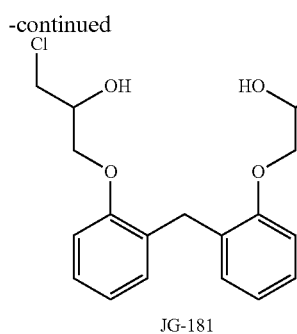

JG-181

EPI-900 (JG-181).

To a solution of racemic bis(2-hydroxyphenyl)methane diglycidyl ether JG-175 (74 mg, 0.24 mmol, 1 equiv) in acetonitrile (2 mL) was added CeCl$_3$.7H$_2$O (238 mg, 0.64 mmol, 2.6 equiv) and the mixture was refluxed for 15 h. The resulting white paste was filtered with dichloromethane and the clear suspension was concentrated under reduced pressure. The resulting residue was purified by flash column chromatography on silica gel (eluent: dichloromethane and 10% ethyl acetate in dichloromethane) to provide JG-181 (24 mg, 26%) as a yellow oil.

$^1$H NMR (400 MHz, DMSO-d$_6$): δ 7.15 (m, 2H), 7.05 (m, 2H) 6.95 (m, 2H), 6.83 (m, 2H), 5.49 (d, J=5.2, 2H), 3.96 (m, 6H), 3.88 (s, 2H), 3.65 (dd, J=10.8, 4.0, 2H), 3.55 (dd, J 10.8, 5.2, 2H).

$^{13}$C NMR (100 MHz, DMSO-d$_6$): δ 156.7, 130.8, 129.3, 127.9, 121.1, 112.2, 69.5, 69.3, 47.5, 30.1.

HRMS (ESI) (m/z): calc'd for C$_{19}$H$_{22}$O$_4$NaCl$_2$ [M+Na]$^+$: 407.0793. found: 407.0803.

TLC (5% methanol in dichloromethane), Rf: 0.55 (UV, p-anisaldehyde).

Example 6

LNCaP cells were transiently cotransfected with PSA (6.1 kb)-luciferase (0.25 μg/well) in 24-well plates for 24 h prior to pre-treatment with compounds for 1 hour before the addition of synthetic androgen, R1881 (1 nM) to induce PSA production or vehicle. The total amount of plasmid DNA transfected was normalized to 0.75 μg/well by the addition of the empty vector. After 48 h of incubation with R1881, the cells were harvested, and relative luciferase activity was determined. Test compounds were added to the cells at various concentrations and activity for each treatment was normalized to the predicted maximal activity induction (in the absence of test compounds, vehicle only). Plotting of sigmoidal curves (Boltzmann Function) and IC$_{50}$ calculations were done using OriginPro 8.1 Sofware (Northampton, Mass., USA).

Furthermore, toxicity was assessed by both microscopic examination and reduction of protein levels. Solubility was assessed both macroscopically (cloudy media) and microscopically (formation of granules or crystals).

TABLE 3 shows the chemical structures for the compounds that showed activity using the above-described assays.

The following Table includes active compounds.

TABLE 3

| COMPOUND | EXPERIMENTAL DATA |
|---|---|
| 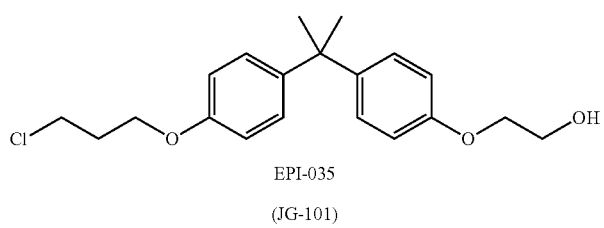 [SMILES: CC(C)(c1ccc(OCCO)cc1)c1ccc(OCCCCl)cc1]<br>EPI-035<br>(JG-101) | Active |
| 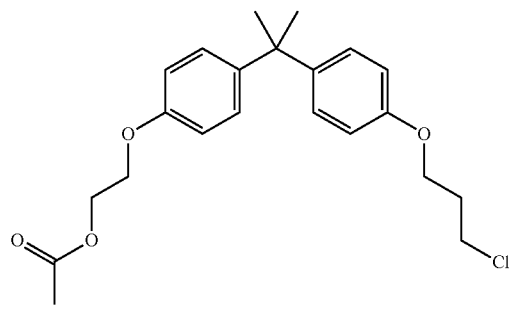<br>EPI-037<br>(JG-148 A) | Active |

TABLE 3-continued
| COMPOUND | EXPERIMENTAL DATA |
|---|---|
| 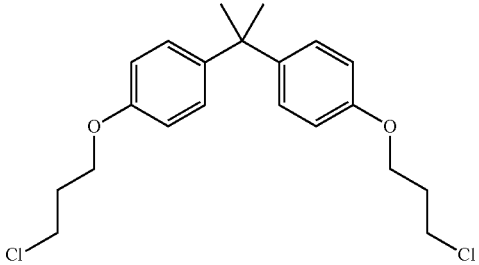<br>EPI-038<br>(JG-147 A) | Active |
| 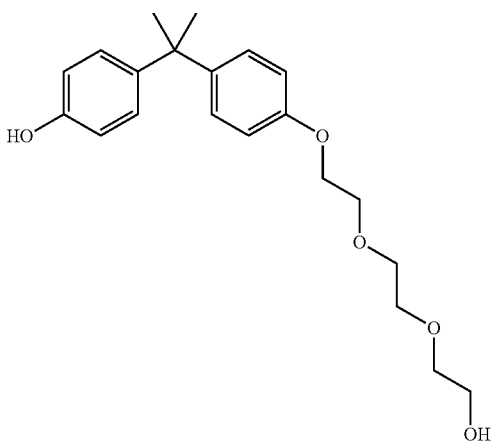<br>EPI-040<br>(JG-122B) | Active |
| 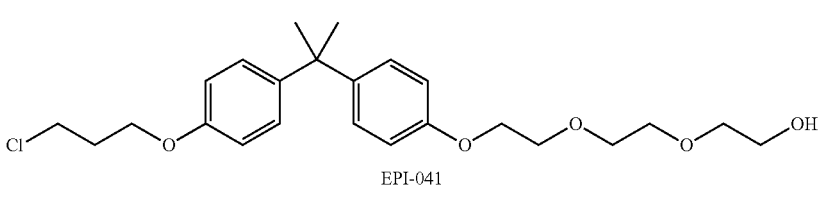<br>EPI-041<br>(JG-140 A) | Active |
| 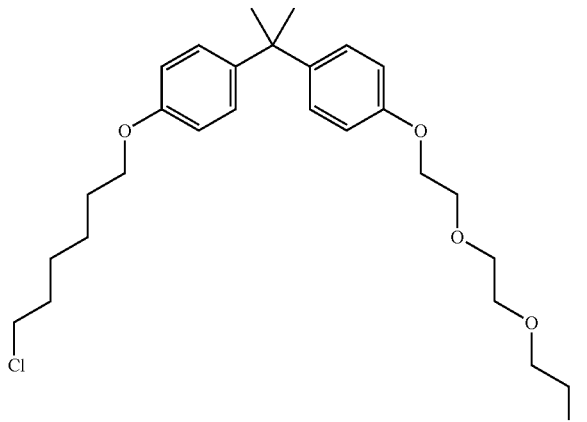<br>EPI-043<br>(JG-201) | Active |

TABLE 3-continued
| COMPOUND | EXPERIMENTAL DATA |
|---|---|
| 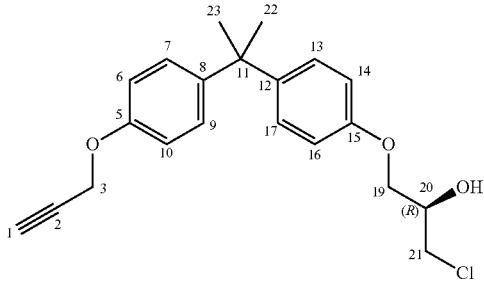<br>EPI-046 (20R)<br>(JG-353) | Active |
| 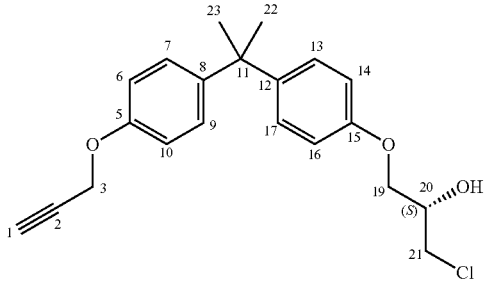<br>EPI-047 (20S)<br>(JG-353) | Active |
| 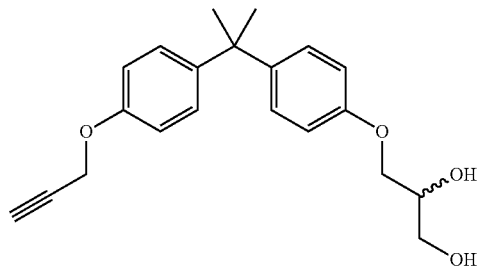<br>EPI-051<br>(JG-341) | Active |
| 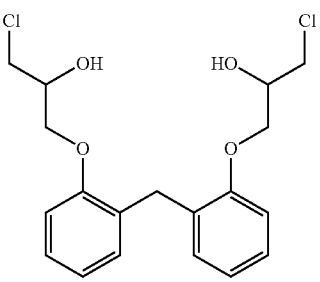<br>EPI-900<br>(JG-181) | Active |

TABLE 3-continued

| COMPOUND | EXPERIMENTAL DATA |
|---|---|
| 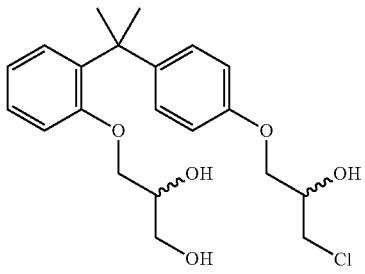<br>EPI-6000, EPI-6001, EPI-6002, and EPI-6003<br>(stereo and regio isomers) | Active |
| 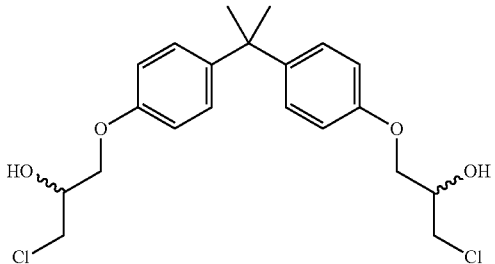<br>EPI-001<br>EPI-001 | Control |
| 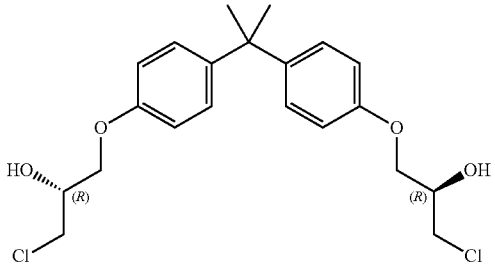<br>EPI-026<br>(2R, 20R) | Control |

Example 7

Figure 2A:
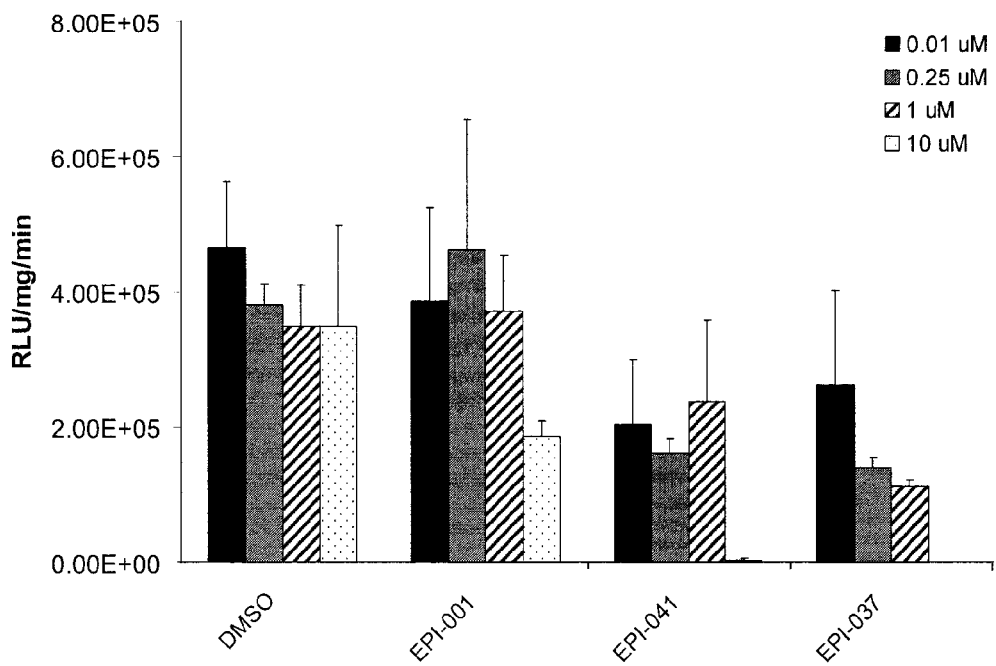
FIG. 2A shows a dose response for EPI-041 and EPI-037 as compared to EPI-001 in a LNCaP PSA (6.1 kb)-luciferase assay.
Figure 2B:
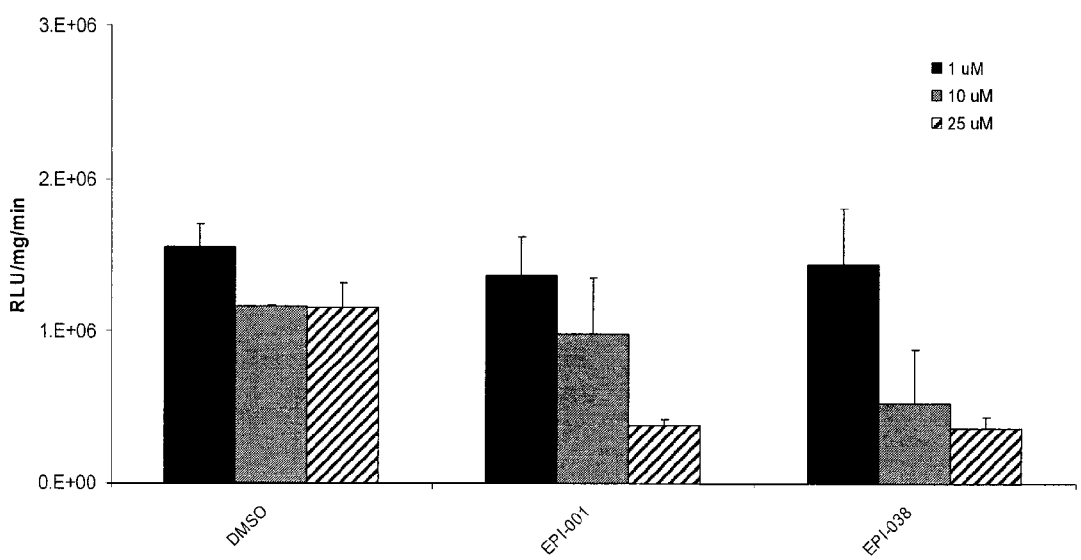
FIG. 2B shows a dose response for EPI-038 as compared to EPI-001 in a LNCaP PSA (6.1 kb)-luciferase assay.
Figure 3A:
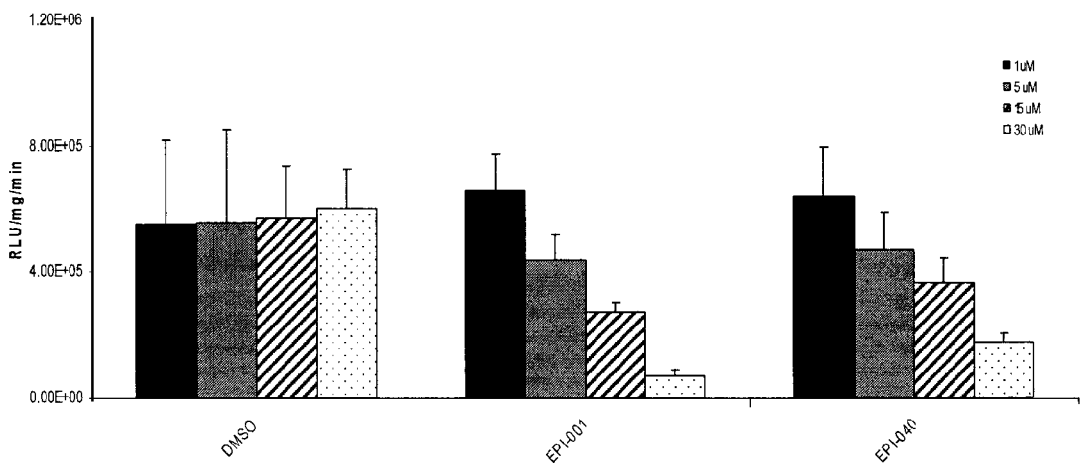
FIG. 3A shows a dose response for EPI-040 as compared to EPI-001 in a LNCaP PSA (6.1 kb)-luciferase assay.
Figure 3B:
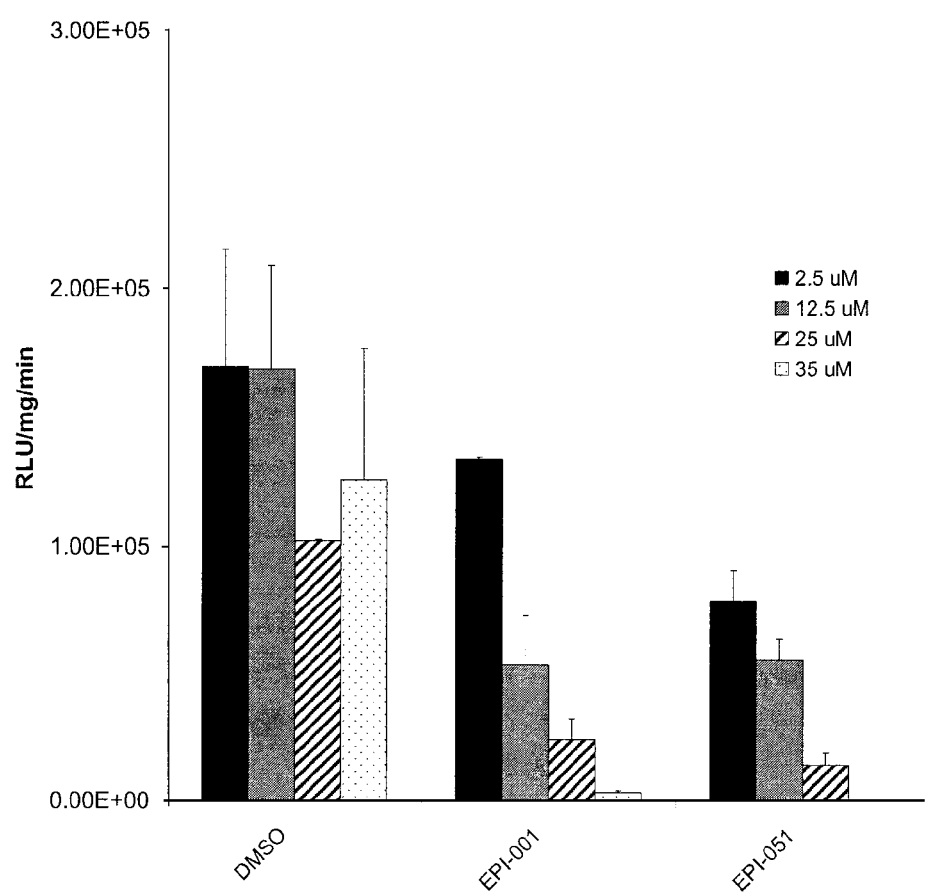
FIG. 3B shows a dose response for EPI-051 as compared to EPI-001 in a LNCaP PSA (6.1 kb)-luciferase assay.
Figure 4A:
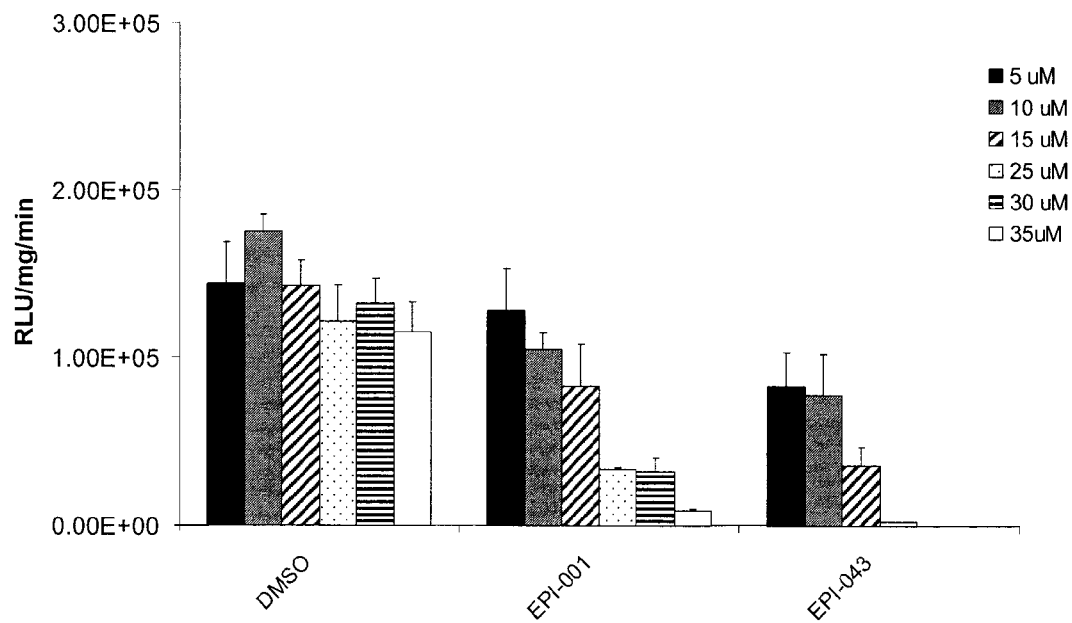
FIG. 4A shows a dose response for EPI-043 as compared to EPI-001 in a LNCaP PSA (6.1 kb)-luciferase assay over a dosage range of 5 μM to 35 μM.
Figure 4B:
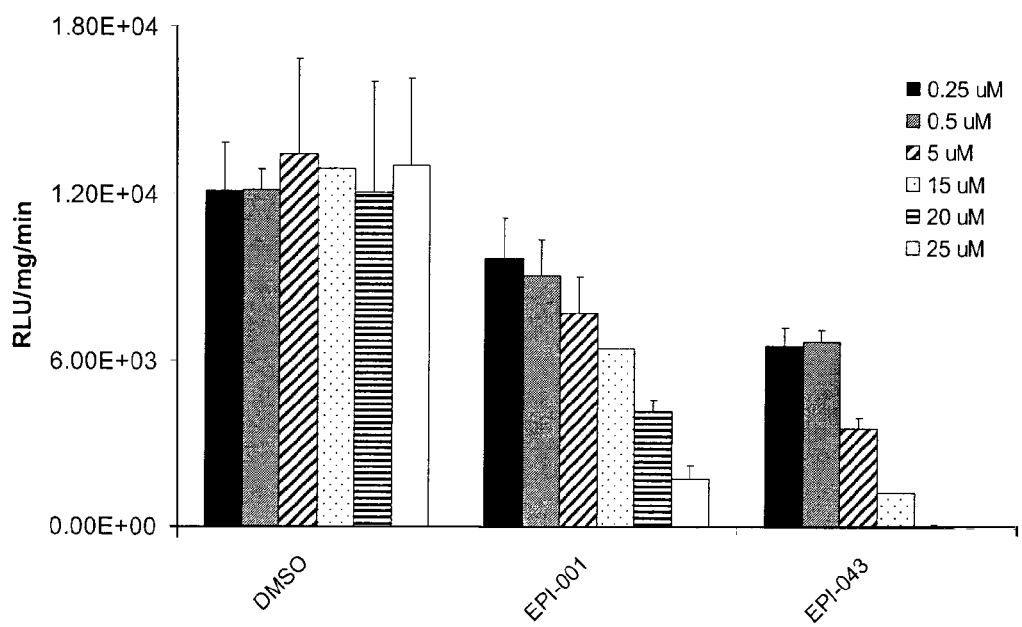
FIG. 4B shows a dose response for EPI-043 as compared to EPI-001 in a LNCaP PSA (6.1 kb)-luciferase assay over a dosage range of 0.25 μM to 25 μM.
Figure 5:
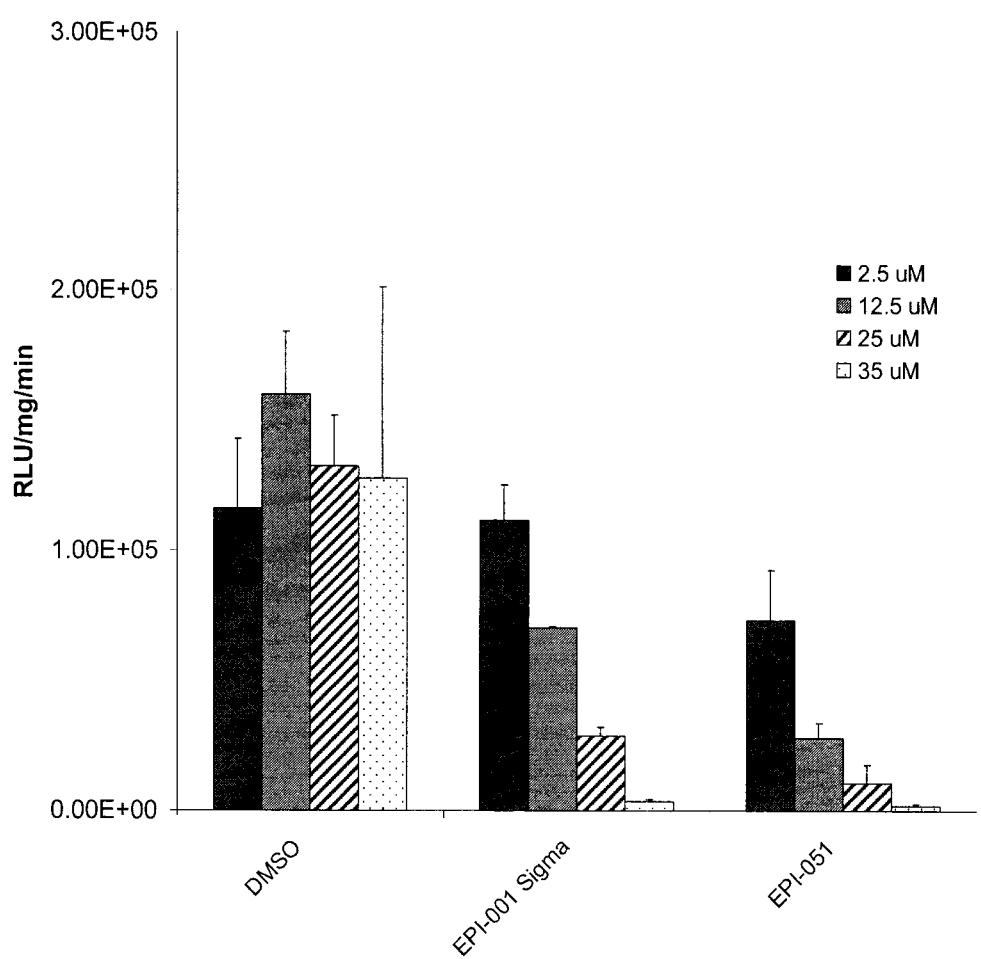
FIG. 5 shows a dose response for EPI-051 as compared to EPI-001 and EPI-026 in a LNCaP PSA (6.1 kb)-luciferase assay.
Figure 6:
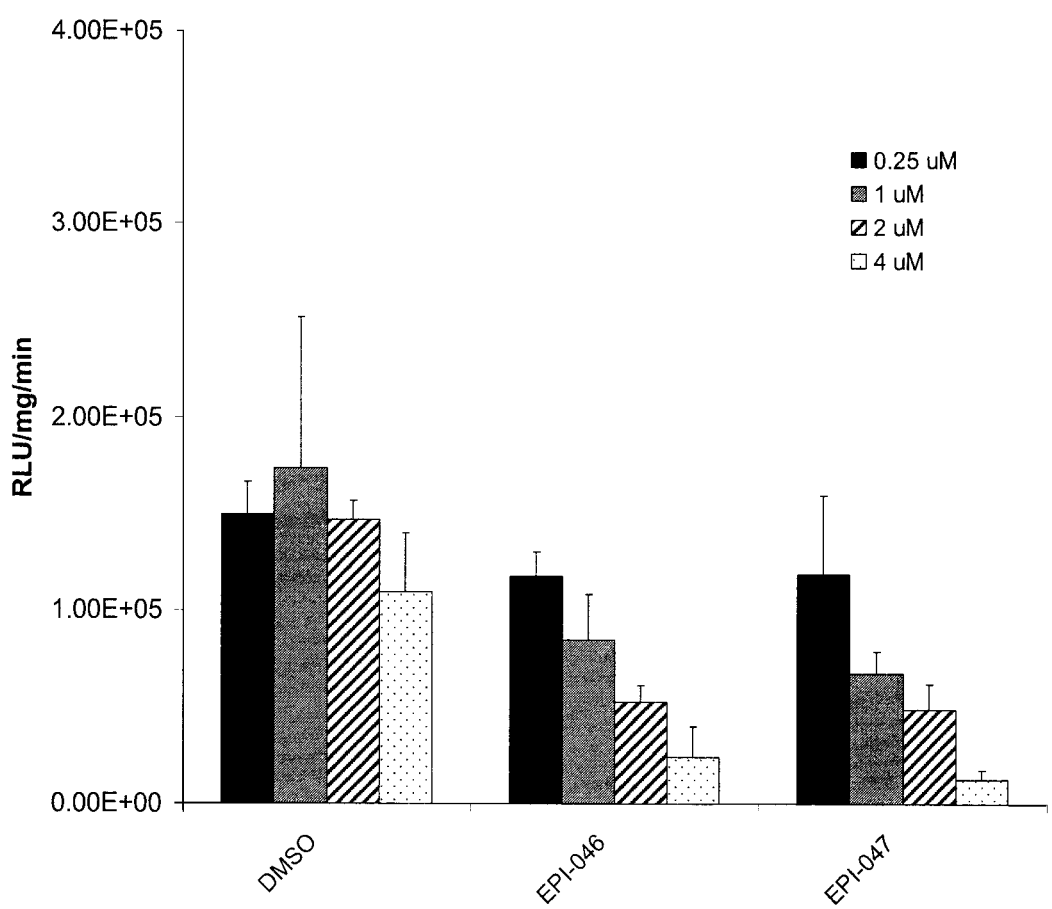
FIG. 6 shows a dose response for EPI-046 and EPI-047 as compared to EPI-001 in a LNCaP PSA (6.1 kb)-luciferase assay.

Using the LNCaP PSA (6.1 kb)-luciferase assay described above, various compounds described herein were tested against DMSO and EPI-001 controls. In FIG. 1, a comparison is made between EPI-035 and DMSO and EPI-001 or EPI-026 from 1 µM to 10 µM. FIG. 2A shows EPI-041 and EPI-037 as compared to DMSO and EPI-001 at 0.01 µM to 10 µM (0.01 µM, 0.25 µM, 1 µM, and 10 µM). FIG. 2B shows EPI-038 as compared to DMSO and EPI-001 at 1 µM, 10 µM, and 25 µM. In FIGS. 3A and 3B, EPI-040 and EPI-051 are compared to DMSO and EPI-001 at 1 µM to 30 µM and 2.5 µM to 35 µM respectively. In FIGS. 4A and 4B, EPI-043 is compared to DMSO and EPI-001 at 5 µM to 35 µM 0.25 µM to 25 µM respectively. FIG. 5 shows EPI-051 in comparison to DMSO and EPI-001 at 2.5 µM to 35 µM. FIG. 6, shows EPI-046 and EPI-047 compared to DMSO at 0.25 µM to 4 µM.

Figure 7A:
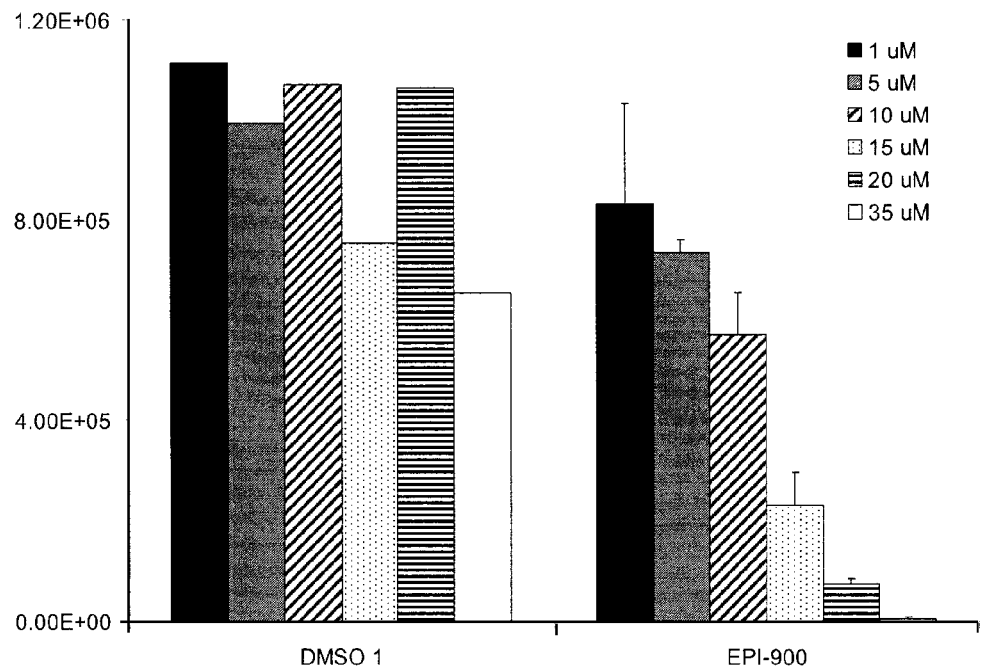
FIG. 7A shows a dose response for EPI-900 in a LNCaP PSA (6.1 kb)-luciferase assay.
Figure 7B:
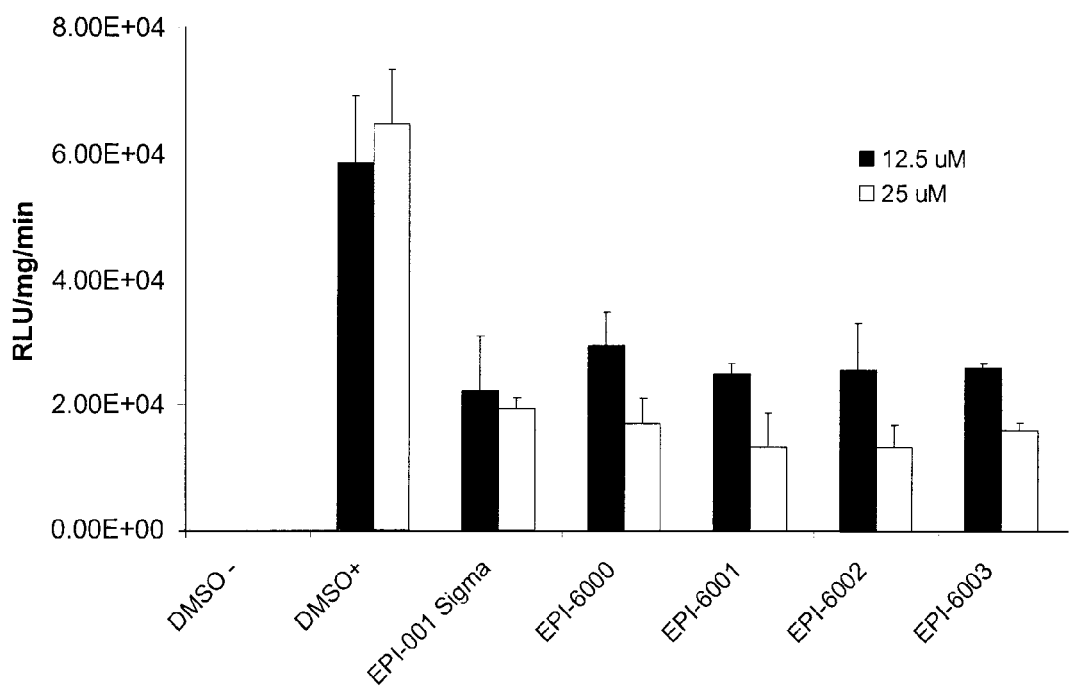
FIG. 7B shows a dose response for EPI-6000, EPI-6001, EPI-6002, and EPI-6003 as compared to EPI-001 in a LNCaP PSA (6.1 kb)-luciferase assay.

FIG. 7A shows a dose response plot for concentrations of EPI-900 and DMSO (control) from 1 µM to 35 µM (1 µM, 5 µM, 10 µM, 15 µM, 20 µM, and 35 µM). EPI-900 showed a dose response as compared to the DMSO control. Similarly, in FIG. 7B concentrations of EPI-6000, EPI-6001, EPI-6002, and EPI-6003 are shown at 12.5 µM and 25 µM as compared to the DMSO control.

Each of EPI-035, EPI-037, EPI-038, EPI-040, EPI-041, EPI-043, EPI-046, EPI-047, EPI-051, EPI-900, EPI-6000, EPI-6001, EPI-6002, and EPI-6003 showed androgen receptor modulating activity.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method for modulating androgen receptor (AR) activity, the method comprising administering a compound to a subject in need thereof, wherein the compound has the following Formula III

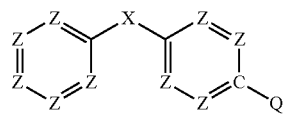

III or a pharmaceutically acceptable salt thereof,
wherein:
X is $CH_2$, $CHR^1$, or $CR^1R^2$;
each of $R^1$ and $R^2$ is independently linear or branched, substituted or unsubstituted, saturated or unsaturated $C_1$-$C_{10}$ alkyl, wherein the optional substituent is selected from the group consisting of $OJ'''$, F, Cl, Br, I, or $NH_2$;
wherein Q is

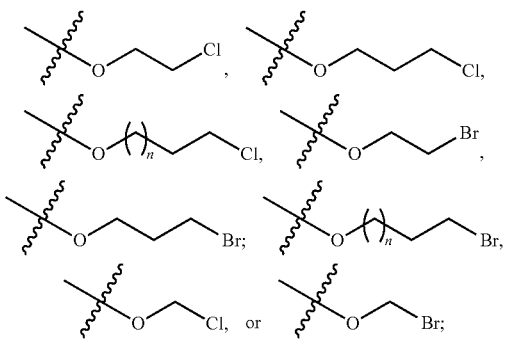

at least one Z of the other aromatic ring may independently be C-T, wherein T is

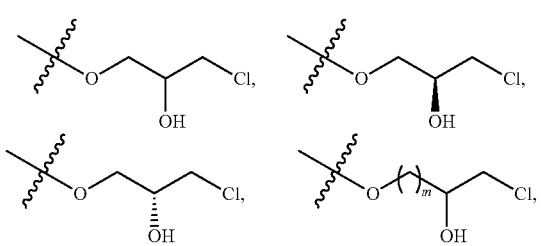

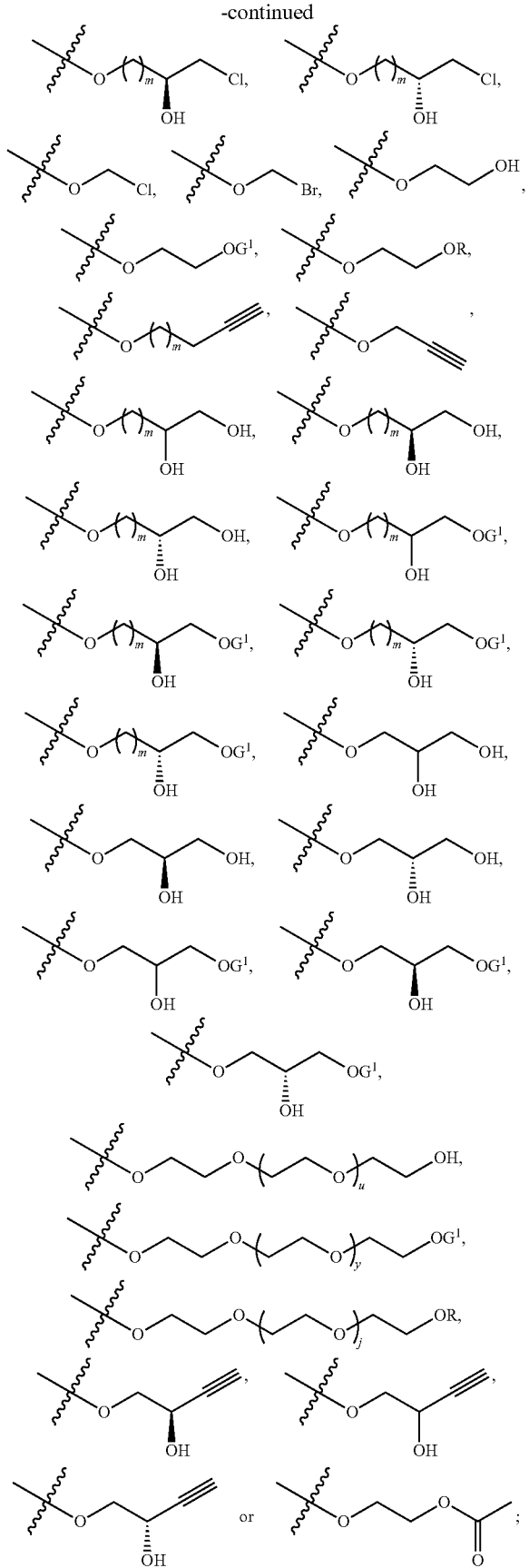

and each remaining Z is independently CG$^1$, N, CH, CF, CCl, CBr, CI, or COH;
n is 0, 1, 2, 3, 4, 5, 6, 7 or 8;
each of u, y and j is independently 0, 1, 2, 3, 4, 5, 6 or 7;
m is 0, 1, 2, 3, 4, 5, 6, 7 or 8;
each of J″ and J‴ is independently a moiety selected from the group consisting of:
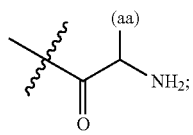(aa)    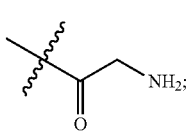
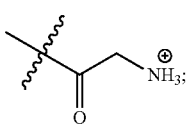    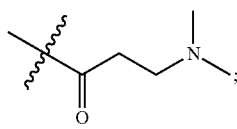
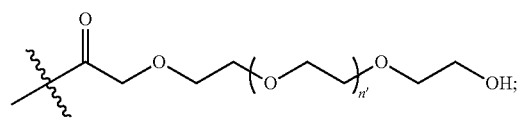
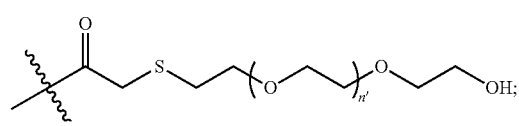
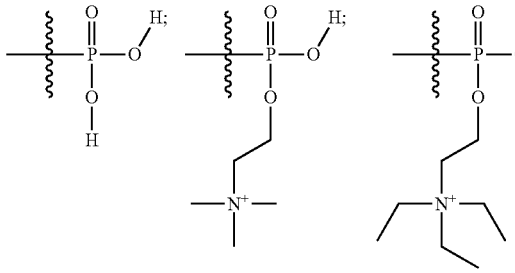
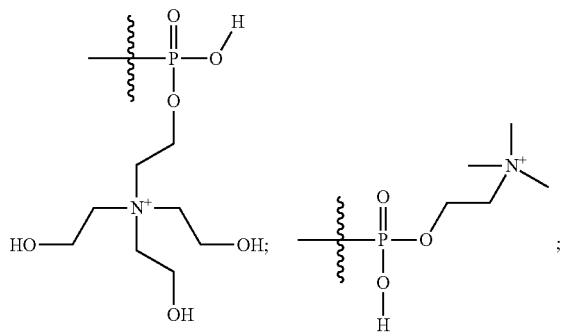
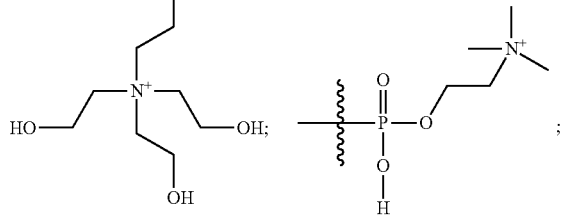
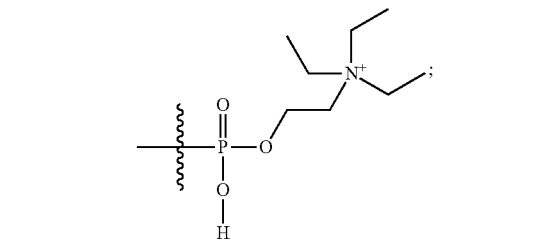
-continued
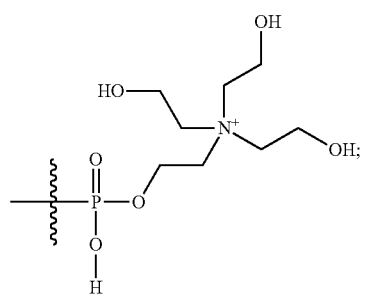
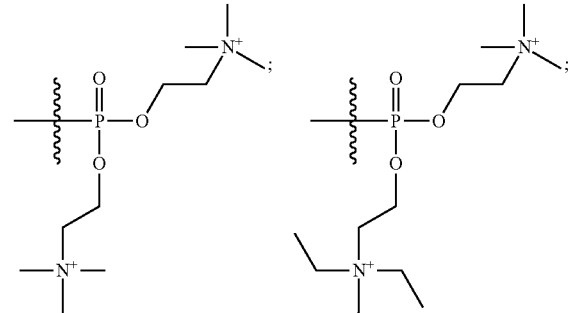
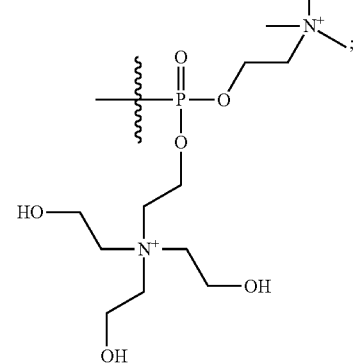
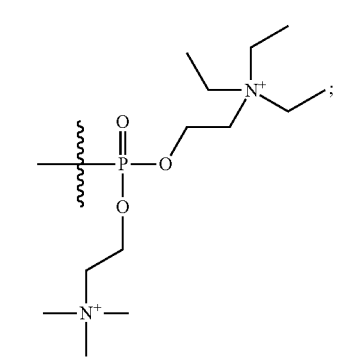

273
-continued

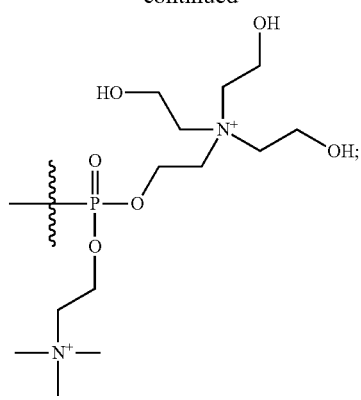

274
-continued

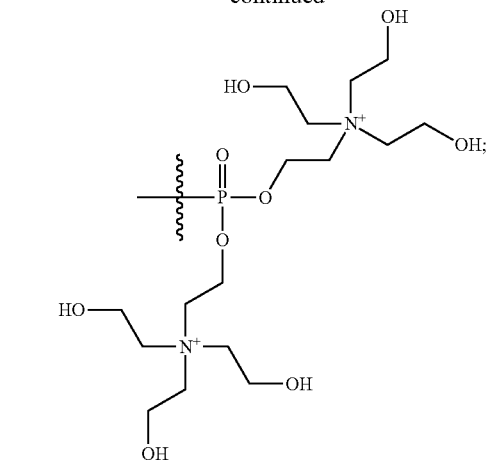

each $G^1$ is independently linear or branched, substituted or unsubstituted, saturated or unsaturated $C_1$-$C_{10}$ alkyl, wherein the optional substituent is selected from the group consisting of oxo, OJ''', COOH, OH, F, Cl, Br, I, $NH_2$, CN, SH, $SO_3H$, $CONH_2$, $OPO_3H_2$, and $NO_2$;

wherein one or more of the OH groups is optionally substituted to replace the H with a moiety selected from the group consisting of:

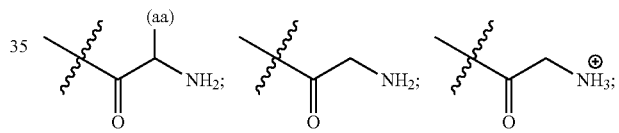

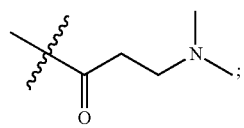

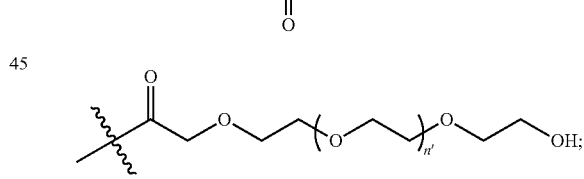

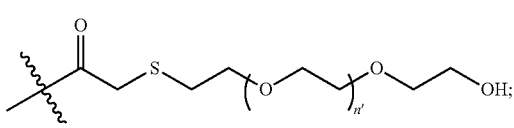

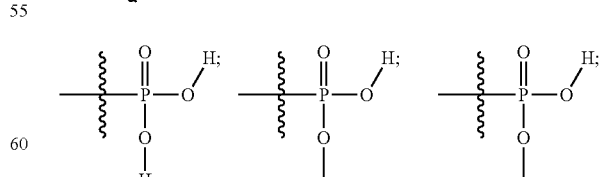

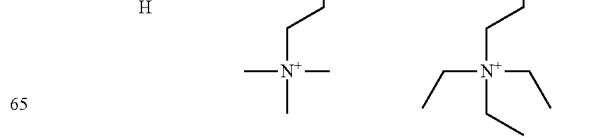

275
-continued
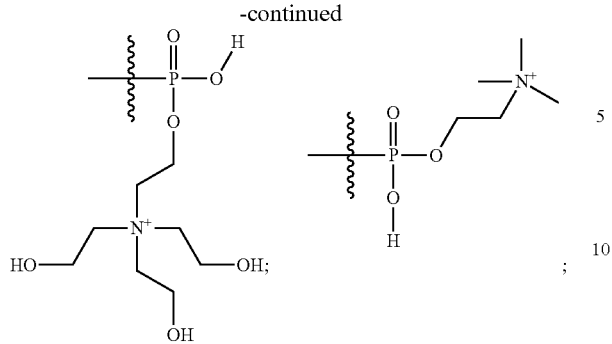
276
-continued
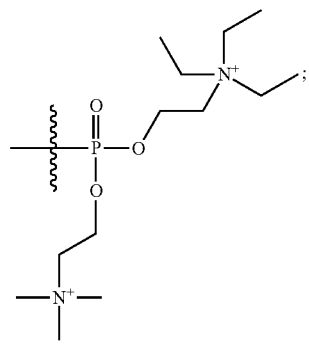
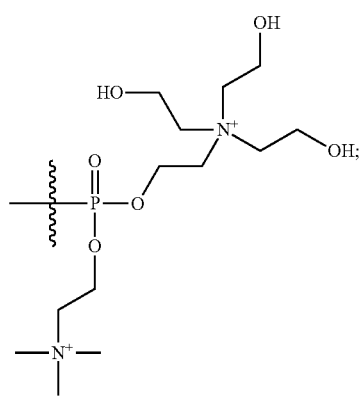
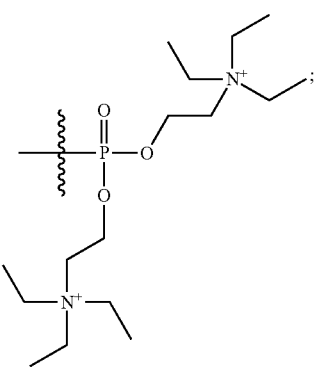
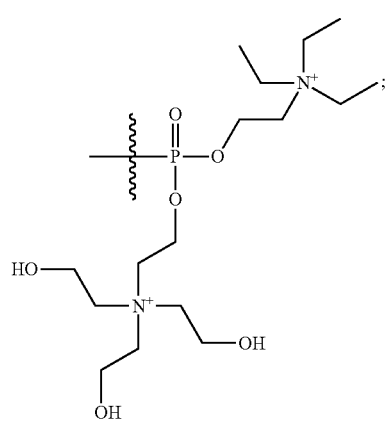

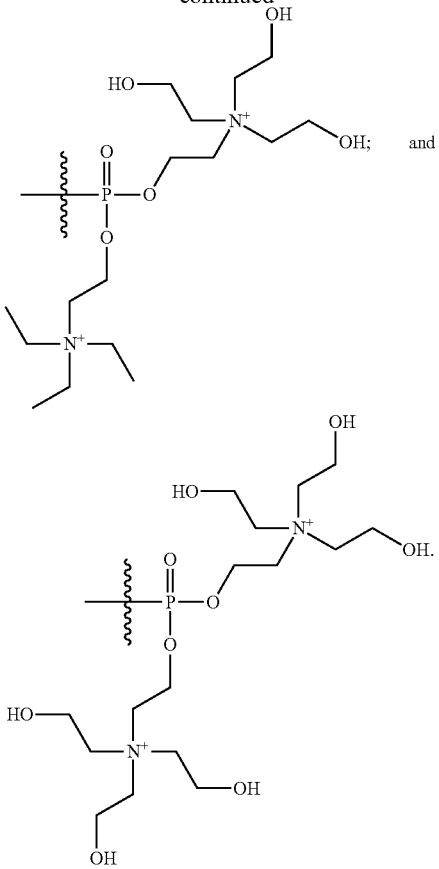

2. The method of claim 1, wherein the modulating of androgen receptor (AR) activity is in a mammalian cell.

3. The method of claim 2, wherein the modulating AR activity is for treatment of at least one indication selected from the group consisting of: prostate cancer, breast cancer, ovarian cancer, endometrial cancer, hair loss, acne, hirsutism, ovarian cysts, polycystic ovary disease, precocious puberty, and age-related macular degeneration.

4. The method of claim 3, wherein the indication is prostate cancer.

5. The method of claim 4, wherein the prostate cancer is androgen-independent prostate cancer.

6. The method of claim 4, wherein the prostate cancer is androgen-dependent prostate cancer.

7. A compound having a structure of Formula III

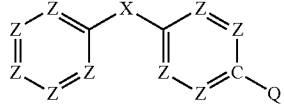

III or a pharmaceutically acceptable salt thereof, wherein:
X is $CH_2$, $CHR^1$, or $CR^1R^2$;
each of $R^1$ and $R^2$ is independently linear or branched, substituted or unsubstituted, saturated or unsaturated $C_1$-$C_{10}$ alkyl, wherein the optional substituent is selected from the group consisting of OJ''', F, Cl, Br, I, or $NH_2$;

wherein Q is

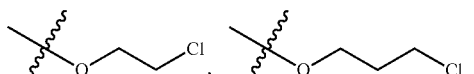
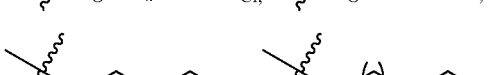
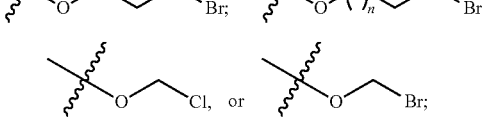

at least one Z of the other aromatic ring may independently be C-T, wherein T is

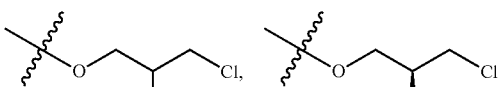
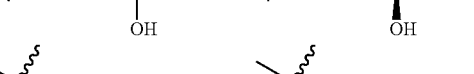
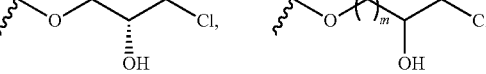
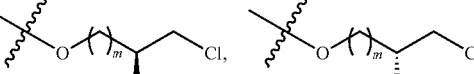
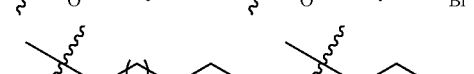
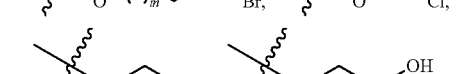
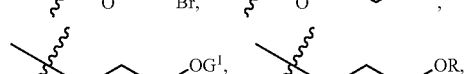
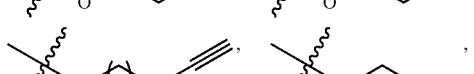
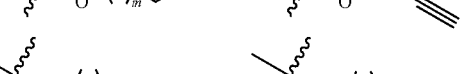
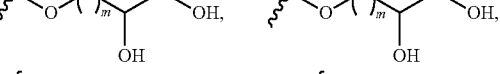
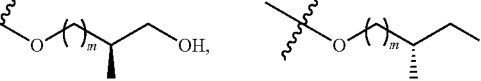
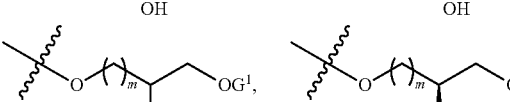

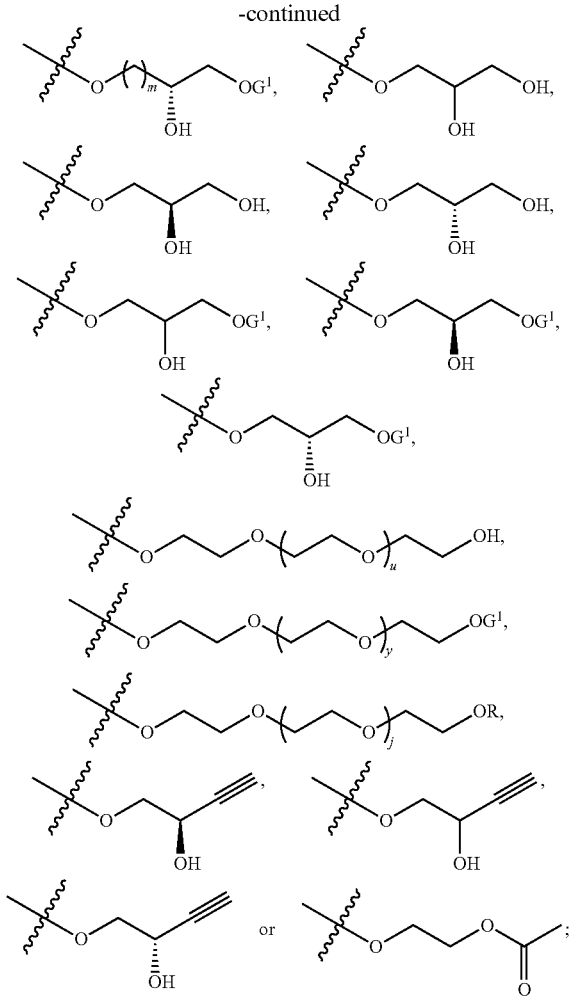

and each remaining Z is independently $CG^1$, N, CH, CF, CCl, CBr, CI, or COH;

n is 0, 1, 2, 3, 4, 5, 6, 7 or 8;

m is 0, 1, 2, 3, 4, 5, 6, 7 or 8;

each of u, j and y is independently 0, 1, 2, 3, 4, 5, 6 or 7;

each $G^1$ is independently linear or branched, substituted or unsubstituted, saturated or unsaturated $C_1$-$C_{10}$ alkyl, wherein the optional substituent is selected from the group consisting of oxo, OJ''', COOH, OH, F, Cl, Br, I, $NH_2$, CN, SH, $SO_3H$, $CONH_2$, $OPO_3H_2$, and $NO_2$; and each J'' and J''' is independently a moiety selected from the group consisting of:

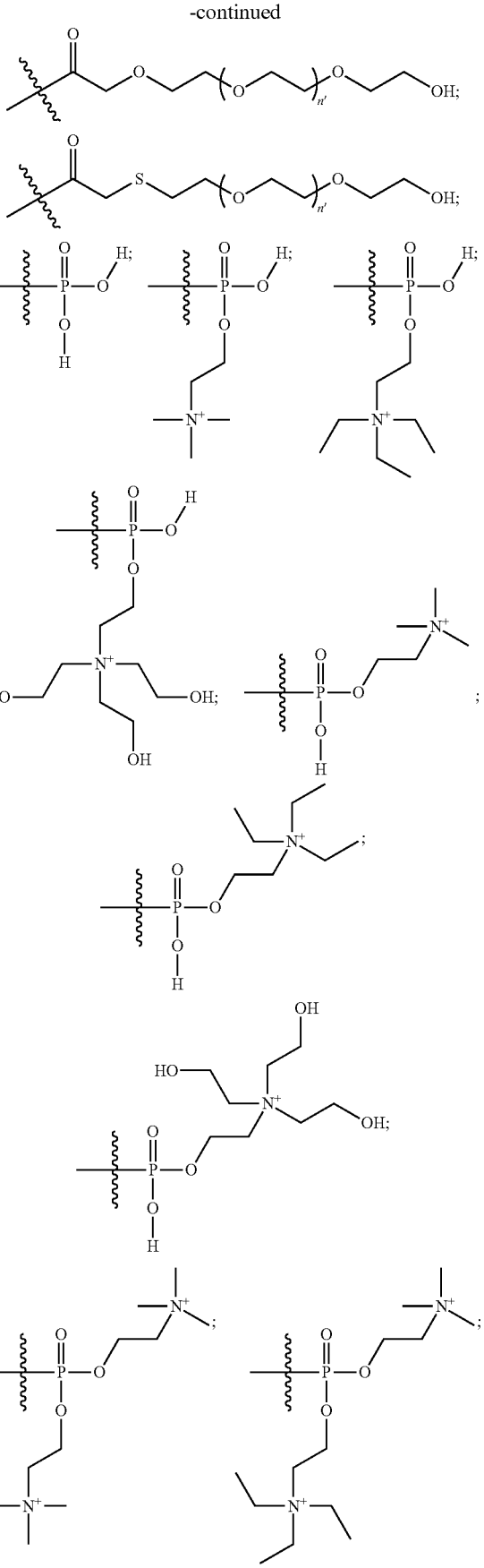

281
-continued
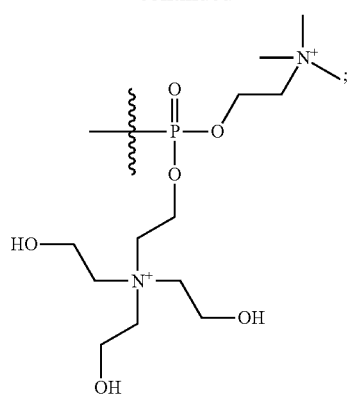
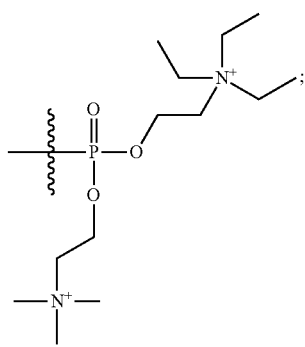
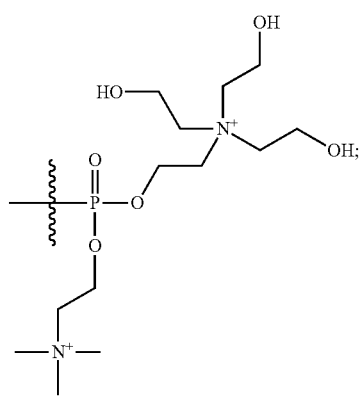
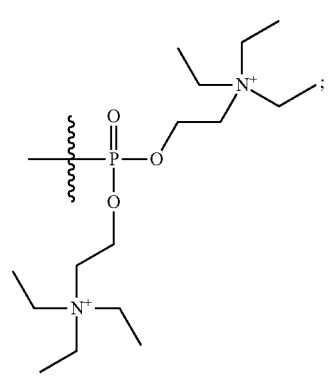
282
-continued
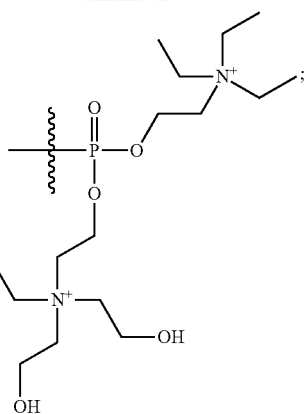
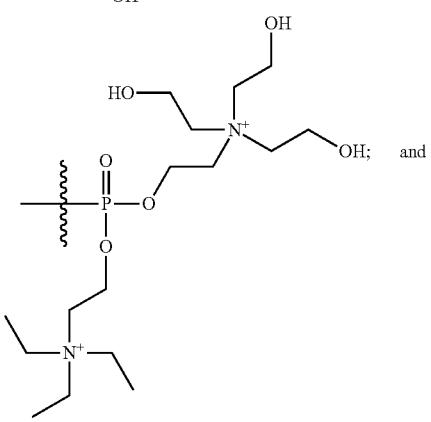
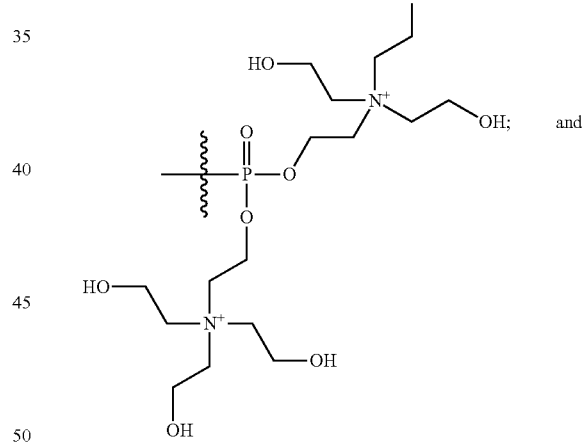
wherein one or more of the OH groups is optionally substituted to replace the H with a moiety selected from the group consisting of:
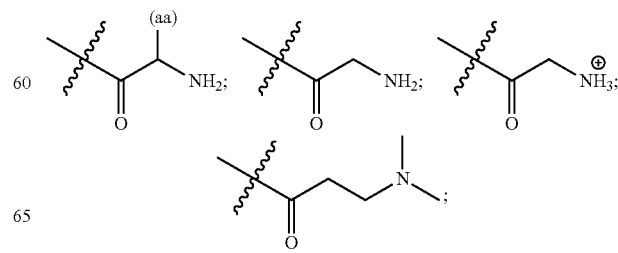

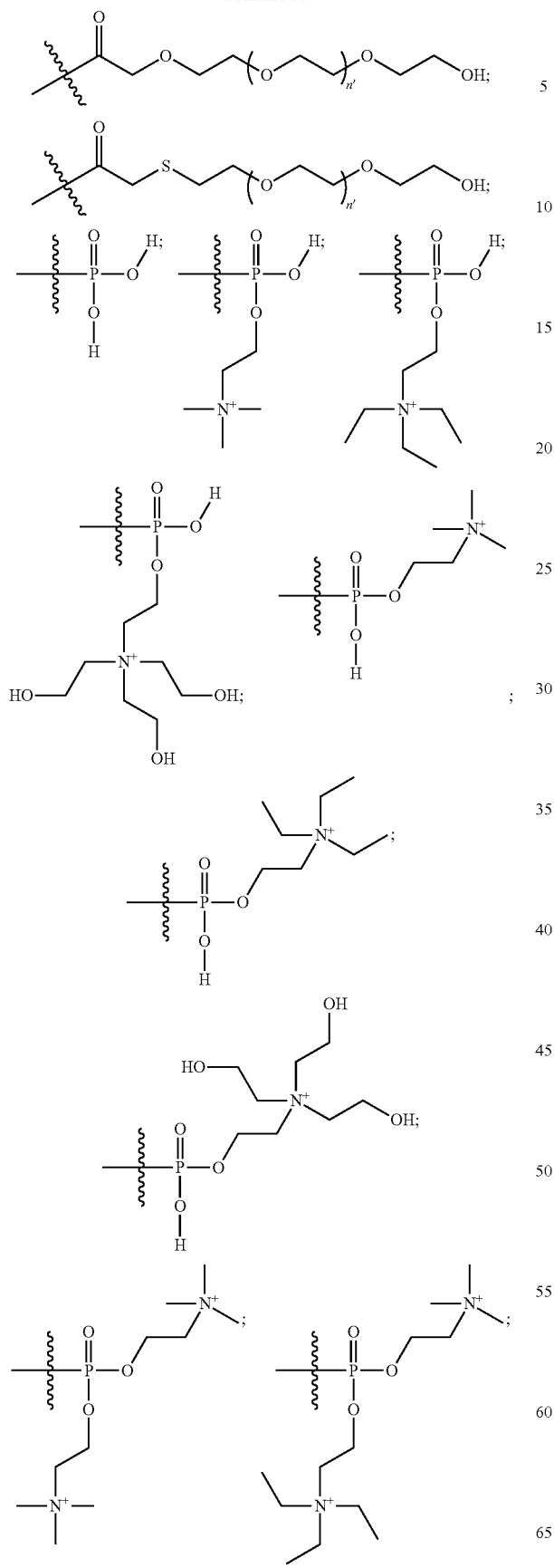
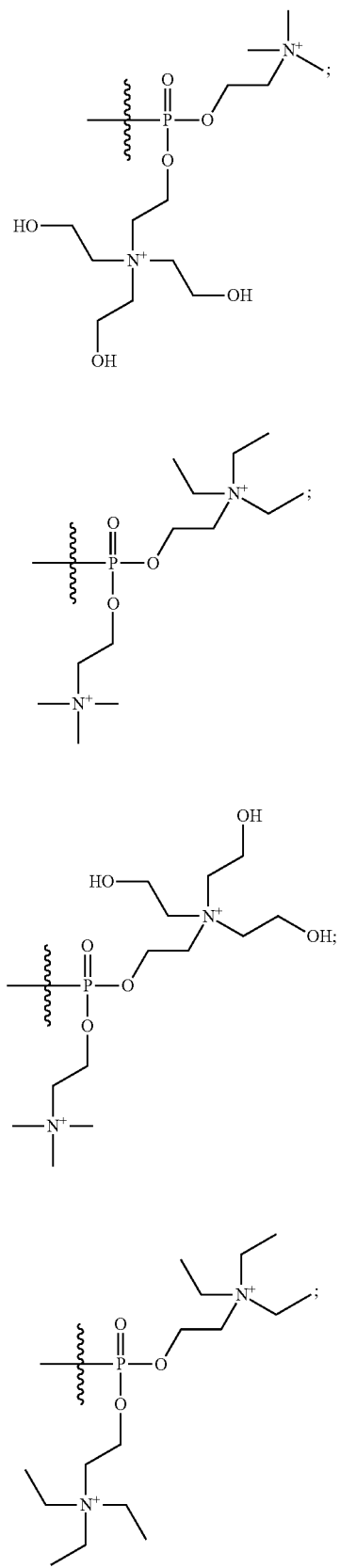

-continued

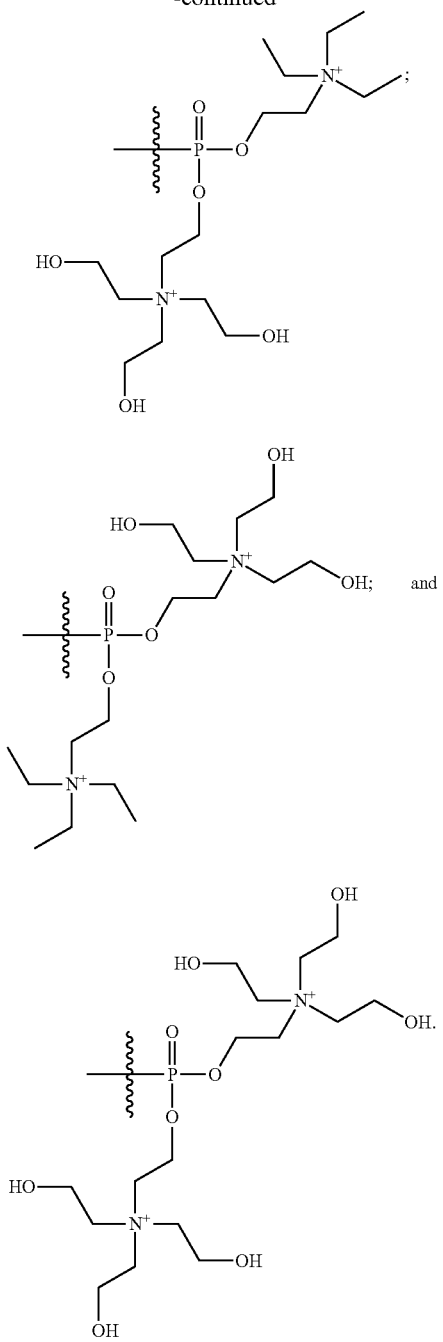

8. The compound or salt according to claim 7, wherein Q is

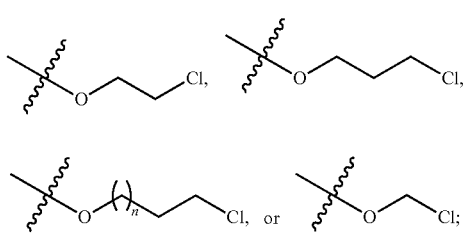

T is

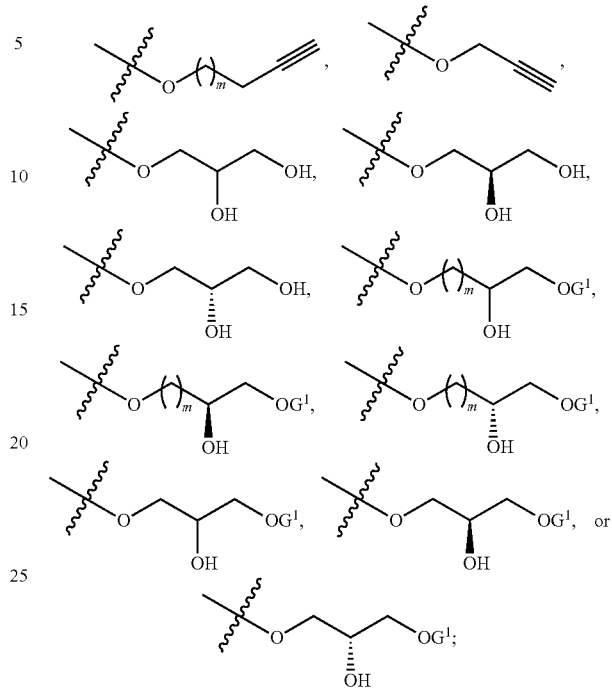

n is 0, 1, 2, 3, 4, 5, 6, 7 or 8; m is 0, 1, 2, 3, 4, 5, 6, 7 or 8; and each $G^1$ is independently linear or branched, substitute or unsubstituted, saturated or unsaturated $C_1$-$C_{10}$ alkyl, wherein the optional substituent is selected from the group consisting of oxo, OJ''', COOH, OH, F, Cl, Br, I, $NH_2$, CN, SH, $SO_3H$, $CONH_2$, $OPO_3H_2$, and $NO_2$.

9. The compound of claim 7, wherein the compound has the following Formula IV

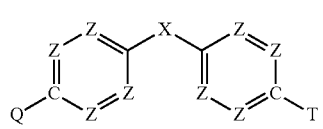

IV or pharmaceutically acceptable salt thereof, wherein:

X is $CH_2$, $CHR^1$, or $CR^1R^2$;

each of $R^1$ and $R^2$ is independently linear or branched, substituted or unsubstituted, saturated or unsaturated $C_1$-$C_{10}$ alkyl, wherein the optional substituent is selected from the group consisting of OJ''', F, Cl, Br, I, or $NH_2$;

each Z is independently $CG^1$, N, CH, CF, CCl, CBr, CI, or COH;

wherein Q is

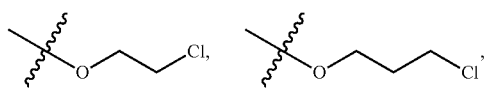

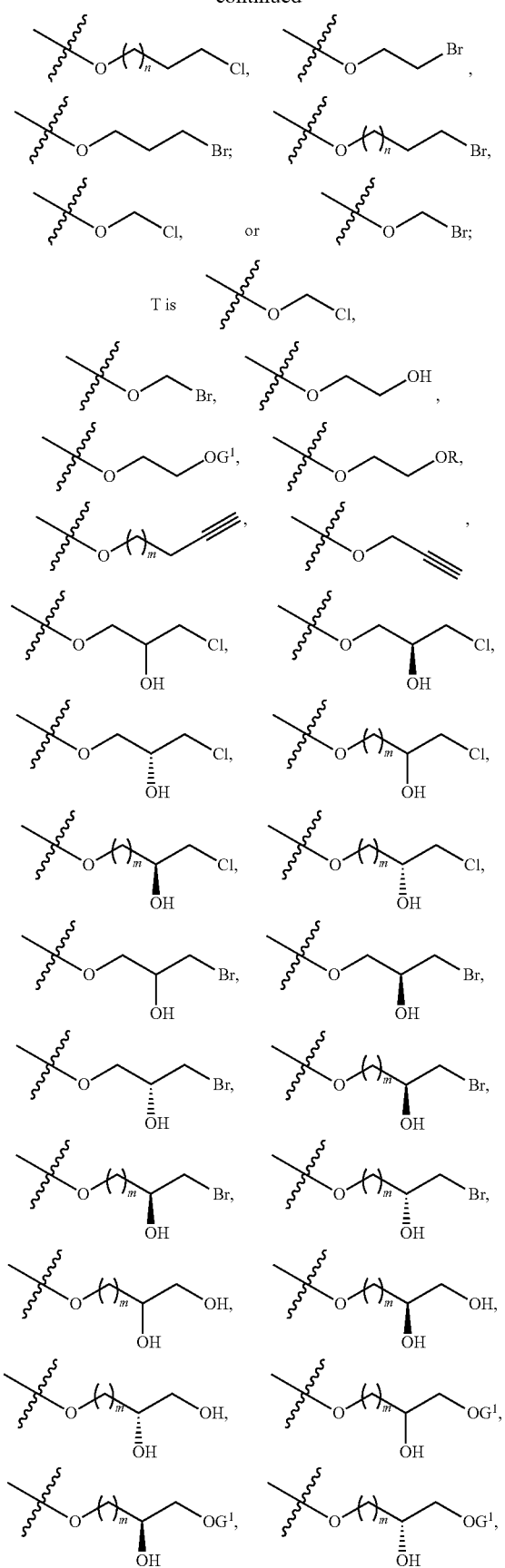

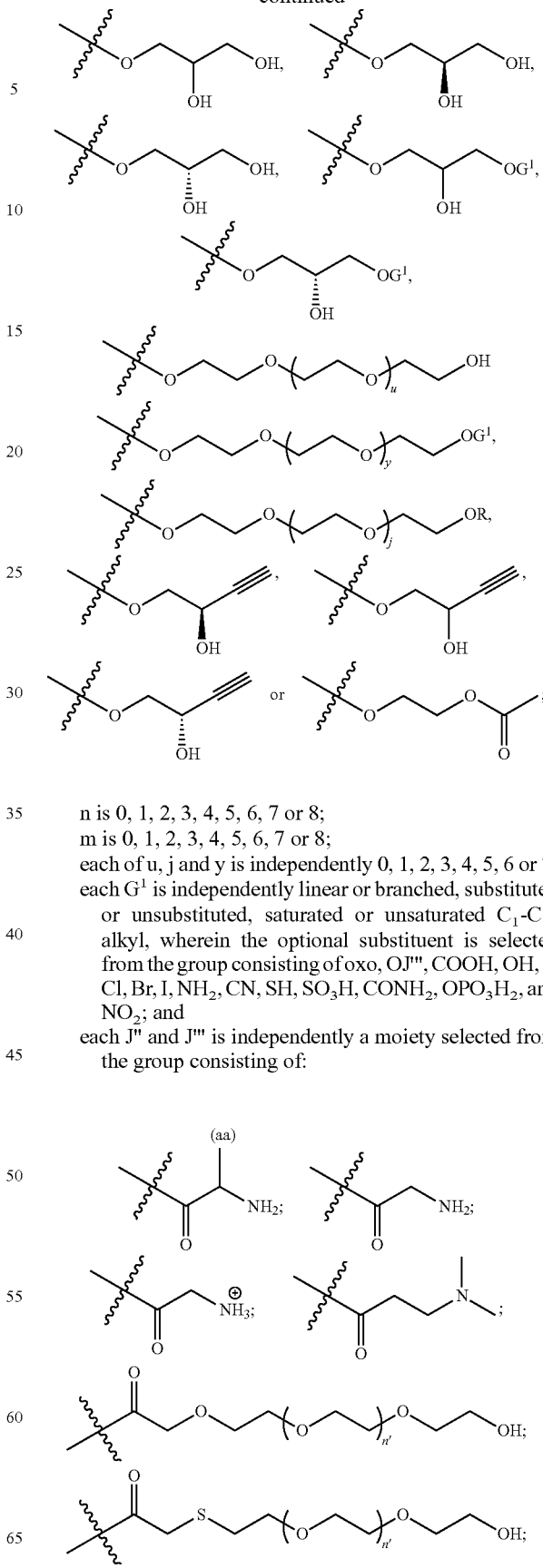

n is 0, 1, 2, 3, 4, 5, 6, 7 or 8;
m is 0, 1, 2, 3, 4, 5, 6, 7 or 8;
each of u, j and y is independently 0, 1, 2, 3, 4, 5, 6 or 7;
each $G^1$ is independently linear or branched, substituted or unsubstituted, saturated or unsaturated $C_1$-$C_{10}$ alkyl, wherein the optional substituent is selected from the group consisting of oxo, OJ''', COOH, OH, F, Cl, Br, I, $NH_2$, CN, SH, $SO_3H$, $CONH_2$, $OPO_3H_2$, and $NO_2$; and
each J''' and J'''' is independently a moiety selected from the group consisting of:

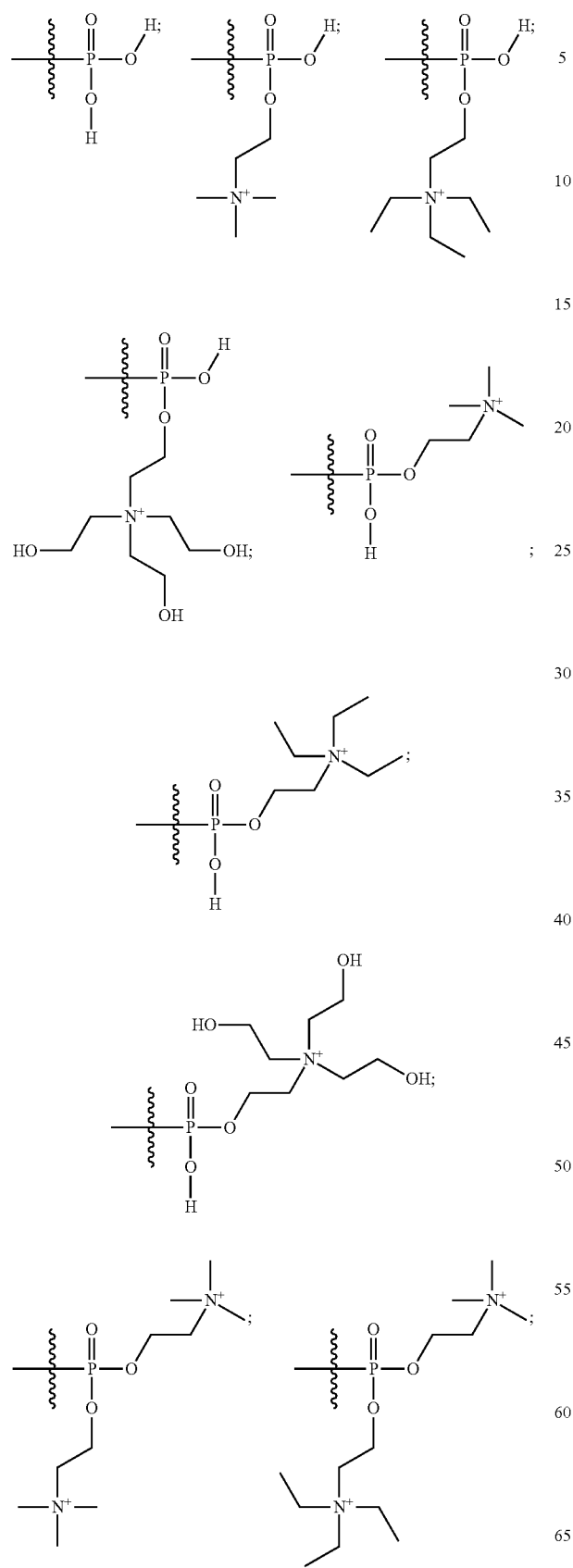
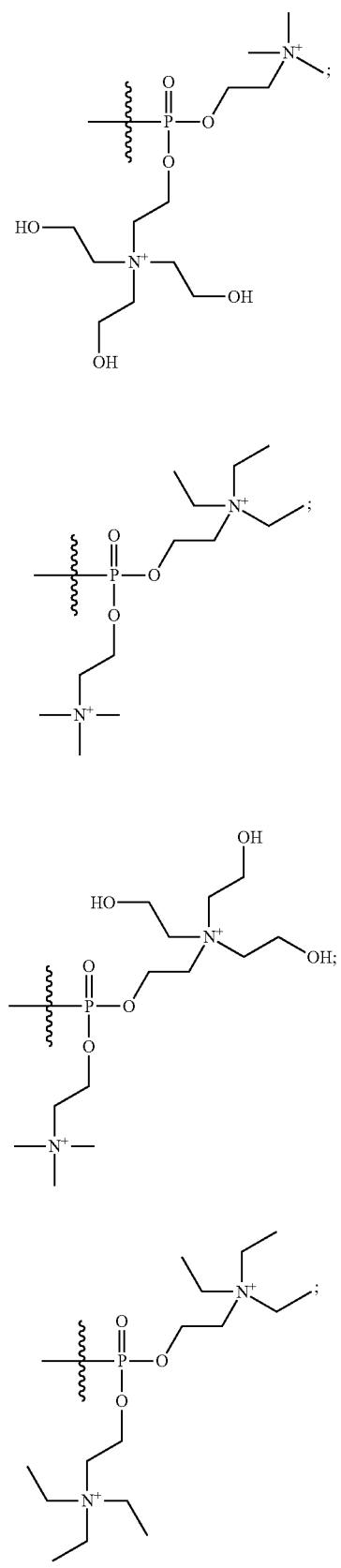

291
-continued
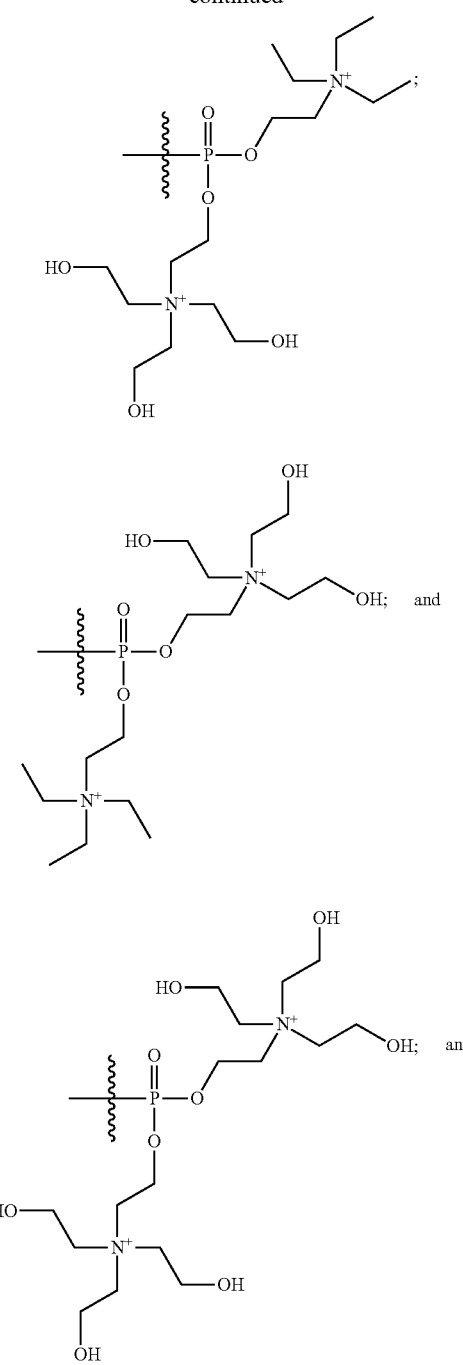
and
wherein one or more of the OH groups is optionally substituted to replace the H with a moiety selected from the group consisting of:
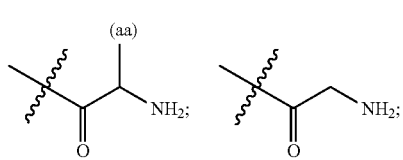
292
-continued
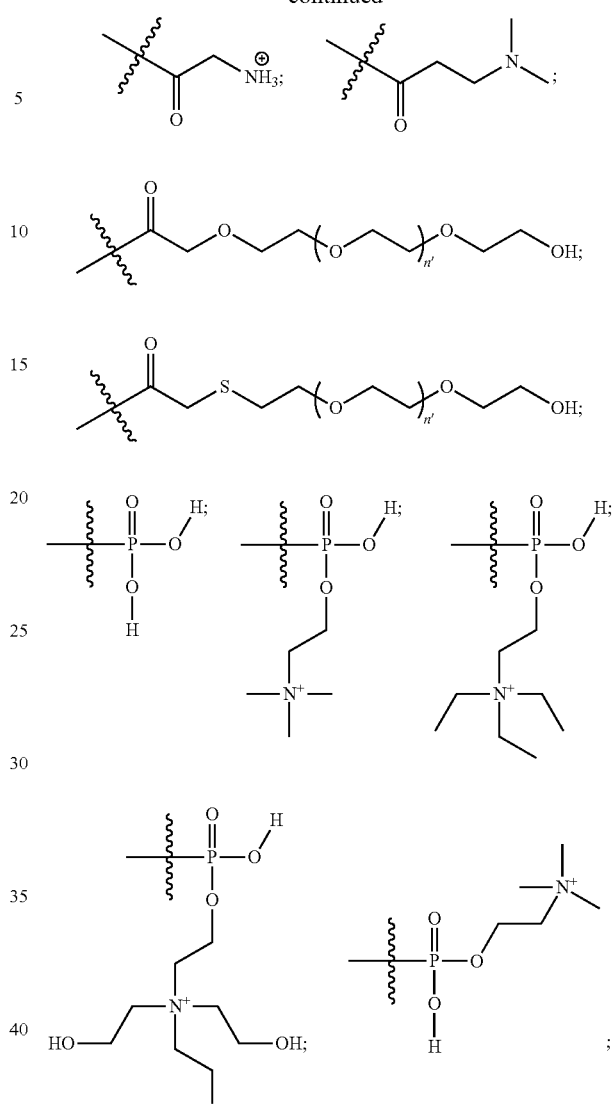
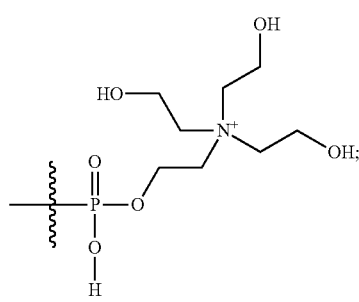

293
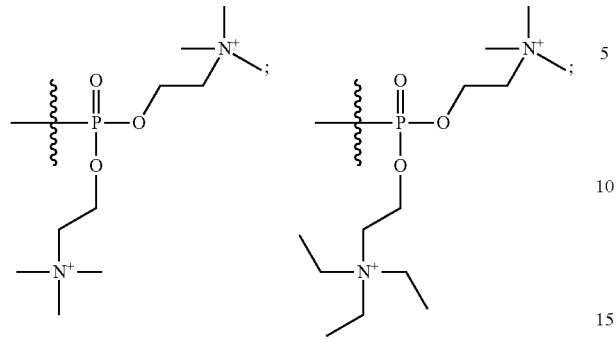
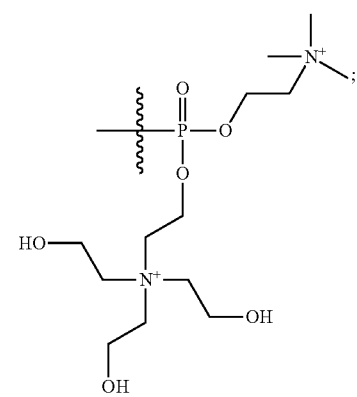
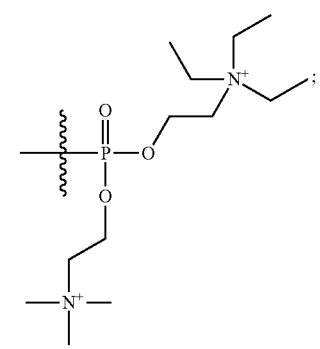
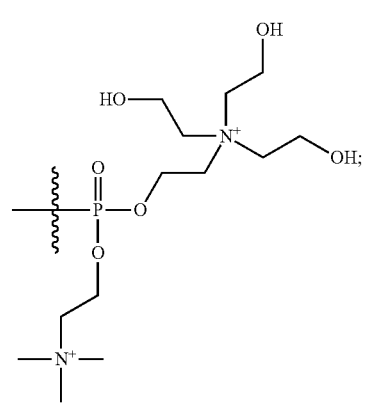
294
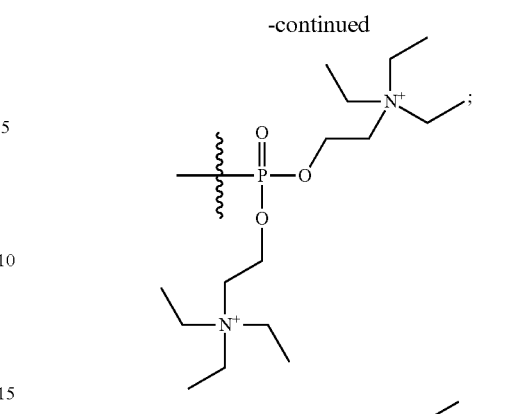
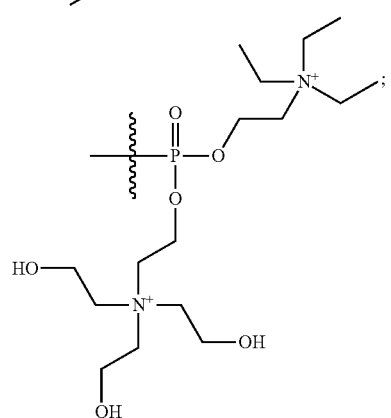
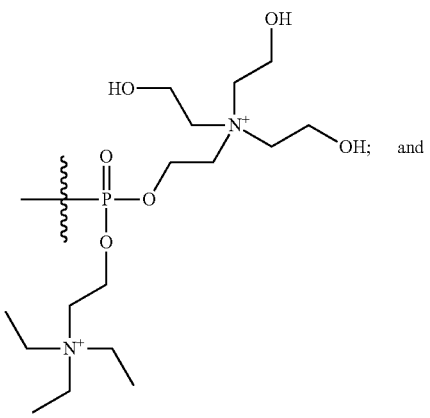; and
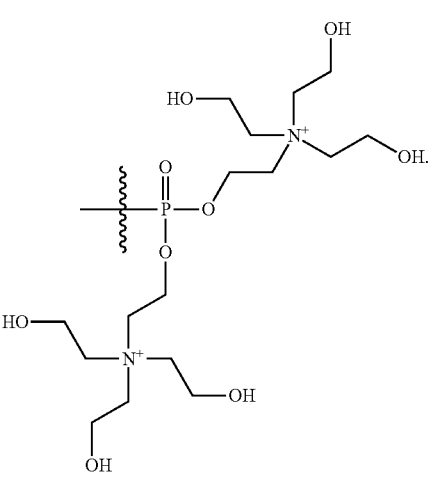

10. The compound or salt according to claim 9, wherein Q is

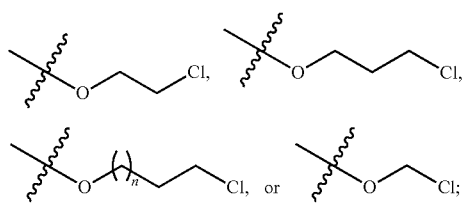

T is

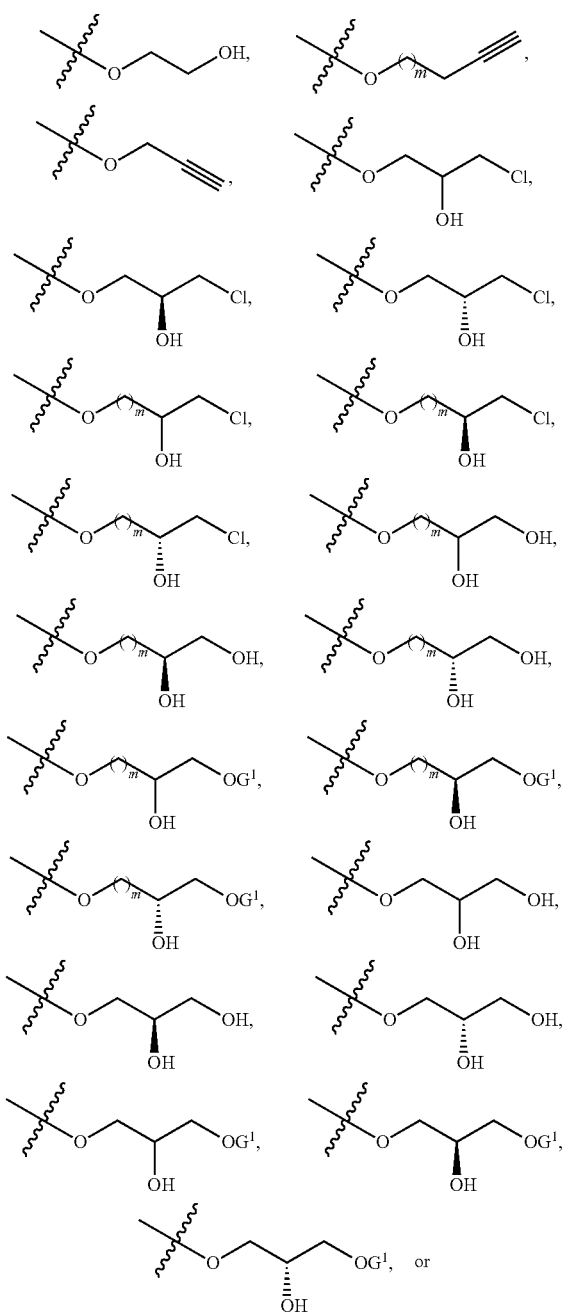

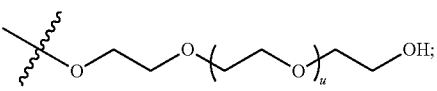

n is 0, 1, 2, 3, 4, 5, 6, 7 or 8;
m is 0, 1, 2, 3, 4, 5, 6, 7 or 8;
u is 0, 1, 2, 3, 4, 5, 6 or 7; and
each $G^1$ is independently linear or branched, substituted or unsubstituted, saturated or unsaturated $C_1$-$C_{10}$ alkyl, wherein the optional substituent is selected from the group consisting of oxo, OJ''', COOH, OH, F, Cl, Br, I, $NH_2$, CN, SH, $SO_3H$, $CONH_2$, $OPO_3H_2$, and $NO_2$.

11. The compound or salt according to claim 9, wherein Q is

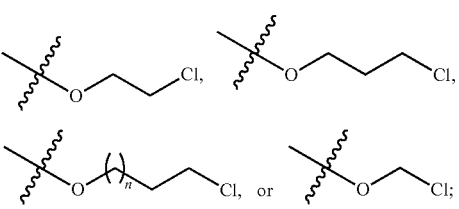

T is

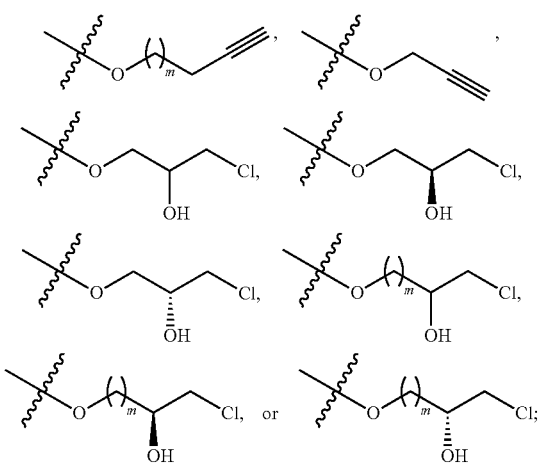

n is 0, 1, 2, 3, 4, 5, 6, 7 or 8; and m is 0, 1, 2, 3, 4, 5, 6, 7 or 8.

12. The compound or salt according to claim 9, wherein Q is

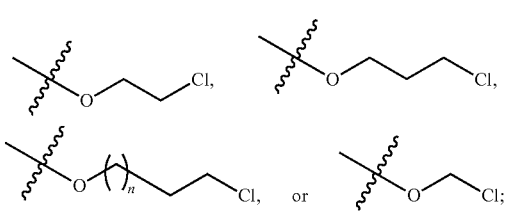

T is

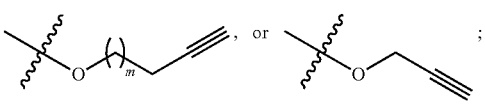

n is 0, 1, 2, 3, 4, 5, 6, 7 or 8; and m is 0, 1, 2, 3, 4, 5, 6, 7 or 8.

13. The compound or salt according to claim 9, wherein Q is

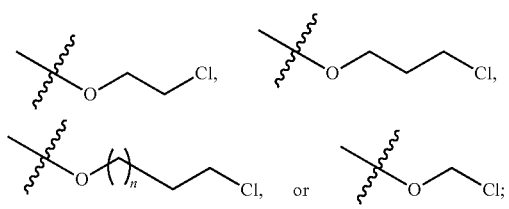

T is

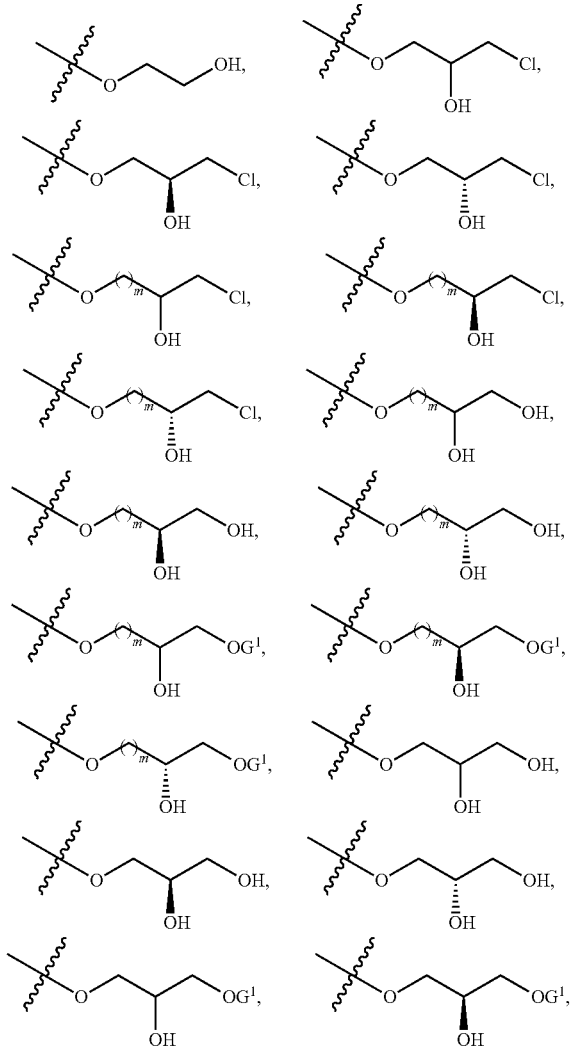

-continued

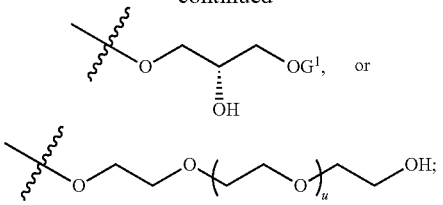

n is 0, 1, 2, 3, 4, 5, 6, 7 or 8;

m is 0, 1, 2, 3, 4, 5, 6, 7 or 8;

u is 0, 1, 2, 3, 4, 5, 6 or 7; and each $G^1$ is independently linear or branched, substituted or unsubstituted, saturated or unsaturated $C_1$-$C_{10}$ alkyl, wherein the optional substituent is selected from the group consisting of oxo, $OJ'''$, COOH, OH, F, Cl, Br, I, $NH_2$, CN, SH, $SO_3H$, $CONH_2$, $OPO_3H_2$, and $NO_2$.

14. The compound or salt according to claim 9, wherein Q is

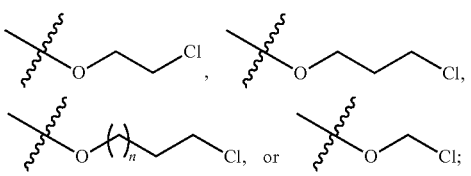

T is

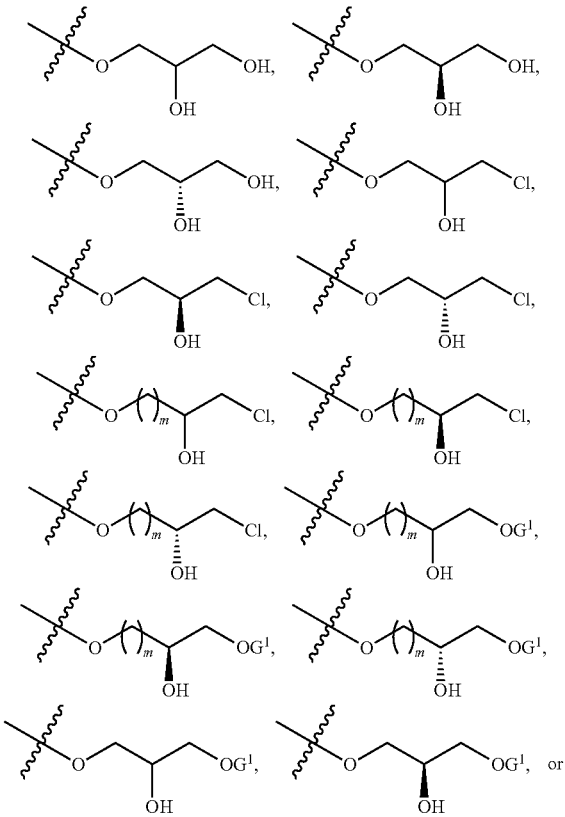

-continued

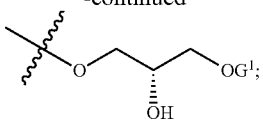

n is 0, 1, 2, 3, 4, 5, 6, 7 or 8; m is 0, 1, 2, 3, 4, 5, 6, 7 or 8; and each $G^1$ is independently linear or branched, substituted or unsubstituted, saturated or unsaturated $C_1$-$C_{10}$ alkyl, wherein the optional substituent is selected from the group consisting of oxo, OJ''', COOH, OH, F, Cl, Br, I, $NH_2$, CN, SH, $SO_3H$, $CONH_2$, $OPO_3H_2$, and $NO_2$.

15. A compound having a structure of Formula IX

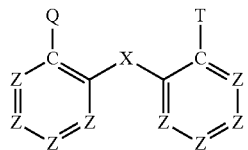

or pharmaceutically acceptable salt thereof,
wherein:
X is $CH_2$, $CHR^1$, or $CR^1R^2$;
each of $R^1$ and $R^2$ is independently linear or branched, substituted or unsubstituted, saturated or unsaturated $C_1$-$C_{10}$ alkyl, wherein the optional substituent is selected from the group consisting of OJ''', F, Cl, Br, I, or $NH_2$;
each Z is independently $CG^1$, N, CH, CF, CCl, CBr, CI, or COH;
wherein Q is

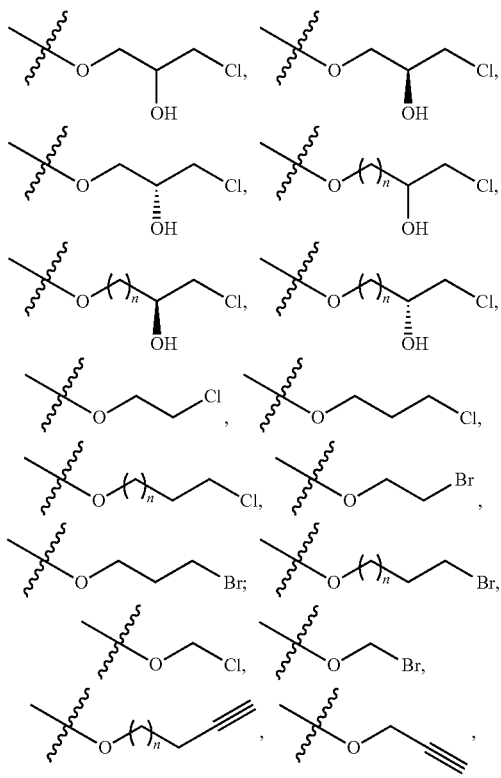

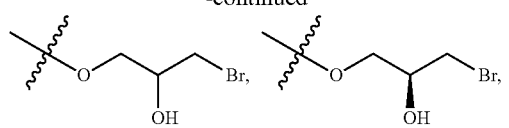

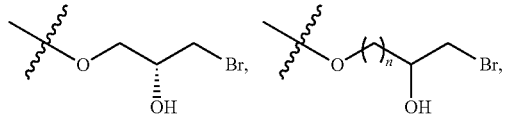

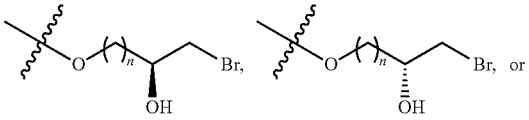

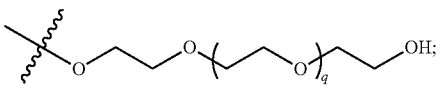

T is

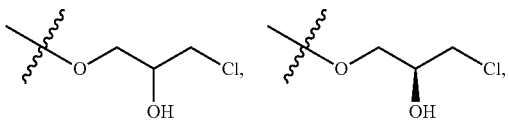

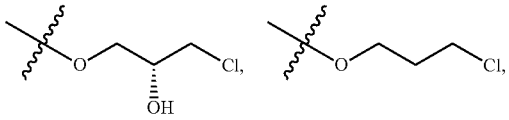

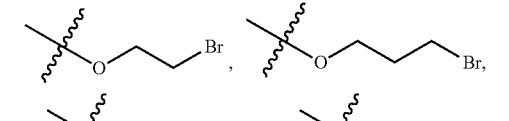

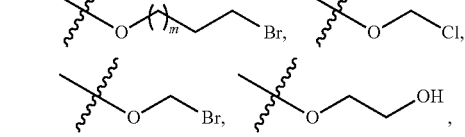

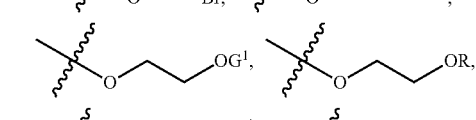

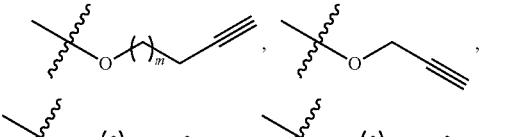

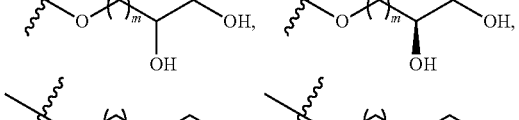

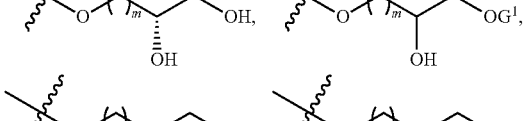

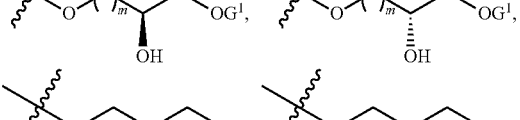

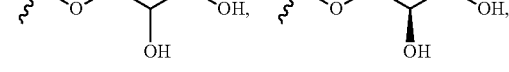

301

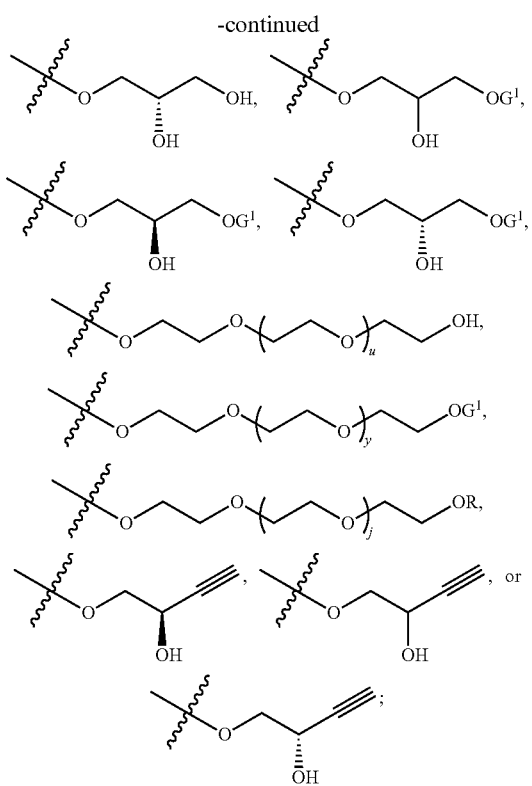

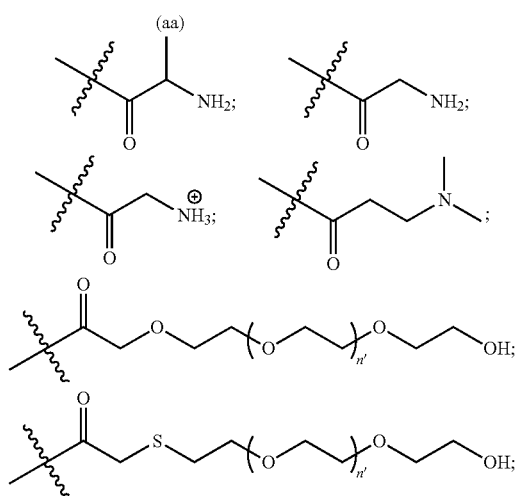

n is 0, 1, 2, 3, 4, 5, 6, 7 or 8;

q is 0, 1, 2, 3, 4, 5, 6, or 7;

m is 0, 1, 2, 3, 4, 5, 6, 7 or 8;

each of u, j and y is independently 0, 1, 2, 3, 4, 5, 6 or 7;

each $G^1$ is independently linear or branched, substituted or unsubstituted, saturated or unsaturated $C_1$-$C_{10}$ alkyl, wherein the optional substituent is selected from the group consisting of oxo, OJ''', COOH, OH, F, Cl, Br, I, $NH_2$, CN, SH, $SO_3H$, $CONH_2$, $OPO_3H_2$, and $NO_2$; and each J'' and J''' is independently a moiety selected from the group consisting of:

302

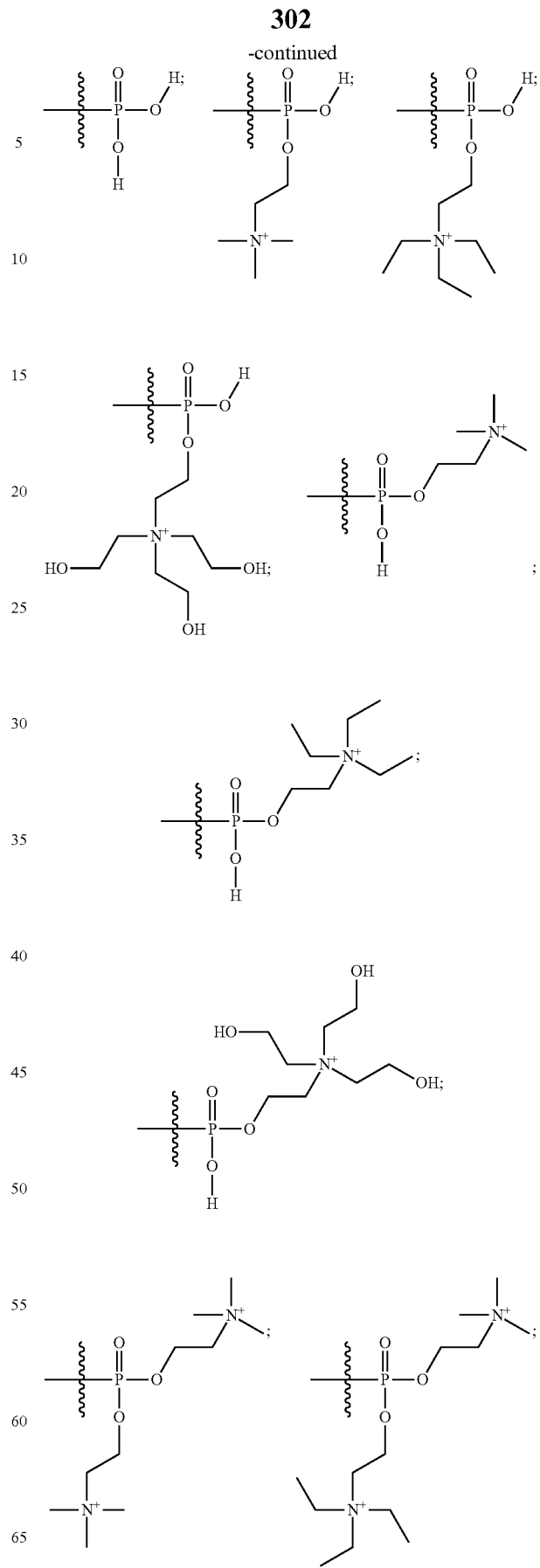

303
-continued
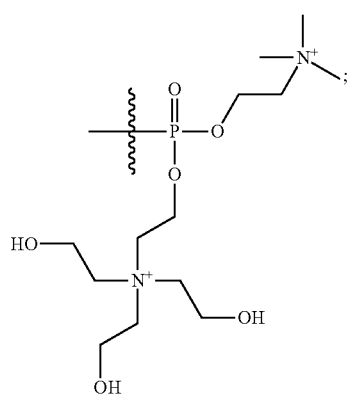
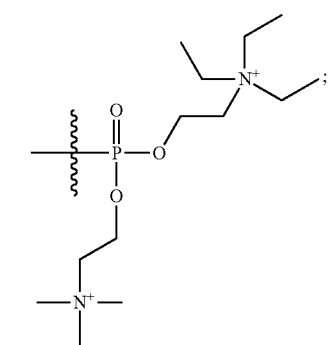
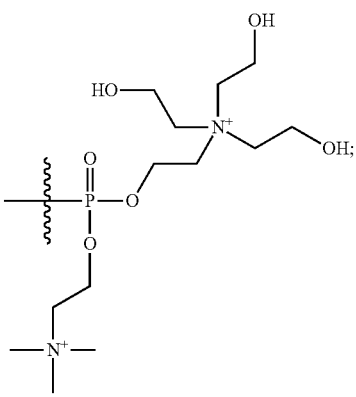
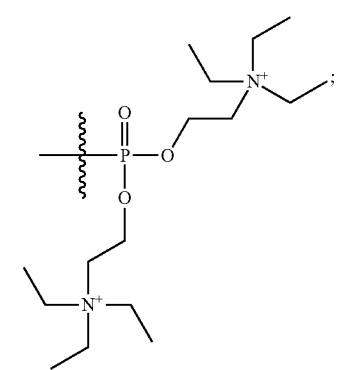
304
-continued
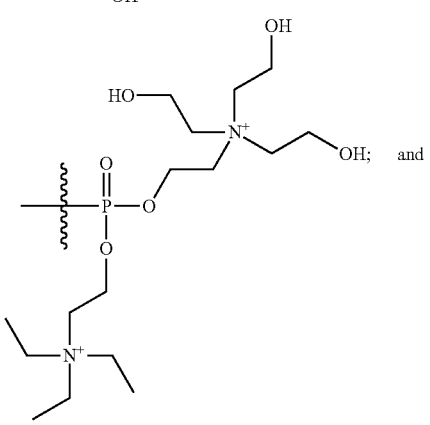
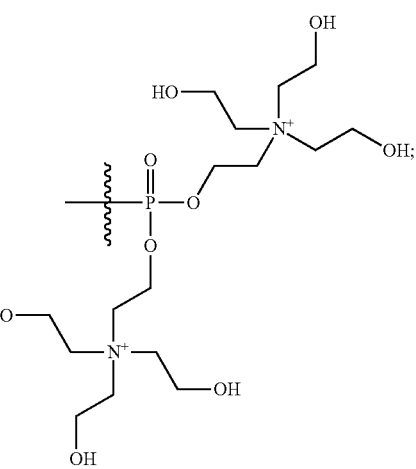
and
wherein one or more of the OH groups is optionally substituted to replace the H with a moiety selected from the group consisting of:
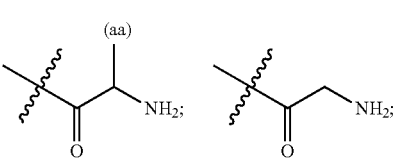
(aa)

305
-continued
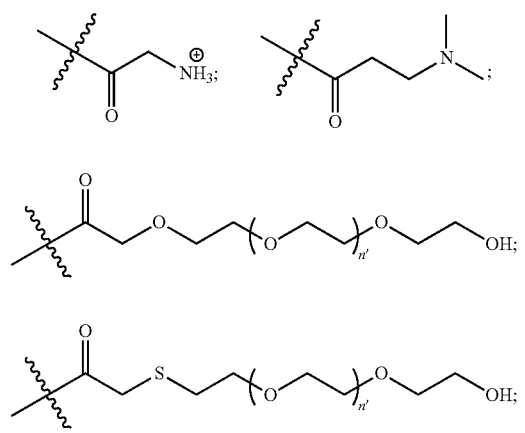
306
-continued
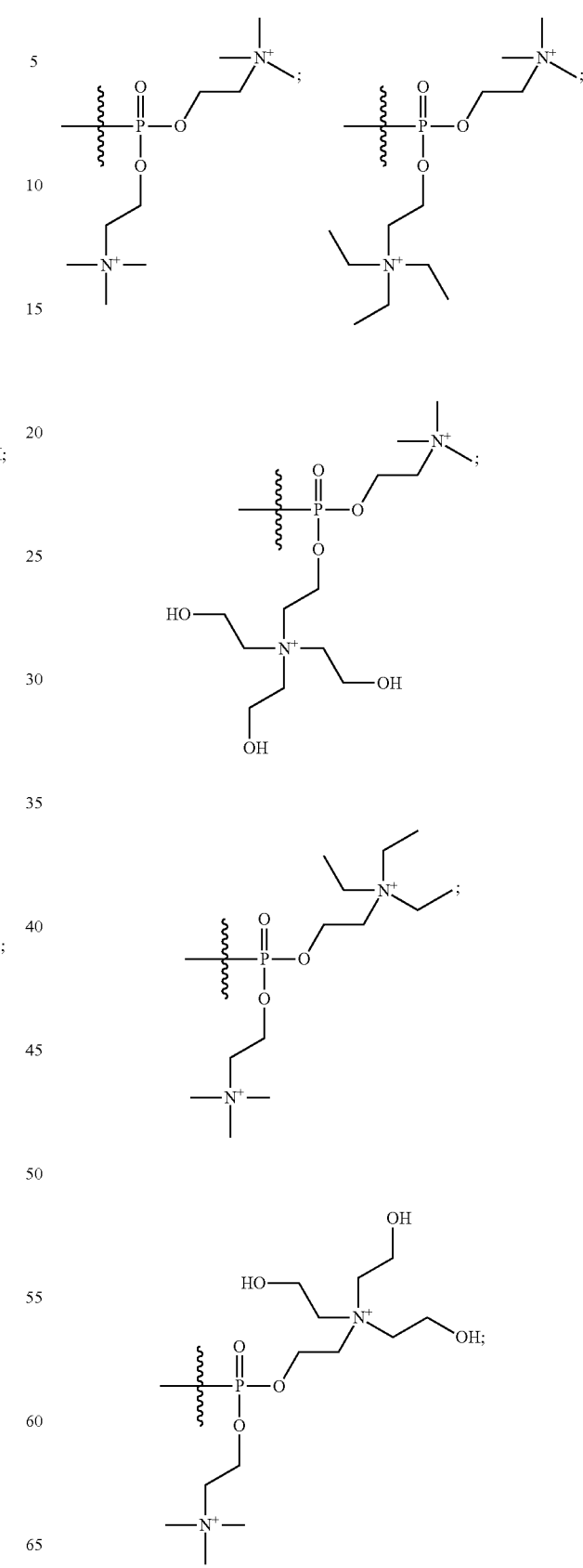

-continued
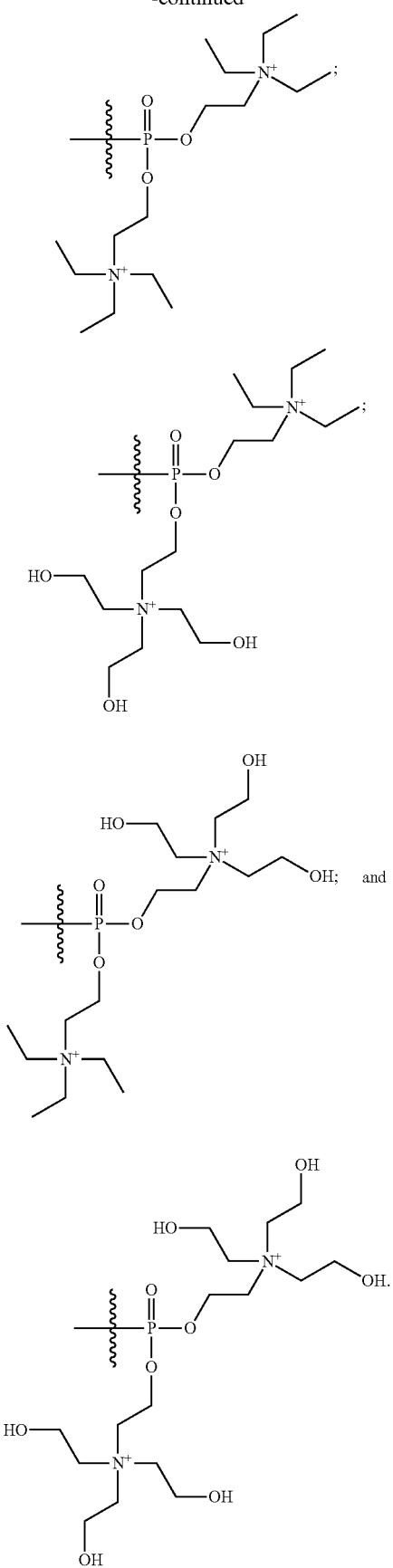
16. The compound or salt according to claim 15, wherein Q is
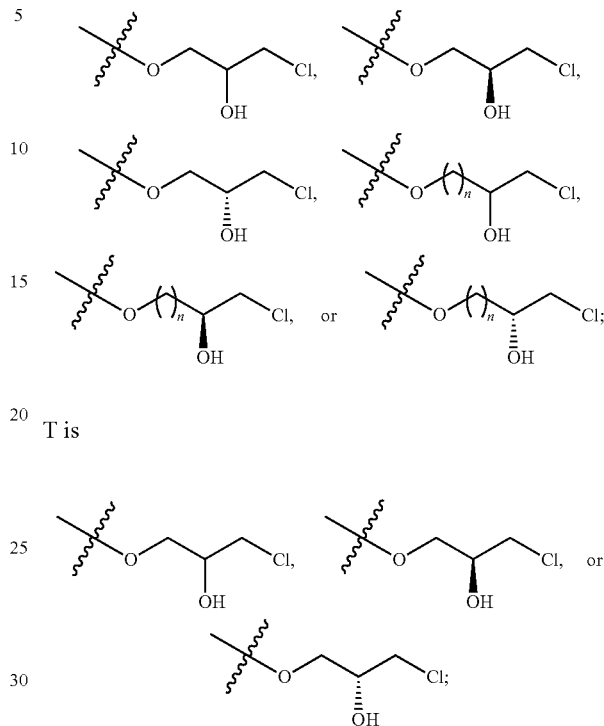
T is
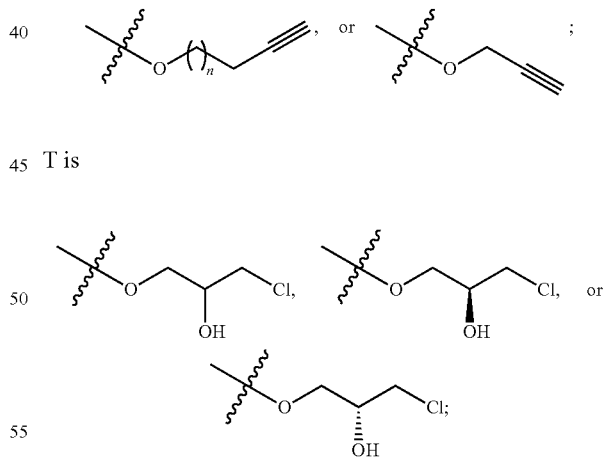
n is 0, 1, 2, 3, 4, 5, 6, 7 or 8.
17. The compound or salt according to claim 15, wherein Q is
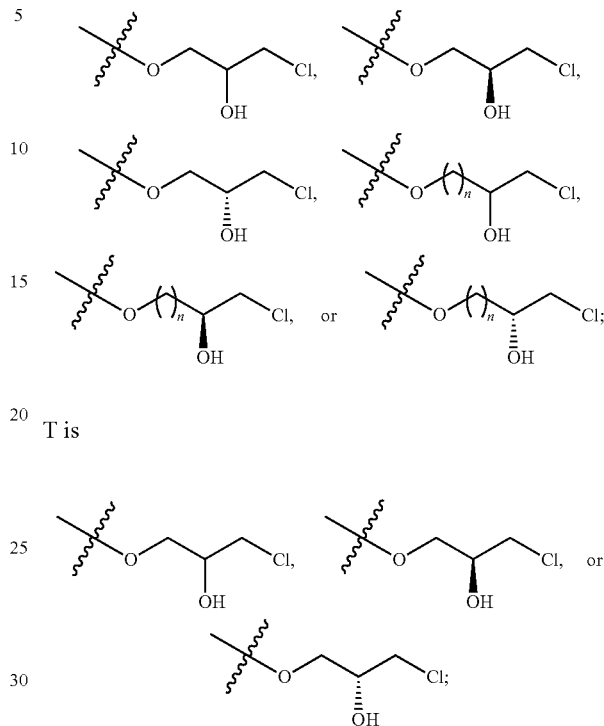
T is
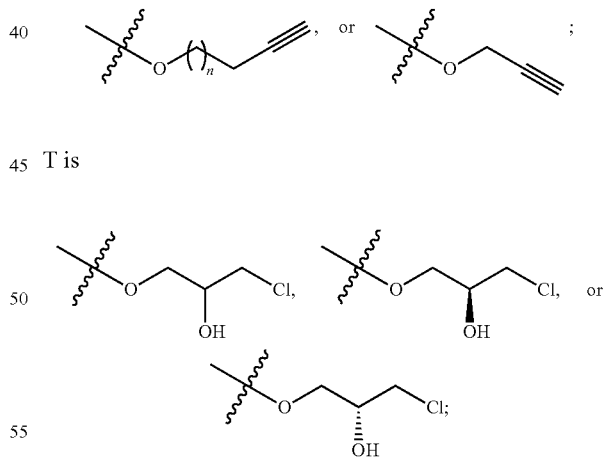
and n is 0, 1, 2, 3, 4, 5, 6, 7 or 8.
18. The compound or salt according to claim 15, wherein Q is
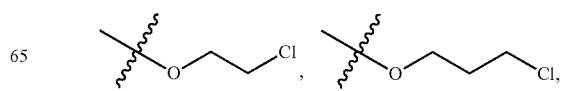

-continued

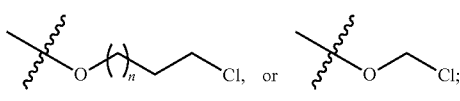

T is

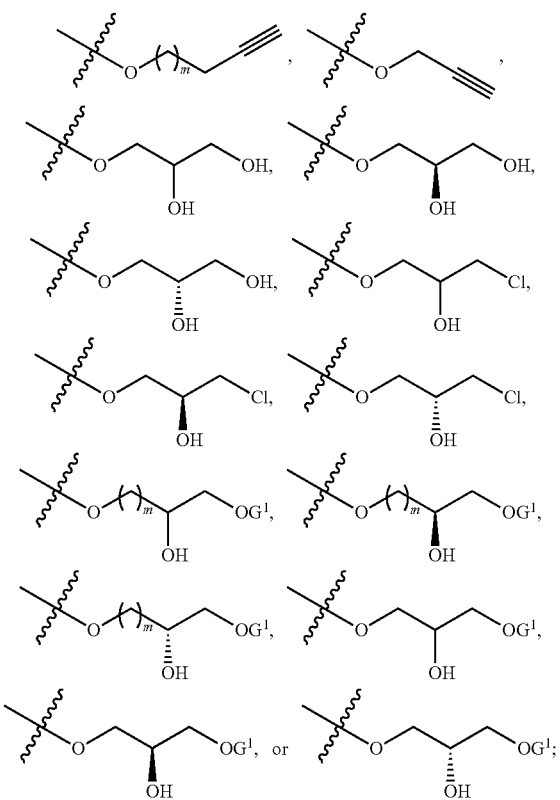

n is 0, 1, 2, 3, 4, 5, 6, 7 or 8; m is 0, 1, 2, 3, 4, 5, 6, 7 or 8; and each $G^1$ is independently linear or branched, substituted or unsubstituted, saturated or unsaturated $C_1$-$C_{10}$ alkyl, wherein the optional substituent is selected from the group consisting of oxo, $OJ'''$, COOH, OH, F, Cl, Br, I, $NH_2$, CN, SH, $SO_3H$, $CONH_2$, $OPO_3H_2$, and $NO_2$.

19. The compound or salt according to claim 7, wherein Q is

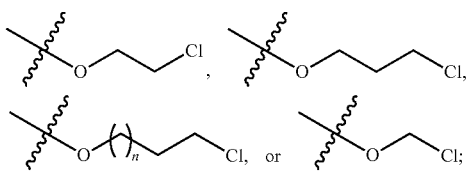

T is

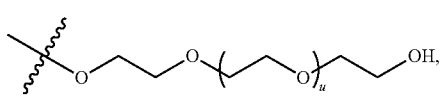

-continued

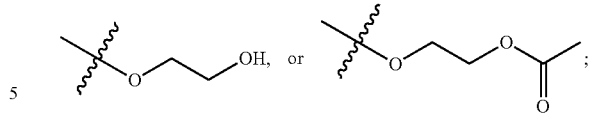

n is 0, 1, 2, 3, 4, 5, 6, 7 or 8; and u is 0, 1, 2, 3, 4, 5, 6, or 7.

20. The compound or salt according to claim 15, wherein Q is

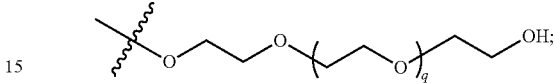

T is

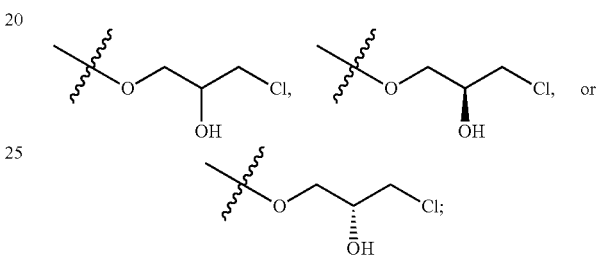

and q is 0, 1, 2, 3, 4, 5, 6, or 7.

21. The compound or salt according to claim 7, wherein Q is

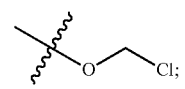 [SMILES: *OCCl]

n is 0, 1, 2, 3, 4, 5, 6, 7 or 8; and m is 0, 1, 2, 3, 4, 5, 6, 7 or 8.

22. The compound or salt according to claim 7, wherein $G^1$, when present, is $CH_2C\equiv CH$ or $CH(CH_3)_2$.

23. The compound or salt according to claim 7, wherein each remaining Z is independently selected from: $CCH_3$; CH; and CBr.

24. The compound or salt according to claim 7, wherein each remaining Z is CH.

25. The compound or salt according to claim 7, wherein X is $CH_2$.

26. The compound or salt according to claim 7, wherein X is $CHR^1$ and $R^1$ is $CH_3$.

27. The compound or salt according to claim 7, wherein X is $CR^1R^2$ and each of $R^1$ and $R^2$ is $CH_3$.

28. The compound or salt according to claim 7, wherein one or more of the OH groups of the compound or salt is optionally substituted to replace the H with a moiety selected from the group consisting of:

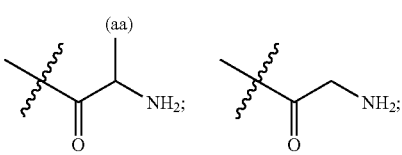

311
-continued
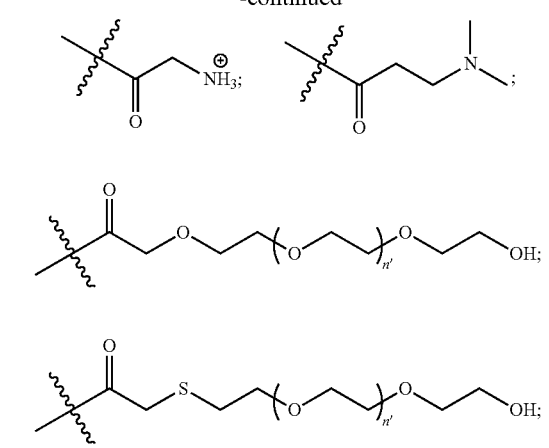
312
-continued
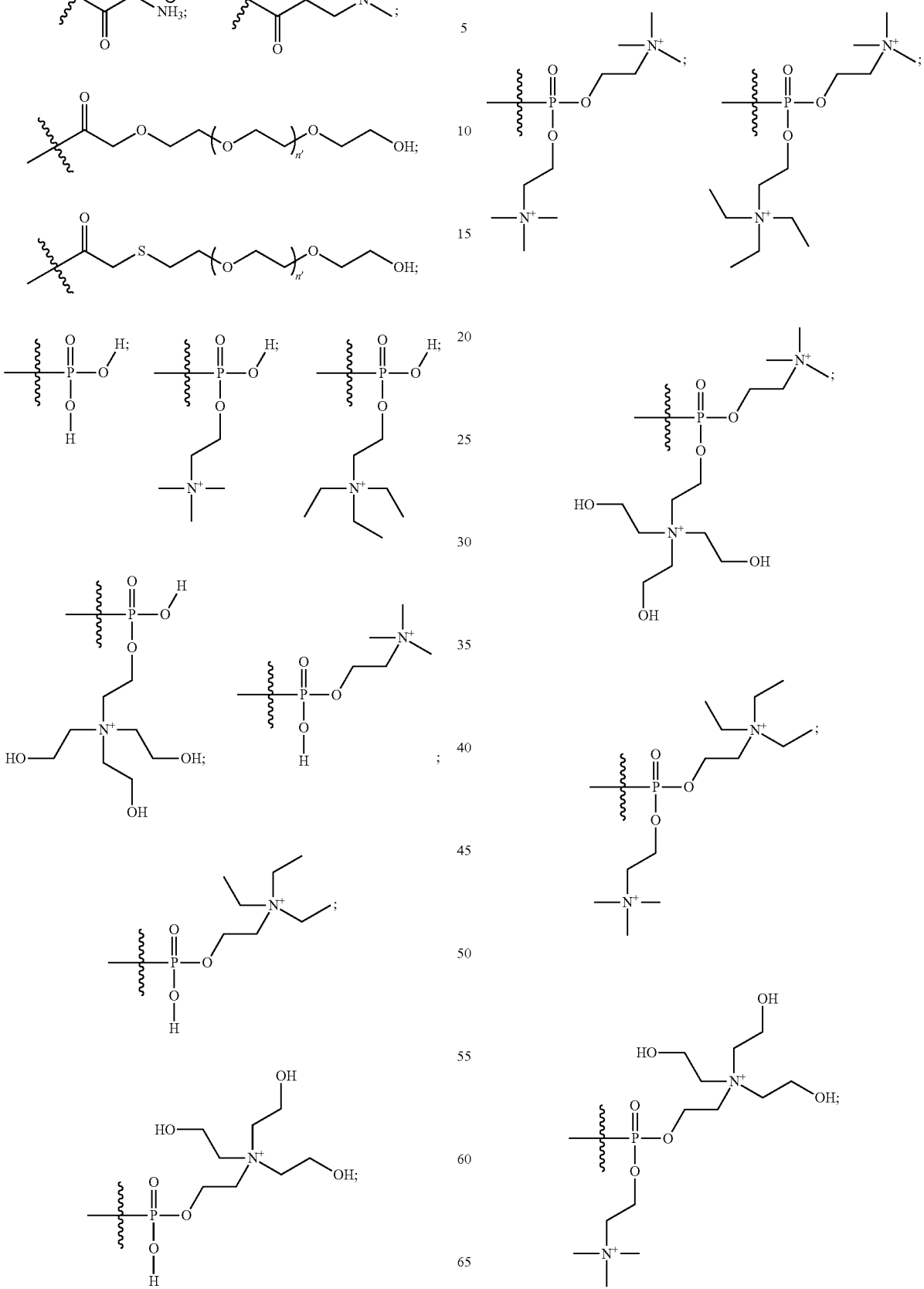

313
-continued
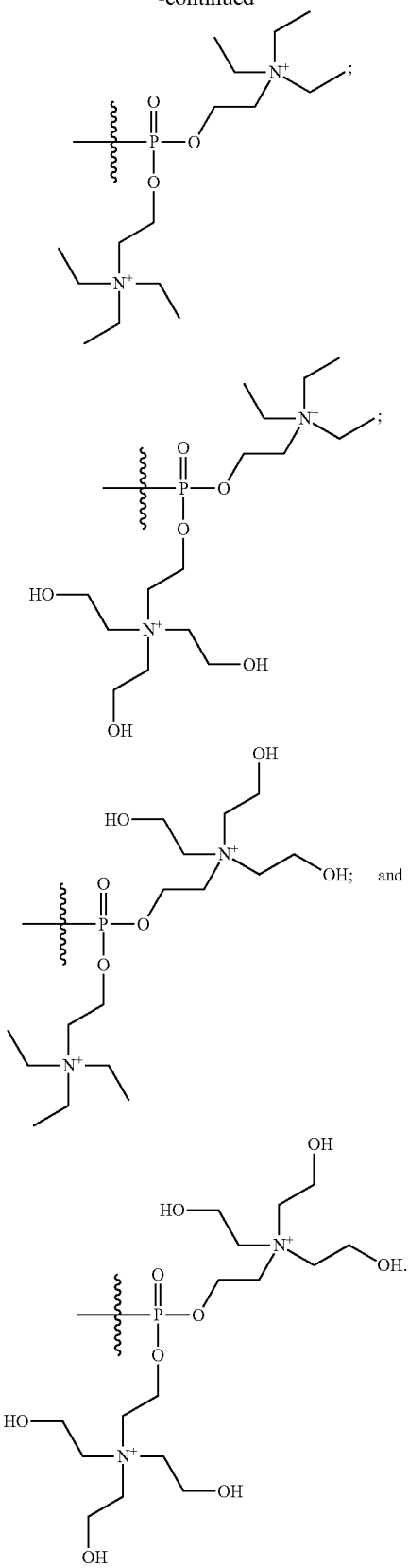
29. The compound or salt according to claim 28, wherein the moiety selected from
314
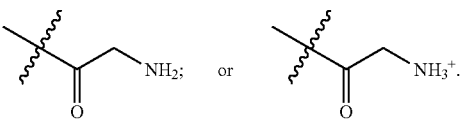
30. The compound of claim 7, wherein the compound has one of the following structures:
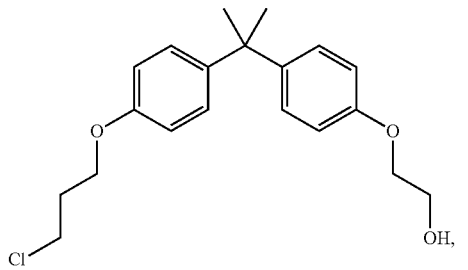
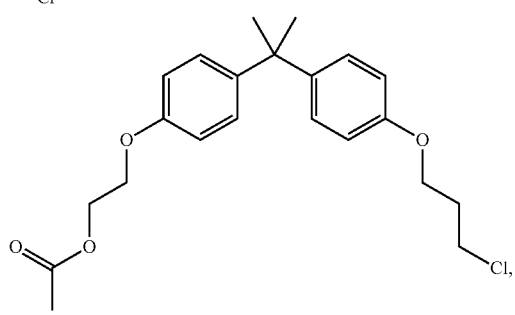
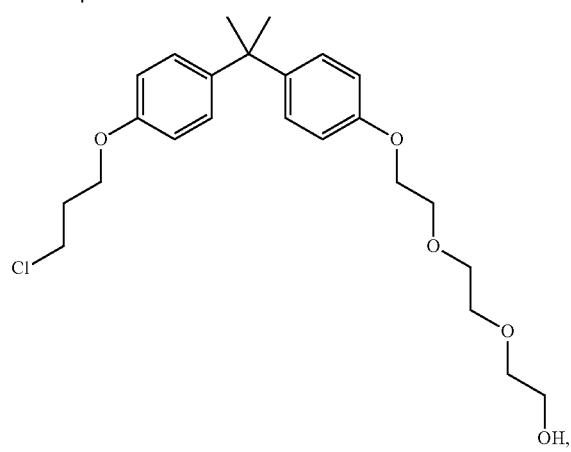
or

315

-continued

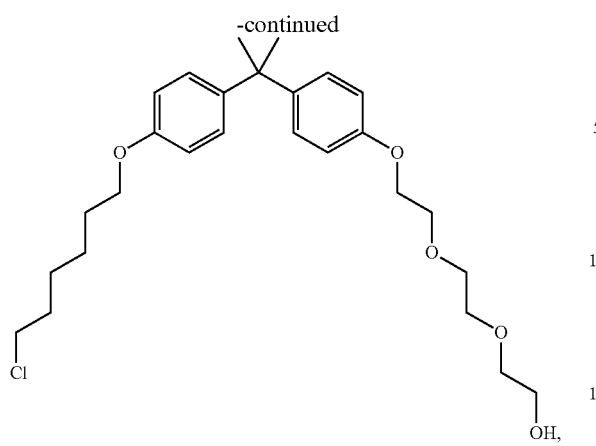

or a pharmaceutically acceptable salt thereof.

31. A pharmaceutical composition comprising a compound or pharmaceutically acceptable salt thereof of claim 7 and a pharmaceutically acceptable carrier.

32. The compound of claim 15, wherein the compound has the following structure:

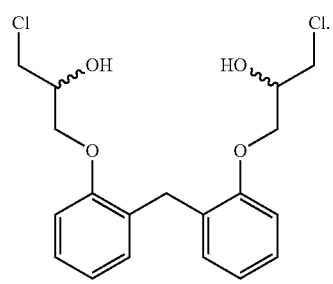 [SMILES: OC(CCl)COc1ccccc1Cc1ccccc1OCC(O)CCl]

33. A compound having the following structure:

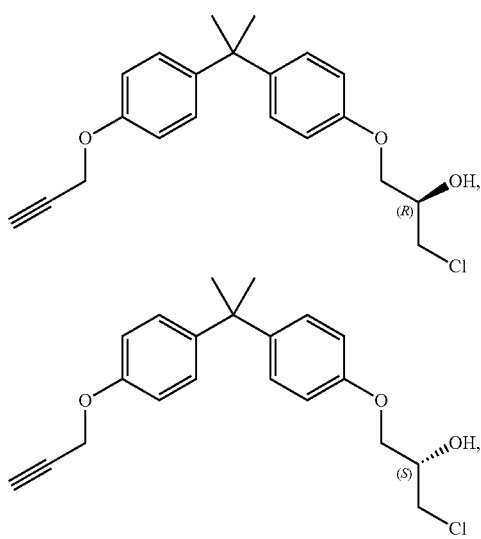

316

-continued

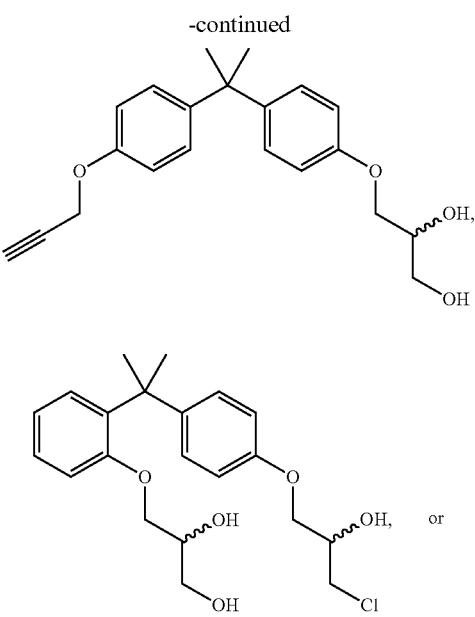

34. The compound or salt according to claim 9, wherein Q is

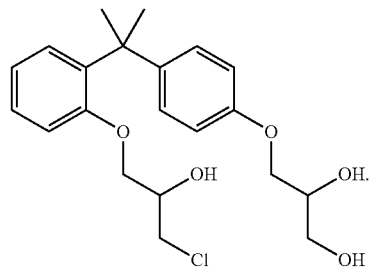

and T is

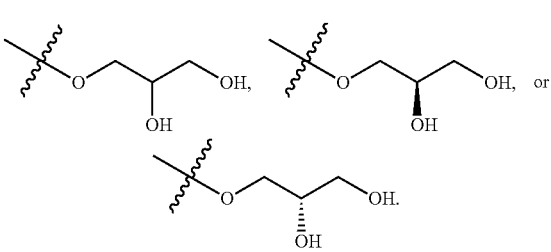

* * * * *